(12) United States Patent
Sommadossi et al.

(10) Patent No.: US 10,000,523 B2
(45) Date of Patent: *Jun. 19, 2018

(54) β-D-2'-DEOXY-2'-α-FLUORO-2'-β-C-SUBSTITUTED-2-MODIFIED-N⁶-SUBSTITUTED PURINE NUCLEOTIDES FOR HCV TREATMENT

(71) Applicant: Atea Pharmaceuticals, Inc., Boston, MA (US)

(72) Inventors: Jean-Pierre Sommadossi, Boston, MA (US); Adel Moussa, Burlington, MA (US)

(73) Assignee: Atea Pharmaceuticals, Inc., Boston, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/782,628

(22) Filed: Oct. 12, 2017

(65) Prior Publication Data

US 2018/0030081 A1 Feb. 1, 2018

Related U.S. Application Data

(63) Continuation of application No. 15/063,461, filed on Mar. 7, 2016, now Pat. No. 9,828,410.

(60) Provisional application No. 62/276,597, filed on Jan. 8, 2016, provisional application No. 62/253,958, filed on Nov. 11, 2015, provisional application No. 62/129,319, filed on Mar. 6, 2015.

(51) Int. Cl.
*A61K 31/7076* (2006.01)
*C07H 19/207* (2006.01)
*C07H 19/16* (2006.01)
*C07H 19/20* (2006.01)

(52) U.S. Cl.
CPC ....... *C07H 19/207* (2013.01); *A61K 31/7076* (2013.01); *C07H 19/16* (2013.01); *C07H 19/20* (2013.01)

(58) Field of Classification Search
None
See application file for complete search history.

(56) References Cited

U.S. PATENT DOCUMENTS

| | | | |
|---|---|---|---|
| 5,977,061 A | 11/1999 | Holy et al. |
| 6,348,587 B1 | 2/2002 | Schinazi et al. |
| 6,660,721 B2 | 12/2003 | Devos et al. |
| 6,777,395 B2 | 8/2004 | Bhat et al. |
| 6,784,166 B2 | 8/2004 | Devos et al. |
| 6,812,219 B2 | 11/2004 | LaColla et al. |
| 6,908,924 B2 | 6/2005 | Watanabe et al. |
| 6,911,424 B2 | 6/2005 | Schinazi et al. |
| 6,914,054 B2 | 7/2005 | Sommadossi et al. |
| 6,949,522 B2 | 9/2005 | Otto et al. |
| 7,094,770 B2 | 8/2006 | Watanabe et al. |
| 7,105,493 B2 | 9/2006 | Sommadossi et al. |
| 7,105,499 B2 | 9/2006 | Carroll et al. |
| 7,125,855 B2 | 10/2006 | Bhat et al. |
| 7,138,376 B2 | 11/2006 | Gosselin et al. |
| 7,148,206 B2 | 12/2006 | Sommadossi et al. |
| 7,157,441 B2 | 1/2007 | Sommadossi et al. |
| 7,163,929 B2 | 1/2007 | Sommadossi et al. |
| 7,169,766 B2 | 1/2007 | Sommadossi et al. |
| 7,192,936 B2 | 3/2007 | LaColla et al. |
| 7,202,224 B2 | 4/2007 | Eldrup et al. |
| 7,211,570 B2 | 5/2007 | Schinazi et al. |
| 7,268,119 B2 | 9/2007 | Cook et al. |
| 7,285,658 B2 | 10/2007 | Cook et al. |
| 7,307,065 B2 | 12/2007 | Schinazi et al. |
| 7,323,449 B2 | 1/2008 | Olsen et al. |
| 7,339,054 B2 | 3/2008 | Xu et al. |
| 7,365,057 B2 | 4/2008 | LaColla et al. |
| 7,384,924 B2 | 6/2008 | LaColla et al. |
| 7,388,002 B2 | 6/2008 | Babu et al. |
| 7,429,571 B2 | 9/2008 | Chand et al. |
| 7,429,572 B2 | 9/2008 | Clark |
| 7,456,155 B2 | 11/2008 | Sommadossi et al. |
| 7,495,006 B2 | 2/2009 | Liotta et al. |
| 7,514,410 B2 | 4/2009 | Babu et al. |
| 7,534,767 B2 | 5/2009 | Butora et al. |
| 7,547,704 B2 | 6/2009 | LaColla et al. |
| 7,560,434 B2 | 7/2009 | Babu et al. |
| 7,560,550 B2 | 7/2009 | Doring et al. |
| 7,582,618 B2 | 9/2009 | Sommadossi et al. |

(Continued)

FOREIGN PATENT DOCUMENTS

| | | |
|---|---|---|
| CN | 103435672 A | 12/2013 |
| EP | 0547008 A1 | 6/1993 |
| EP | 0398231 B1 | 7/1997 |
| WO | WO 1998/16184 | 4/1998 |
| WO | WO 2001/90121 A2 | 11/2001 |

(Continued)

OTHER PUBLICATIONS

Ahmad, T. et al. "Cardiac dysfunction associated with a nucleotide polymerase inhibitor for treatment of hepatitis C" Hepatology 2015, 62, 409.

(Continued)

*Primary Examiner* — Traviss C McIntosh, III
(74) *Attorney, Agent, or Firm* — Knowles Intellectual Property Strategies, LLC

(57) ABSTRACT

A compound of the structure:

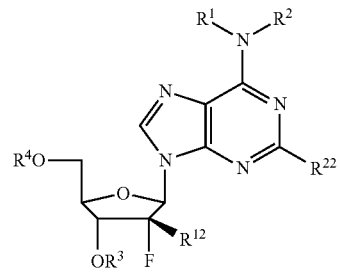

or a pharmaceutically acceptable salt or composition thereof for the treatment of a host infected with or exposed to an HCV virus or other disorders more fully described herein.

30 Claims, 11 Drawing Sheets

(56) References Cited

U.S. PATENT DOCUMENTS

| | | |
|---|---|---|
| 7,601,820 B2 | 10/2009 | Wang et al. |
| 7,608,597 B2 | 10/2009 | Sommadossi et al. |
| 7,608,599 B2 | 10/2009 | Klumpp et al. |
| 7,608,600 B2 | 10/2009 | Storer et al. |
| 7,608,601 B2 | 10/2009 | Devos et al. |
| 7,625,875 B2 | 12/2009 | Gosselin et al. |
| 7,632,821 B2 | 12/2009 | Butora et al. |
| 7,635,689 B2 | 12/2009 | LaColla et al. |
| 7,638,502 B2 | 12/2009 | Schinazi et al. |
| 7,662,798 B2 | 2/2010 | LaColla et al. |
| 7,662,938 B2 | 2/2010 | Schinazi et al. |
| 7,713,941 B2 | 5/2010 | Cook et al. |
| 7,718,790 B2 | 5/2010 | Stuyver et al. |
| 7,772,208 B2 | 8/2010 | Schinazi et al. |
| 7,824,851 B2 | 11/2010 | Sommadossi et al. |
| 7,842,672 B2 | 11/2010 | Boojamra et al. |
| RE42,015 E | 12/2010 | Watanabe et al. |
| 7,879,815 B2 | 2/2011 | MacCoss et al. |
| 7,902,202 B2 | 3/2011 | Sommadossi et al. |
| 7,919,247 B2 | 4/2011 | Stuyver et al. |
| 7,932,240 B2 | 4/2011 | Dousson et al. |
| 7,951,789 B2 | 5/2011 | Sommadossi et al. |
| 7,964,580 B2 | 6/2011 | Sofia et al. |
| 7,973,013 B2 | 7/2011 | Cho et al. |
| 7,994,139 B2 | 8/2011 | Babu et al. |
| 8,008,264 B2 | 8/2011 | Butler et al. |
| 8,012,941 B2 | 9/2011 | Cho et al. |
| 8,012,942 B2 | 9/2011 | Butler et al. |
| 8,071,567 B2 | 12/2011 | Devos et al. |
| 8,071,568 B2 | 12/2011 | Narjes et al. |
| 8,093,380 B2 | 1/2012 | Wang et al. |
| 8,114,994 B2 | 2/2012 | Liotta et al. |
| 8,114,997 B2 | 2/2012 | Otto et al. |
| 8,119,607 B2 | 2/2012 | Francom et al. |
| 8,133,870 B2 | 3/2012 | Babu et al. |
| 8,148,349 B2 | 4/2012 | Meppen et al. |
| 8,163,703 B2 | 4/2012 | Babu et al. |
| 8,168,583 B2 | 5/2012 | Schinazi et al. |
| 8,173,621 B2 | 5/2012 | Du et al. |
| 8,193,372 B2 | 6/2012 | Dousson et al. |
| 8,242,085 B2 | 8/2012 | Babu et al. |
| 8,299,038 B2 | 10/2012 | Sommadossi et al. |
| 8,318,682 B2 | 11/2012 | Butler et al. |
| 8,324,179 B2 | 12/2012 | Chen et al. |
| 8,334,270 B2 | 12/2012 | Sofia et al. |
| 8,343,937 B2 | 1/2013 | Sommadossi et al. |
| 8,362,068 B2 | 1/2013 | Dousson et al. |
| 8,399,429 B2 | 3/2013 | Jonckers et al. |
| 8,415,308 B2 | 4/2013 | Cho et al. |
| 8,415,309 B2 | 4/2013 | Francom et al. |
| 8,415,322 B2 | 4/2013 | Clark |
| 8,431,588 B2 | 4/2013 | Jonckers et al. |
| 8,440,813 B2 | 5/2013 | Babu et al. |
| 8,455,451 B2 | 6/2013 | Cho et al. |
| 8,470,834 B2 | 6/2013 | Kwong et al. |
| 8,481,510 B2 | 7/2013 | Jonckers et al. |
| 8,481,712 B2 | 7/2013 | Bhat et al. |
| 8,481,713 B2 | 7/2013 | Wang et al. |
| 8,492,539 B2 | 7/2013 | Chun et al. |
| 8,501,699 B2 | 8/2013 | Francom et al. |
| 8,507,460 B2 | 8/2013 | Surleraux et al. |
| 8,541,434 B2 | 9/2013 | Kwong et al. |
| 8,551,973 B2 | 10/2013 | Bao et al. |
| 8,552,021 B2 | 10/2013 | Jonckers et al. |
| 8,563,530 B2 | 10/2013 | Chang et al. |
| 8,575,119 B2 | 11/2013 | Wang et al. |
| 8,580,765 B2 | 11/2013 | Sofia et al. |
| 8,609,627 B2 | 12/2013 | Cho et al. |
| 8,618,076 B2 | 12/2013 | Ross et al. |
| 8,629,263 B2 | 1/2014 | Ross et al. |
| 8,633,309 B2 | 1/2014 | Ross et al. |
| 8,637,475 B1 | 1/2014 | Storer et al. |
| 8,642,756 B2 | 2/2014 | Ross et al. |
| 8,673,926 B2 | 3/2014 | Chu |
| 8,674,085 B2 | 3/2014 | Sommadossi et al. |
| 8,680,071 B2 | 3/2014 | Surleraux et al. |
| 8,691,788 B2 | 4/2014 | Sommadossi et al. |
| 8,697,694 B2 | 4/2014 | Arasappan et al. |
| 8,715,638 B2 | 5/2014 | Kwong et al. |
| 8,716,262 B2 | 5/2014 | Sofia et al. |
| 8,716,263 B2 | 5/2014 | Chun et al. |
| 8,735,345 B2 | 5/2014 | Porter et al. |
| 8,735,372 B2 | 5/2014 | Du et al. |
| 8,735,569 B2 | 5/2014 | Ross et al. |
| 8,742,101 B2 | 6/2014 | Storer et al. |
| 8,759,318 B2 | 6/2014 | Chamberlain et al. |
| 8,759,510 B2 | 6/2014 | Du et al. |
| 8,765,710 B2 | 7/2014 | Sofia et al. |
| 8,772,474 B2 | 7/2014 | Beigelman et al. |
| 8,802,840 B2 | 8/2014 | Francom et al. |
| 8,815,829 B2 | 8/2014 | Schinazi et al. |
| 8,816,074 B2 | 8/2014 | Chu et al. |
| 8,841,275 B2 | 9/2014 | Du et al. |
| 8,846,638 B2 | 9/2014 | Or et al. |
| 8,846,896 B2 | 9/2014 | Serebryany et al. |
| 8,853,171 B2 | 10/2014 | Butler et al. |
| 8,859,595 B2 | 10/2014 | Coats et al. |
| 8,871,737 B2 | 10/2014 | Smith et al. |
| 8,871,785 B2 | 10/2014 | Boojamra et al. |
| 8,877,731 B2 | 11/2014 | Beigelman et al. |
| 8,877,733 B2 | 11/2014 | Cho et al. |
| 8,889,159 B2 | 11/2014 | Cleary et al. |
| 8,889,701 B1 | 11/2014 | Ivachtchenko et al. |
| 8,895,531 B2 | 11/2014 | Shi |
| 8,895,723 B2 | 11/2014 | Serebryany et al. |
| 8,906,880 B2 | 12/2014 | Du et al. |
| 8,912,321 B2 | 12/2014 | Axt et al. |
| 8,921,384 B2 | 12/2014 | Chu |
| 8,933,052 B2 | 1/2015 | Jonckers et al. |
| 8,946,244 B2 | 2/2015 | Chu et al. |
| 8,951,985 B2 | 2/2015 | Surleraux et al. |
| 8,957,045 B2 | 2/2015 | Sofia et al. |
| 8,957,046 B2 | 2/2015 | Du et al. |
| 8,980,865 B2 | 3/2015 | Wang et al. |
| 9,012,427 B2 | 4/2015 | Blatt et al. |
| 9,012,428 B2 | 4/2015 | Jonckers et al. |
| 9,045,520 B2 | 6/2015 | Chun et al. |
| 9,061,041 B2 | 6/2015 | Girijavallabhan et al. |
| 9,085,573 B2 | 7/2015 | Du et al. |
| 9,085,599 B2 | 7/2015 | Or et al. |
| 9,090,642 B2 | 7/2015 | Cho et al. |
| 9,109,001 B2 | 8/2015 | Parsy et al. |
| 9,139,604 B2 | 9/2015 | Boojamra et al. |
| 9,156,872 B2 | 10/2015 | Girijavallabhan et al. |
| 9,173,893 B2 | 11/2015 | Cho et al. |
| 9,187,515 B2 | 11/2015 | Mayes et al. |
| 9,211,300 B2 | 12/2015 | Mayes et al. |
| 9,243,025 B2 | 1/2016 | Surleraux et al. |
| 9,603,863 B2 | 3/2017 | Blatt et al. |
| 9,603,864 B2 | 3/2017 | Blatt et al. |
| 2004/0063658 A1 | 4/2004 | Roberts et al. |
| 2004/0229839 A1 | 11/2004 | Babu et al. |
| 2004/0259934 A1 | 12/2004 | Olsen et al. |
| 2010/0249068 A1 | 9/2010 | Beigelman et al. |
| 2010/0279969 A1 | 11/2010 | Schinazi et al. |
| 2011/0257121 A1 | 10/2011 | Chang et al. |
| 2012/0070411 A1 | 3/2012 | Beigelman et al. |
| 2012/0135951 A1 | 5/2012 | Schinazi et al. |
| 2013/0064794 A1 | 3/2013 | Surleraux et al. |
| 2014/0038916 A1 | 2/2014 | Wang et al. |
| 2014/0066395 A1 | 3/2014 | Cho et al. |
| 2014/0212382 A1 | 7/2014 | Schinazi et al. |
| 2014/0235566 A1 | 8/2014 | Amblard et al. |
| 2015/0011497 A1 | 1/2015 | Beigelman et al. |
| 2015/0105341 A1 | 4/2015 | Beigelman et al. |
| 2016/0002281 A1 | 1/2016 | Mayes et al. |
| 2016/0257706 A1 | 9/2016 | Sommadossi et al. |

FOREIGN PATENT DOCUMENTS

| | | |
|---|---|---|
| WO | WO 2001/92282 A2 | 12/2001 |
| WO | WO 2002/32920 A2 | 4/2002 |
| WO | WO 2003/039523 A2 | 5/2003 |

(56) References Cited

FOREIGN PATENT DOCUMENTS

| | | |
|---|---|---|
| WO | WO 2003/062256 A1 | 7/2003 |
| WO | WO 2003/093290 A2 | 11/2003 |
| WO | WO 2004/002999 A2 | 1/2004 |
| WO | WO 2004/003000 A2 | 1/2004 |
| WO | WO 2004/014312 A2 | 2/2004 |
| WO | WO 2004/091499 A2 | 10/2004 |
| WO | WO 2004/106356 A1 | 12/2004 |
| WO | WO 2005/000864 A1 | 1/2005 |
| WO | WO 2005/021568 A2 | 3/2005 |
| WO | WO 2005/084192 A2 | 9/2005 |
| WO | WO 2005/090370 A1 | 9/2005 |
| WO | WO 2006/012078 A2 | 2/2006 |
| WO | WO 2006/063149 A1 | 6/2006 |
| WO | WO 2006/063717 A2 | 7/2006 |
| WO | WO 2006/094347 A1 | 9/2006 |
| WO | WO 2006/102533 A2 | 9/2006 |
| WO | WO 2006/121820 A1 | 11/2006 |
| WO | WO 2006/130217 A2 | 12/2006 |
| WO | WO 2007/022073 A2 | 2/2007 |
| WO | WO 2007/112028 A2 | 10/2007 |
| WO | WO 2007/130783 A1 | 11/2007 |
| WO | WO 2008/012555 A1 | 1/2008 |
| WO | WO 2008/048128 A1 | 4/2008 |
| WO | WO 2008/062206 A2 | 5/2008 |
| WO | WO 2008/095040 A2 | 10/2008 |
| WO | WO 2009/001097 A2 | 12/2008 |
| WO | WO 2009/003042 A1 | 12/2008 |
| WO | WO 2009/067409 A1 | 5/2009 |
| WO | WO 2009/086192 A1 | 7/2009 |
| WO | WO 2009/086201 A1 | 7/2009 |
| WO | WO 2009/129120 A2 | 10/2009 |
| WO | WO 2010/081082 A2 | 7/2010 |
| WO | WO 2010/091386 A2 | 8/2010 |
| WO | WO 2010/108135 A1 | 9/2010 |
| WO | WO 2010/145778 | 12/2010 |
| WO | WO 2011/005595 A1 | 1/2011 |
| WO | WO 2011/005860 A2 | 1/2011 |
| WO | WO 2012/041965 A1 | 4/2012 |
| WO | WO 2012/048013 A2 | 4/2012 |
| WO | WO 2012/092484 A2 | 7/2012 |
| WO | WO 2012/125900 A1 | 9/2012 |
| WO | WO 2012/154321 A1 | 11/2012 |
| WO | WO 2012/158811 A2 | 11/2012 |
| WO | WO 2013/009737 A1 | 1/2013 |
| WO | WO 2013/019874 A1 | 2/2013 |
| WO | WO 2013/039855 A1 | 3/2013 |
| WO | WO 2013/039920 A1 | 3/2013 |
| WO | WO 2013/044030 A1 | 3/2013 |
| WO | WO 2013/090420 A2 | 6/2013 |
| WO | WO 2013/096680 A1 | 6/2013 |
| WO | WO 2013/142125 A1 | 9/2013 |
| WO | WO 2013/142157 A1 | 9/2013 |
| WO | WO 2013/142159 A1 | 9/2013 |
| WO | WO 2013/151975 A1 | 10/2013 |
| WO | WO 2013/177219 A1 | 11/2013 |
| WO | WO 2013/187978 A1 | 12/2013 |
| WO | WO 2014/008236 A1 | 1/2014 |
| WO | WO 2014/047117 A1 | 3/2014 |
| WO | WO 2014/052638 A1 | 4/2014 |
| WO | WO 2014/063019 A1 | 4/2014 |
| WO | WO 2014/076490 A1 | 5/2014 |
| WO | WO 2014/082935 A1 | 6/2014 |
| WO | WO 2014/100498 A1 | 6/2014 |
| WO | WO 2014/100505 A1 | 6/2014 |
| WO | WO 2014/124430 A1 | 8/2014 |
| WO | WO 2014/137930 A1 | 9/2014 |
| WO | WO 2014/169278 A1 | 10/2014 |
| WO | WO 2014/169280 A2 | 10/2014 |
| WO | WO 2014/209979 A1 | 12/2014 |
| WO | WO 2015/038596 A1 | 3/2015 |
| WO | WO 2015/053662 A1 | 4/2015 |
| WO | WO 2015/081133 A2 | 6/2015 |
| WO | WO 2015/095305 A1 | 6/2015 |
| WO | WO 2015/158913 A1 | 10/2015 |
| WO | WO 2016/041877 A1 | 3/2016 |
| WO | WO 2016/100441 A1 | 6/2016 |
| WO | WO 2016/100569 A1 | 6/2016 |
| WO | WO 2016/144918 A1 | 9/2016 |
| WO | WO 2016/145142 A1 | 9/2016 |

OTHER PUBLICATIONS

Chang, W. et al. "Discovery of PSI-353661, a Novel Purine Nucleotide Prodrug for the Treatment of HCV Infection" ACS Med Chem Lett. 2011, 2, 130.

Cretton-Scott, E. et al. "In Vitro Antiviral Activity and Pharmacology of IDX184, A Novel and Potent Inhibitor of HCV Replication" (Abstract 588) J. Hepatol. 2008, 48, Supplement 2, S220.

Freeman et al. 2-amino-9(3-azido-2,3-dideoxy-β-D-erythropentofuranosyl)-6-Substituted-9H-Purines: Synthesis and Anti-HIV Activity. Bioorganic and Medicinal Chemistry, 1995; 3(4): 447-448.

Herman, B. et al. "Substrate mimicry: HIV-1 reverse transcriptase recognizes 6-modified-30-azido-20,30-dideoxyguanosine-50-triphosphates as adenosine analogs" Nucleic Acids Research 2012, 40, 381.

McGuigan, C. et al. "Design, synthesis and evaluation of a novel double pro-drug: INX-08189. A new clinical candidate for hepatitis C virus" Bioorganic & Medicinal Chemistry Letters 2010, 20, 4850.

McGuigan, C. et al. "Dual pro-drugs of 2'-C-methyl guanosine monophosphate as potent and selective inhibitors of hepatitis C virus" Bioorganic & Medicinal Chemistry Letters 2011, 21, 6007.

Murakami, E. et al. "Adenosine Deaminase-like Protein 1 (ADAL1): Characterization and Substrate Specificity in the Hydrolysis of N6- or O6-Substituted Purine or 2-Aminopurine Nucleoside Monophosphates" J Med Chem 2011, 54, 5902.

Pradere, U. et al. "Synthesis of 5'-Methylene-Phosphonate Furanonucleoside Prodrugs: Application to D-2'-Deoxy-2'-α-fluoro-2'-β-C-methyl Nucleosides" Organic Letters 2012, 14, 4426.

Reddy, P. et al. "2'-Deoxy-2'-α-fluoro-2'-β-C-methyl 3',5'-cyclic phosphate nucleotide prodrug analogs as inhibitors of HCV NS5B polymerase: Discovery of PSI-352938" Bioorganic & Medicinal Chemistry Letters 2010, 20, 7376.

Tao, S., Zhou, L., Zhang, H., Zhou, S., Amiralaei, S., Shelton, J.R., Coats, S.J., Schinazi, R.F.: Comparison of Three 2'-C-Methyl Guanosine Prodrugs for Hepatitis C including a Novel $^2$-D-2'-C-Me-2,6-Diaminopurine Ribonucleoside Phosphoramidate (RS-1389): Interspecies Hepatocyte and Human Cardiomyocyte Metabolism Profiles. The Liver Meeting 2014. Boston, MA, USA. Nov. 6-11, 2014.

Zhang et al. "Synthesis and evaluation of 30-azido-20,30-dideoxypurine nucleosides as inhibitors of human immunodeficiency virus" Bioorganic and Medicinal Chemistry Letters 2010, 20, 60.

Zhou, L. et al. "β-D-2'-C-Methyl-2,6-diaminopurine Ribonucleoside Phosphoramidates are Potent and Selective Inhibitors of Hepatitis C Virus (HCV) and Are Bioconverted Intracellularly to Bioactive 2,6-Diaminopurine and Guanosine 5'-Triphosphate Forms" J Med Chem 2015, 58, 3445.

PCT/US2016/021276 International Search Report and Written Opinion, dated Jun. 17, 2016.

β-D-2'-DEOXY-2'-α-FLUORO-2'-β-C-SUBSTITUTED-2-MODIFIED-N⁶-SUBSTITUTED PURINE NUCLEOTIDES FOR HCV TREATMENT

PRIORITY

This application is a continuation of U.S. Ser. No. 15/063,461 filed on Mar. 7, 2016 and claims priority to U.S. Ser. No. 62/129,319 filed on Mar. 6, 2015; U.S. Ser. No. 62/253,958 filed on Nov. 11, 2015; and, U.S. Ser. No. 62/276,597 filed on Jan. 8, 2016. Each of these references is incorporated herewith in their entirety.

FIELD OF THE INVENTION

The present invention is directed to nucleotide compounds and compositions and uses thereof to treat the Hepatitis C virus ("HCV").

BACKGROUND OF THE INVENTION

Hepatitis C (HCV) is an RNA single stranded virus and member of the Hepacivirus genus. It is estimated that 75% of all cases of liver disease are caused by HCV. HCV infection can lead to cirrhosis and liver cancer, and if left to progress, liver failure which may require a liver transplant. Approximately 170-200 million people worldwide are infected, with an estimated 3-4 million infections in the United States.

RNA polymerase is a key component in the targeting of RNA single stranded viruses. The HCV non-structural protein NS5B RNA-dependent RNA polymerase is a key enzyme responsible for initiating and catalyzing viral RNA synthesis. As a result, HCV NS5B is an attractive target for the current drug discovery and development of anti-HCV agents. There are two major subclasses of NS5B inhibitors: nucleoside analogs, which are anabolized to their active triphosphates—which act as alternative substrates for the polymerase—and non-nucleoside inhibitors (NNIs), which bind to allosteric regions on the protein. Nucleoside or nucleotide inhibitors mimic natural polymerase substrate and act as chain terminators. They inhibit the initiation of RNA transcription and elongation of a nascent RNA chain.

In addition to targeting RNA polymerase, other RNA viral proteins may also be targeted in combination therapies. For example, HCV proteins that are additional targets for therapeutic approaches are NS3/4A (a serine protease) and NS5A (a non-structural protein that is an essential component of HCV replicase and exerts a range of effects on cellular pathways).

In December 2013, the first nucleoside NS5B polymerase inhibitor sofosbuvir (Sovaldi®, Gilead Sciences) was approved. Sovaldi® is a uridine phosphoramidate prodrug that is taken up by hepatocytes and undergoes intracellular activation to afford the active metabolite; 2'-deoxy-2'-α-fluoro-β-C-methyluridine-5'-triphosphate; see structures below:

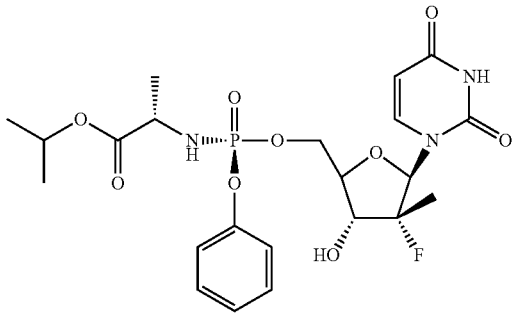

Sovaldi®

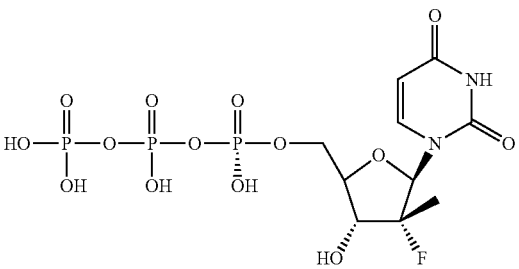

2'-Deoxy-2'-α-fluoro-β-C-methyluridine-5'-triphosphate

Sovaldi® is the first drug that has demonstrated safety and efficacy to treat certain types of HCV infection without the need for co-administration of interferon. Sovaldi® is the third drug with breakthrough therapy designation to receive FDA approval.

In 2014, the U.S. FDA approved Harvoni® (ledispasvir, a NS5A inhibitor, and sofosbuvir) to treat chronic hepatitis C virus genotype 1 infection. Harvoni® is the first combination pill approved to treat chronic HCV genotype 1 infection. It is also the first approved regimen that does not require administration with interferon or ribavirin. In addition, the FDA approved simeprevir (Olysio™) in combination with sofosbuvir (Sovaldi®) as a once-daily, all oral, interferon and ribavirin-free treatment for adults with genotype 1 HCV infection.

The U.S. FDA also approved AbbVie's VIEKIRA Pak™ in 2014, a multipill pack containing dasabuvir (a non-nucleoside NS5B polymerase inhibitor), ombitasvir (a NS5A inhibitor), paritaprevir (a NS3/4A inhibitor), and ritonavir. The VIEKIRA Pak™ can be used with or without the ribavirin to treat genotype 1 HCV infected patients including patients with compensated cirrhosis. VIEKIRA Pak™ does not require interferon co-therapy.

In July 2015, the U.S. FDA approved Technivie™ and Daklinza™ for the treatment of HCV genotype 4 and HCV genotype 3 respectively. Technivie™ (Ombitasvir/paritaprevir/ritonavir) was approved for use in combination with ribavirin for the treatment of HCV genotype 4 in patients without scarring and cirrhosis and is the first option for HCV-4 infected patients who do not require co-administration with interferon. Daklinza™ was approved for use with Sovaldi® to treat HCV genotype 3 infections. Daklinza™ is the first drug that has demonstrated safety and efficacy in treating HCV genotype 3 without the need for co-administration of interferon or ribavirin.

In October 2015, the U.S. FDA warned that HCV treatments Viekira Pak and Technivie can cause serious liver injury primarily in patients with underlying advanced liver disease, and required that additional information about safety be added to the label.

Other current approved therapies for HCV include interferon alpha-2b or pegylated interferon alpha-2b (Pegintron®), which can be administered with ribavirin (Rebetol®), NS3/4A telaprevir (Incivek®, Vertex and Johnson & Johnson), boceprevir (Victrelis™, Merck), simeprevir (Olysio™, Johnson & Johnson), paritaprevir (AbbVie), Ombitasvir (AbbVie), (NNI) Dasabuvir (ABT-333) and Merck's Zepatier™ (a single-tablet combination of the two drugs grazoprevir and elbasvir).

Additional NS5B polymerase inhibitors are currently under development. Merck is developing the uridine nucleotide prodrug MK-3682 (formerly Idenix IDX21437). The drug is currently in Phase II combination trials.

United States patents and WO applications which describe nucleoside polymerase inhibitors for the treatment of Flaviviridae, including HCV, include those filed by Idenix Pharmaceuticals (U.S. Pat. Nos. 6,812,219; 6,914,054; 7,105,493; 7,138,376; 7,148,206; 7,157,441; 7,163,929; 7,169,766; 7,192,936; 7,365,057; 7,384,924; 7,456,155; 7,547,704; 7,582,618; 7,608,597; 7,608,600; 7,625,875; 7,635,689; 7,662,798; 7,824,851; 7,902,202; 7,932,240; 7,951,789; 8,193,372; 8,299,038; 8,343,937; 8,362,068; 8,507,460; 8,637,475; 8,674,085; 8,680,071; 8,691,788; 8,742,101, 8,951,985; 9,109,001; 9,243,025; US2016/0002281; US2013/0064794; WO/2015/095305; WO/2015/081133; WO/2015/061683; WO/2013/177219; WO/2013/039920; WO/2014/137930; WO/2014/052638; WO/2012/154321); Merck (U.S. Pat. Nos. 6,777,395; 7,105,499; 7,125,855; 7,202,224; 7,323,449; 7,339,054; 7,534,767; 7,632,821; 7,879,815; 8,071,568; 8,148,349; 8,470,834; 8,481,712; 8,541,434; 8,697,694; 8,715,638, 9,061,041; 9,156,872 and WO/2013/009737); Emory University (U.S. Pat. Nos. 6,348,587; 6,911,424; 7,307,065; 7,495,006; 7,662,938; 7,772,208; 8,114,994; 8,168,583; 8,609,627; US 2014/0212382; and WO2014/1244430); Gilead Sciences/Pharmasset Inc. (U.S. Pat. Nos. 7,842,672; 7,973,013; 8,008,264; 8,012,941; 8,012,942; 8,318,682; 8,324,179; 8,415,308; 8,455,451; 8,563,530; 8,841,275; 8,853,171; 8,871,785; 8,877,733; 8,889,159; 8,906,880; 8,912,321; 8,957,045; 8,957,046; 9,045,520; 9,085,573; 9,090,642; and 9,139,604) and (U.S. Pat. Nos. 6,908,924; 6,949,522; 7,094,770; 7,211,570; 7,429,572; 7,601,820; 7,638,502; 7,718,790; 7,772,208; RE42,015; 7,919,247; 7,964,580; 8,093,380; 8,114,997; 8,173,621; 8,334,270; 8,415,322; 8,481,713; 8,492,539; 8,551,973; 8,580,765; 8,618,076; 8,629,263; 8,633,309; 8,642,756; 8,716,262; 8,716,263; 8,735,345; 8,735,372; 8,735,569; 8,759,510 and 8,765,710); Hoffman La-Roche (U.S. Pat. No. 6,660,721), Roche (U.S. Pat. Nos. 6,784,166; 7,608,599, 7,608,601 and 8,071,567); Alios BioPharma Inc. (U.S. Pat. Nos. 8,895,723; 8,877,731; 8,871,737, 8,846,896, 8,772,474; 8,980,865; 9,012,427; US 2015/0105341; US 2015/0011497; US 2010/0249068; US2012/0070411; WO 2015/054465; WO 2014/209979; WO 2014/100505; WO 2014/100498; WO 2013/142159; WO 2013/142157; WO 2013/096680; WO 2013/088155; WO 2010/108135), Enanta Pharmaceuticals (U.S. Pat. Nos. 8,575,119; 8,846,638; 9,085,599; WO 2013/044030; WO 2012/125900), Biota (U.S. Pat. Nos. 7,268,119; 7,285,658; 7,713,941; 8,119,607; 8,415,309; 8,501,699 and 8,802,840), Biocryst Pharmaceuticals (U.S. Pat. Nos. 7,388,002; 7,429,571; 7,514,410; 7,560,434; 7,994,139; 8,133,870; 8,163,703; 8,242,085 and 8,440,813), Alla Chem, LLC (U.S. Pat. No. 8,889,701 and WO 2015/053662), Inhibitex (U.S. Pat. No. 8,759,318 and WO/2012/092484), Janssen Products (U.S. Pat. Nos. 8,399,429; 8,431,588, 8,481,510, 8,552,021, 8,933,052; 9,006,29 and 9,012,428) the University of Georgia Foundation (U.S. Pat. Nos. 6,348,587; 7,307,065; 7,662,938; 8,168,583; 8,673,926, 8,816,074; 8,921,384 and 8,946,244), RFS Pharma, LLC (U.S. Pat. Nos. 8,895,531; 8,859,595; 8,815,829; 8,609,627; 7,560,550; US 2014/0066395; US 2014/0235566; US 2010/0279969; WO/2010/091386 and WO 2012/158811) University College Cardiff Consultants Limited (WO/2014/076490, WO 2010/081082; WO/2008/062206), Achillion Pharmaceuticals, Inc. (WO/2014/169278 and WO 2014/169280), Cocrystal Pharma, Inc. (U.S. Pat. No. 9,173,893), Katholieke Universiteit Leuven (WO 2015/158913), Catabasis (WO 2013/090420) and the Regents of the University of Minnesota (WO 2006/004637).

Nonetheless, there remains a strong medical need to develop anti-HCV therapies that are safe, effective and well-tolerated. The need is accentuated by the expectation that drug resistance. More potent direct-acting antivirals could significantly shorten treatment duration and improve compliance and SVR rates for patients infected with all HCV genotypes.

It is therefore an object of the present invention to provide compounds, pharmaceutical compositions, and methods and uses to treat and/or prevent infections of HCV.

SUMMARY OF THE INVENTION

It has been discovered that the compounds of Formula I, Formula II, Formula III, Formula IV, Formula V, Formula VI, Formula VII and including β-D-2'-deoxy-2'-α-fluoro-2'-β-C-substituted-$N^6$-(mono- or di-methyl) purine nucleotides, are highly active against the HCV virus when administered in an effective amount to a host in need thereof. The host can be a human or any animal that carries the viral infection.

Disclosed nucleotides include those with nanomolar activity against HCV in vitro and therapeutic indices that range to 25,000 or more.

Surprisingly, the parent $N^6$-(methyl) purine nucleosides of disclosed compounds had not been developed or specifically disclosed as drug candidates prior to this invention. For example, it was reported in 2010 that 3'-azido-$N^6$-dimethyl-2,6-diaminopurine is not substantially deaminated by adenosine deaminase over a long period (120 minutes), and for that reason it had been considered an inappropriate compound to derivatize as a drug (see for example, WO 2010/091386, page 86 and corresponding U.S. Pat. No. 8,609,627).

However, it has now been discovered that compounds of the present invention are anabolized to a 5-monophosphate of the $N^6$-substituted-purine without substantial $N^6$-deamination and then subsequently anabolized at the 6-position to generate active guanine triphosphate compounds, in a manner that provides exceptional activity and therapeutic index.

In particular, it has been discovered that a 5'-stabilized phosphate prodrug or derivative of β-D-2'-deoxy-2'-α-fluoro-2'-β-methyl-$N^6$-methyl-2,6-diaminopurine nucleotide, as well as β-D-2'-deoxy-2'-α-fluoro-2'-β-methyl-$N^6$-dimethyl-2,6-diaminopurine nucleotide, and other β-D -2'-D-2'-α-fluoro-2'-β-C-substituted-2-modified-$N^6$-substituted purine nucleotides as described below, are highly active against HCV. This is surprising because the activity of the parent nucleoside β-D-2'-deoxy-2'-α-fluoro-2'-β-methyl-$N^6$-methyl-2,6-diaminopurine in a replicon assay ($EC_{50}$=15.7 micromolar) indicates that it is not suitable for use as a human drug due to insufficient activity (in combination with the reference WO 2010/091386, page 86 and corresponding U.S. Pat. No. 8,609,627 that suggests that $N^6$-methyl-2,6-diaminopurines are not deaminated in vivo) however, the stabilized racemic phosphate prodrug (phosphoramidate) exhibits an $EC_{50}$=26 nanomolar (nM), in a replicon assay, which is at least an 600 fold increase in activity. The corresponding (S)-phosphoramidate exhibits an $EC_{50}$=4 nM, which is at least a 3,900 fold increase in activity; see the structure below and compound 5-2 in Table 7. With a TC$_{50}$ greater than one hundred micromolar, the compound thus has a therapeutic index of greater than 25,000. For comparison, Sofosbuvir has an EC$_{50}$=53 nM, a TC$_{50}$ greater than one hundred micromolar and a therapeutic index greater than 1,920.

Compound 5-2 (Table 7)

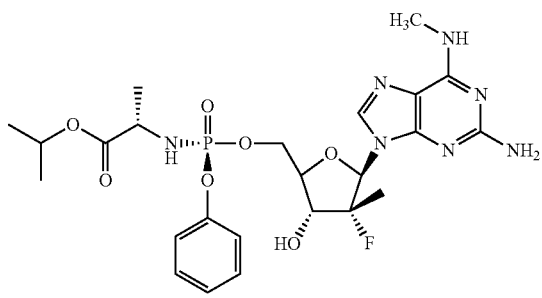

Likewise, the activity of the parent nucleoside β-D-2'-deoxy-2'-α-fluoro-2'-β-methyl-N$^6$-dimethyl-2,6-diaminopurine in a replicon assay (EC$_{50}$=10.7 micromolar, "µM") indicates that it is also not suitable for use as a human drug due to insufficient activity, however, the stabilized racemic phosphate prodrug (phosphoramidate) exhibits an EC$_{50}$=12 nM, in a replicon assay, which is more than a 890 fold increase in activity. The corresponding (S)-phosphoramidate (compound 25, Table 7) also exhibits an EC$_{50}$=4 nM, which is at least a 2,600 fold increase in activity; see the structure below. In addition, compound 25 also has a therapeutic index of greater than 25,000.

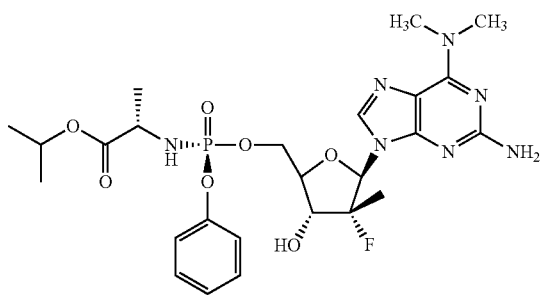 [SMILES: CC(C)OC(=O)[C@H](C)N[P@](=O)(OCC1O[C@@H](n2cnc3c(N(C)C)nc(N)nc32)[C@](C)(F)[C@@H]1O)Oc1ccccc1]

In another example, the compound isopropyl ((((R,S)-(2R,3R,4R,5R)-5-(2-amino-6-(N-methyl-N-cyclopropyl-amino)-9H-purin-9-yl)-4-fluoro-3-hydroxy-4-methyltetra-hydrofuran-2-yl)methoxy)-phenoxy-phosphoryl)-L-alaninate exhibited an EC$_{50}$=7 nM and the corresponding (S)-phosphoramidate exhibited an EC$_{50}$=5 nM in a replicon assay; see compound 27 in Table 7 and the structure below.

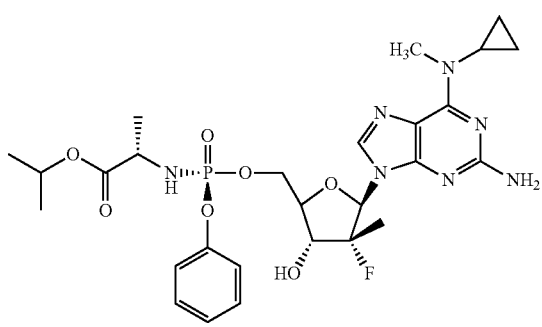 [SMILES: CC(C)OC(=O)[C@H](C)N[P@](=O)(OCC1O[C@@H](n2cnc3c(N(C)C4CC4)nc(N)nc32)[C@](C)(F)[C@@H]1O)Oc1ccccc1]

As stated above, the metabolism of the β-D-2'-deoxy-2'-α-fluoro-2'-β-methyl-N$^6$-methyl-2,6-diaminopurine nucleoside as a phosphoramidate involves the production of a 5'-monophosphate and the subsequent anabolism of the N$^6$-methyl-2,6-diaminopurine base to generate the β-D-2'-deoxy-2'-α-fluoro-2'-β-methyl-guanine nucleoside as the 5'-monophosphate. The monophosphate is then further anabolized to the active species; the 5'-triphosphate. The β-D-2'-deoxy-2'-α-fluoro-2'-β-methyl-guanine triphosphate has an IC$_{50}$=0.15 µM against the HCV genotype 1b NS5B polymerase.

Thus, in one embodiment, the invention is:

Formula I

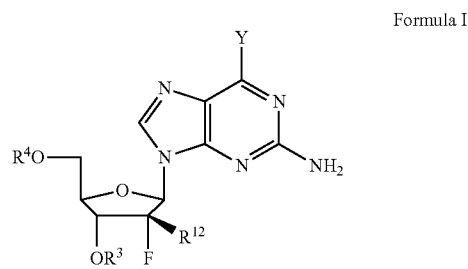

wherein:

Y is NR$^1$R$^2$;

R$^1$ is C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CH$_2$F, CHF$_2$, CF$_3$, CH$_2$CF$_3$, CF$_2$CH$_3$ and CF$_2$CF$_3$), C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(heterocycle), —(C$_0$-C$_2$alkyl)(aryl), —(C$_0$-C$_2$alkyl)(heteroaryl), —OR$^{25}$, —C(O)R$^{3C}$(including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$ each of which can be optionally substituted;

R$^2$ is hydrogen, C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CHF$_2$, CHF$_2$, CF$_3$, CH$_2$CF$_3$ and CF$_2$CF$_3$), —(C$_0$-C$_2$alkyl)(C$_3$-C$_6$cycloalkyl), —C(O)R$^{3C}$ (including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —(C$_0$-C$_2$alkyl)(aryl), —(C$_0$-C$_2$alkyl)(heterocycle), —(C$_0$-C$_2$alkyl)(heteroaryl); and wherein at least one of R$^1$ and R$^2$ is methyl, CH$_2$F, CHF$_2$ or CF$_3$;

R$^3$ is hydrogen,

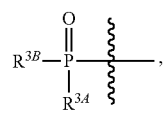

diphosphate, triphosphate, an optionally substituted carbonyl linked amino acid, or —C(O)R$^{3C}$;

R$^{3A}$ can be selected from O$^-$, OH, an —O-optionally substituted aryl, an —O-optionally substituted heteroaryl, or an optionally substituted heterocyclyl;

R$^{3B}$ can be selected from O$^-$, OH, an optionally substituted N-linked amino acid or an optionally substituted N-linked amino acid ester;

R$^{3C}$ is alkyl, alkenyl, alkynyl, —(C$_0$-C$_2$)(cycloalkyl), —(C$_0$-C$_2$)(heterocyclo), —(C$_0$-C$_2$)(aryl), —(C$_0$-C$_2$)(heteroaryl), —O-alkyl, —O-alkenyl, —O-alkynyl, —O—(C$_0$-C$_2$)(cycloalkyl), —O—(C$_0$-C$_2$)(heterocyclo), —O—(C$_0$-C$_2$)(aryl), or —O—(C$_0$-C$_2$)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug, including but not limited to, a 3',5'-cyclic phosphate prodrug;

$R^{12}$ is $CH_3$, $CH_2F$, $CHF_2$, $CF_3$, or ethynyl.

In one embodiment, the invention is:

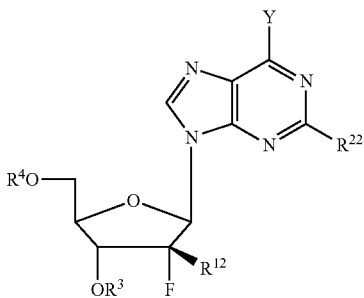

Formula II wherein:

Y is $NR^1R^2$;

$R^1$ is $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CH_2F$, $CHF_2$, $CF_3$, $CH_2CF_3$, $CF_2CH_3$ and $CF_2CF_3$), $C_2$-$C_6$ alkenyl, $C_2$-$C_6$ alkynyl, —($C_0$-$C_2$alkyl)($C_3$-$C_6$cycloalkyl), —($C_0$-$C_2$alkyl)(heterocycle), —($C_0$-$C_2$alkyl)(aryl), —($C_0$-$C_2$alkyl)(heteroaryl), —$OR^{25}$, —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$ each of which can be optionally substituted;

$R^2$ is hydrogen, optionally substituted $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CHF_2$, $CF_3$, $CH_2CF_3$ and $CF_2CF_3$), optionally substituted —($C_0$-$C_2$alkyl)($C_3$-$C_6$cycloalkyl), optionally substituted —($C_0$-$C_2$alkyl)(heterocycle), optionally substituted —($C_0$-$C_2$alkyl)(aryl), optionally substituted —($C_0$-$C_2$alkyl)(heteroaryl), —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$; and wherein at least one of $R^1$ and $R^2$ is methyl, $CH_2F$, $CHF_2$ or $CF_3$;

$R^3$ is hydrogen,

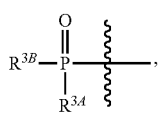

diphosphate, triphosphate, an optionally substituted carbonyl linked amino acid, or —$C(O)R^{3C}$;

$R^{3A}$ can be selected from $O^-$, OH, an —O-optionally substituted aryl, an —O-optionally substituted heteroaryl, or an optionally substituted heterocyclyl;

$R^{3B}$ can be selected from $O^-$, OH, an optionally substituted N-linked amino acid or an optionally substituted N-linked amino acid ester;

$R^{3C}$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), —O—($C_0$-$C_2$)(heteroaryl), —S-alkyl, —S-alkenyl, —S-alkynyl, —S—($C_0$-$C_2$)(cycloalkyl), —S—($C_0$-$C_2$)(heterocyclo), —S—($C_0$-$C_2$)(aryl), or —S—($C_0$-$C_2$)(heteroaryl) each of which can be optionally substituted;

$R^{3D}$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), or —O—($C_0$-$C_2$)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or $R^3$ and $R^4$ together with the oxygens that they are bonded to can form a 3',5'-cyclic prodrug, including but not limited to, a 3',5'-cyclic phosphate prodrug;

$R^5$ is $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CHF_2$, $CF_3$, $CH_2CF_3$ and $CF_2CF_3$), $C_2$-$C_6$ alkenyl, $C_2$-$C_6$ alkynyl, —($C_0$-$C_2$alkyl)($C_3$-$C_6$cycloalkyl), —($C_0$-$C_2$alkyl)(heterocycle), —($C_0$-$C_2$alkyl)(aryl), —($C_0$-$C_2$alkyl)(heteroaryl), —$OR^{25}$, —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$ each of which can be optionally substituted;

$R^6$ is hydrogen, optionally substituted $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CHF_2$, $CF_3$, $CH_2CF_3$ and $CF_2CF_3$), optionally substituted —($C_0$-$C_2$alkyl)($C_3$-$C_6$cycloalkyl), optionally substituted —($C_0$-$C_2$alkyl)(heterocycle), optionally substituted —($C_0$-$C_2$alkyl)(aryl), optionally substituted —($C_0$-$C_2$alkyl)(heteroaryl), —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$; or $R^5$ and $R^6$ together with the nitrogen that they are bonded to can form a heterocyclic ring;

$R^{12}$ is $CH_3$, $CH_2F$, $CHF_2$, $CF_3$, or ethynyl;

$R^{22}$ is Cl, Br, F, CN, $N_3$, $C_1$-$C_6$ alkyl, $C_2$-$C_6$ alkenyl, $C_2$-$C_6$ alkynyl, —($C_1$-$C_2$alkyl)($C_3$-$C_6$cycloalkyl), —($C_0$-$C_2$alkyl)($C_3$-$C_6$heterocycle), —($C_0$-$C_2$alkyl)(aryl), —($C_0$-$C_2$alkyl)(heteroaryl); —$ONHC(=O)OR^{23}$, —$NHOR^{24}$, —$OR^{25}$, —$SR^{25}$, —$NH(CH_2)_{1-4}N(R^{26})_2$, —$NHNHR^{26}$, —$N=NR^{27}$, —$NHC(O)NHNHR^{27}$, —$NHC(S)NHNHR^{27}$, —$C(O)NHNHR^{27}$, —$NR^{27}SO_2R^{28}$, —$SO_2NR^{27}R^{29}$, —$C(O)NR^{27}R^{29}$, —$CO_2R^{29}$, —$SO_2R^{29}$,

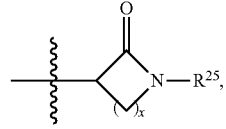

—$P(O)H(OR^{29})$, —$P(O)(OR^{29})(OR^{30})$, —$P(O)(OR^{29})(NR^{29}R^{30})$ or —$NR^5R^6$;

for example including but not limited to the following embodiments, chloro, bromo, fluoro, cyano, azido, ethyl, n-propyl, iso-propyl, n-butyl, iso-butyl, sec-butyl, tert-butyl and n-pentyl, 1,1-dimethylpropyl, 2,2-dimtheylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —($CH_2$)-cyclopropyl, —($CH_2$)-cyclobutyl, —($CH_2$)-cyclopentyl, —($CH_2$)-cyclohexyl, aziridine, oxirane, thiirane, azetidine, oxetane, thietane, pyrrolidine, tetrahydrofuran, thiolane, pyrazolidine, piperidine, oxane, thiane, —($CH_2$)-aziridine, —($CH_2$)-oxirane, —($CH_2$)-thiirane, —($CH_2$)-azetidine, —($CH_2$)-oxetane, —($CH_2$)-thietane, —($CH_2$)-pyrrolidine, —($CH_2$)-tetrahydrofuran, —($CH_2$)-thiolane, —($CH_2$)-pyrazolidine, —($CH_2$)-piperidine, —($CH_2$)-oxane, —($CH_2$)-thiane, phenyl, pyridyl, —ONHC(=O)O$CH_3$, —ONHC(=O)O$CH_2CH_3$, —NHOH, NHO$CH_3$, —O$CH_3$, O$C_2H_5$, —OPh, O$CH_2$Ph, —S$CH_3$, —S$C_2H_5$, —SPh, S$CH_2$Ph, —NH($CH_2)_2NH_2$, —NH($CH_2)_2N(CH_3)_2$, —NHN$H_2$, —NHNH$CH_3$, —N=NH, —N=N$CH_3$, —N=N$CH_2CH_3$, —NHC(O)NHN$H_2$, —NHC(S)NHN$H_2$, —C(O)NHN$H_2$, —NHS$O_2CH_3$, —NHS$O_2CH_2CH_3$, —S$O_2$NH$CH_3$, —S$O_2$N($CH_3)_2$, —C(O)N$H_2$, —C(O)NH$CH_3$, —C(O)N($CH_3)_2$, —C$O_2CH_3$, —C$O_2CH_2CH_3$, —C$O_2$Ph, —C$O_2CH_2$Ph, —S$O_2CH_3$, —S$O_2CH_2CH_3$, —S$O_2$Ph, —S$O_2CH_2$Ph,

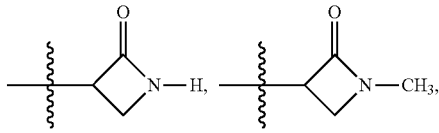

—P(O)H(OH), —P(O)H(O$CH_3$), —P(O)(OH)(OH), —P(O)(OH)(O$CH_3$), —P(O)(O$CH_3$)(O$CH_3$), —P(O)(OH)(N$H_2$), —P(O)(OH)(NH$CH_3$), —P(O)(OH)N($CH_3)_2$, —NHC(O)$CH_3$, —NHC(O)$CH_2CH_3$, —NHC(O)CH($CH_3)_2$, —NHC(O)O$CH_3$, —NHC(O)O$CH_2CH_3$, —NHC(O)OCH($CH_3)_2$, —NHC(O)O$CH_2CH_2CH_3$, —NHC(O)O$CH_2CH_2CH_2CH_3$ and —NHC(O)O$CH_2CH_2CH_2CH_2CH_3$;

$R^{23}$ is $C_1$-$C_5$alkyl, —($C_0$-$C_2$alkyl)($C_3$-$C_6$cycloalkyl), —($C_0$-$C_2$alkyl)(heterocycle)-($C_0$-$C_2$alkyl)(aryl) or —($C_0$-$C_2$alkyl)(heteroaryl) each of which can be optionally substituted;

$R^{24}$ is hydrogen, $C_1$-$C_6$ alkyl, —($C_1$-$C_2$alkyl)($C_3$-$C_6$cycloalkyl), —($C_1$-$C_2$alkyl)($C_3$-$C_6$heterocycle) —($C_0$-$C_2$alkyl)(aryl) or —($C_0$-$C_2$alkyl)(heteroaryl) wherein except for the hydrogen each of which can be optionally substituted;

$R^{25}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted;

$R^{26}$ is independently selected from hydrogen, $C_1$-$C_6$alkyl, —($C_0$-$C_2$alkyl)($C_3$-$C_6$cycloalkyl), —($C_0$-$C_2$alkyl)(heterocycle), —($C_0$-$C_2$alkyl)(aryl), or —($C_0$-$C_2$alkyl)(heteroaryl) wherein except for the hydrogen each of which can be optionally substituted;

$R^{27}$ hydrogen or optionally substituted $C_1$-$C_6$ alkyl;

$R^{28}$ is $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) each of which can be optionally substituted;

$R^{29}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{27}$ and $R^{29}$ together with the nitrogen that they are bonded to can form a heterocyclic ring;

$R^{30}$ is hydrogen, $C_1$-$C_6$ alkyl, $C_2$-$C_6$ alkenyl, $C_2$-$C_6$ alkynyl, —($C_0$-$C_2$alkyl)($C_3$-$C_6$cycloalkyl), —($C_0$-$C_2$alkyl)($C_3$-$C_6$heterocycle), —($C_0$-$C_2$alkyl)(aryl) or —($C_0$-$C_2$alkyl)(heteroaryl) wherein except for the hydrogen each of which can be optionally substituted; or $R^{29}$ and $R^{30}$ can be bonded together to form a heterocyclic ring;

x is 1, 2 or 3.

The metabolism of the β-D-2'-deoxy-2'-α-fluoro-2'-β-methyl-$N^6$-dimethyl-2,6-diaminopurine nucleotide involves both the formation of the β-D-2'-deoxy-2'-α-fluoro-2'-β-methyl-$N^6$-dimethyl-2,6-diaminopurine nucleoside triphosphate as well as the generation of the corresponding guanine nucleoside triphosphate. See Scheme 2 and 3.

2'-Deoxy-2'-α-fluoro-2'-β-C-substituted-$N^6$-substituted-2,6-diaminopurine nucleotides can be further substituted at the $N^2$-position by alkylation or acylated which can modify the lipophilicity, pharmacokinetics and/or targeting of the nucleotide to the liver. It has been discovered that 2'-deoxy-2'-α-fluoro-2'-β-C-substituted-$N^6$-substituted-2,6-diaminopurine nucleotides modified at the 2-position of the diaminopurine can be dealkylated or deacylated by hepatic enzymes to further increase the specificity of the nucleotide derivatives both in vitro and in vivo, unless the $N^2$-amino group is completely replaced by a different moiety, as described herein, such as fluoro. For example, the nucleoside phosphoramidate 2'-deoxy-2'-α-fluoro-2'-β-methyl-$N^2$-methyl-$N^6$-methyl-2,6-diaminopurine nucleoside phosphoramidate is dealkylated to 2'-deoxy-2'-α-fluoro-2'-β-methyl-$N^6$-methyl-2,6-diaminopurine nucleoside phosphoramidate when incubated with a human liver S9 fraction in vitro, up to 60 minutes, these conditions mimics in vivo conditions. In one embodiment, $N^2$ modifications will increase cell permeability and hepatitic targeting.

Despite the volume of antiviral nucleoside literature and patent filings, the 5'-stabilized phosphate derivative of 2'-deoxy-2'-α-fluoro-2'-β-methyl-$N^6$-methyl-2,6-diaminopurine nucleoside, 2'-deoxy-2'-α-fluoro-2'-β-methyl-$N^6$-dimethyl-2,6-diaminopurine nucleoside, and other β-D-2'-D-2'-α-fluoro-2'-β-C-substituted-2-modified-$N^6$-substituted purine nucleoside derivatives as described herein have not been specifically disclosed, nor have their advantageous activities been described.

Unless otherwise specified, the compounds described herein are provided in the β-D-configuration. Likewise, when in phosphoramide or thiophosphoramidate form, the amino acid portion can be in the L- or D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$ stabilized phosphate prodrug, it can be provided as an R or S chiral phosphorus derivative or a mixture thereof, including a racemic mixture. All of the combinations of these stereoconfigurations are included in the invention described herein.

Accordingly, the present invention includes a compound of Formula I-VII, or a pharmaceutically acceptable composition, salt, or prodrug thereof, as described herein:

Formula I

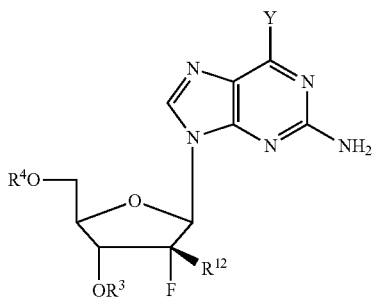

In one specific embodiment, the parent nucleoside, i.e., the nucleoside wherein $R^4$ is hydrogen and the 5'-position thus has a hydroxyl group, is not substantially deaminated by adenosine deaminase under conditions that mimic the in vivo environment (e.g., ambient temperature and aqueous physiological pH), for a period of 7 minutes, 10 minutes, 30 minutes, 60 minutes or 120 minutes. Unless otherwise stated, the time period is 30 minutes. In this embodiment, the term "not substantially deaminated" means that the parent compound is not converted to the corresponding guanine derivative, or 6-oxo derivative, in an amount sufficient to provide a therapeutic effect in vivo.

Compounds, methods, and compositions are provided for the treatment of a host infected with a HCV virus via administration of an effective amount of the compound or its pharmaceutically acceptable salt.

The compounds and compositions can also be used to treat related conditions such as anti-HCV antibody positive and antigen positive conditions, viral-based chronic liver inflammation, liver cancer resulting from advanced hepatitis C, cirrhosis, chronic or acute hepatitis C, fulminant hepatitis C, chronic persistent hepatitis C and anti-HCV-based fatigue. The compound or formulations that include the compounds can also be used prophylactically to prevent or restrict the progression of clinical illness in individuals who are anti-HCV antibody or antigen positive or who have been exposed to hepatitis C.

In another embodiment, compounds of Formula Ia are disclosed:

Formula Ia

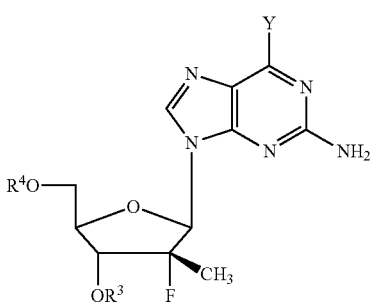

wherein:
Y, $R^3$ and $R^4$ are as defined above.
In one embodiment of Formula Ia, $R^3$ is hydrogen.
In one embodiment of Formula Ia, when Y is $NR^1R^2$, $R^1$ is methyl and $R^2$ is hydrogen.

In one embodiment of Formula Ia, when Y is $NR^1R^2$, both $R^1$ and $R^2$ are methyl.
In one embodiment of Formula Ia, when Y is $NR^1R^2$, $R^1$ is methyl and $R^2$ is cyclopropyl.
In another embodiment, compounds of Formula Ib are disclosed:

Formula Ib

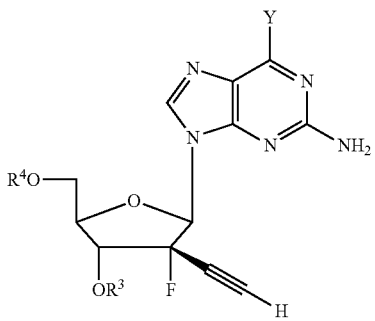

wherein:
Y, $R^3$ and $R^4$ are as defined above.
In one embodiment of Formula Ib, $R^3$ is hydrogen.
In one embodiment of Formula Ib, when Y is $NR^1R^2$, $R^1$ is methyl and $R^2$ is hydrogen.
In one embodiment of Formula Ib, when Y is $NR^1R^2$, both $R^1$ and $R^2$ are methyl.
In one embodiment, compounds of Formula II are disclosed:

Formula II

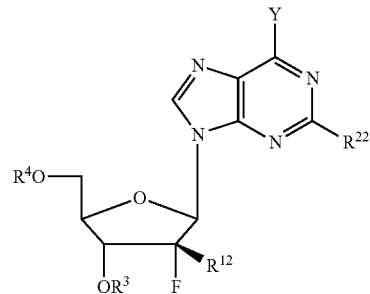

wherein:
Y, $R^1$, $R^4$, $R^{12}$ and $R^{22}$ are as defined above.
In another embodiment, compounds of Formula IIa are disclosed:

Formula IIa

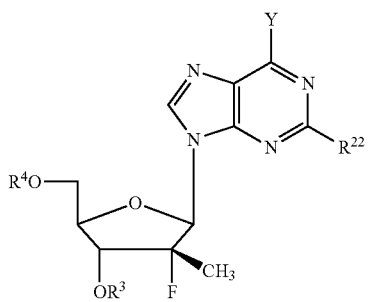

wherein:
Y, $R^3$, $R^4$ and $R^{22}$ are as defined above.

In another embodiment, compounds of Formula IIb are disclosed:

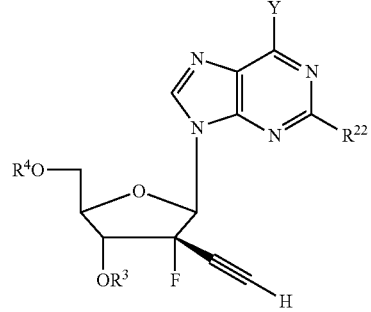

Formula IIb wherein:

Y, $R^3$, $R^4$, and $R^{22}$ are as defined above.

In one embodiment, compounds of Formula III are disclosed:

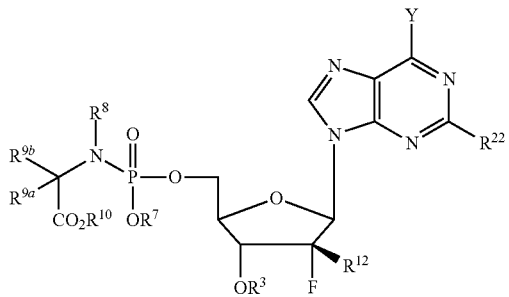

Formula III wherein the variables Y, $R^3$, $R^7$, $R^8$, $R^{9a}$, $R^{9b}$, $R^{10}$, $R^{12}$ and $R^{22}$ are described herein.

In one embodiment, compounds of Formula IV are disclosed:

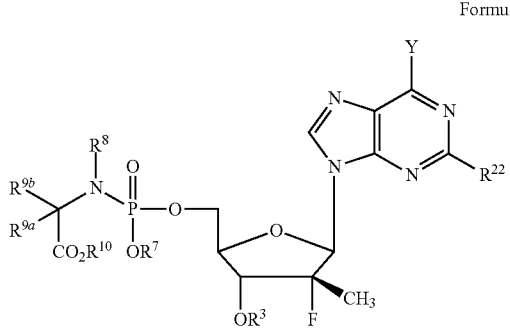

Formula IV wherein the variables Y, $R^3$, $R^7$, $R^8$, $R^{9a}$, $R^{9b}$, $R^{10}$ and $R^{22}$ are described herein.

In one embodiment, compounds of Formula V are disclosed:

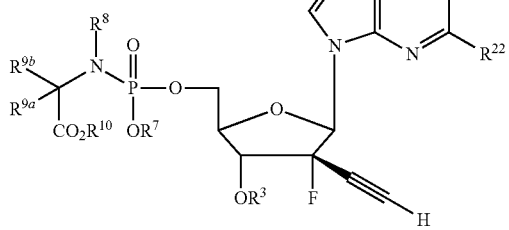

Formula V wherein the variables Y, $R^3$, $R^7$, $R^8$, $R^{9a}$, $R^{9b}$, $R^{10}$ and $R^{22}$ are described herein.

In one embodiment, compounds of Formula VI are disclosed:

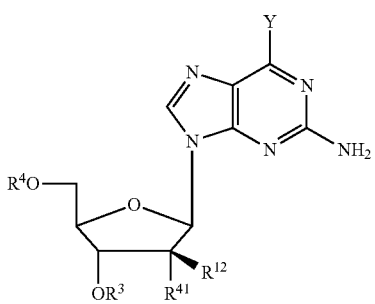

Formula VI wherein:

$R^{41}$ is halogen (in particular F or Cl), $OR^3$, $N_3$, $NH_2$ or CN; and the variables Y, $R^3$, $R^4$, and $R^{12}$ are described herein.

In one embodiment, compounds of Formula VII are disclosed:

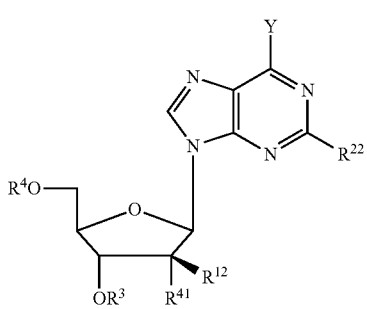

Formula VII

Wherein the variables Y, $R^3$, $R^4$, $R^{12}$ and $R^{41}$ are described herein.

The phosphorus in any of the Formulas above may be chiral and thus can be provided as an R or S enantiomer or mixture thereof, including a racemic mixture.

Compound 5 was separated into the enantiomer compounds 5-1 and 5-2. Compound 5-2 was also prepared by chiral synthesis and assigned compound 24.

In one embodiment, compounds, methods, and compositions are provided for the treatment of a host infected with or exposed to hepatitis C described herein. The compounds of the invention can be administered in an effective amount alone or in combination with another anti-HCV drug, to treat the infected host. In certain embodiments, it is useful to administer a combination of drugs that modulates the same or a different pathway or inhibits a different target in the virus. As the disclosed β-D-2'-D-2'-α-fluoro-2'-β-C-substituted-2-modified-$N^6$-substituted purine nucleotides are NS5B polymerase inhibitors, it may be useful to administer the compound to a host in combination with a protease inhibitor, such as an NS3/4A protease inhibitor (for example, telaprevir (Incivek®) boceprevir (Victrelis™) simeprevir (Olysio™), or paritaprevir, or an NS5A inhibitor (for example, Ombitasvir). The compounds of the invention can also be administered in combination with a structurally different NS5B polymerase inhibitor such as another compound described herein or below, including Gilead's Sovaldi®. The compounds of the invention can also be administered in combination with interferon alfa-2a, which may be pegylated or otherwise modified, and/or ribavirin.

The β-D-2'-D-2'-α-fluoro-2'-β-C-substituted-2-modified-$N^6$-substituted purine nucleotides of the invention are typically administered orally, for example in pill or tablet form, but may be administered via an other route which the attending physician considers appropriate, including via intravenous, transdermal, subcutaneous, topical, parenteral, or other suitable route.

DETAILED DESCRIPTION OF THE INVENTION

Figure 1:
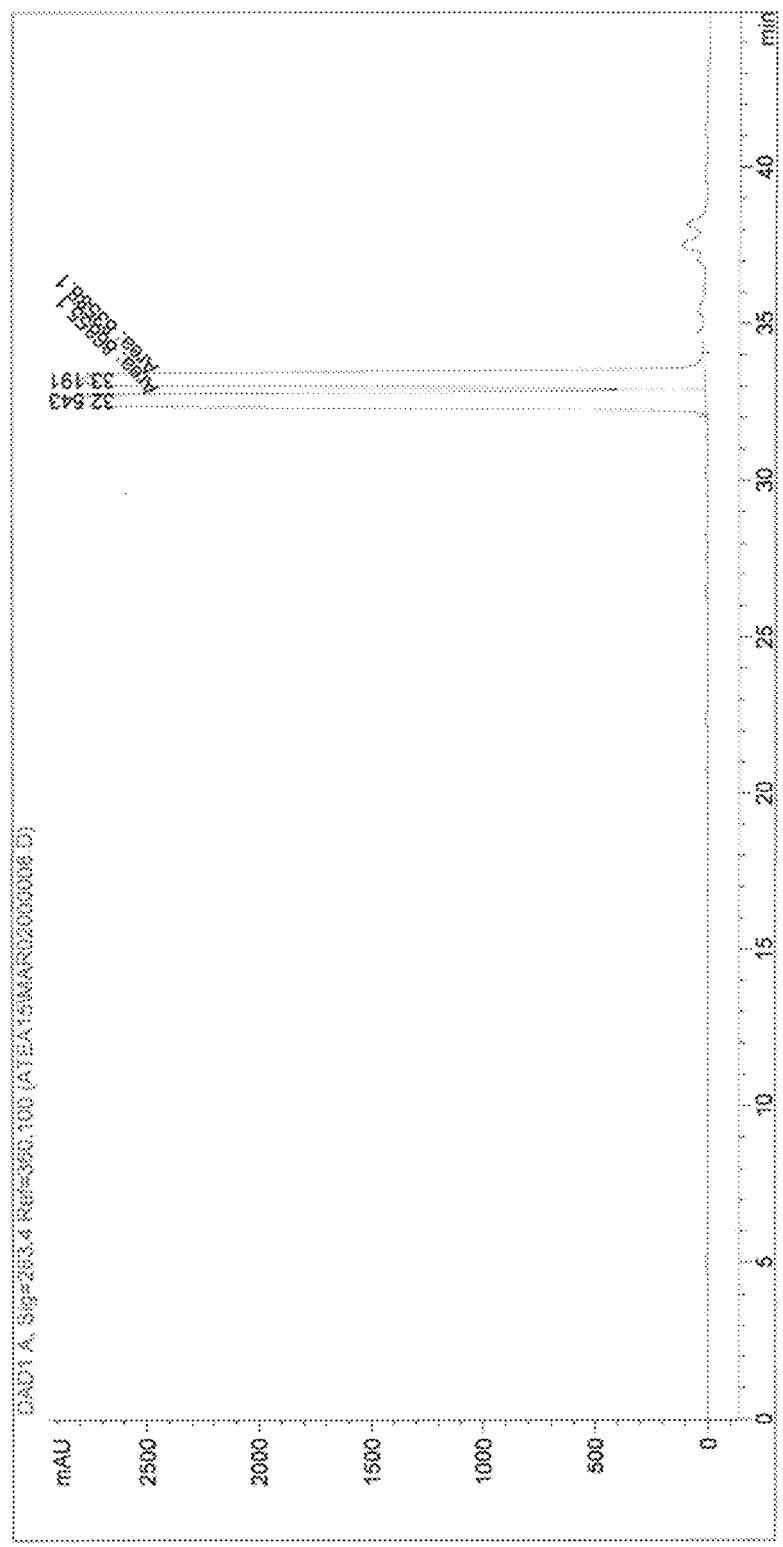
FIG. 1 is a sample chromatogram of a semi-prep run illustrating the separation of the stereoisomers of Compound 5 using a Phenominex Luna column as disclosed in Example 9. The y axis is shown in mAU and the x axis is measured in minutes.

The invention disclosed herein is a compound, method, and composition for the treatment of infections in or exposure to humans and other host animals of the HCV virus that includes the administration of an effective amount of a compound of Formula I-VII as described herein or a pharmaceutically acceptable salt or prodrug thereof, optionally in a pharmaceutically acceptable carrier. The compounds of this invention either possess antiviral activity, or are metabolized to a compound that exhibits such activity.

The compounds and compositions can also be used to treat conditions related to or occurring as a result of a HCV viral exposure. For example, the active compound can be used to treat HCV antibody positive and HCV antigen positive conditions, viral-based chronic liver inflammation, liver cancer resulting from advanced hepatitis C, cirrhosis, acute hepatitis C, fulminant hepatitis C, chronic persistent hepatitis C, and anti-HCV-based fatigue. In one embodiment, the compounds or formulations that include the compounds can also be used prophylactically to prevent or retard the progression of clinical illness in individuals who are HCV antibody or HCV antigen positive or who have been exposed to hepatitis C.

In particular, it has been discovered that a 5'-stabilized phosphate prodrug or derivative of β-D-2'-deoxy-2'-α-fluoro-2'-β-methyl-$N^6$-methyl-2,6-diamino purine nucleotide, as well as β-D-2'-deoxy-2'-α-fluoro-2'-β-methyl-$N^6$-dimethyl-2,6-diamino purine nucleotide, and other β-D-2'-D-2'-α-fluoro-2'-β-C-substituted-2-modified-$N^6$-substituted purine nucleotides as described below, are highly active against HCV. This is surprising because the activity of the parent nucleoside β-D-2'-deoxy-2'-α-fluoro-2'-β-methyl-$N^6$-methyl-2,6-diamino purine in a replicon assay ($EC_{50}$=15.7 micromolar) indicates that it is not suitable for use as a human drug due to insufficient activity, however, the stabilized phosphate prodrug (phosphoramidate) exhibits an $EC_{50}$=26 nanomolar, in a replicon assay, which is at least an 870 fold increase in activity. Likewise, the activity of the parent nucleoside β-D-2'-deoxy-2'-α-fluoro-2'-β-methyl-$N^6$-dimethyl-2,6-diaminopurine in a replicon assay ($EC_{50}$=10.7 micromolar, "μM") indicates that it is also not suitable for use as a human drug due to insufficient activity, however, the stabilized phosphate prodrug (phosphoramidate) exhibits an $EC_{50}$=12 nanomolar, ("nM"), in a replicon assay, which is more than a 1,300 fold increase in activity.

Despite the volume of antiviral nucleoside literature and patent filings, the 5'-stabilized phosphate derivative of 2'-deoxy-2'-α-fluoro-2'-β-methyl-$N^6$-methyl-2,6-diamino purine nucleotide, 2'-deoxy-2'-α-fluoro-2'-β-methyl-$N^6$-dimethyl-2,6-diamino purine nucleotide, and other β-D-2'-D-2'-α-fluoro-2'-β-C-substituted-2-modified-$N^6$-substituted purine nucleotides have not been specifically disclosed.

Unless otherwise specified, the compounds described herein are provided in the β-D-configuration. In an alternative embodiment, the compounds can be provided in a β-L-configuration. Likewise, any substituent group that exhibits chirality can be provided in racemic, enantiomeric, diastereomeric form or any mixture thereof. Where a phosphoramidate, thiophosphoramidate or other stabilized phosphorus prodrug in which the phosphorus exhibits chirality is used as the $R^4$ stabilized phosphate prodrug, it can be provided as an R or S chiral phosphorus derivative or a mixture thereof, including a racemic mixture. The amino acid of the phosphoramidate or thiophosphoramidate can be in the D- or L-configuration, or a mixture thereof, including a racemic mixture. All of the combinations of these stereo configurations are included in the invention described herein.

The present invention includes the following features:

(a) a compound of Formula I-VII as described herein, and pharmaceutically acceptable salts and prodrugs thereof;

(b) Formulas I-VII as described herein, and pharmaceutically acceptable salts and prodrugs thereof for use in the treatment or prophylaxis of a hepatitis C virus infection;

(c) use of Formulas I-VII, and pharmaceutically acceptable salts and prodrugs thereof in the manufacture of a medicament for treatment of a hepatitis C virus infection;

(d) a method for manufacturing a medicament intended for the therapeutic use for treating a hepatitis C virus infection, characterized in that a Formulas I-VII as described herein is used in the manufacture;

(e) a pharmaceutical formulation comprising an effective host-treating amount of the Formulas I-VII or a pharmaceutically acceptable salt or prodrug thereof together with a pharmaceutically acceptable carrier or diluent;

(f) Formulas I-VII as described herein substantially in the absence of stereoisomers of the described compound, or substantially isolated from other chemical entities; and, (g) processes for the preparation of therapeutic products that contain an effective amount of a Formulas I-VII, as described herein.

I. 2'-Deoxy-2'-α-Fluoro-2'-β-C-Substituted-2-Modified-$N^6$-Substituted Purine Nucleotides of the Invention The active compounds of the invention are those depicted, for example, in Formula I, which can be provided in a pharmaceutically acceptable composition, salt or prodrug thereof:

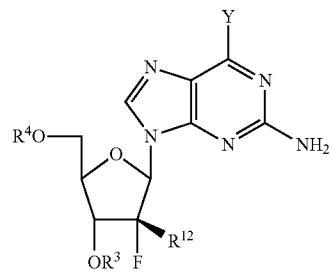

Formula I wherein:

Y is $NR^1R^2$;

$R^1$ is $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CH_2F$, $CH_2F$, $CF_3$, $CH_2CF_3$, $CF_2CH_3$ and $CF_2CF_3$), $C_2$-$C_6$ alkenyl, $C_2$-$C_6$ alkynyl, —($C_0$-$C_2$alkyl)($C_3$-$C_6$cycloalkyl), —($C_0$-$C_2$alkyl)(heterocycle), —($C_0$-$C_2$alkyl)(aryl), —($C_0$-$C_2$alkyl)(heteroaryl), —$OR^{25}$, —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$ each of which can be optionally substituted;

$R^2$ is hydrogen, optionally substituted $C_1$-$C_5$alkyl (including methyl, ethyl, n-propyl, iso-propyl, n-butyl, iso-butyl, sec-butyl, tert-butyl and pentyl), $C_1$-$C_5$haloalkyl (including $CHF_2$, $CH_2F$, $CF_3$, $CH_2CF_3$ and $CF_2CF_3$), optionally substituted —($C_0$-$C_2$alkyl)($C_3$-$C_6$cycloalkyl), optionally substituted —($C_0$-$C_2$alkyl)(heterocycle), optionally substituted —($C_0$-$C_2$alkyl)(aryl), optionally substituted —($C_0$-$C_2$alkyl)(heteroaryl), —$C(O)R^{3C}$ (including —$C(O)CH_3$, —$C(O)CH_2CH_3$—$C(O)CH(CH_3)_2$, —$C(O)OCH_3$, —$C(O)OC_2H_5$, —$C(O)OC_3H_7$, —$C(O)OC_4H_9$, and —$C(O)OC_5H_{11}$), —$C(S)R^{3D}$, or —$SO_2R^{28}$; and wherein at least one of $R^1$ and $R^2$ is methyl, $CH_2F$, $CHF_2$ or $CF_3$;

$R^3$ is hydrogen,

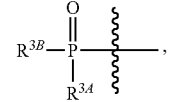

diphosphate, triphosphate, an optionally substituted carbonyl linked amino acid, or —$C(O)R^{3C}$;

$R^{3A}$ can be selected from $O^-$, OH, an —O-optionally substituted aryl, an —O-optionally substituted heteroaryl, or an optionally substituted heterocyclyl;

$R^{3B}$ can be selected from $O^-$, OH, an optionally substituted N-linked amino acid or an optionally substituted N-linked amino acid ester;

$R^{3C}$ is alkyl, alkenyl, alkynyl, —($C_0$-$C_2$)(cycloalkyl), —($C_0$-$C_2$)(heterocyclo), —($C_0$-$C_2$)(aryl), —($C_0$-$C_2$)(heteroaryl), —O-alkyl, —O-alkenyl, —O-alkynyl, —O—($C_0$-$C_2$)(cycloalkyl), —O—($C_0$-$C_2$)(heterocyclo), —O—($C_0$-$C_2$)(aryl), or —O—($C_0$-$C_2$)(heteroaryl), each of which can be optionally substituted;

$R^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or R$^3$ and R$^4$ together with the oxygens that they are bonded to can form a 3',5'-cyclic prodrug, including but not limited to, a 3',5'-cyclic phosphate prodrug;

R$^{12}$ is CH$_3$, CH$_2$F, CHF$_2$, CF$_3$, or ethynyl.

A stabilized phosphate prodrug is any moiety that can deliver a mono, di, or triphosphate.

In another embodiment, compounds of Formula Ia are disclosed:
wherein:

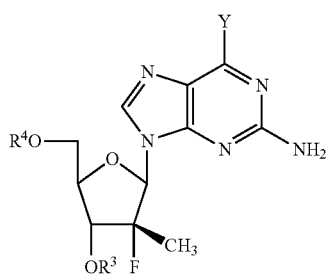

Formula Ia

Y, R$^3$ and R$^4$ are as defined above.

In another embodiment, compounds of Formula Ib are disclosed:

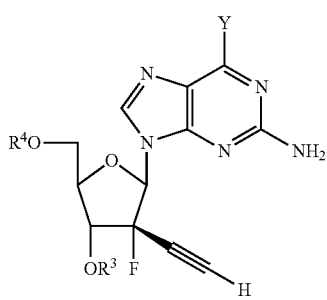

Formula Ib wherein:
Y, R$^3$ and R$^4$ are as defined above.

In another embodiment, the compound is according to Formula Ic:

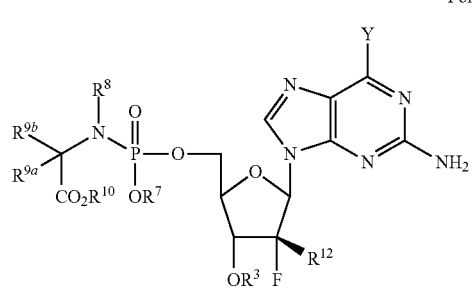

Formula Ic wherein:
R$^7$ is hydrogen, C$_{1-6}$alkyl; C$_{3-7}$-cycloalkyl; heteroaryl, heterocyclic, or aryl, which includes, but is not limited to, phenyl or naphthyl, where phenyl or naphthyl are optionally substituted with C$_{1-6}$alkyl, C$_{2-6}$alkenyl, C$_{2-6}$ alkynyl, C$_{1-6}$alkoxy, F, Cl, Br, I, nitro, cyano, C$_{1-6}$haloalkyl, —N(R$^{7'}$)$_2$, C$_{1-6}$acylamino, NHSO$_2$C$_{1-6}$alkyl, —SO$_2$N(R$^{7'}$)$_2$, COR$^{7''}$, and —SO$_2$C$_{1-6}$alkyl; (R$^{7'}$ is independently hydrogen or C$_{1-6}$alkyl; R$^{7''}$ is —OR$^{11}$ or —N(R$^7$)$_2$);

R$^8$ is hydrogen, C$_{1-6}$alkyl, or R$^{9a}$ or R$^{9b}$ and R$^8$ together are (CH$_2$)$_n$ so as to form a cyclic ring that includes the adjoining N and C atoms; where n is 2 to 4;

R$^{9a}$ and R$^{9b}$ are (i) independently selected from hydrogen, C$_{1-6}$alkyl, cycloalkyl, —(CH$_2$)$_c$(NR$^{9'}$)$_2$, C$_{1-6}$hydroxyalkyl, —CH$_2$SH, —(CH$_2$)$_2$S(O)(Me), —(CH$_2$)$_3$NHC(=NH)NH$_2$, (1H-indol-3-yl)methyl, (1H-imidazol-4-yl)methyl, —(CH$_2$)$_c$COR$^{9''}$, aryl and aryl(C$_{1-3}$alkyl)-, the aryl groups can be optionally substituted with a group selected from hydroxyl, C$_{1-6}$alkyl, C$_{1-6}$alkoxy, halogen, nitro and cyano; (ii) R$^{9a}$ and R$^{9b}$ both are C$_{1-6}$alkyl; (iii) R$^{9a}$ and R$^{9b}$ together are (CH$_2$)$_r$ so as to form a spiro ring; (iv) R$^{9a}$ is hydrogen and R$^{9b}$ and R$^8$ together are (CH$_2$)$_n$ so as to form a cyclic ring that includes the adjoining N and C atoms (v) R$^{9b}$ is hydrogen and R$^{9a}$ and R$^8$ together are (CH$_2$)$_n$ so as to form a cyclic ring that includes the adjoining N and C atoms, where c is 1 to 6, n is 2 to 4, r is 2 to 5 and where R$^{9'}$ is independently hydrogen or C$_{1-6}$ alkyl and R$^{9''}$ is —OR$^{11}$ or —N(R$^{11'}$)$_2$); (vi) R$^{9a}$ is hydrogen and R$^{9b}$ is hydrogen, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl; or (vii) R$^{9a}$ is CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH)NH$_2$, CH$_2$-imidazol-4-yl, CH$_2$OH, CH(OH)CH$_3$, CH$_2$((4'-OH)-Ph), CH$_2$SH, or lower cycloalkyl and R$^{9b}$ is hydrogen;

R$^{10}$ is hydrogen, C$_{1-6}$alkyl optionally substituted with an alkoxy, di(lower alkyl)-amino, or halogen, C$_{1-6}$haloalkyl, C$_{3-7}$-cycloalkyl, heterocycloalkyl, aminoacyl, aryl, such as phenyl, heteroaryl, such as, pyridinyl, substituted aryl, or substituted heteroaryl;

R$^{11}$ is an optionally substituted C$_{1-6}$alkyl, an optionally substituted cycloalkyl; an optionally substituted C$_{2-6}$alkynyl, an optionally substituted C$_{2-6}$alkenyl, or optionally substituted acyl, which includes but is not limited to C(O)(C$_{1-6}$ alkyl); and Y, R$^3$ and R$^{12}$ are as defined herein.

In one embodiment, compounds of Formula II are disclosed:

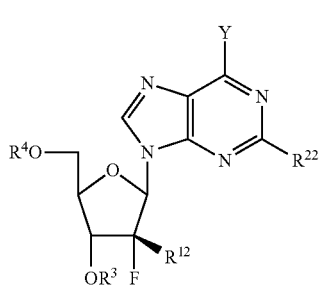

Formula II wherein:
Y is NR$^1$R$^2$;

R$^1$ is C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CH$_2$F, CHF$_2$, CF$_3$, CH$_2$CF$_3$, CF$_2$CH$_3$ and CF$_2$CF$_3$), C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(heterocycle), —(C$_0$-C$_2$alkyl)(aryl), —(C$_0$-C$_2$alkyl)(heteroaryl), —OR$^{25}$, —C(O)R$^{3c}$ (including —C(O)CH$_3$, —C(O)CH$_2$CH$_3$—C (O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$ each of which can be optionally substituted;

R$^2$ is hydrogen, optionally substituted C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CHF$_2$, CHF$_2$, CF$_3$, CH$_2$CF$_3$ and CF$_2$CF$_3$), optionally substituted —(C$_0$-C$_2$alkyl)(C$_3$-C$_6$cycloalkyl), optionally substituted —(C$_0$-C$_2$alkyl)(heterocycle), optionally substituted —(C$_0$-C$_2$alkyl)(aryl), optionally substituted —(C$_0$-C$_2$alkyl)(heteroaryl), —C(O)R$^{3C}$ (including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$; and wherein at least one of R and R$^2$ is methyl, CH$_2$F, CHF$_2$ or CF$_3$;

R$^3$ is hydrogen,

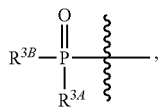

diphosphate, triphosphate, an optionally substituted carbonyl linked amino acid, or —C(O)R$^{3C}$;

R$^{3A}$ can be selected from O$^-$, OH, an —O-optionally substituted aryl, an —O-optionally substituted heteroaryl, or an optionally substituted heterocyclyl;

R$^{3B}$ can be selected from O$^-$, OH, an optionally substituted N-linked amino acid or an optionally substituted N-linked amino acid ester;

R$^{3C}$ is alkyl, alkenyl, alkynyl, —(C$_0$-C$_2$)(cycloalkyl), —(C$_0$-C$_2$)(heterocyclo), —(C$_0$-C$_2$)(aryl), —(C$_0$-C$_2$)(heteroaryl), —O-alkyl, —O-alkenyl, —O-alkynyl, —O—(C$_0$-C$_2$)(cycloalkyl), —O—(C$_0$-C$_2$)(heterocyclo), —O—(C$_0$-C$_2$)(aryl), —O—(C$_0$-C$_2$)(heteroaryl), —S-alkyl, —S-alkenyl, —S-alkynyl, —S—(C$_0$-C$_2$)(cycloalkyl), —S—(C$_0$-C$_2$)(heterocyclo), —S—(C$_0$-C$_2$)(aryl), or —S—(C$_0$-C$_2$)(heteroaryl) each of which can be optionally substituted;

R$^{3D}$ is alkyl, alkenyl, alkynyl, —(C$_0$-C$_2$)(cycloalkyl), —(C$_0$-C$_2$)(heterocyclo), —(C$_0$-C$_2$)(aryl), —(C$_0$-C$_2$)(heteroaryl), —O-alkyl, —O-alkenyl, —O-alkynyl, —O—(C$_0$-C$_2$)(cycloalkyl), —O—(C$_0$-C$_2$)(heterocyclo), —O—(C$_0$-C$_2$)(aryl), or —O—(C$_0$-C$_2$)(heteroaryl), each of which can be optionally substituted;

R$^4$ is a monophosphate, diphosphate, triphosphate, or a stabilized phosphate prodrug, including but not limited to a phosphoramidate, a thiophosphoramidate, or any other moiety that is metabolized to a monophosphate, diphosphate or triphosphate in vivo in the host human or animal; or R$^3$ and R$^4$ together with the oxygens that they are bonded to can form a 3',5'-cyclic prodrug, including but not limited to, a 3',5'-cyclic phosphate prodrug;

R$^5$ is C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CHF$_2$, CHF$_2$, CF$_3$, CH$_2$CF$_3$ and CF$_2$CF$_3$), C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(heterocycle), —(C$_0$-C$_2$alkyl)(aryl), —(C$_0$-C$_2$alkyl)(heteroaryl), —OR$^{25}$, —C(O)R$^{3C}$ (including —C(O)CH$_3$, —C(O)CH$_2$CH$_3$, —C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$ each of which can be optionally substituted;

R$^6$ is hydrogen, optionally substituted C$_1$-C$_5$alkyl (including methyl, ethyl, n-propyl, iso-propyl, n-butyl, iso-butyl, sec-butyl, tert-butyl and pentyl), C$_1$-C$_5$haloalkyl (including CHF$_2$, CH$_2$F, CF$_3$, CH$_2$CF$_3$ and CF$_2$CF$_3$), optionally substituted —(C$_0$-C$_2$alkyl)(C$_3$-C$_6$cycloalkyl), optionally substituted —(C$_0$-C$_2$alkyl)(heterocycle), optionally substituted —(C$_0$-C$_2$alkyl)(aryl), optionally substituted —(C$_0$-C$_2$alkyl)(heteroaryl), —C(O)R$^{3C}$ (including —C(O)CH$_3$, —C(O)CH$_2$CH$_3$—C(O)CH(CH$_3$)$_2$, —C(O)OCH$_3$, —C(O)OC$_2$H$_5$, —C(O)OC$_3$H$_7$, —C(O)OC$_4$H$_9$, and —C(O)OC$_5$H$_{11}$), —C(S)R$^{3D}$, or —SO$_2$R$^{28}$; or R$^5$ and R$^6$ together with the nitrogen that they are bonded to can form a heterocyclic ring;

R$^{12}$ is CH$_3$, CH$_2$F, CHF$_2$, CF$_3$, or ethynyl;

R$^{22}$ is Cl, Br, F, CN, N$_3$, C$_1$-C$_6$ alkyl, C$_2$-C$_6$ alkenyl, C$_2$-C$_6$ alkynyl, —(C$_1$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl), —(C$_0$-C$_2$alkyl)(heteroaryl); —ONHC(=O)OR$^{23}$, —NHOR$^{24}$, —OR$^{25}$, —SR$^{25}$, —NH(CH$_2$)$_{1-4}$N(R$^{26}$)$_2$, —NHNHR$^{26}$, —N=NR$^{27}$, —NHC(O)NHNHR$^{27}$, —NHC(S)NHNHR$^{27}$, —C(O)NHNHR$^{27}$, —NR$^{27}$SO$_2$R$^{28}$, —SO$_2$NR$^{27}$R$^{29}$, —C(O)NR$^{27}$R$^{29}$, —CO$_2$R$^{29}$, —SO$_2$R$^{29}$,

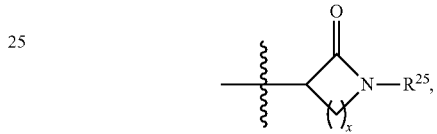

—P(O)H(OR$^{29}$), —P(O)(OR$^{29}$)(OR$^{30}$), —P(O)(OR$^{29}$)(NR$^{29}$R$^{30}$) or —NR$^5$R$^6$;

for example including but not limited to the following embodiments, chloro, bromo, fluoro, cyano, azido, ethyl, n-propyl, iso-propyl, n-butyl, iso-butyl, sec-butyl, tert-butyl and n-pentyl, 1,1-dimethylpropyl, 2,2-dimtheylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, —CO$_2$CH$_2$Ph, —SO$_2$CH$_3$, —SO$_2$CH$_2$CH$_3$, —SO$_2$Ph, —SO$_2$CH$_2$Ph,

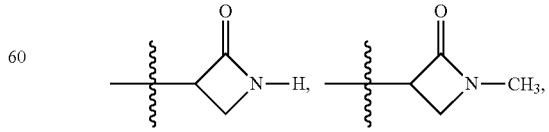

—P(O)H(OH), —P(O)H(OCH$_3$), —P(O)(OH)(OH), —P(O)(OH)(OCH$_3$), —P(O)(OCH$_3$)(OCH$_3$), —P(O)(OH)(NH$_2$), —P(O)(OH)(NHCH$_3$), —P(O)(OH)N(CH$_3$)$_2$, —NHC(O)CH$_3$, —NHC(O)CH$_2$CH$_3$, —NHC(O)CH (CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ and —NHC(O)OCH$_2$CH$_2$CH$_2$CH$_2$CH$_3$;

R$^{23}$ is C$_1$-C$_5$alkyl, —(C$_0$-C$_2$alkyl)(C$_3$-C$_6$cycloalkyl), —(C$_0$-C$_2$alkyl)(heterocycle)-(C$_{0-2}$alkyl)(aryl) or —(C$_0$-C$_2$alkyl)(heteroaryl) each of which can be optionally substituted;

R$^{24}$ is hydrogen, C$_1$-C$_6$ alkyl, —(C$_1$-C$_2$alkyl)(C$_3$-C$_6$cycloalkyl), —(C$_1$-C$_2$alkyl)(C$_3$-C$_6$heterocycle) —(C$_0$-C$_2$alkyl)(aryl) or —(C$_0$-C$_2$alkyl)(heteroaryl) wherein except for the hydrogen each of which can be optionally substituted;

R$^{25}$ is hydrogen, C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted;

R$^{26}$ is independently selected from hydrogen, C$_1$-C$_6$alkyl, —(C$_0$-C$_2$alkyl)(C$_3$-C$_6$cycloalkyl), —(C$_0$-C$_2$alkyl)heterocycle), —(C$_0$-C$_2$alkyl)(aryl), or —(C$_0$-C$_2$alkyl)(heteroaryl) wherein except for the hydrogen each of which can be optionally substituted;

R$^{27}$ hydrogen or optionally substituted C$_1$-C$_6$ alkyl;

R$^{28}$ is C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) each of which can be optionally substituted;

R$^{29}$ is hydrogen, C$_1$-C$_6$ alkyl, C$_2$-C$_6$ alkenyl, C$_2$-C$_6$ alkynyl, —(C$_0$-C$_2$alkyl)(C$_3$-C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted; or R$^{27}$ and R$^{29}$ together with the nitrogen that they are bonded to can form a heterocyclic ring;

R$^{30}$ is hydrogen, C$_1$-C$_6$ alkyl, C$_2$-C$_6$ alkenyl, C$_2$-C$_6$ alkynyl, —(C$_0$-C$_2$alkyl)(C$_3$C$_6$cycloalkyl), —(C$_0$-C$_2$alkyl)(C$_3$-C$_6$heterocycle), —(C$_0$-C$_2$alkyl)(aryl) or —(C$_0$-C$_2$alkyl)(heteroaryl) wherein except for the hydrogen each of which can be optionally substituted; or R$^{29}$ and R$^{30}$ can be bonded together to form a heterocyclic ring;

x is 1, 2 or 3.

In another embodiment, compounds of Formula IIa are disclosed:

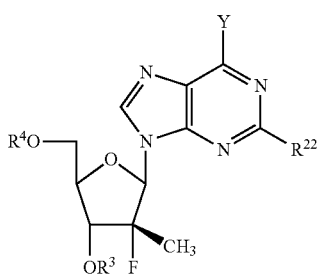

Formula IIa wherein:
Y, R$^3$, R$^4$ and R$^{22}$ are as defined above.

In another embodiment, compounds of Formula IIb are disclosed:

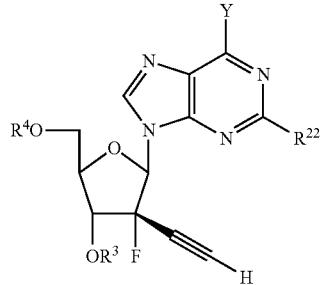

Formula IIb wherein:
Y, R$^3$, R$^4$ and R$^{22}$ are as defined above.

In a typical embodiment, the compound is a β-D isomer with reference to the corresponding nucleoside (i.e., in the naturally occurring configuration). In an alternative configuration, the compound is provided as a β-L isomer. The compound is typically at least 90% free of the opposite enantiomer, and can be at least 98%, 99% or even 100% free of the opposite enantiomer. Unless described otherwise, the compound is at least 90% free of the opposite enantiomer.

In another embodiment, the compound is according to Formula III:

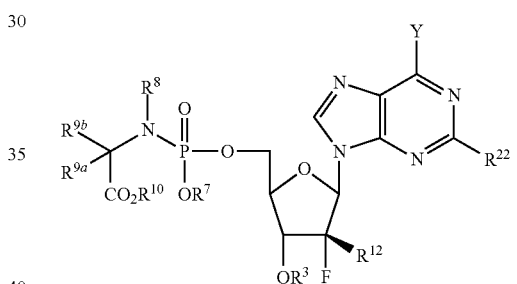

Formula III wherein:
R$^7$ is hydrogen, C$_{1-6}$alkyl; C$_{3-7}$cycloalkyl; heteroaryl, heterocyclic, or aryl, which includes, but is not limited to, phenyl or naphthyl, where phenyl or naphthyl are optionally substituted with C$_{1-6}$alkyl, C$_{2-6}$alkenyl, C$_{2-6}$ alkynyl, C$_{1-6}$alkoxy, F, Cl, Br, I, nitro, cyano, C$_{1-6}$haloalkyl, —N(R$^{7'}$)$_2$, C$_{1-6}$acylamino, NHSO$_2$C$_{1-6}$alkyl, —SO$_2$N(R$^{7'}$)$_2$, COR$^{7''}$, and —SO$_2$C$_{1-6}$alkyl; (R$^{7'}$ is independently hydrogen or C$_{1-6}$alkyl; R$^{7''}$ is —OR$^{11}$ or —N(R$^{7'}$)$_2$);

R$^8$ is hydrogen, C$_{1-6}$alkyl, or R$^{9a}$ or R$^{9b}$ and R$^8$ together are (CH$_2$)$_n$ so as to form a cyclic ring that includes the adjoining N and C atoms; where n is 2 to 4;

R$^{9a}$ and R$^{9b}$ are (i) independently selected from hydrogen, C$_{1-6}$alkyl, cycloalkyl, —(CH$_2$)$_c$(NR$^{9'}$)$_2$, C$_{1-6}$hydroxyalkyl, —CH$_2$SH, —(CH$_2$)$_2$S(O)(Me, —(CH$_2$)$_3$NHC(=NH)NH$_2$, (1H-indol-3-yl)methyl, (1H-imidazol-4-yl)methyl, —(CH$_2$)$_c$COR$^{9'''}$, aryl and aryl(C$_{1-3}$alkyl)-, the aryl groups can be optionally substituted with a group selected from hydroxyl, C$_{1-6}$alkyl, C$_{1-6}$alkoxy, halogen, nitro and cyano; (ii) R$^{9a}$ and R$^{9b}$ both are C$_{1-6}$alkyl; (iii) R$^{9a}$ and R$^{9b}$ together are (CH$_2$)$_r$ so as to form a spiro ring; (iv) R$^{9a}$ is hydrogen and R$^{9b}$ and R$^8$ together are (CH$_2$)$_n$ so as to form a cyclic ring that includes the adjoining N and C atoms (v) R$^{9b}$ is hydrogen and R$^{9a}$ and R$^8$ together are (CH$_2$)$_n$ so as to form a cyclic ring that includes the adjoining N and C atoms, where c is 1 to 6, n is 2 to 4, r is 2 to 5 and where R$^{9'}$ is independently hydrogen or $C_{1-6}$ alkyl and $R^{9''}$ is —$OR^{11}$ or —$N(R^{11})_2$); (vi) $R^{9a}$ is hydrogen and $R^{9b}$ is hydrogen, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (vii) $R^{9a}$ is $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{9b}$ is hydrogen;

$R^{10}$ is hydrogen, $C_{1-6}$alkyl optionally substituted with an alkoxy, di(lower alkyl)-amino, or halogen, $C_{1-6}$haloalkyl, $C_{3-7}$cycloalkyl, heterocycloalkyl, aminoacyl, aryl, such as phenyl, heteroaryl, such as, pyridinyl, substituted aryl, or substituted heteroaryl;

$R^{11}$ is an optionally substituted $C_{1-6}$alkyl, an optionally substituted cycloalkyl; an optionally substituted $C_{2-6}$alkynyl, an optionally substituted $C_{2-6}$alkenyl, or optionally substituted acyl, which includes but is not limited to $C(O)$ ($C_{1-6}$ alkyl); and Y, $R^3$ $R^{12}$ and $R^{22}$ are as defined above.

In one embodiment, compounds of Formula IV are disclosed:

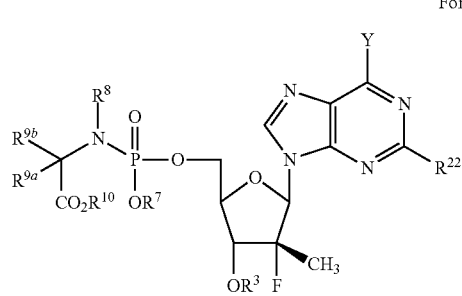

Formula IV wherein the variables Y, $R^3$, $R^7$, $R^8$, $R^{9a}$, $R^{9b}$, $R^{10}$ and $R^{22}$ are described herein.

In one embodiment, compounds of Formula V are disclosed:

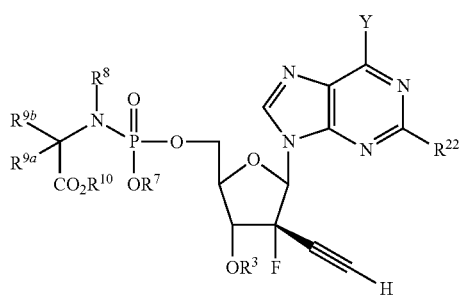

Formula V wherein the variables Y, $R^3$, $R^7$, $R^8$, $R^{9a}$, $R^{9b}$, $R^{10}$ and $R^{22}$ are described herein.

In an alternative embodiment, compounds, methods, and compositions are provided for the treatment of a host infected with or exposed to hepatitis C.

In one embodiment, compounds of Formula VI are disclosed:

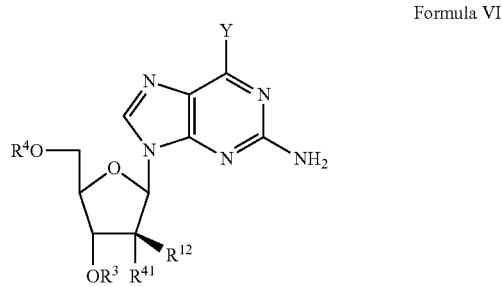

Formula VI wherein:
$R^{41}$ is halogen (in particular F or Cl), $OR^3$ (including OH), $N_3$, $NH_2$ or CN; and
the variables Y, $R^3$, $R^4$, and $R^{12}$ are described herein.

In one embodiment, compounds of Formula VII are disclosed:

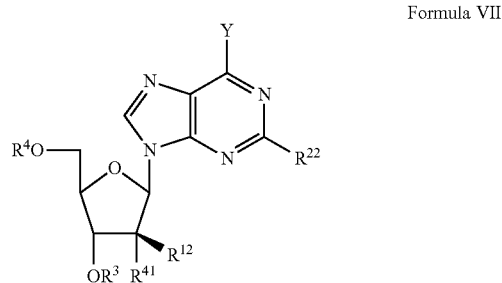

Formula VII

Wherein the variables Y, $R^3$, $R^4$, $R^{12}$ and $R^{41}$ are described herein.

Metabolism of β-D-2'-deoxy-2'-α-fluoro-2'-β-C-substituted-$N^6$-substituted-2,6-diaminopurine nucleotides The metabolism of the β-D-2'-deoxy-2'-α-fluoro-2'-β-methyl-$N^6$-methyl-2,6-diaminopurine nucleoside phosphoramidate involves the production of a 5'-monophosphate and the subsequent anabolism of the $N^6$-methyl-2,6-diaminopurine base to generate the β-D-2'-deoxy-2'-α-fluoro-2'-β-methyl-guanine nucleoside as the 5'-monophosphate. The monophosphate is then further anabolized to the active species; the 5'-triphosphate. The β-D-2'-deoxy-2'-α-fluoro-2'-β-methyl-guanine triphosphate has an $IC_{50}$=0.15 μM against the HCV genotype 1b NS5B polymerase. The metabolic pathway for the β-D-2'-deoxy-2'-α-fluoro-2'-β-methyl-$N^6$-methyl-2,6-diaminopurine nucleoside phosphoramidate is illustrated in Scheme 1 below.

Scheme 1

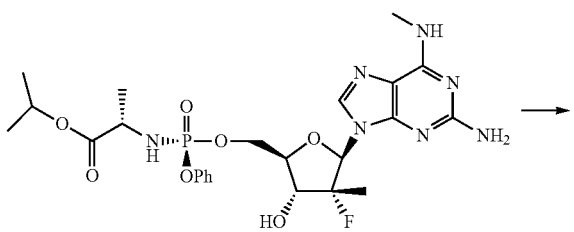

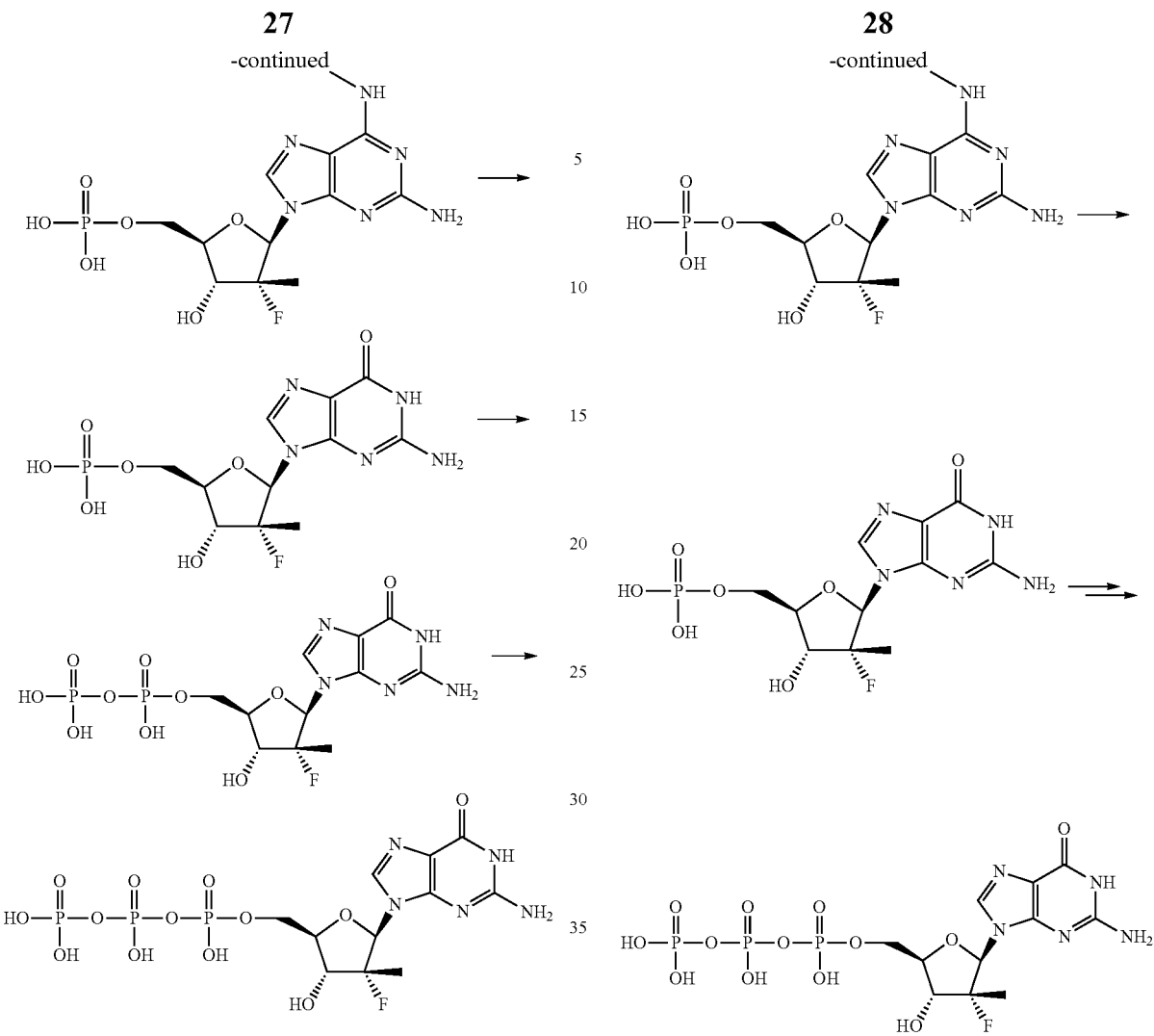

The metabolism of the β-D-2'-deoxy-2'-α-fluoro-2'-β-methyl-N⁶-dimethyl-2,6-diaminopurine nucleotide involves both the formation of the β-D-2'-deoxy-2'-α-fluoro-2'-β-methyl-N⁶-dimethyl-2,6-diaminopurine nucleoside triphosphate as well as the generation of the corresponding guanine nucleoside triphosphate. These metabolic pathways are illustrated in Schemes 2 and 3 below.

Scheme 2

Scheme 3

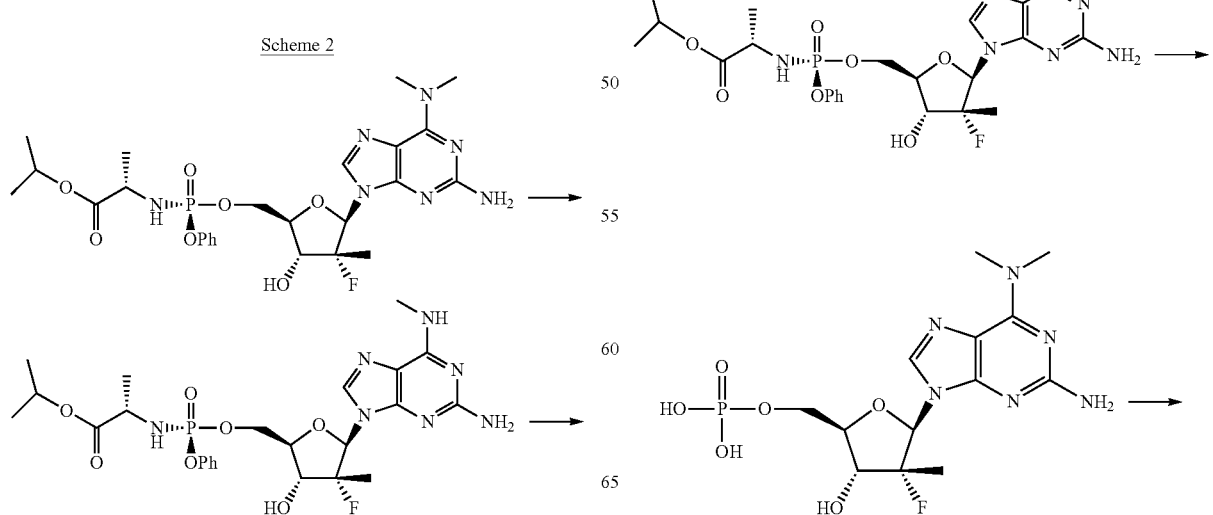

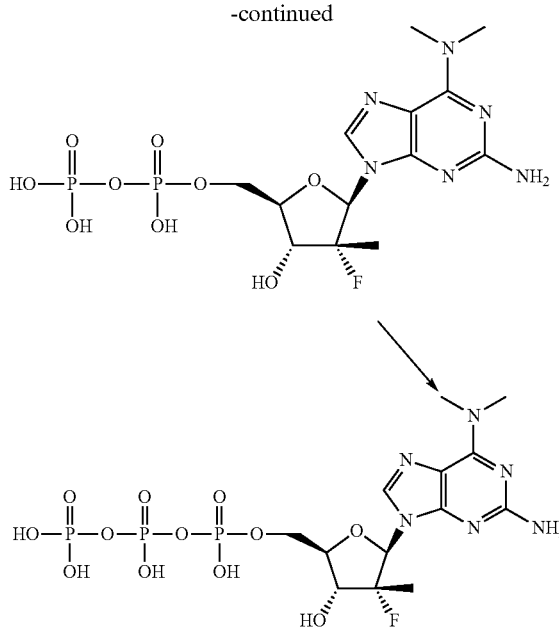

Stabilized Phosphate Prodrugs

Stabilized phosphate prodrugs are moieties that can deliver a mono, di, or triphosphate in vivo. For example, McGuigan has disclosed phosphoramidates in U.S. Pat. Nos. 8,933,053; 8,759,318; 8,658,616; 8,263,575; 8,119,779; 7,951,787 and 7,115,590. Alios has disclosed thiophosphoramidates in U.S. Pat. Nos. 8,895,723 and 8,871,737 incorporated by reference herein. Alios has also disclosed cyclic nucleotides in U.S. Pat. No. 8,772,474 incorporated by reference herein. Idenix has disclosed cyclic phosphoramidates and phosphoramidate/SATE derivatives in WO 2013/177219 incorporated by reference herein. Idenix has also disclosed substituted carbonyloxymethylphosphoramidate compounds in WO 2013/039920 incorporated by reference herein. Hostetler has disclosed lipid phosphate prodrugs, see, for example, U.S. Pat. No. 7,517,858. Hostetler has also disclosed lipid conjugates of phosphonate prodrugs, see, for example, U.S. Pat. Nos. 8,889,658; 8,846,643; 8,710,030; 8,309,565; 8,008,308; and 7,790,703. Emory University has disclosed nucleotide sphingoid and lipid derivatives in WO 2014/124430. RFS Pharma has disclosed purine nucleoside monophosphate prodrugs in WO 2010/091386. Cocrystal Pharma Inc. has also disclosed purine nucleoside monophosphate prodrugs in U.S. Pat. No. 9,173,893 incorporated by reference herein. HepDirect™ technology is disclosed in the article "Design, Synthesis, and Characterization of a Series of Cytochrome P(450) 3A-Activated Prodrugs (HepDirect Prodrugs) Useful for Targeting Phosph(on)ate-Based Drugs to the Liver," (J. Am. Chem. Soc. 126, 5154-5163 (2004). Additional phosphate prodrugs include, but are not limited to phosphate esters, 3',5'-cyclic phosphates including CycloSAL, SATE derivatives (S-acyl-2thioesters) and DTE (dithiodiethyl) prodrugs. For literature reviews that disclose non-limiting examples see: A. Ray and K. Hostetler, "Application of kinase bypass strategies to nucleoside antivirals," Antiviral Research (2011) 277-291; M. Sofia, "Nucleotide prodrugs for HCV therapy," Antiviral Chemistry and Chemotherapy 2011; 22-23-49; and S. Peyrottes et al., "SATE Pronucleotide Approaches: An Overview," Mini Reviews in Medicinal Chemistry 2004, 4, 395. In one embodiment, a 5'-prodrug described in any of these patent filings or literature can be used in the $R^4$ position of the presented compounds.

In one alternative embodiment, the stabilized phosphate prodrugs, include, but are not limited to those described in U.S. Pat. Nos. 9,173,893 and 8,609,627, incorporated by reference herein, including for processes of preparation. For example, 5'-prodrugs of Formula I-V can be represented by the group:

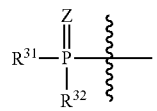

In an alternate embodiment, 3',5'-prodrugs of Formula I-V can be represented by the group:

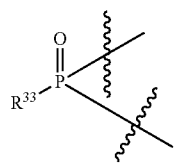

wherein:
when chirality exists at the phosphorous center it may be wholly or partially $R_p$ or $S_p$ or any mixture thereof.
Z is O or S;
$R^{33}$ is selected from $OR^{34}$,

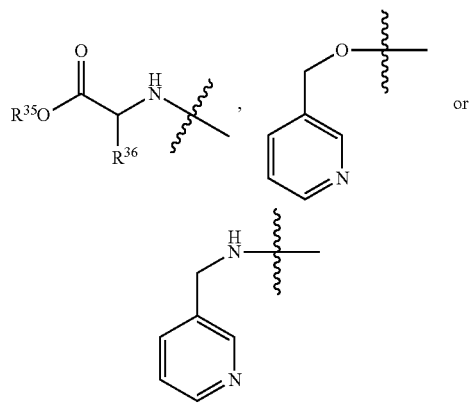

and fatty alcohol derived (for example but not limited to:

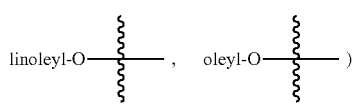

wherein $R^{34}$, $R^{35}$, and $R^{36}$ are as defined below;
$R^{31}$ and $R^{32}$, when administered in vivo, are capable of providing the nucleoside monophosphate or thiomonophosphate, which may or may not be partially or fully resistant to 6-$NH_2$ deamination in a biological system. Representative $R^{31}$ and $R^{32}$ are independently selected from:

(a) $OR^{34}$ where $R^{34}$ is selected from H, Li, Na, K, phenyl and pyridinyl; phenyl and pyridinyl are substituted with one to three substituents independently selected from the group consisting of $(CH_2)_{0-6}CO_2R^{37}$ and $(CH_2)_{0-6}CON(R^{37})_2$; $R^{37}$ is independently H, $C_{1-20}$ alkyl, the carbon chain derived from a fatty alcohol (such as oleyl alcohol, octacosanol, triacontanol, linoleyl alcohol, and etc) or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(b)

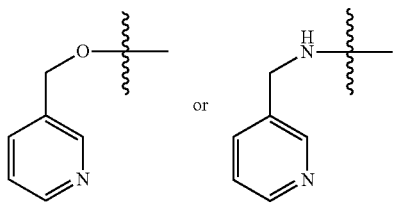 [SMILES: *OCc1cccnc1 ; *NCc1cccnc1]

(c) the ester of a D-amino acid or L-amino acid

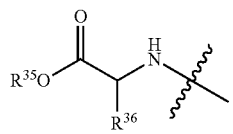

where $R^{36}$ is restricted to those sidechains occurring in natural L-amino acids, and $R^{35}$ is H, $C_{1-20}$ alkyl, the carbon chain derived from a fatty alcohol (such as oleyl alcohol, octacosanol, triacontanol, linoleyl alcohol, and etc) or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(d) $R^{31}$ and $R^{32}$ can come together to form a ring

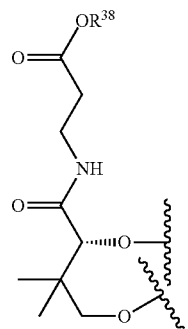

where $R^{38}$ is H, $C_{1-20}$ alkyl, $C_{1-20}$ alkenyl, the carbon chain derived from a fatty alcohol (such as oleyl alcohol, octacosanol, triacontanol, linoleyl alcohol, etc) or $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as, pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl;

(e) $R^{31}$ and $R^{32}$ can come together to form a ring selected from

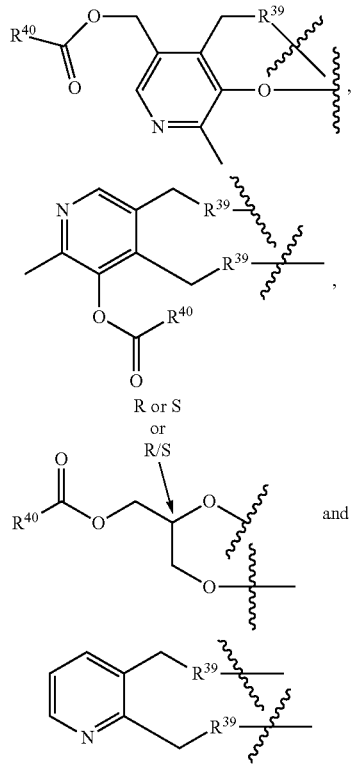

where $R^{39}$ is O or NH and $R^{40}$ is selected from H, $C_{1-20}$ alkyl, $C_{1-20}$ alkenyl, the carbon chain derived from a fatty acid (such as oleic acid, linoleic acid, and the like), and $C_{1-20}$ alkyl substituted with a lower alkyl, alkoxy, di(lower alkyl)-amino, fluoro, $C_{3-10}$ cycloalkyl, cycloalkyl alkyl, cycloheteroalkyl, aryl, such as phenyl, heteroaryl, such as pyridinyl, substituted aryl, or substituted heteroaryl; wherein the substituents are $C_{1-5}$ alkyl, or $C_{1-5}$ alkyl substituted with a lower alkyl, alkoxy, di(lower alkyl)-amino, fluoro, $C_{3-10}$ cycloalkyl, or cycloalkyl.

The compounds can be prepared, for example, by preparing the 5'-OH analogs, then converting these to the monophosphate analogs.

Embodiments

In particular embodiments:
(i) in Formula Ia, Y is $NR^1R^2$, $R^1$ is methyl, $R^2$ is hydrogen, $R^3$ is hydrogen, $R^4$ is a stabilized phosphate prodrug;
(ii) in Formula Ia, Y is $NR^1R^2$, $R^1$ is methyl, $R^2$ is hydrogen, $R^3$ is hydrogen, and $R^4$ is a stabilized thiophosphate prodrug;
(iii) in Formula Ia, Y is $NR^1R^2$, $R^1$ is methyl, $R^2$ is hydrogen, $R^3$ is hydrogen, and $R^4$ is a phosphoramidate;

(iv) in Formula Ia, Y is $NR^1R^2$, $R^1$ is methyl, $R^2$ is hydrogen, $R^3$ is hydrogen, and $R^4$ is a thiophosphoramidate:
(v) in Formula Ia, Y is $NR^1R^2$, $R^1$ is methyl, $R^2$ is hydrogen, $R^3$ is hydrogen, and $R^4$ is a monophosphate;
(vi) in Formula Ia, Y is $NR^1R^2$, $R^1$ is methyl, $R^2$ is hydrogen, $R^3$ is hydrogen, and $R^4$ is a diphosphate;
(vii) in Formula Ia, Y is $NR^1R^2$, $R^1$ is methyl, $R^2$ is hydrogen, $R^3$ is hydrogen, and $R^4$ is a triphosphate;
(viii) in Formula Ia, Y is $NR^1R^2$, $R^1$ is methyl, $R^2$ is methyl, $R^3$ is hydrogen, $R^4$ is a stabilized phosphate prodrug;
(ix) in Formula Ia, Y is $NR^1R^2$, $R^1$ is methyl, $R^2$ is methyl, $R^3$ is hydrogen, and $R^4$ is a stabilized thiophosphate prodrug;
(x) in Formula Ia, Y is $NR^1R^2$, $R^1$ is methyl, $R^2$ is methyl, $R^3$ is hydrogen, and $R^4$ is a phosphoramidate;
(xi) in Formula Ia, Y is $NR^1R^2$, $R^1$ is methyl, $R^2$ is methyl, $R^3$ is hydrogen, and $R^4$ is a thiophosphoramidate:
(xii) in Formula Ia, Y is $NR^1R^2$, $R^1$ is methyl, $R^2$ is methyl, $R^3$ is hydrogen, and $R^4$ is a monophosphate;
(xiii) in Formula Ia, Y is $NR^1R^2$, $R^1$ is methyl, $R^2$ is methyl, $R^3$ is hydrogen, and $R^4$ is a diphosphate;
(xiv) in Formula Ia, Y is $NR^1R^2$, $R^1$ is methyl, $R^2$ is methyl, $R^3$ is hydrogen, and $R^4$ is a triphosphate;
(xv) in Formula Ia, Y is $NR^1R^2$, $R^1$ is methyl, $R^2$ is cyclopropyl, $R^3$ is hydrogen, $R^4$ is a stabilized phosphate prodrug;
(xvi) in Formula Ia, Y is $NR^1R^2$, $R^1$ is methyl, $R^2$ is cyclopropyl, $R^3$ is hydrogen, and $R^4$ is a stabilized thiophosphate prodrug;
(xvii) in Formula Ia, Y is $NR^1R^2$, $R^1$ is methyl, $R^2$ is cyclopropyl, $R^3$ is hydrogen, and $R^4$ is a phosphoramidate;
(xviii) in Formula Ia, Y is $NR^1R^2$, $R^1$ is methyl, $R^2$ is cyclopropyl, $R^3$ is hydrogen, and $R^4$ is a thiophosphoramidate:
(xix) in Formula Ia, Y is $NR^1R^2$, $R^1$ is methyl, $R^2$ is cyclopropyl, $R^3$ is hydrogen, and $R^4$ is a monophosphate;
(xx) in Formula Ia, Y is $NR^1R^2$, $R^1$ is methyl, $R^2$ is cyclopropyl, $R^3$ is methyl, and $R^4$ is a diphosphate;
(xxi) in Formula Ia, Y is $NR^1R^2$, $R^1$ is methyl, $R^2$ is cyclopropyl, $R^3$ is hydrogen, and $R^4$ is a triphosphate;
(xxii) in Formula Ia, Y is $NR^1R^2$, $R^1$ is methyl, $R^2$ is propyl, $R^3$ is hydrogen, $R^4$ is a stabilized phosphate prodrug;
(xxiii) in Formula Ia, Y is $NR^1R^2$, $R^1$ is methyl, $R^2$ is propyl, $R^3$ is hydrogen, and $R^4$ is a stabilized thiophosphate prodrug;
(xxiv) in Formula Ia, Y is $NR^1R^2$, $R^1$ is methyl, $R^2$ is propyl, $R^3$ is hydrogen, and $R^4$ is a phosphoramidate;
(xxv) in Formula Ia, Y is $NR^1R^2$, $R^1$ is methyl, $R^2$ is propyl, $R^3$ is hydrogen, and $R^4$ is a thiophosphoramidate:
(xxvi) in Formula Ia, Y is $NR^1R^2$, $R^1$ is methyl, $R^2$ is propyl, $R^3$ is hydrogen, and $R^4$ is a monophosphate;
(xxvii) in Formula Ia, Y is $NR^1R^2$, $R^1$ is methyl, $R^2$ is propyl, $R^3$ is hydrogen, and $R^4$ is a diphosphate;
(xxviii) in Formula Ia, Y is $NR^1R^2$, Y is $NR^1R^2$, $R^1$ is methyl, $R^2$ is propyl, $R^3$ is hydrogen, and $R^4$ is a triphosphate;
(xxix) in Formula Ia, Y is $NR^1R^2$, $R^1$ is methyl, $R^2$ is ethyl, $R^3$ is hydrogen, and $R^4$ is a stabilized phosphate prodrug;
(xxx) in Formula Ia, Y is $NR^1R^2$, $R^1$ is methyl, $R^2$ is ethyl, $R^3$ is hydrogen, and $R^4$ is a stabilized thiophosphate prodrug;
(xxxi) in Formula Ia, Y is $NR^1R^2$, $R^1$ is methyl, $R^2$ is ethyl, $R^3$ is hydrogen, and $R^4$ is a phosphoramidate;
(xxxii) in Formula Ia, Y is $NR^1R^2$, $R^1$ is methyl, $R^2$ is ethyl, $R^3$ is hydrogen, and $R^4$ is a thiophosphoramidate:
(xxxiii) in Formula Ia, Y is $NR^1R^2$, $R^1$ is methyl, $R^2$ is ethyl, $R^3$ is hydrogen, and $R^4$ is a monophosphate;
(xxxiv) in Formula Ia, Y is $NR^1R^2$, $R^1$ is methyl, $R^2$ is ethyl, $R^3$ is hydrogen, and $R^4$ is a diphosphate;
(xxxv) in Formula Ia, Y is $NR^1R^2$, $R^1$ is methyl, $R^2$ is ethyl, $R^3$ is hydrogen, and $R^4$ is a triphosphate;
(xxxvi) in Formula Ib, Y is $NR^1R^2$, $R^1$ is methyl, $R^2$ is methyl, $R^3$ is hydrogen, $R^4$ is a stabilized phosphate prodrug;
(xxxvii) in Formula Ib, Y is $NR^1R^2$, $R^1$ is methyl, $R^2$ is methyl, $R^3$ is hydrogen, and $R^4$ is a stabilized thiophosphate prodrug;
(xxxviii) in Formula Ib, Y is $NR^1R^2$, $R^1$ is methyl, $R^2$ is methyl, $R^3$ is hydrogen, and $R^4$ is a phosphoramidate;
(xxxix) in Formula Ib, Y is $NR^1R^2$, $R^1$ is methyl, $R^2$ is methyl, $R^3$ is hydrogen, and $R^4$ is a thiophosphoramidate:
(xl) in Formula Ib, Y is $NR^1R^2$, $R^1$ is methyl, $R^2$ is methyl, $R^3$ is hydrogen, and $R^4$ is a monophosphate;
(xli) in Formula Ib, Y is $NR^1R^2$, $R^1$ is methyl, $R^2$ is methyl, $R^3$ is hydrogen, and $R^4$ is a diphosphate;
(xlii) in Formula Ib, Y is $NR^1R^2$, $R^1$ is methyl, $R^2$ is methyl, $R^3$ is hydrogen, and $R^4$ is a triphosphate;
(xliii) in Formula Ib, Y is $NR^1R^2$, $R^1$ is methyl, $R^2$ is hydrogen, $R^3$ is hydrogen, $R^4$ is a stabilized phosphate prodrug;
(xliv) in Formula Ib, Y is $NR^1R^2$, $R^1$ is methyl, $R^2$ is hydrogen, $R^3$ is hydrogen, and $R^4$ is a stabilized thiophosphate prodrug;
(xlv) in Formula Ib, Y is $NR^1R^2$, $R^1$ is methyl, $R^2$ is hydrogen, $R^3$ is hydrogen, and $R^4$ is a phosphoramidate;
(xlvi) in Formula Ib, Y is $NR^1R^2$, $R^1$ is methyl, $R^2$ is hydrogen, $R^3$ is hydrogen, and $R^4$ is a thiophosphoramidate:
(xlvii) in Formula Ib, Y is $NR^1R^2$, $R^1$ is methyl, $R^2$ is hydrogen, $R^3$ is hydrogen, and $R^4$ is a monophosphate;
(xlviii) in Formula Ib, Y is $NR^1R^2$, $R^1$ is methyl, $R^2$ is hydrogen, $R^3$ is hydrogen, and $R^4$ is a diphosphate;
(xlix) in Formula Ib, Y is $NR^1R^2$, $R^1$ is methyl, $R^2$ is hydrogen, $R^3$ is hydrogen, and $R^4$ is a triphosphate;
(l) in Formula Ib, Y is $NR^1R^2$, $R^1$ is methyl, $R^2$ is cyclopropyl, $R^3$ is hydrogen, $R^4$ is a stabilized phosphate prodrug;
(li) in Formula Ib, Y is $NR^1R^2$, $R^1$ is methyl, $R^2$ is cyclopropyl, $R^3$ is hydrogen, and $R^4$ is a stabilized thiophosphate prodrug;
(lii) in Formula Ib, Y is $NR^1R^2$, $R^1$ is methyl, $R^2$ is cyclopropyl, $R^3$ is hydrogen, and $R^4$ is a phosphoramidate;
(liii) in Formula Ib, Y is $NR^1R^2$, $R^1$ is methyl, $R^2$ is cyclopropyl, $R^3$ is hydrogen, and $R^4$ is a thiophosphoramidate:
(liv) in Formula Ib, Y is $NR^1R^2$, $R^1$ is methyl, $R^2$ is cyclopropyl, $R^3$ is hydrogen, and $R^4$ is a monophosphate;
(lv) in Formula Ib, Y is $NR^1R^2$, $R^1$ is methyl, $R^2$ is cyclopropyl, $R^3$ is methyl, and $R^4$ is a diphosphate;
(lvi) in Formula Ia, Y is $NR^1R^2$, $R^1$ is methyl, $R^2$ is cyclopropyl, $R^3$ is hydrogen, and $R^4$ is a triphosphate.

In alternative embodiments of any of the above, the compound has an $R^{22}$ substituent. In some of these specific embodiments, the $R^{22}$ is F, amide or carbamate. In other specific aspects of the embodiments above, $R^{22}$ is chloro, bromo, cyano, azido, ethyl, n-propyl, iso-propyl, n-butyl, iso-butyl, sec-butyl, tert-butyl and n-pentyl, 1,1-dimethylpropyl, 2,2-dimtheylpropyl, 3-methylbutyl, 1-methylbutyl, 1-ethylpropyl, vinyl, allyl, 1-butynyl, 2-butynyl, acetylenyl, cyclopropyl, cyclobutyl, cyclopentyl, cyclohexyl, —(CH$_2$)-cyclopropyl, —(CH$_2$)-cyclobutyl, —(CH$_2$)-cyclopentyl, —(CH$_2$)-cyclohexyl, aziridine, oxirane, thiirane, azetidine, oxetane, thietane, pyrrolidine, tetrahydrofuran, thiolane, pyrazolidine, piperidine, oxane, thiane, —(CH$_2$)-aziridine, —(CH$_2$)-oxirane, —(CH$_2$)-thiirane, —(CH$_2$)-azetidine, —(CH$_2$)-oxetane, —(CH$_2$)-thietane, —(CH$_2$)-pyrrolidine, —(CH$_2$)-tetrahydrofuran, —(CH$_2$)-thiolane, —(CH$_2$)-pyrazolidine, —(CH$_2$)-piperidine, —(CH$_2$)-oxane, —(CH$_2$)-thiane, phenyl, pyridyl, —ONHC(=O)OCH$_3$, —ONHC(=O)OCH$_2$CH$_3$, —NHOH, NHOCH$_3$, —OCH$_3$, OC$_2$H$_5$, —OPh, OCH$_2$Ph, —SCH$_3$, —SC$_2$H$_5$, —SPh, SCH$_2$Ph, —NH(CH$_2$)$_2$NH$_2$, —NH(CH$_2$)$_2$N(CH$_3$)$_2$, —NHNH$_2$, —NHNHCH$_3$, —N=NH, —N=NCH$_3$, —N=NCH$_2$CH$_3$, —NHC(O)NHNH$_2$, —NHC(S)NHNH$_2$, —C(O)NHNH$_2$, —NHSO$_2$CH$_3$, —NHSO$_2$CH$_2$CH$_3$, —SO$_2$NHCH$_3$, —SO$_2$N(CH$_3$)$_2$, —C(O)NH$_2$, —C(O)NHCH$_3$, —C(O)N(CH$_3$)$_2$, —CO$_2$CH$_3$, —CO$_2$CH$_2$CH$_3$, —CO$_2$Ph, CO$_2$CH$_2$Ph, —SO$_2$CH$_3$, —SO$_2$CH$_2$CH$_3$, —SO$_2$Ph, —SO$_2$CH$_2$Ph,

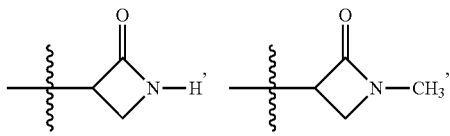

—P(O)H(OH), —P(O)H(OCH$_3$), —P(O)(OH)(OH), —P(O)(OH)(OCH$_3$), —P(O)(OCH$_3$)(OCH$_3$), —P(O)(OH)(NH$_2$), —P(O)(OH)(NHCH$_3$), —P(O)(OH)N(CH$_3$)$_2$, —NHC(O)CH$_3$, —NHC(O)CH$_2$CH$_3$, —NHC(O)CH(CH$_3$)$_2$, —NHC(O)OCH$_3$, —NHC(O)OCH$_2$CH$_3$, —NHC(O)OCH(CH$_3$)$_2$, —NHC(O)OCH$_2$CH$_2$CH$_3$, —NHC(O)OCH$_2$CH$_2$CH$_2$CH$_3$ and —NHC(O)OCH$_2$CH$_2$CH$_2$CH$_2$CH$_3$;

In alternative embodiments of compounds (i) through (lvi), an L-nucleoside is used in Formula I-VII.

In an alternate embodiment, the Formula I $R^{12}$ variable is CH$_2$F.

In an alternate embodiment, the Formula I $R^{12}$ variable is CHF$_2$.

In an alternate embodiment, the Formula I $R^{12}$ variable is CF$_3$.

In one embodiment, a compound of Formula Ia is provided. Non-limiting examples of compounds of Formula Ia include:

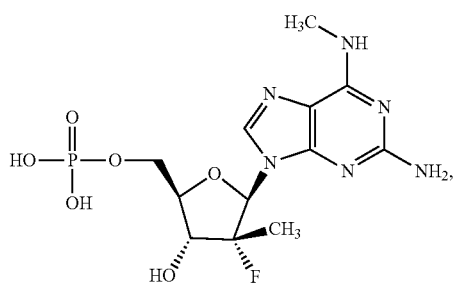

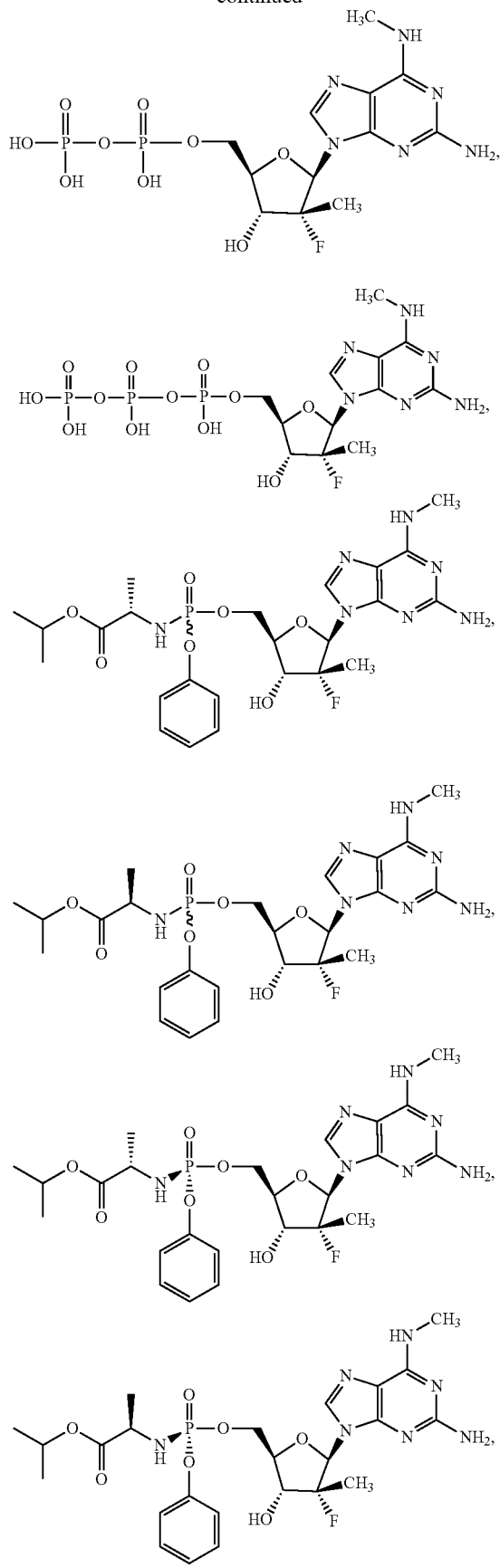

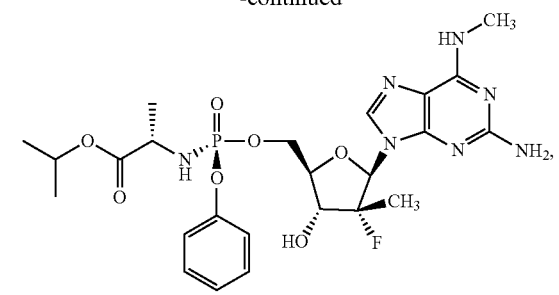
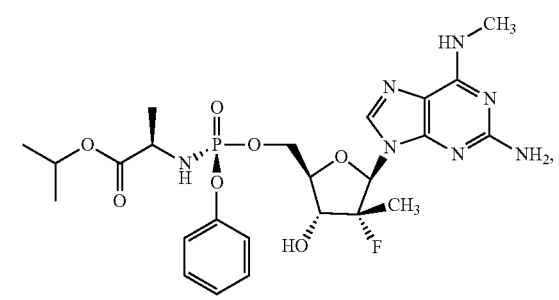
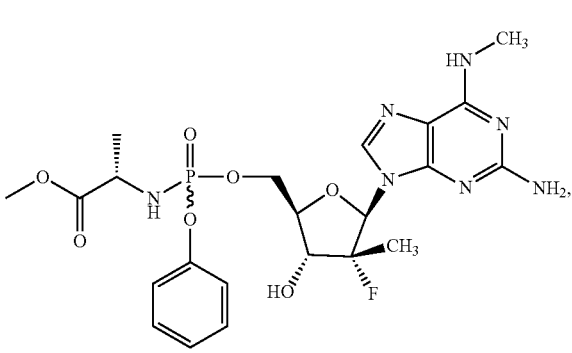
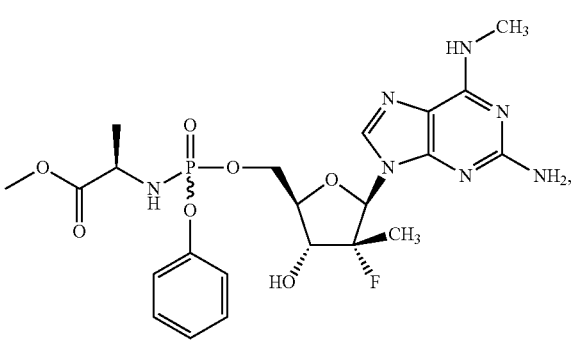
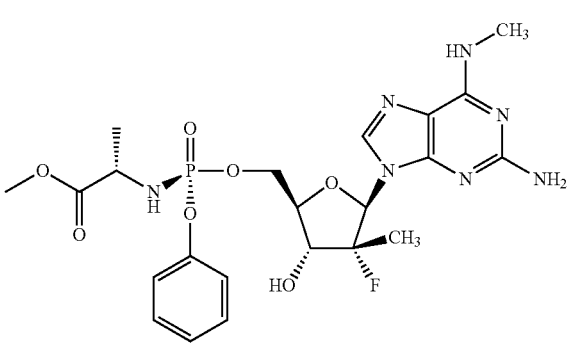
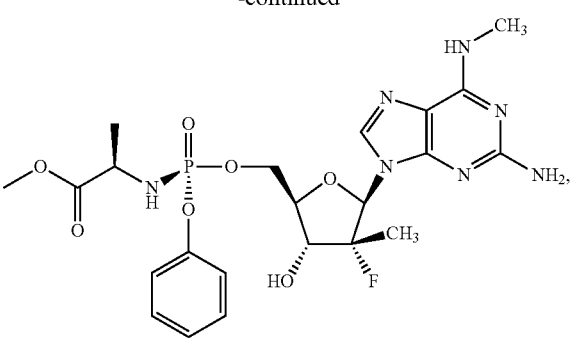
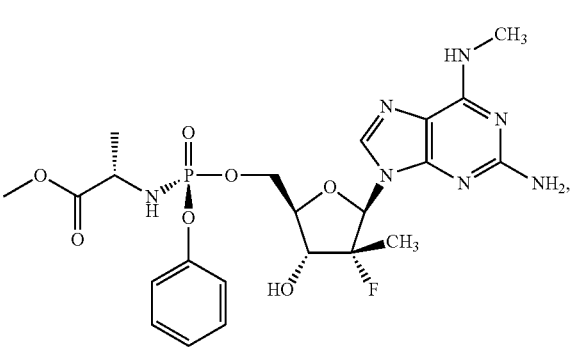
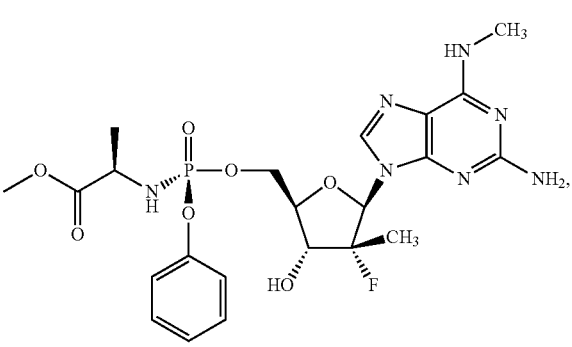
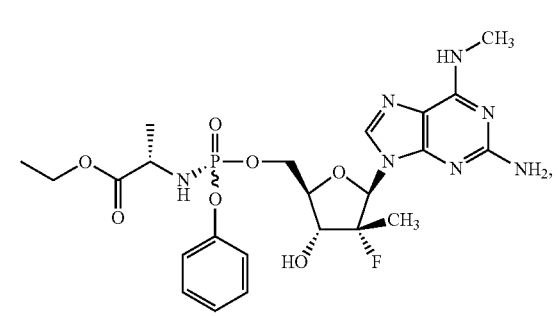
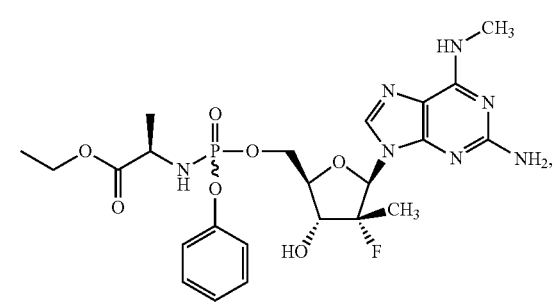

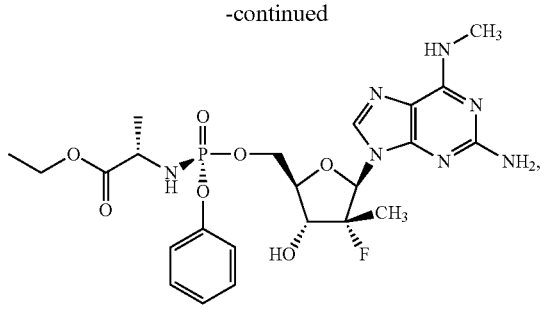
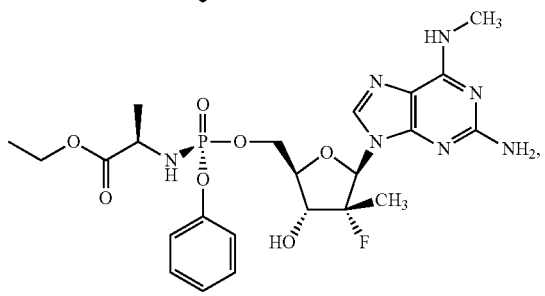
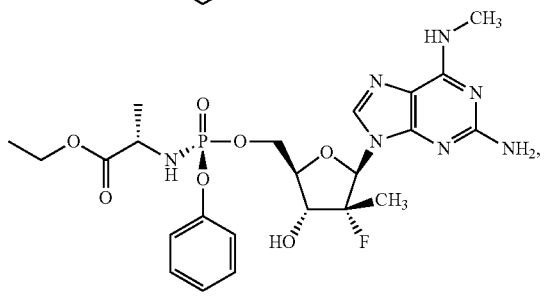
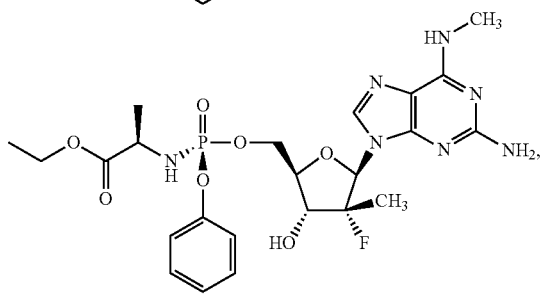
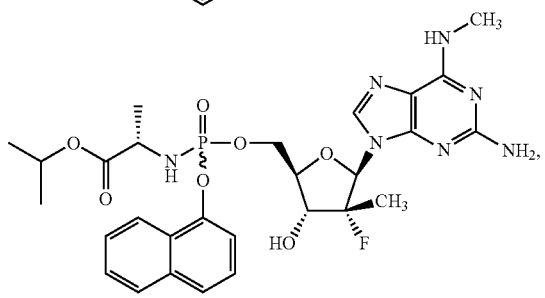
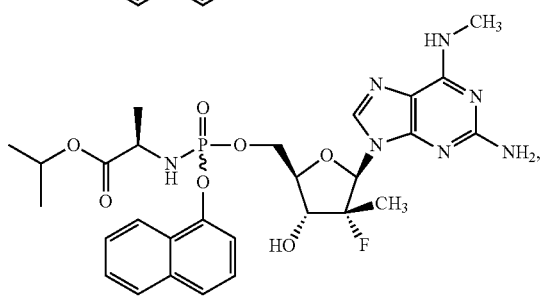
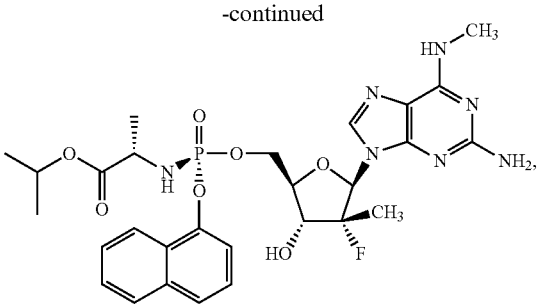
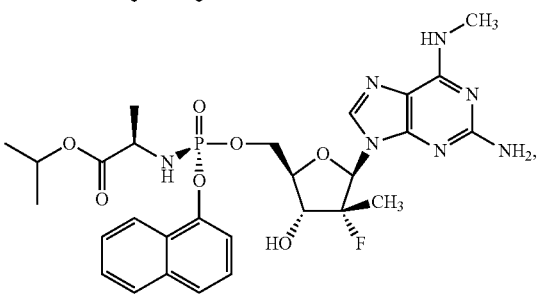
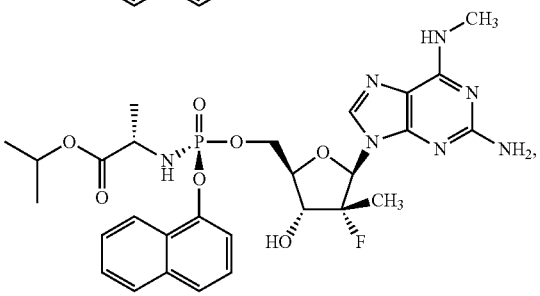
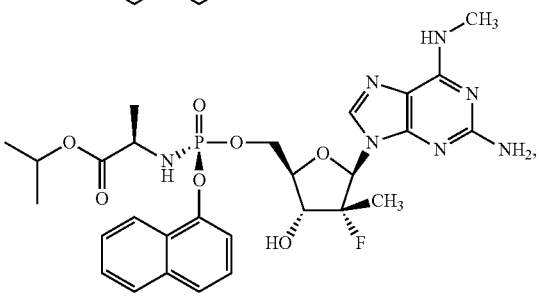
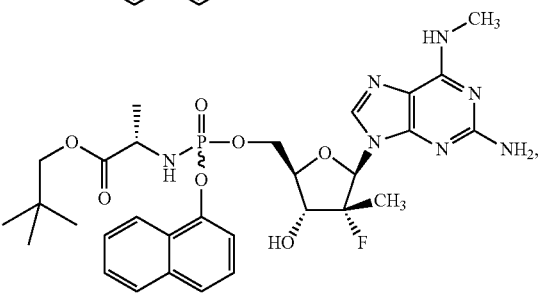
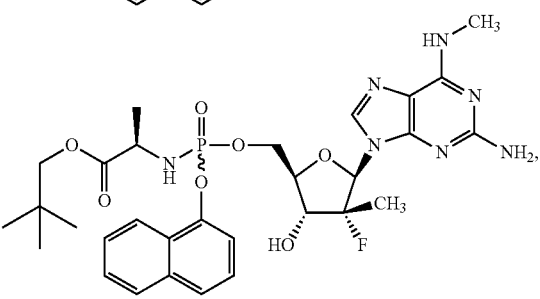

41
-continued
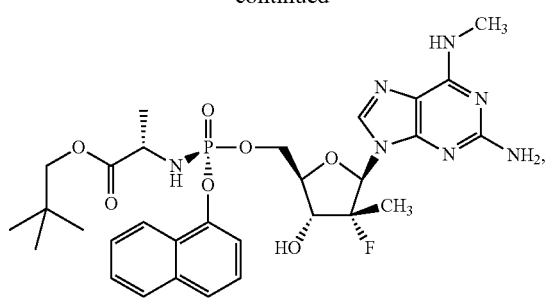
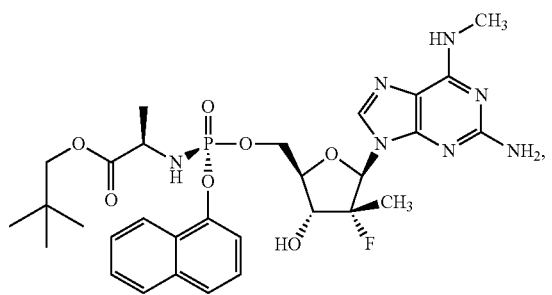
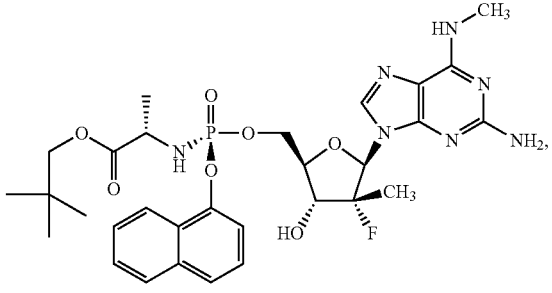
and
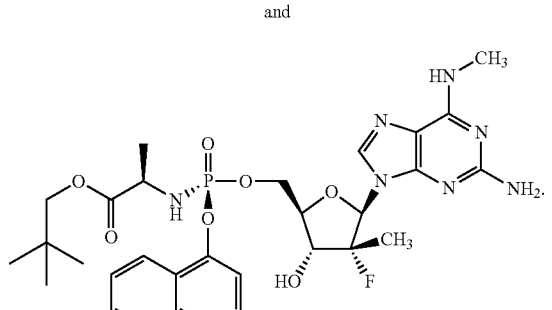
In one embodiment, a thiophosphoramidate of Formula Ia is provided. Non-limiting examples of thiophosphoramidates of Formula Ia include, but are not limited to:
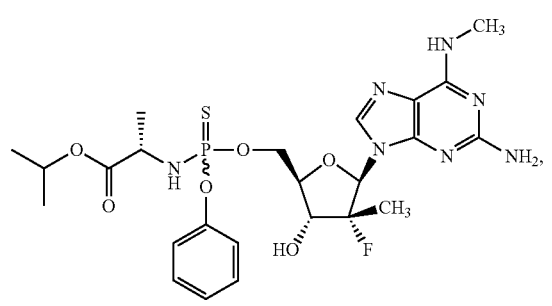
42
-continued
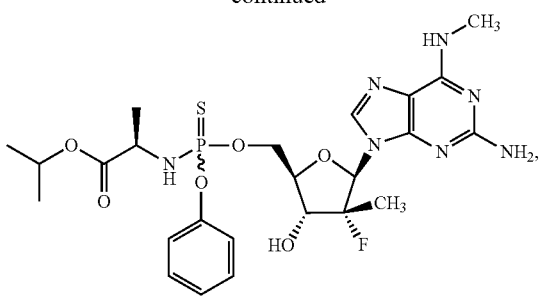
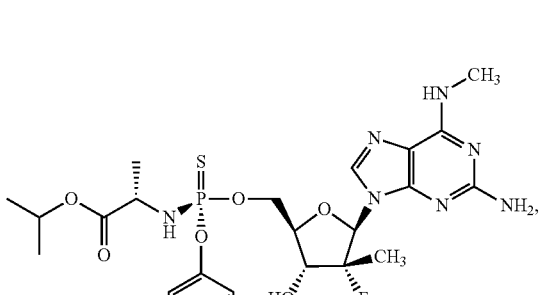
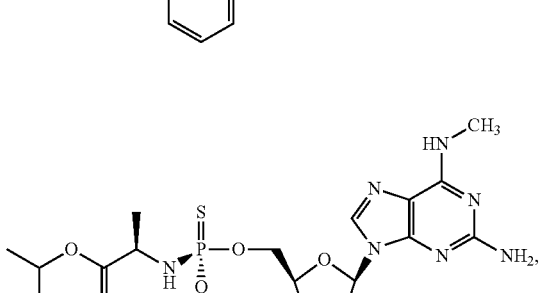
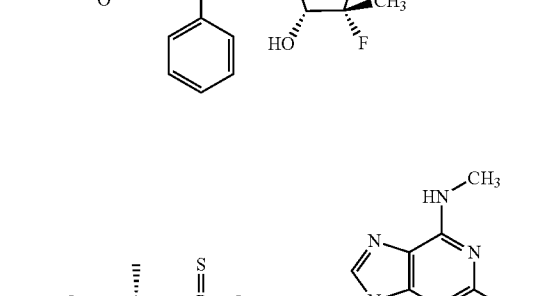
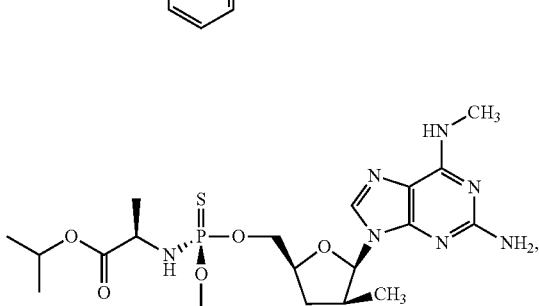

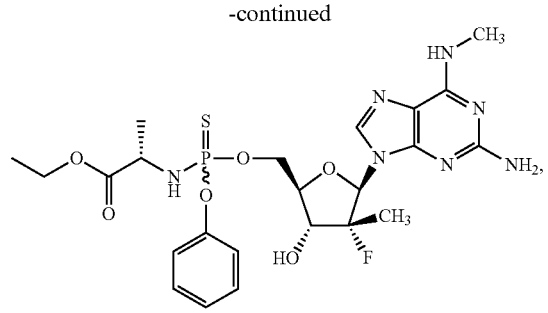
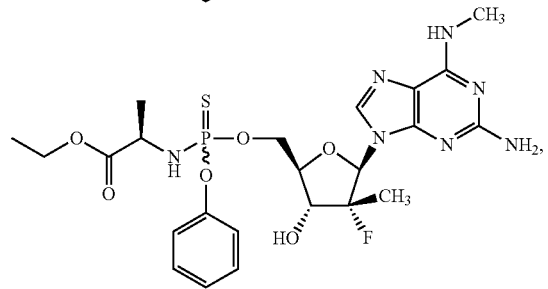
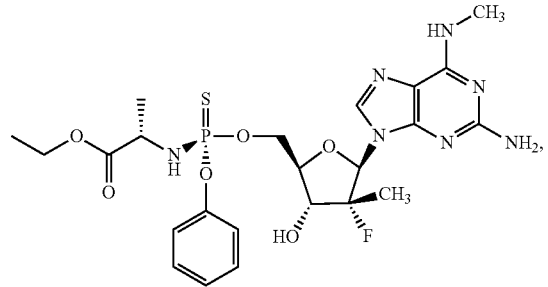
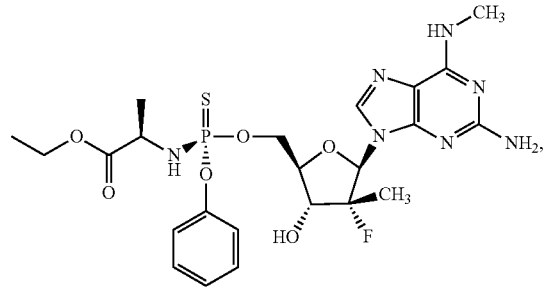
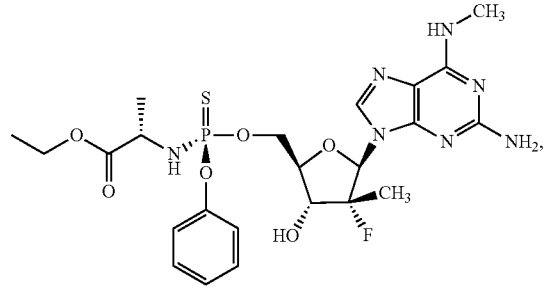
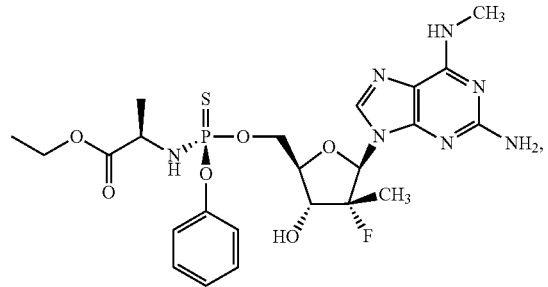
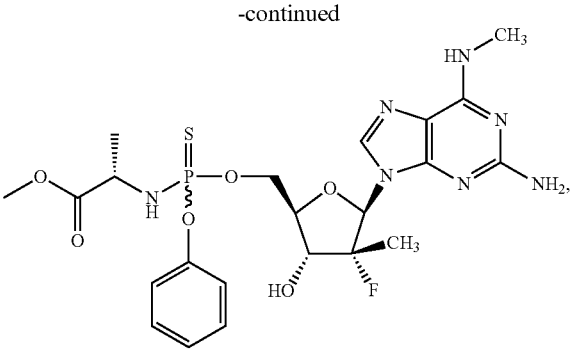
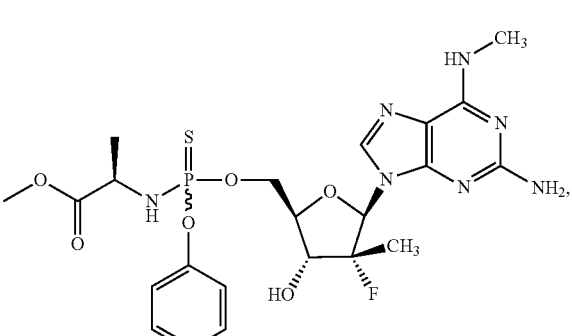
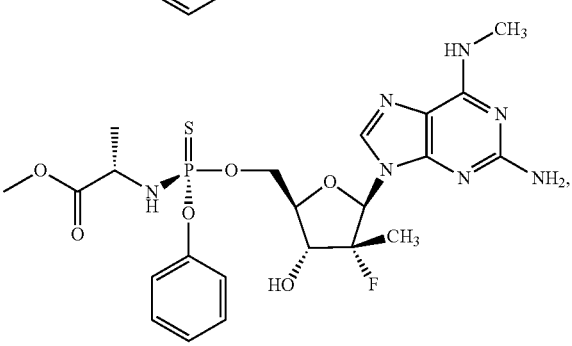
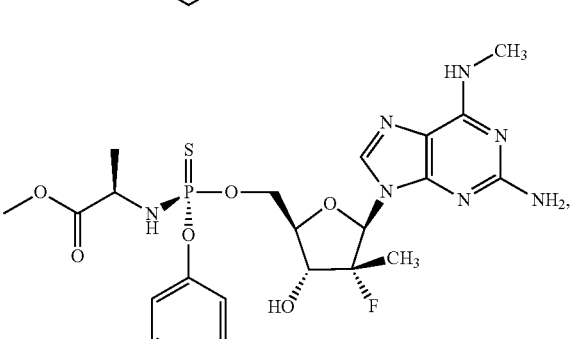
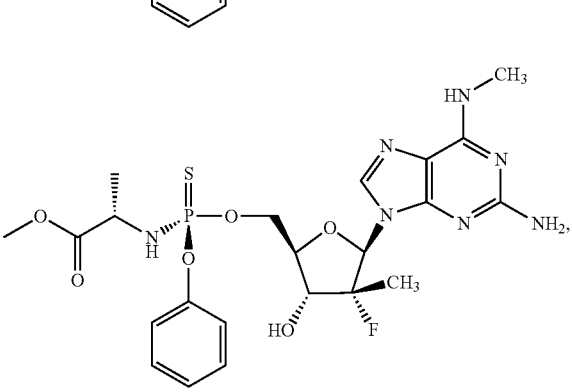

45
-continued
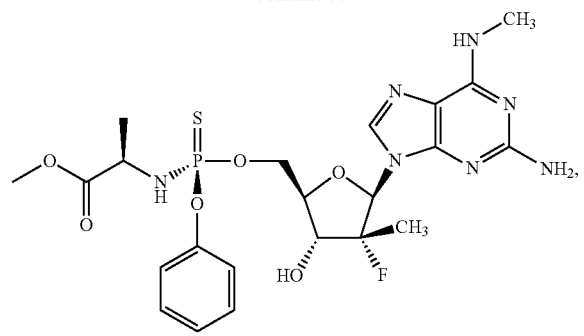
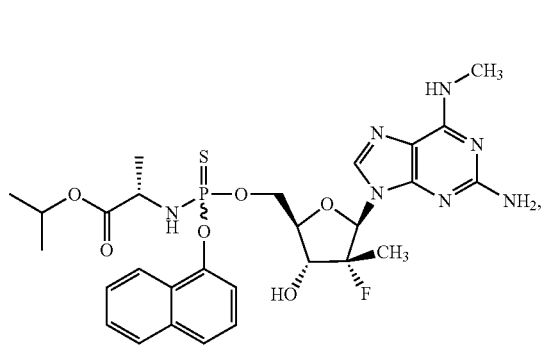
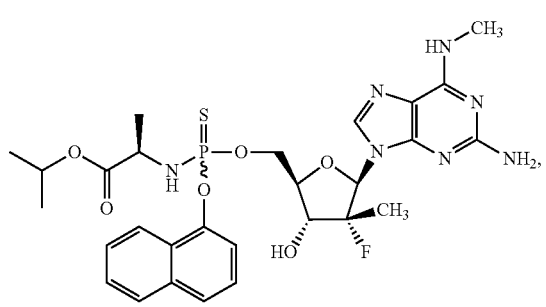
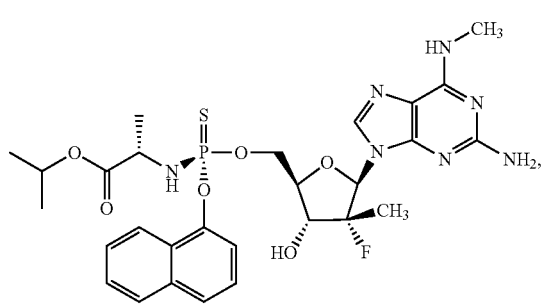
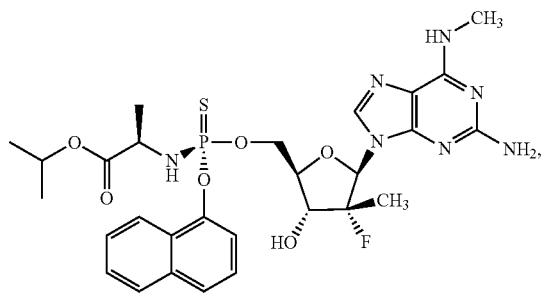
46
-continued
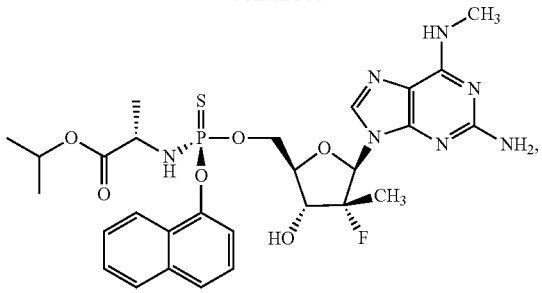
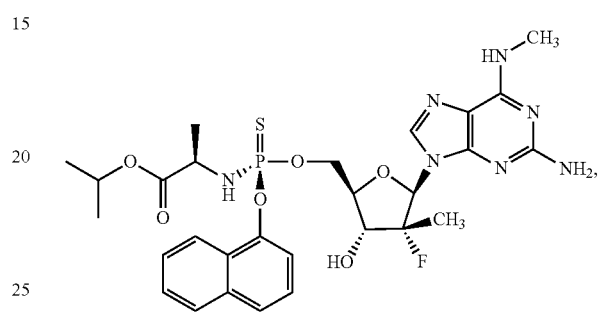
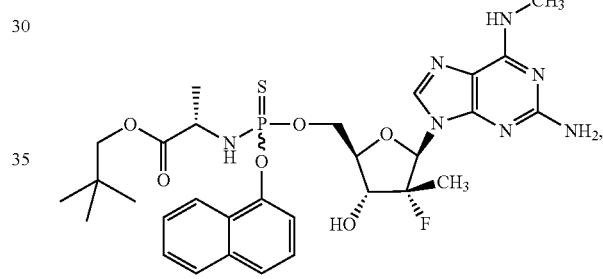
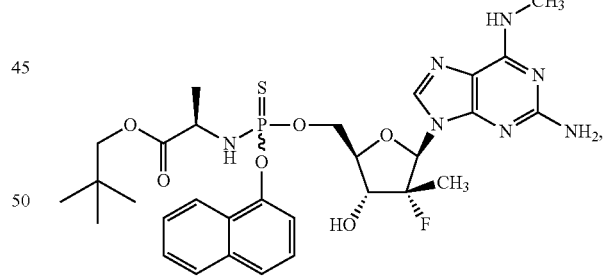
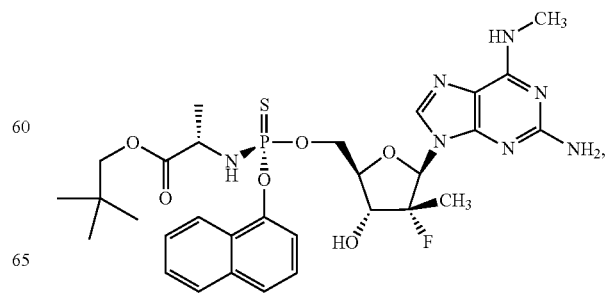

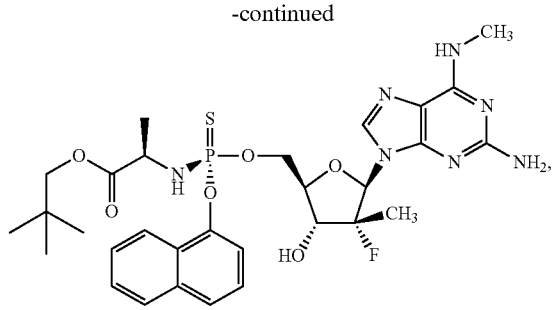
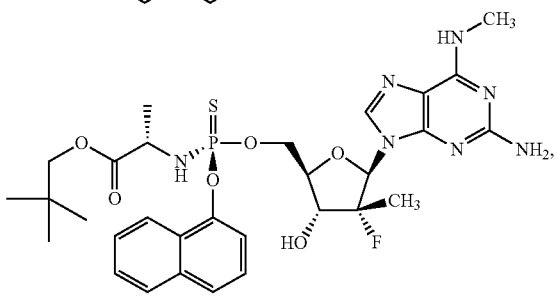
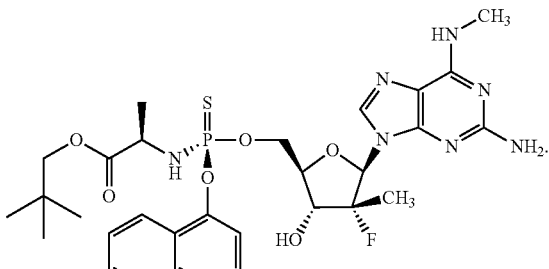
In one embodiment, a stabilized phosphate prodrug of Formula Ia is provided. Non-limiting examples of stabilized phosphate prodrugs of Formula Ia are illustrated below:
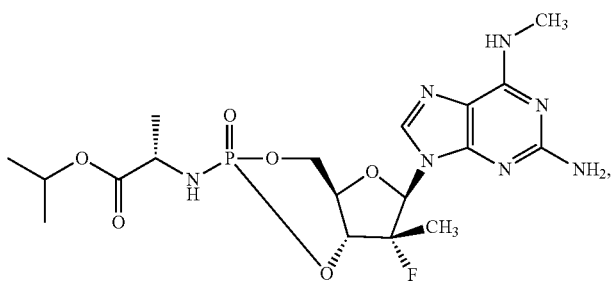
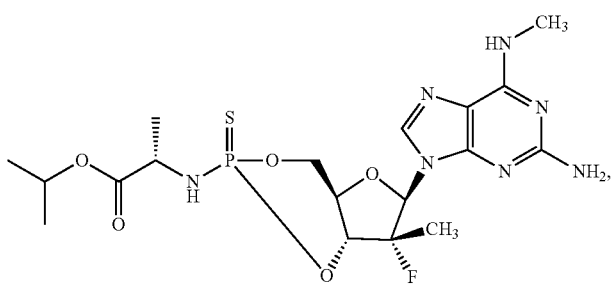
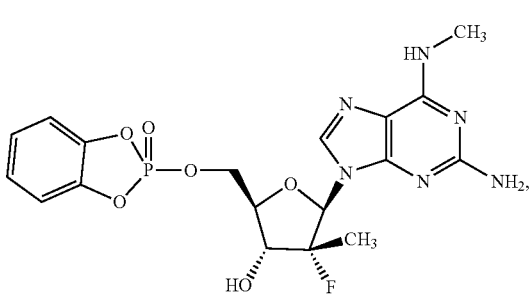
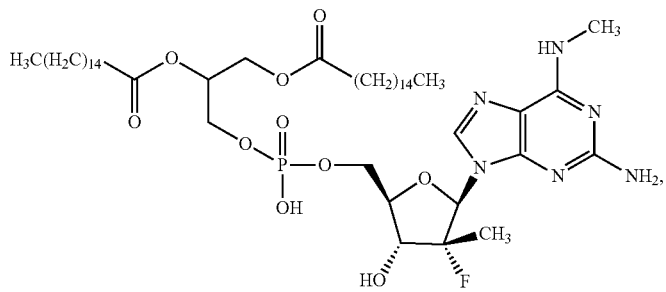

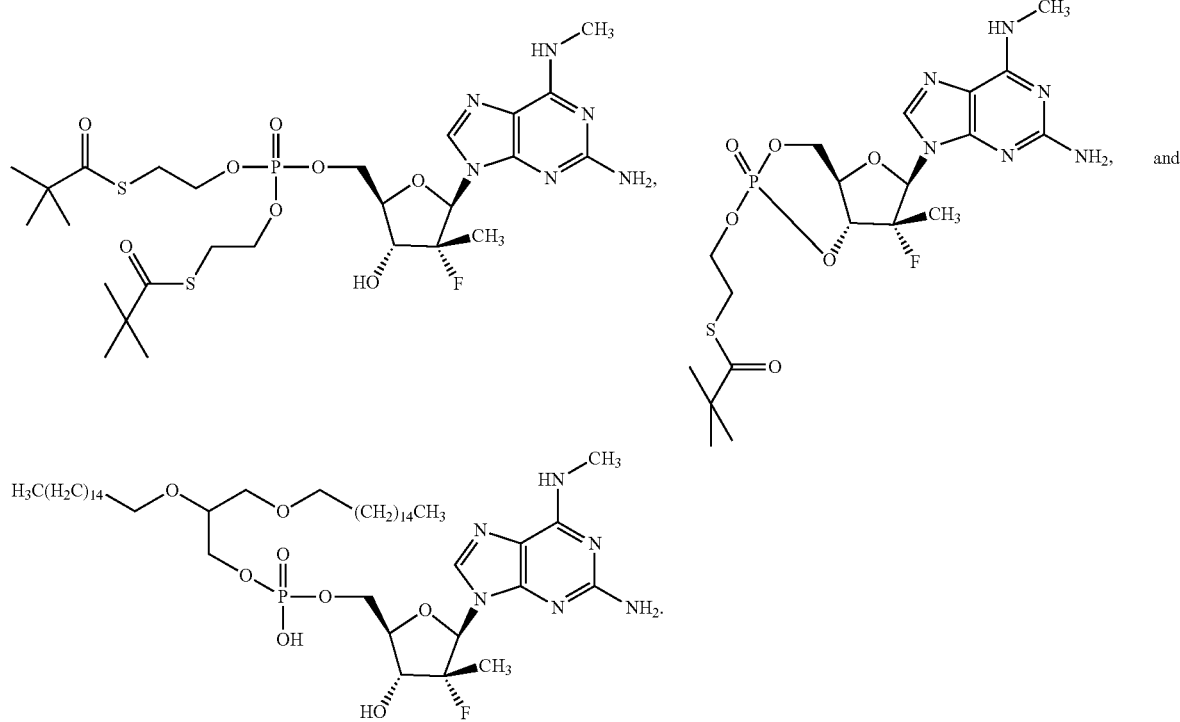
In another embodiment, a compound of Formula Ia is provided. Non-limiting examples of compounds of Formula Ia include:
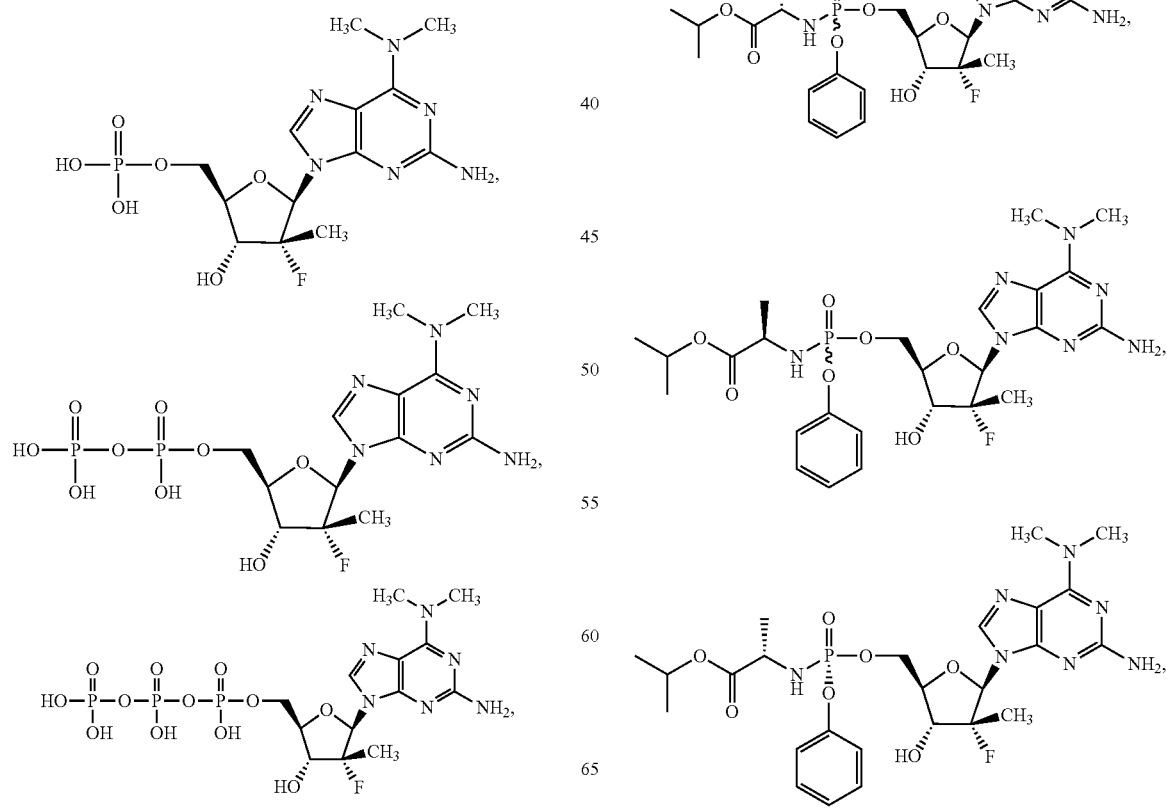

-continued
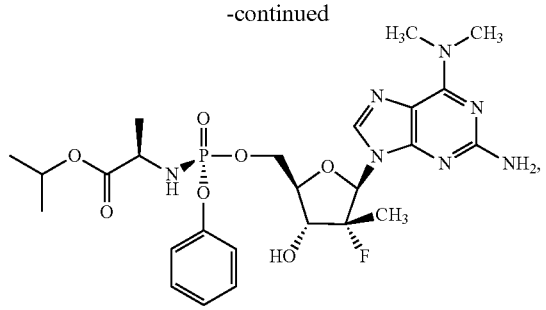
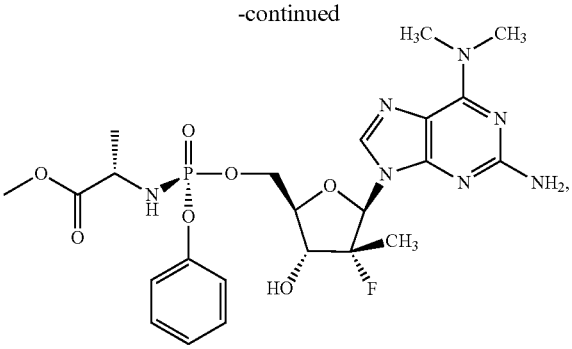
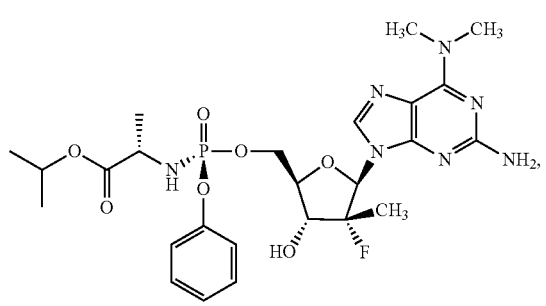
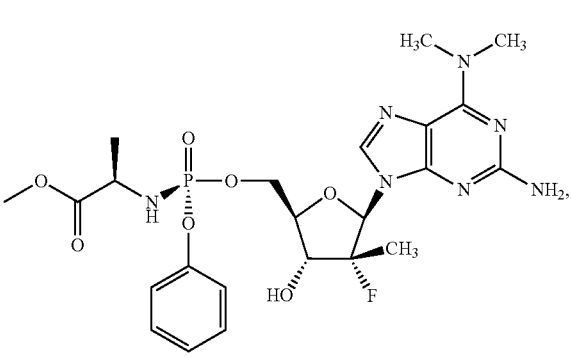
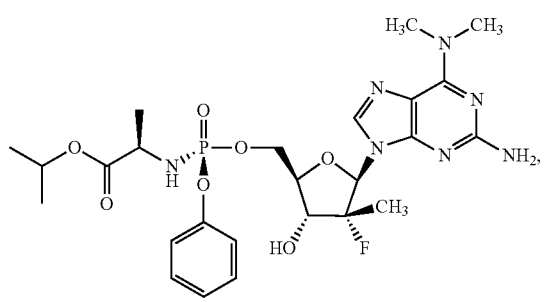
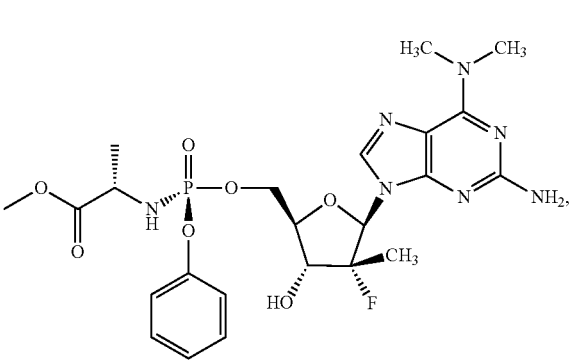
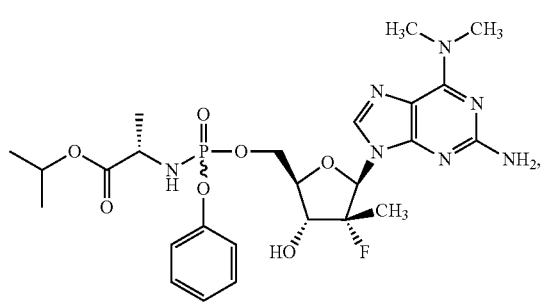
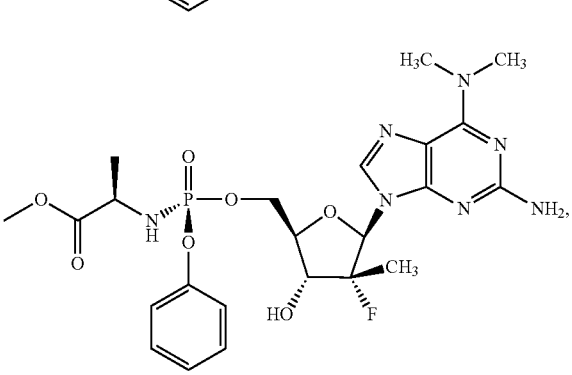
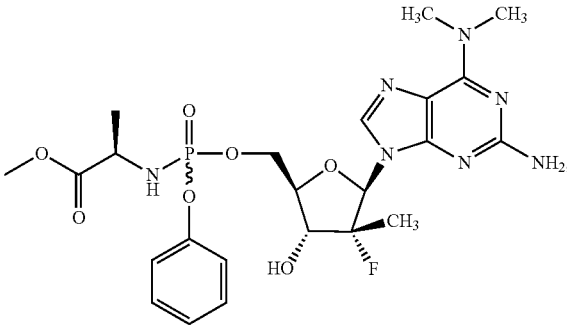
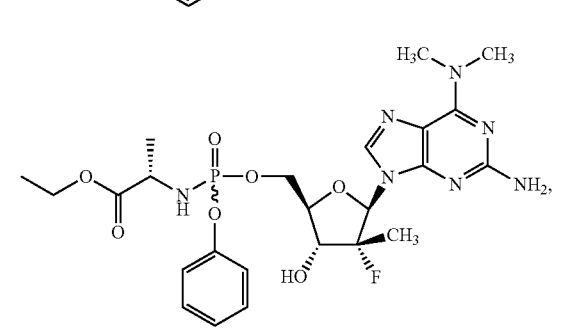

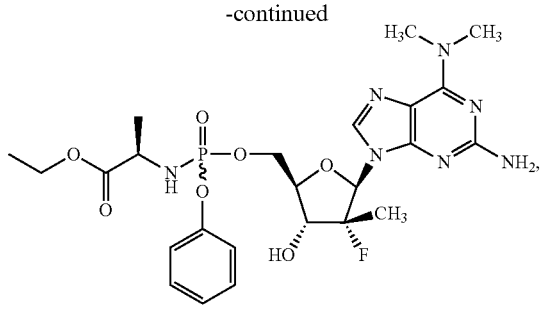
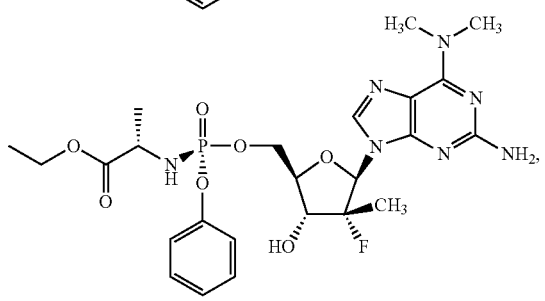
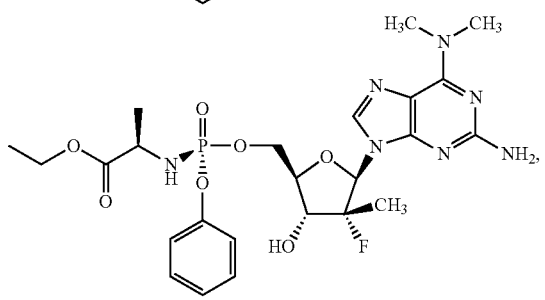
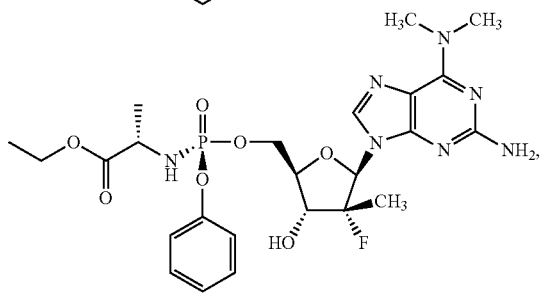
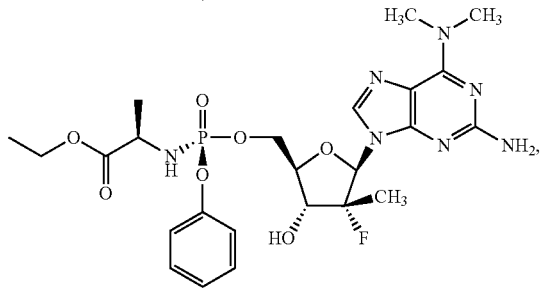
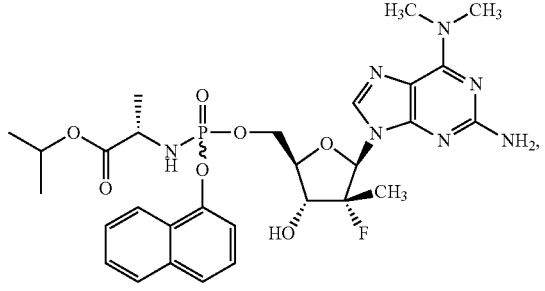
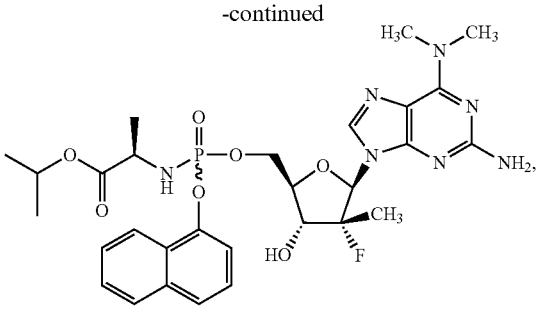

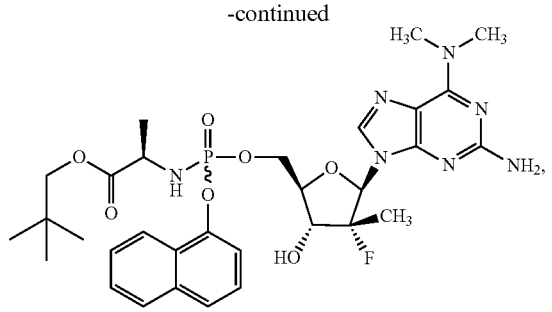
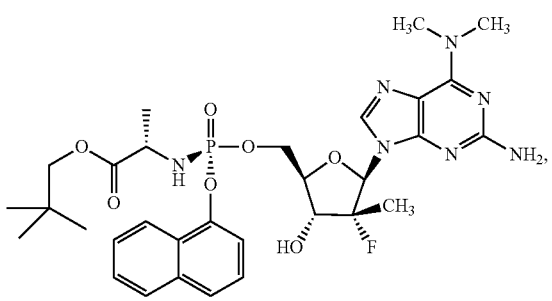
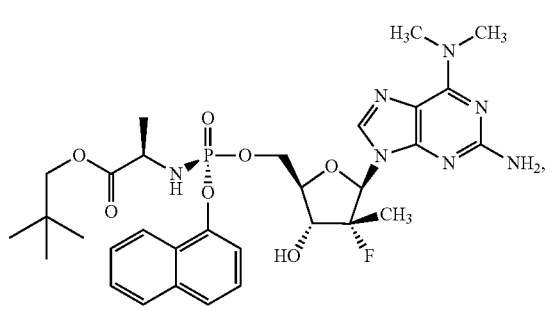
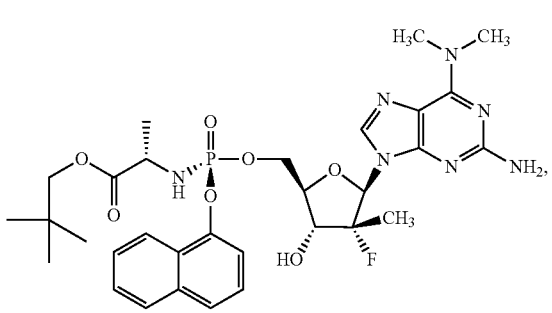
and
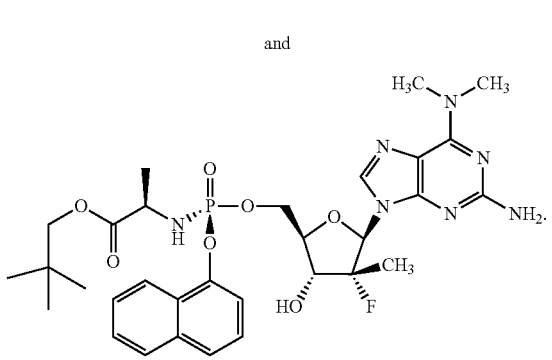
In one embodiment, a thiophosphoramidate of Formula Ia is provided. Non-limiting examples of thiophosphoramidates of Formula Ia include, but are not limited to:
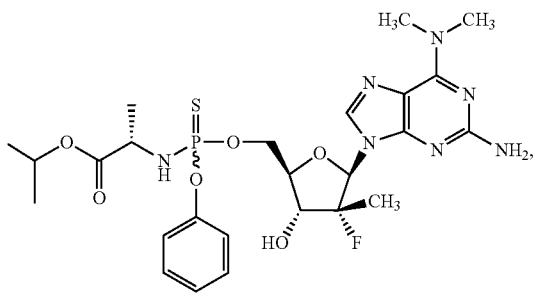
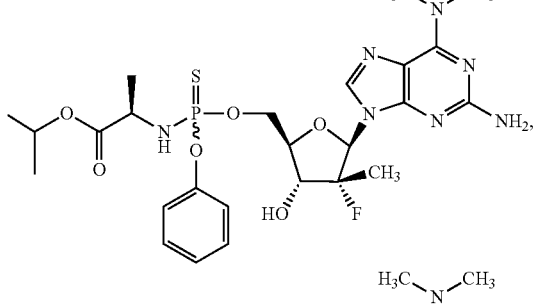
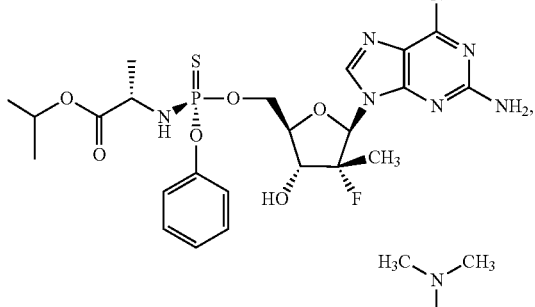
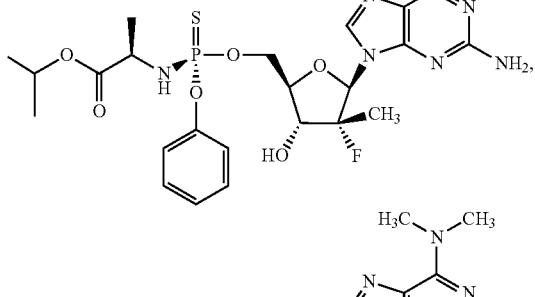
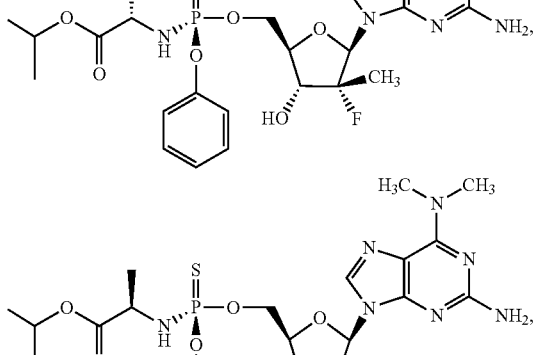

-continued
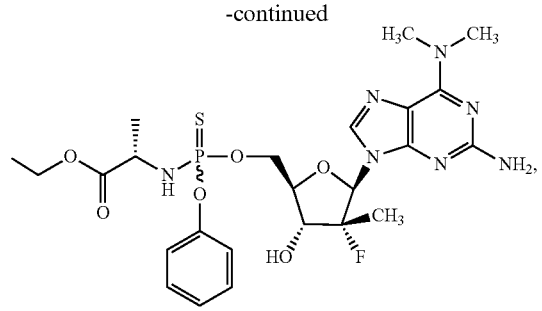
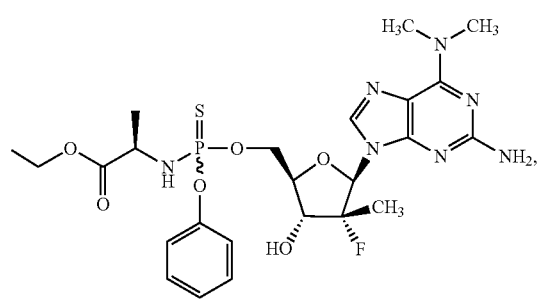
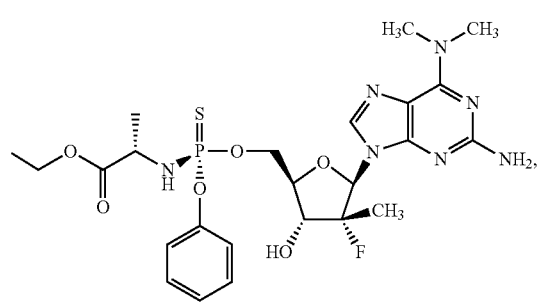
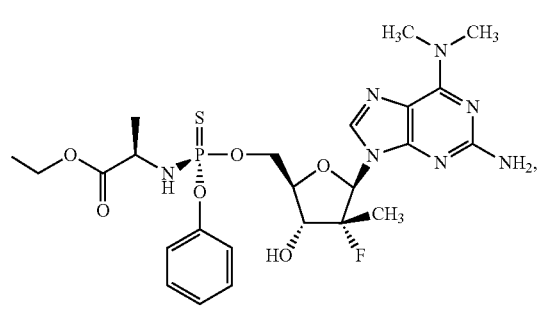
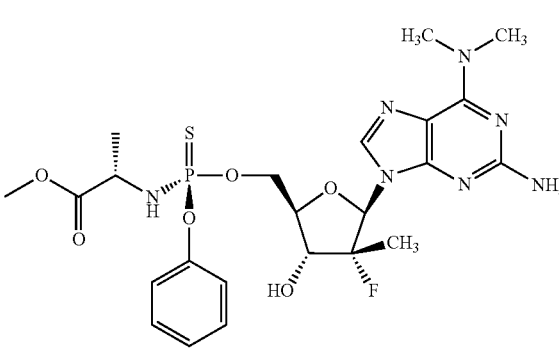
-continued
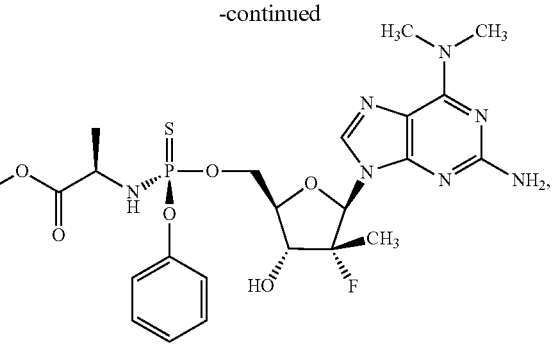
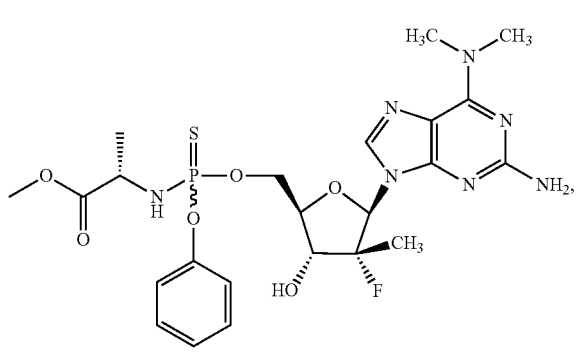
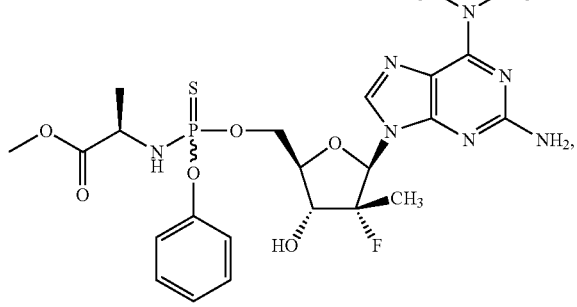
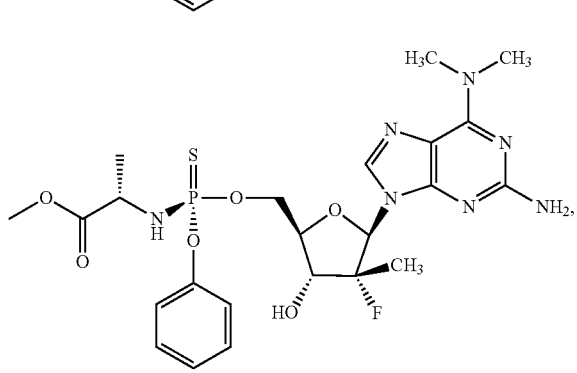
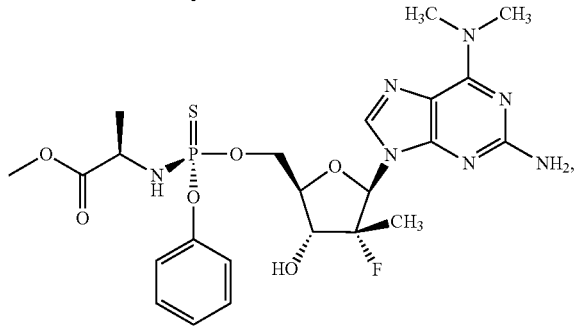

-continued
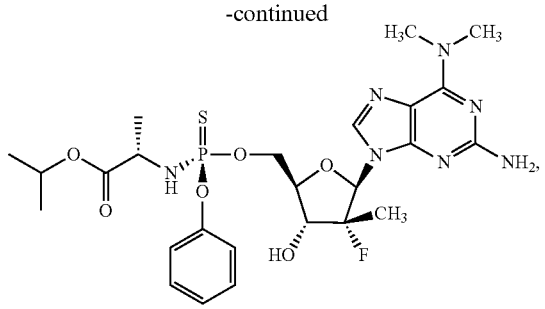
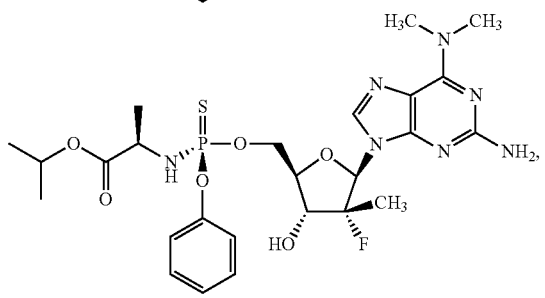
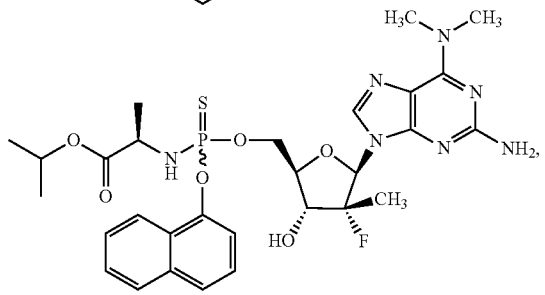
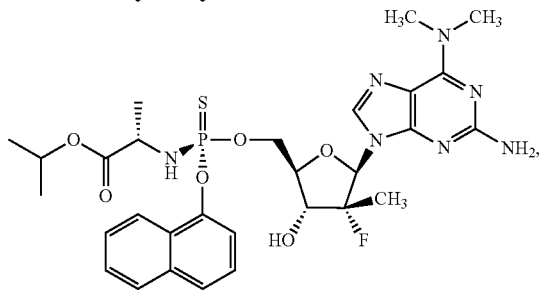
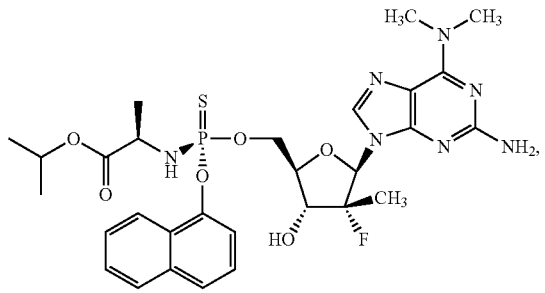 [SMILES: CC(C)OC(=O)[C@@H](C)N[P@](=S)(OC[C@H]1O[C@@H](n2cnc3c(N(C)C)nc(N)nc32)[C@](C)(F)[C@@H]1O)Oc1cccc2ccccc12]
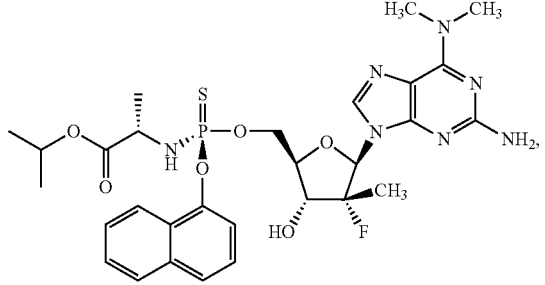
-continued
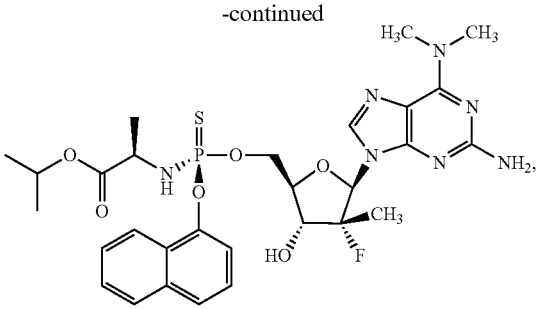
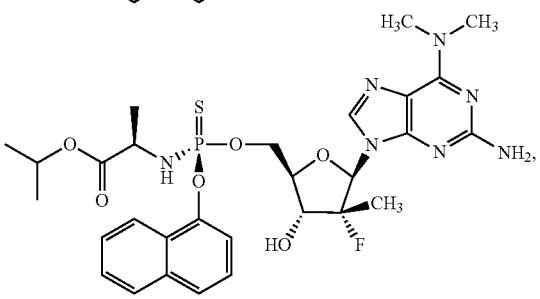
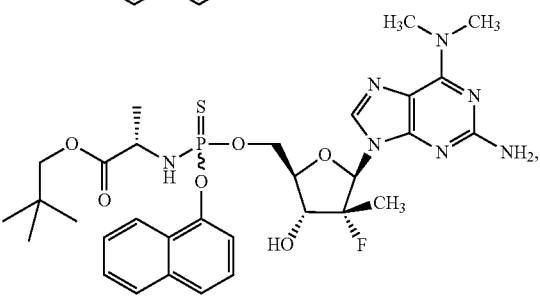
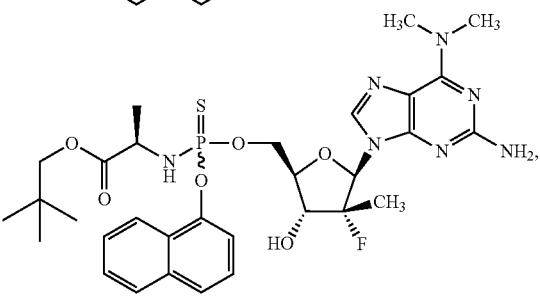
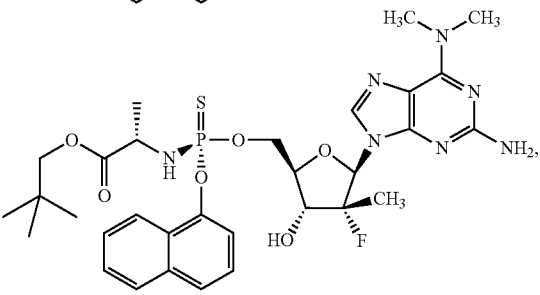
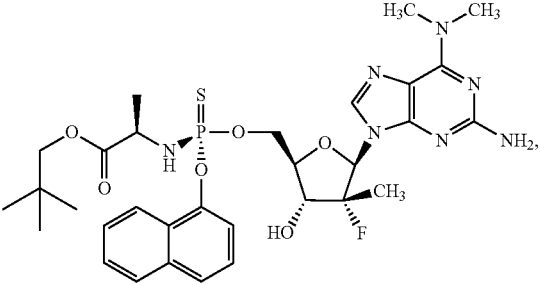

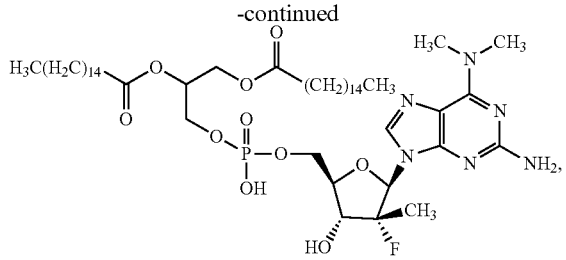
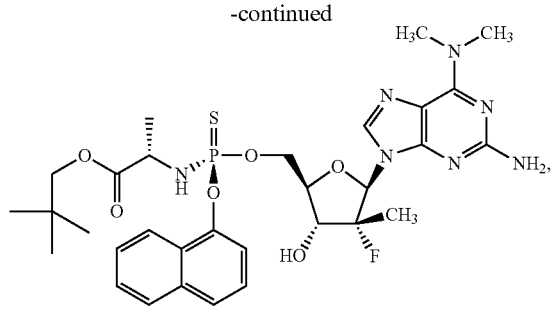
and
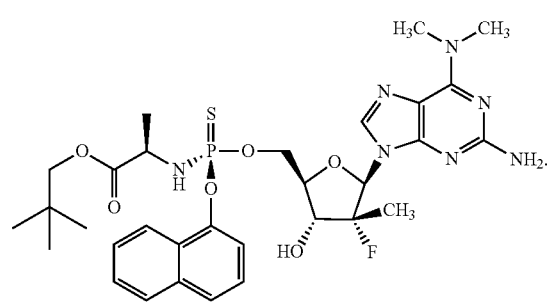
In one embodiment, a stabilized phosphate prodrug of Formula Ia is provided. Non-limiting examples of stabilized phosphate prodrugs of Formula Ia are illustrated below:
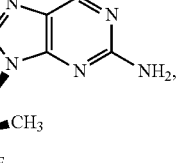
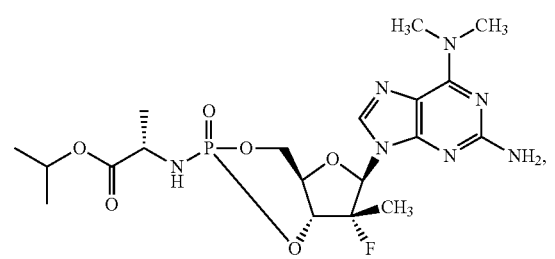
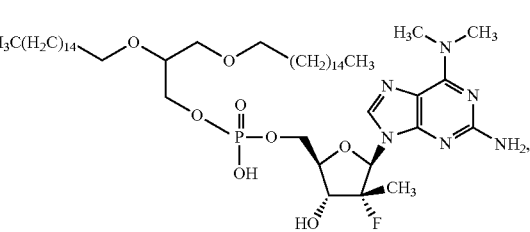
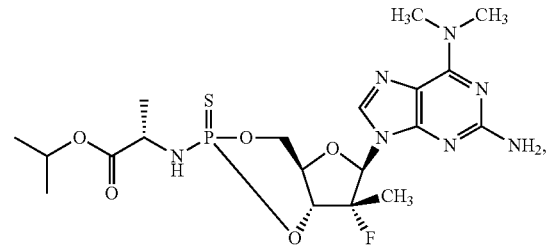
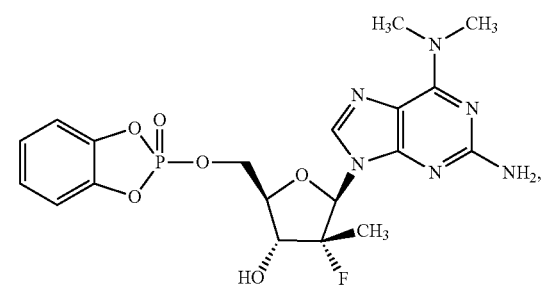
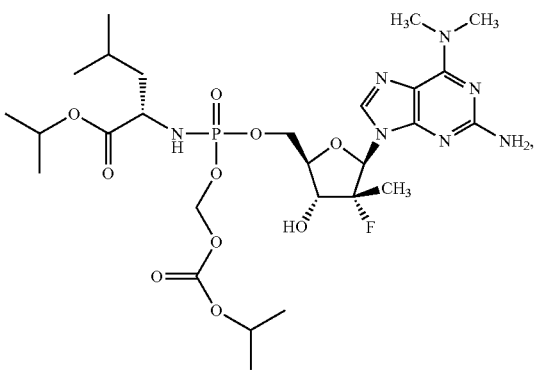
and -continued
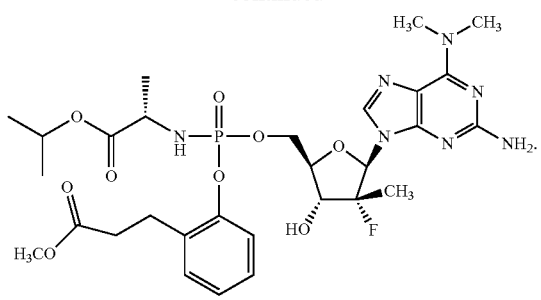
In one embodiment, a compound of Formula II is provided. Non-limiting examples of compounds of Formula II include:
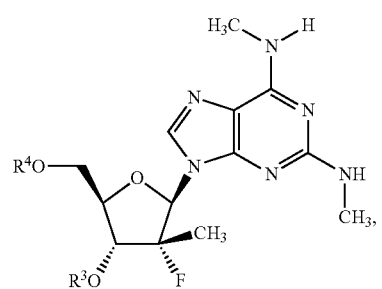
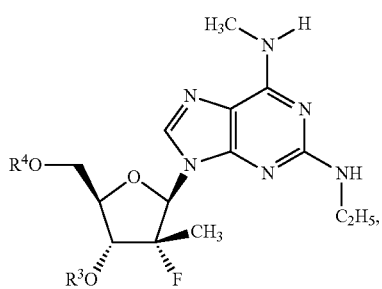
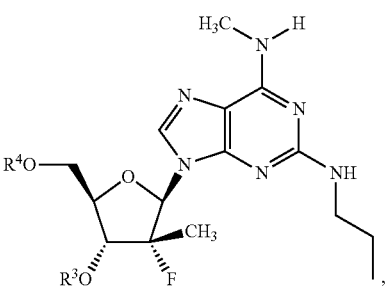
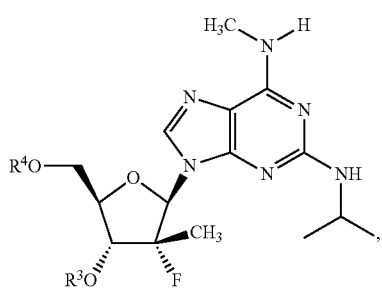
-continued
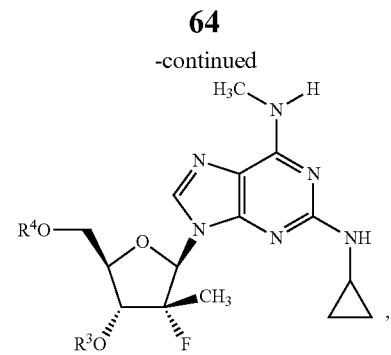
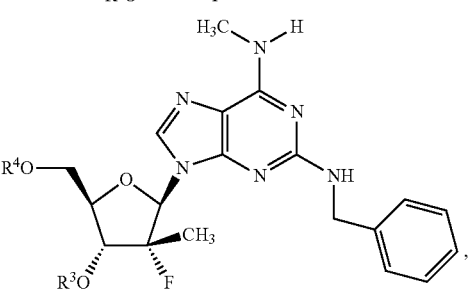
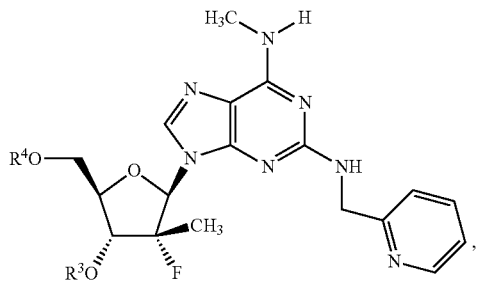
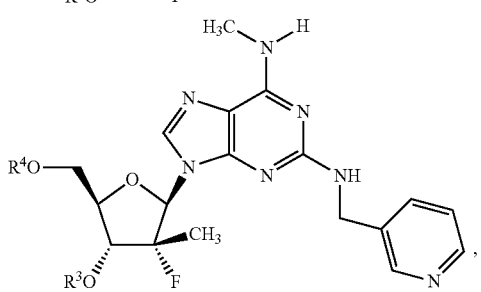
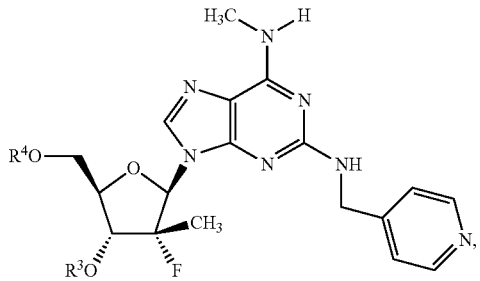
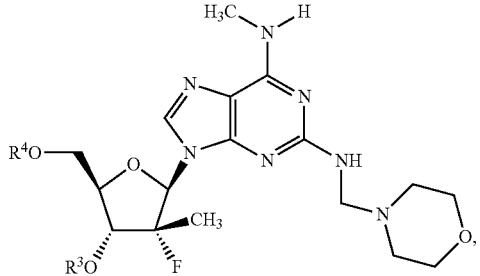

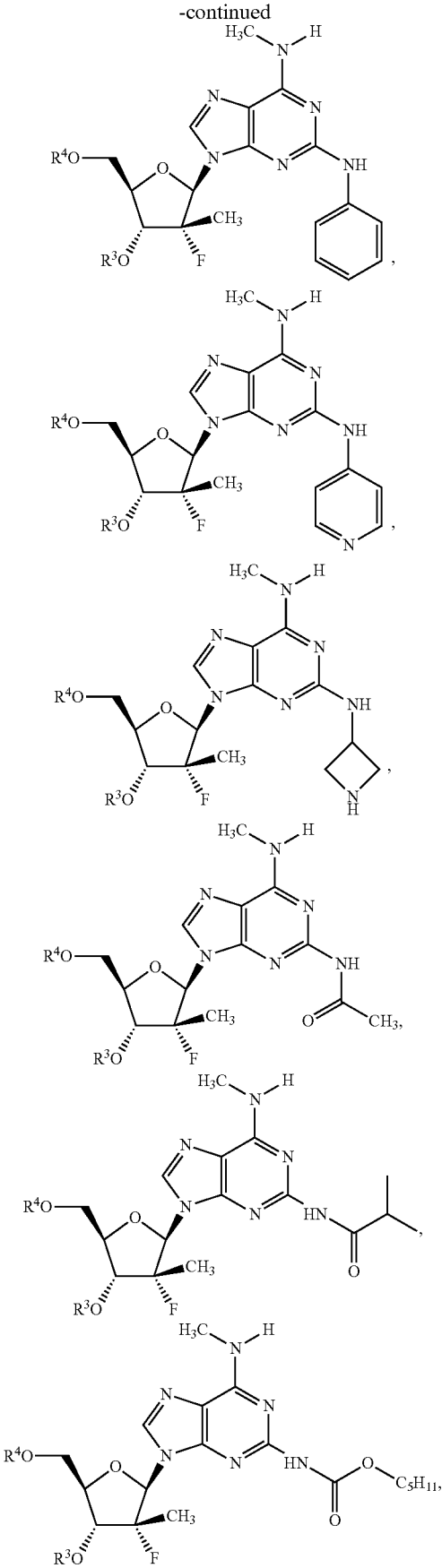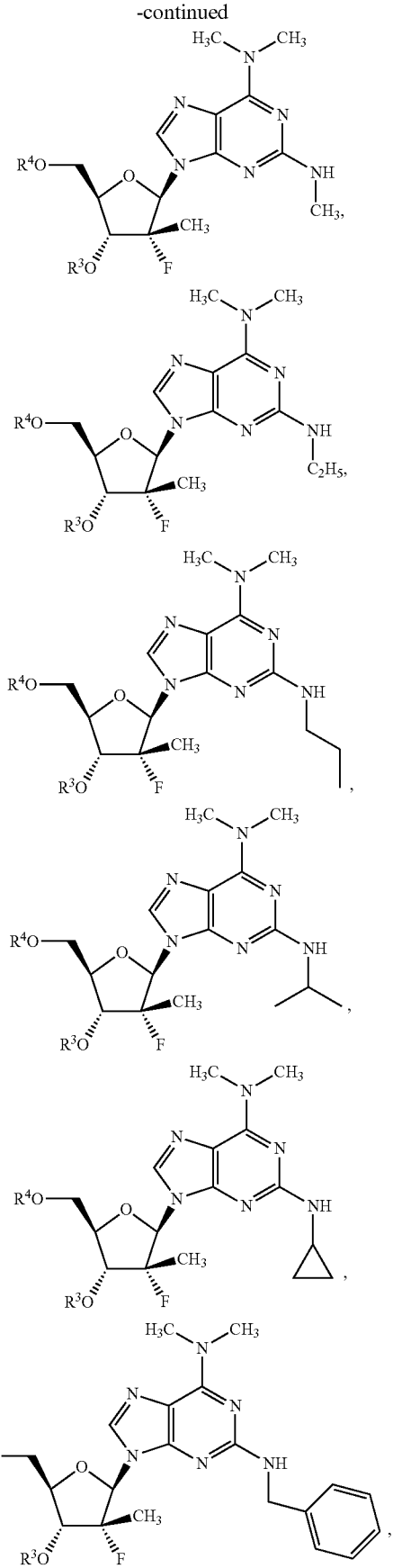

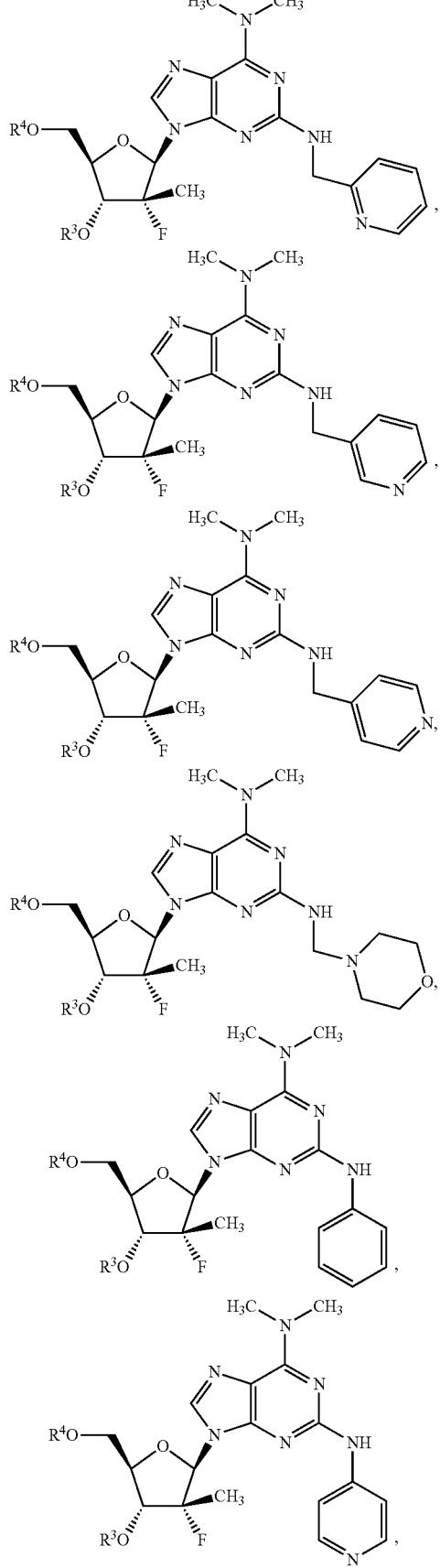
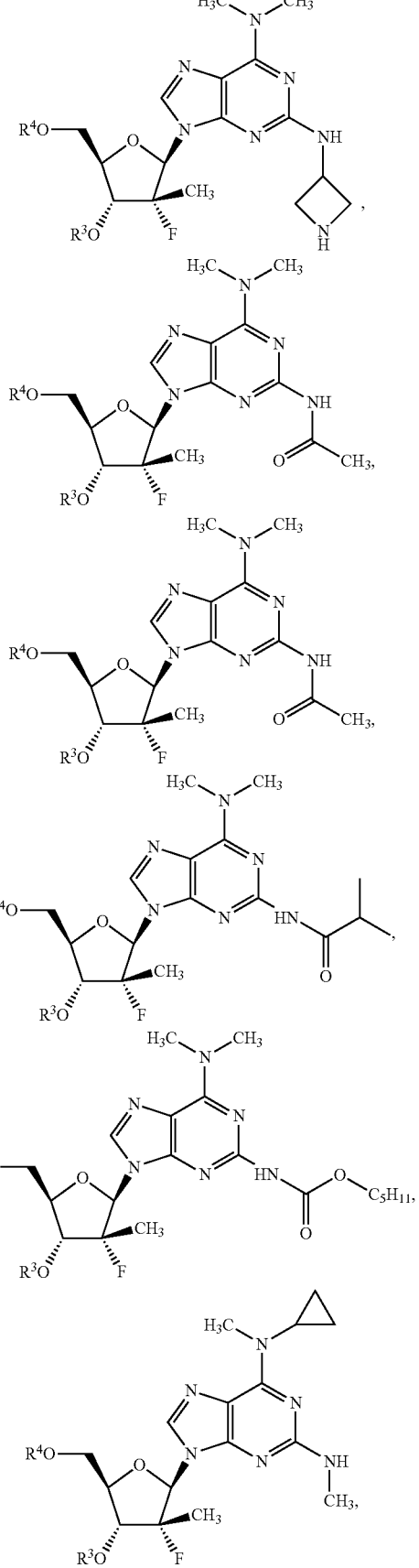

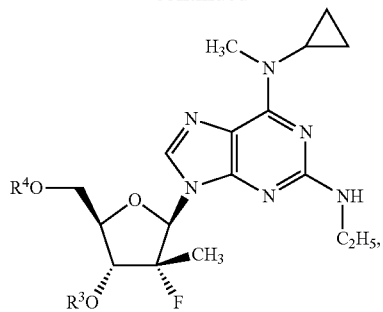
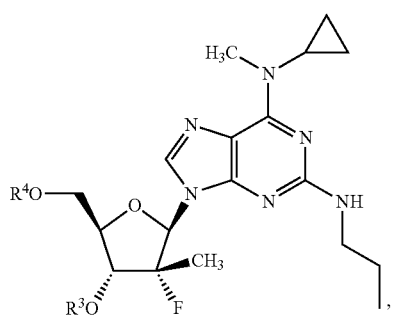
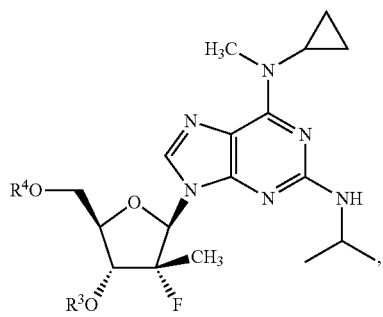
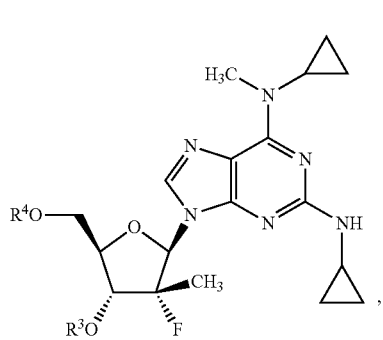
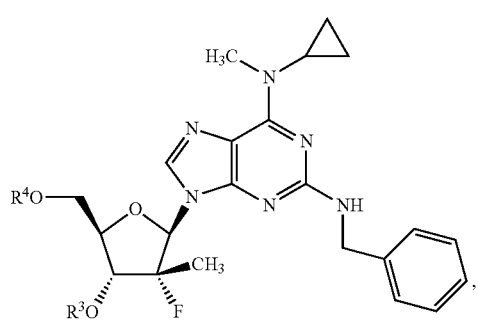
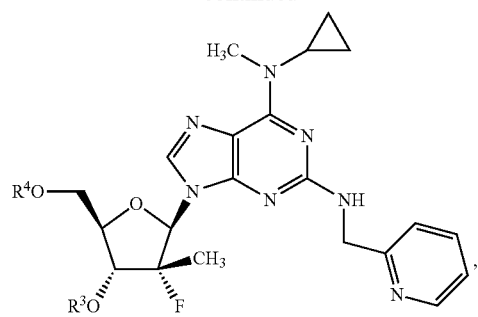
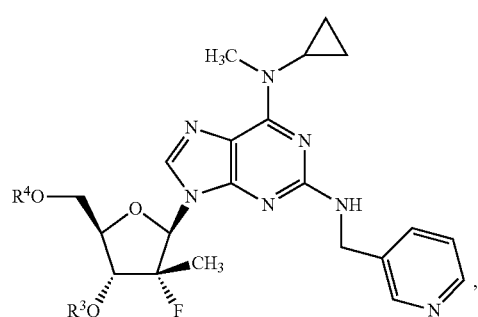
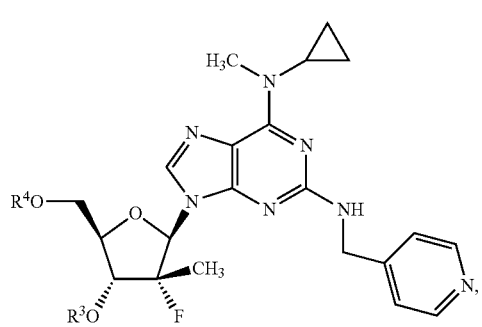
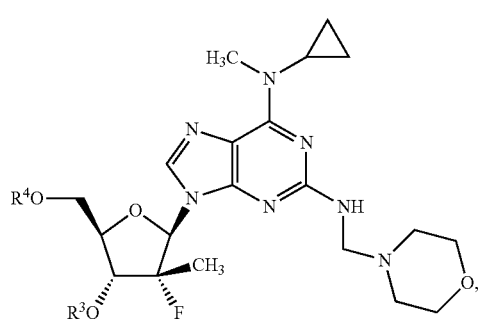
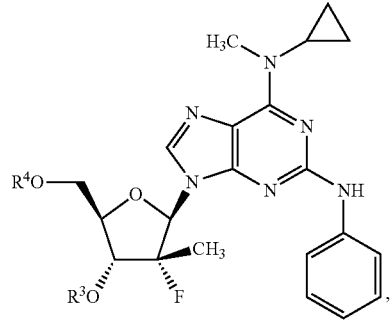

71
-continued
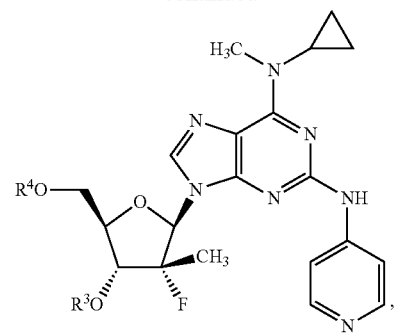
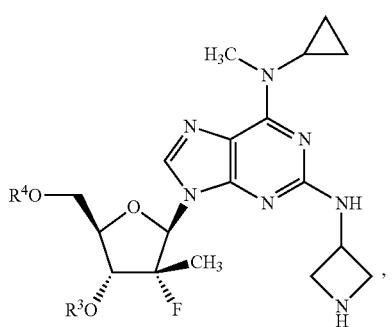
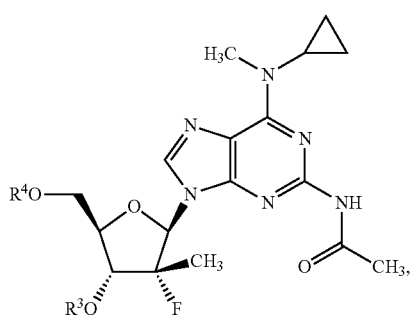
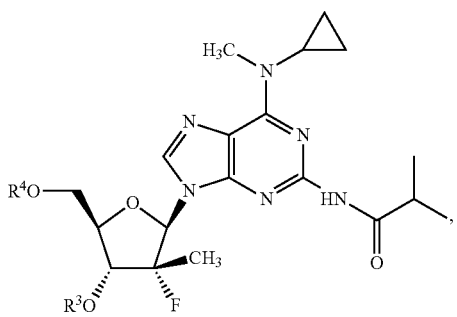
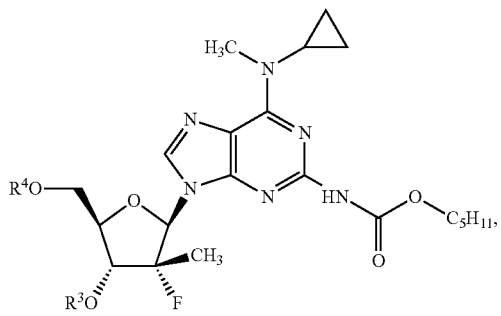
72
-continued
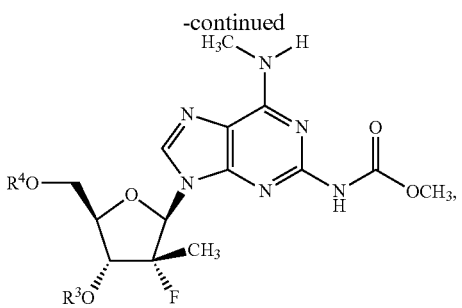
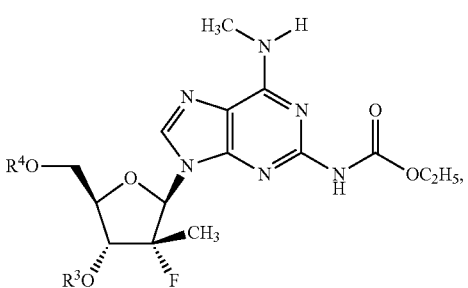
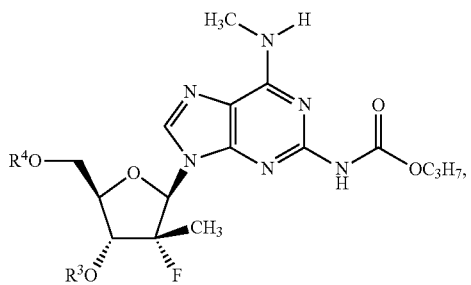
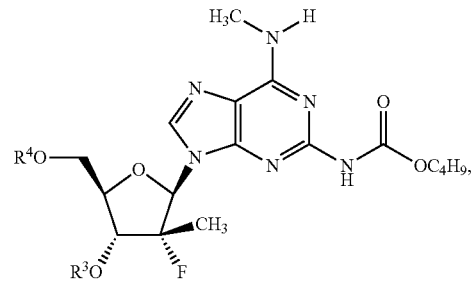
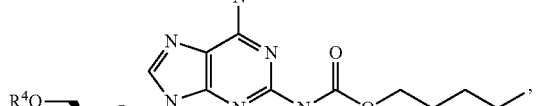
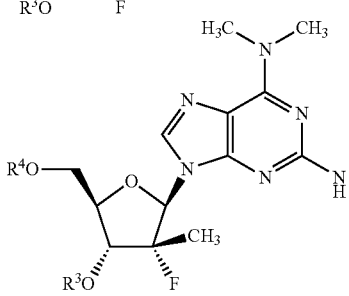

-continued
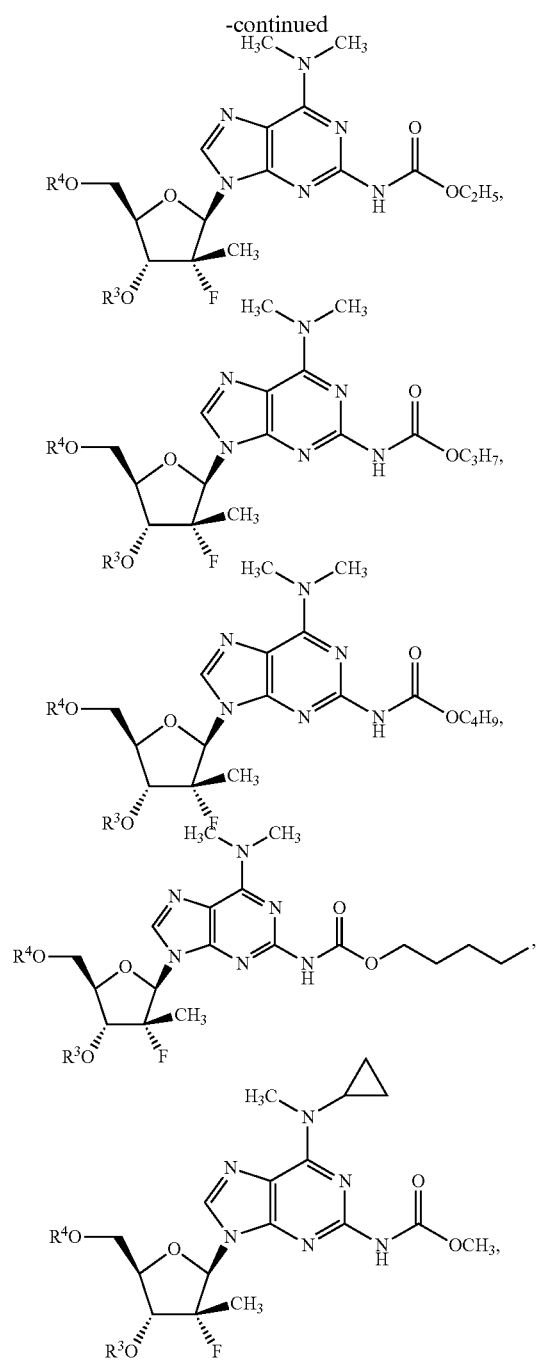
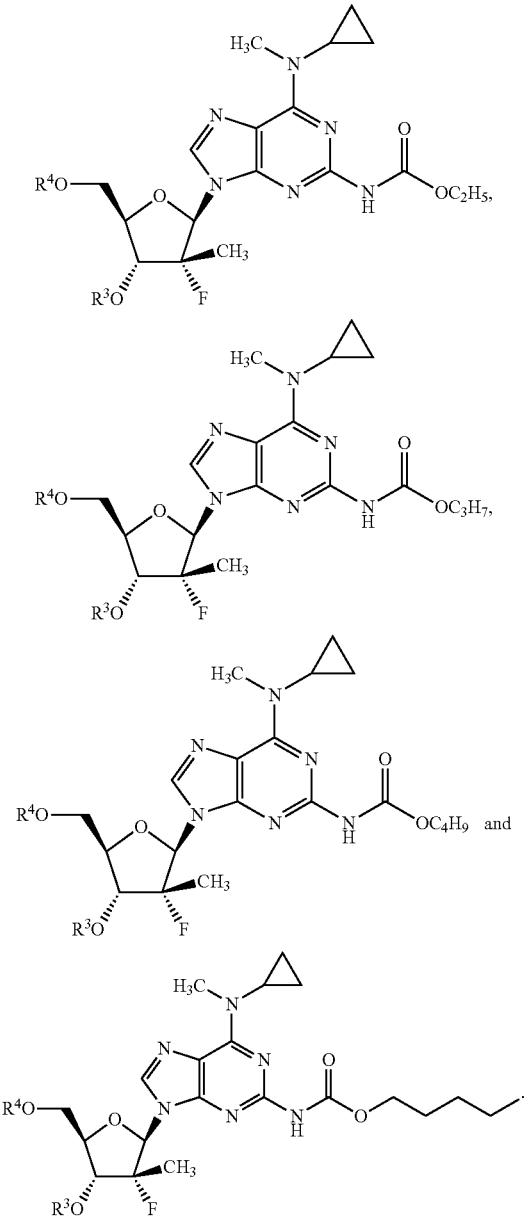
In one embodiment, a compound of Formula I is provided. Non-limiting examples of compounds of Formula I include:
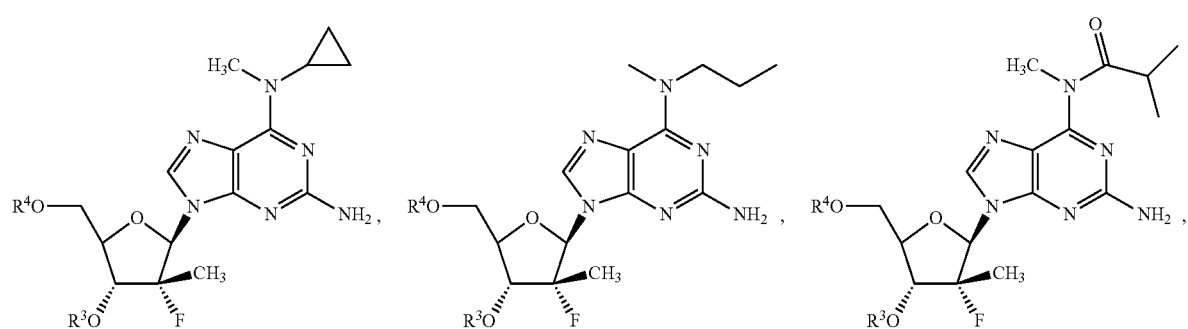

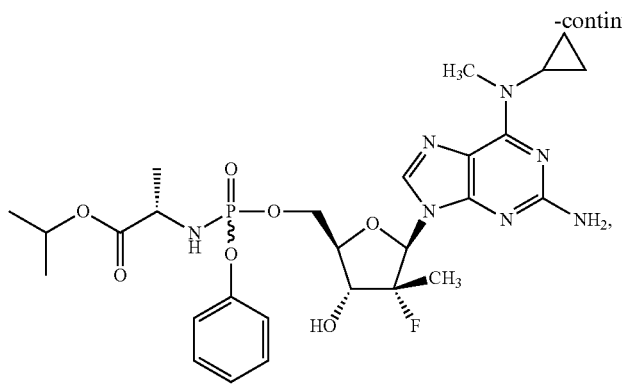
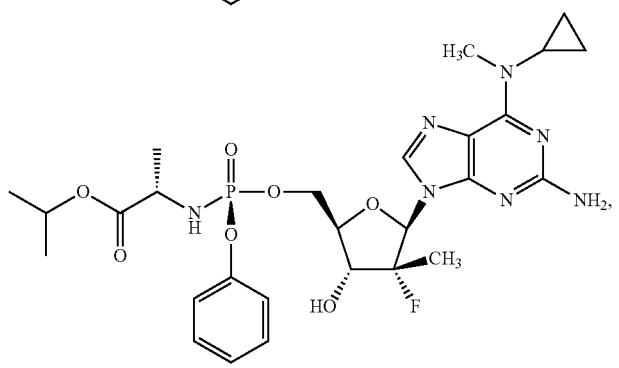
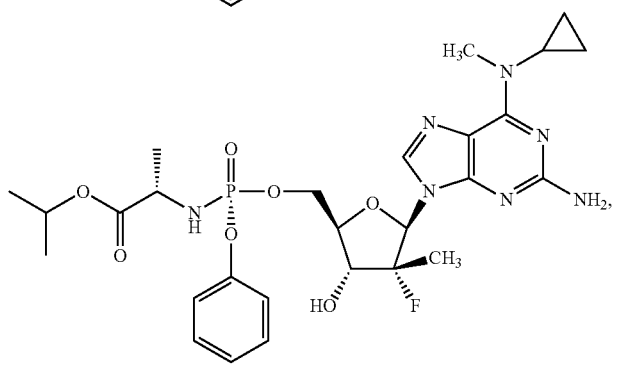
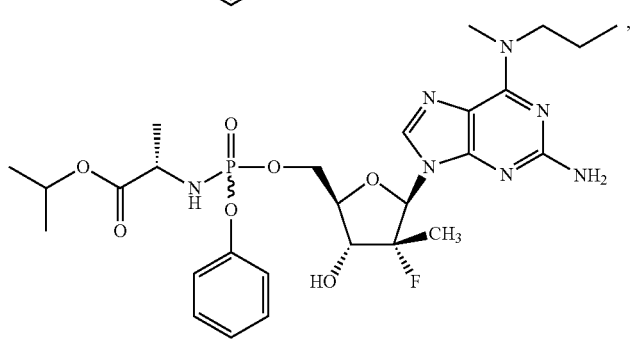
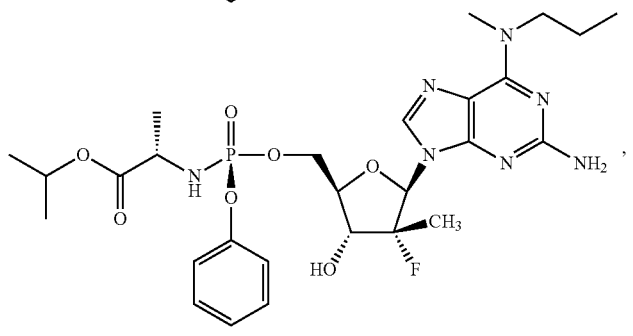

-continued
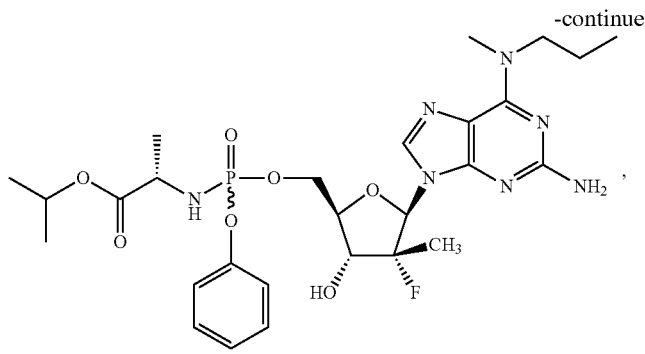
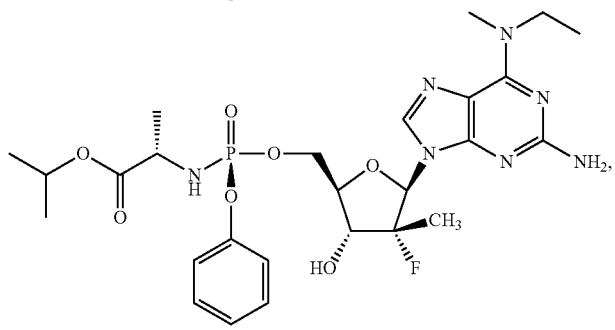
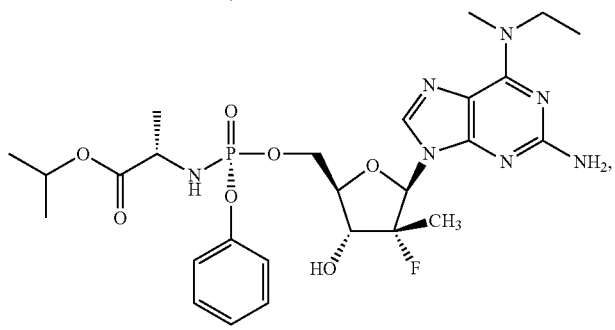
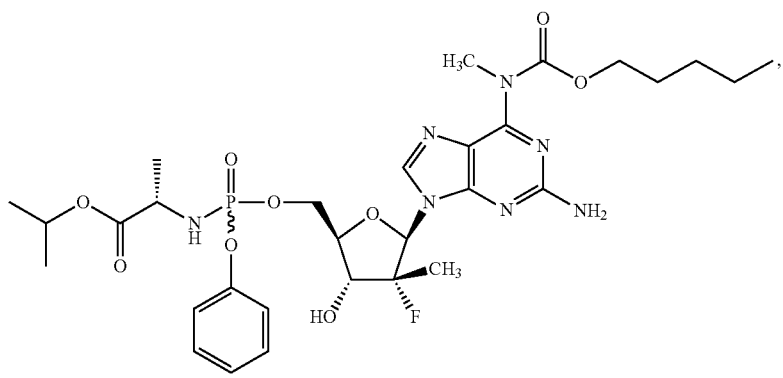
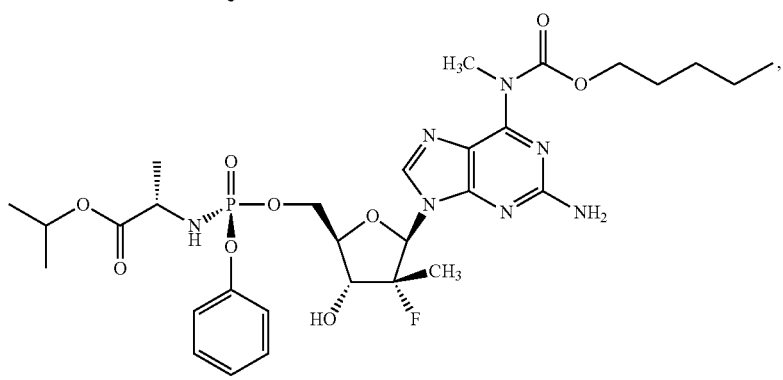

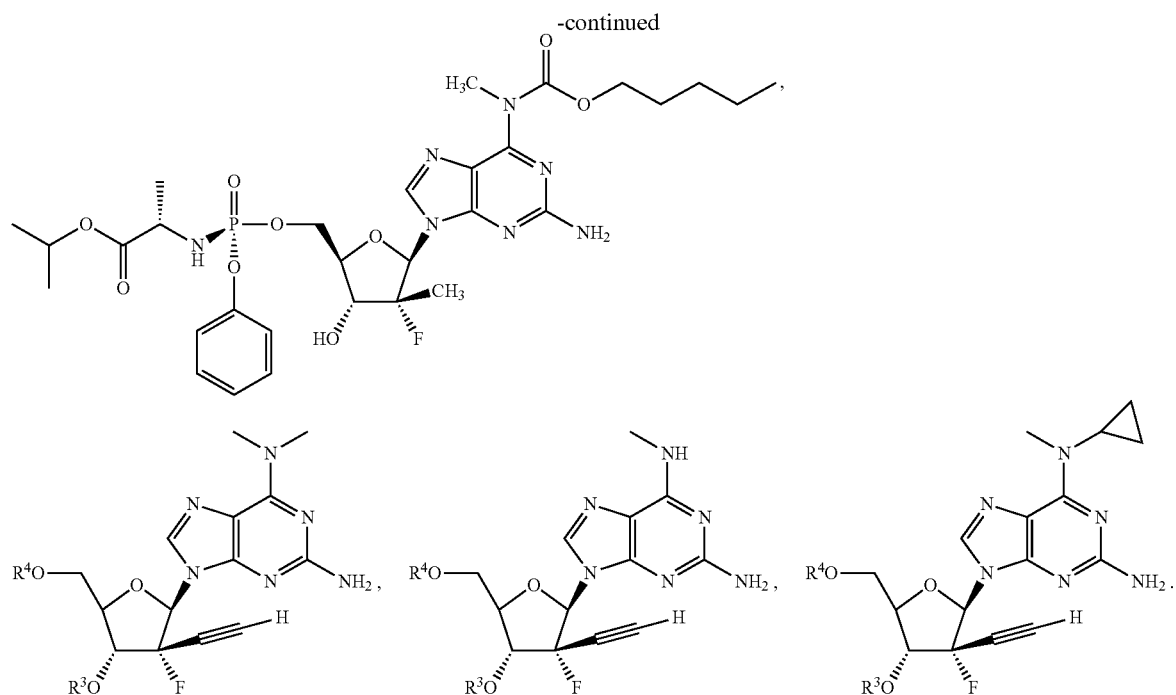
In one embodiment, a compound of Formula II is provided. Non-limiting examples of compounds of Formula II include:
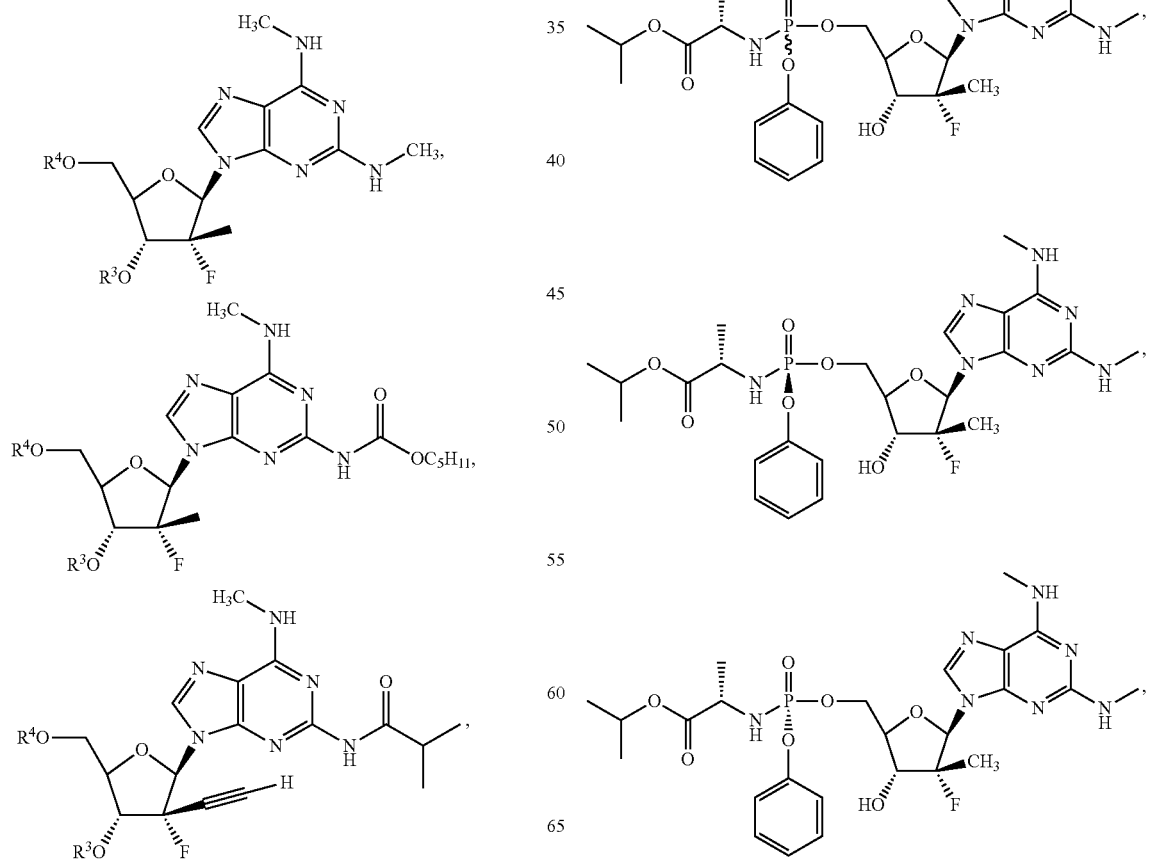

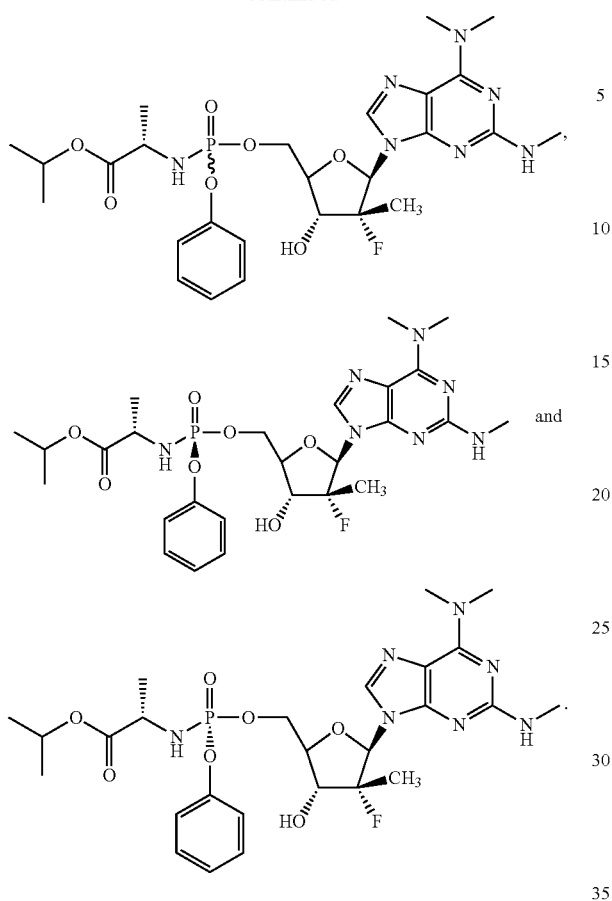
In one embodiment, and R⁴ is
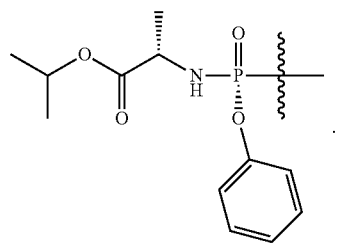 [SMILES: *[P@](=O)(N[C@@H](C)C(=O)OC(C)C)Oc1ccccc1]
In one embodiment, a compound of Formula II is provided. Non-limiting examples of compounds of Formula II include:
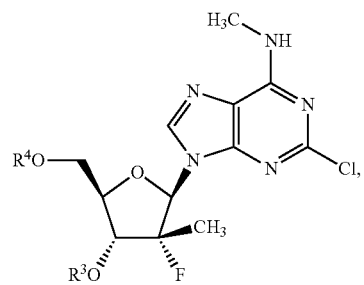
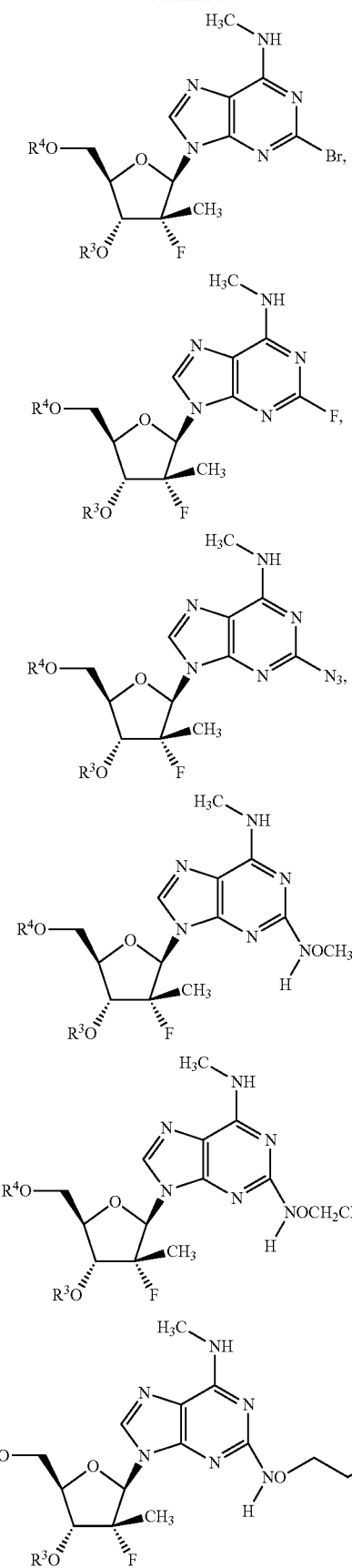

-continued
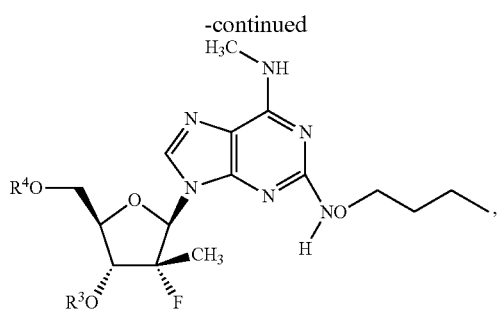
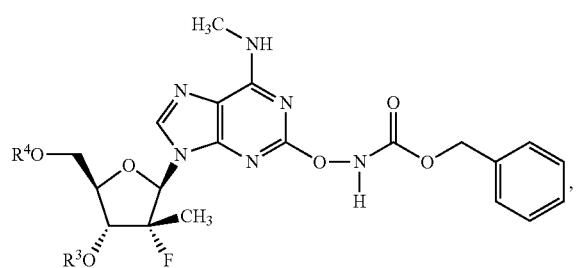
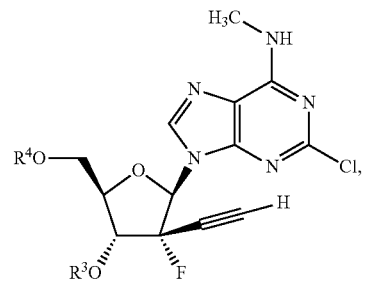
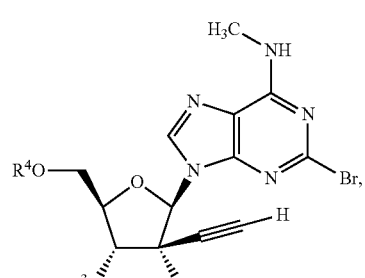
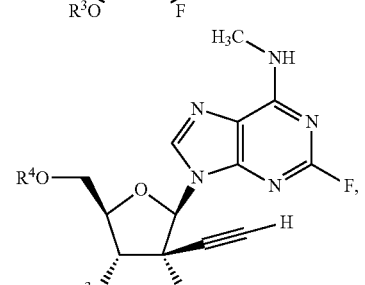
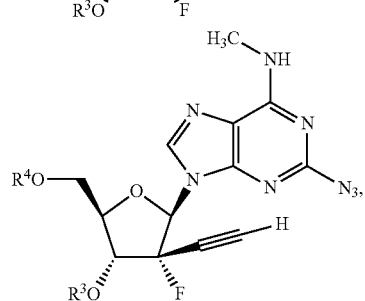
-continued
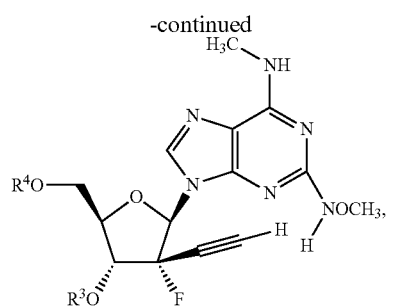
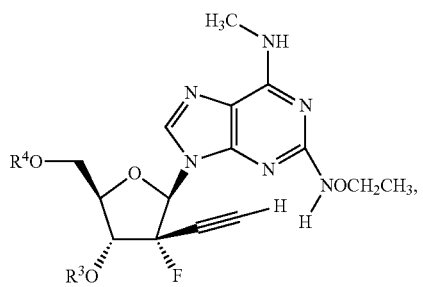
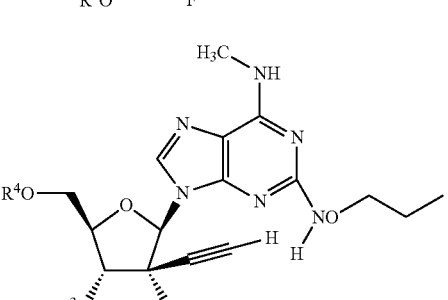
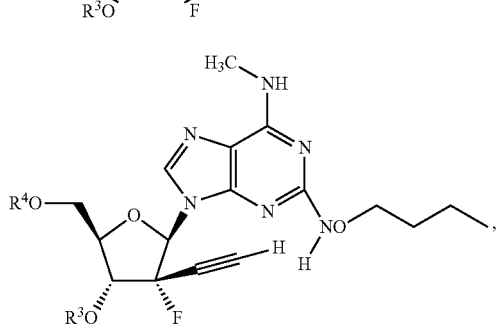
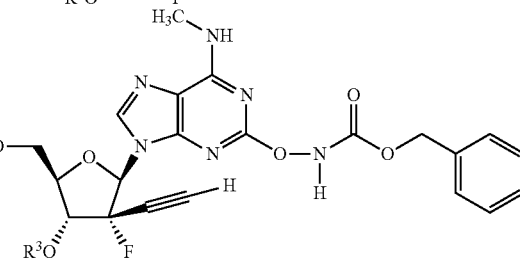
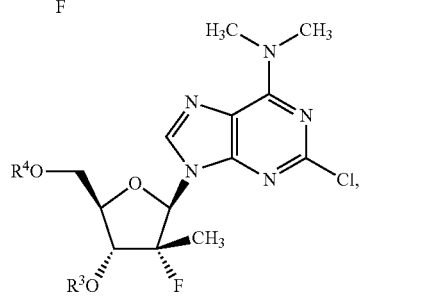

85
-continued
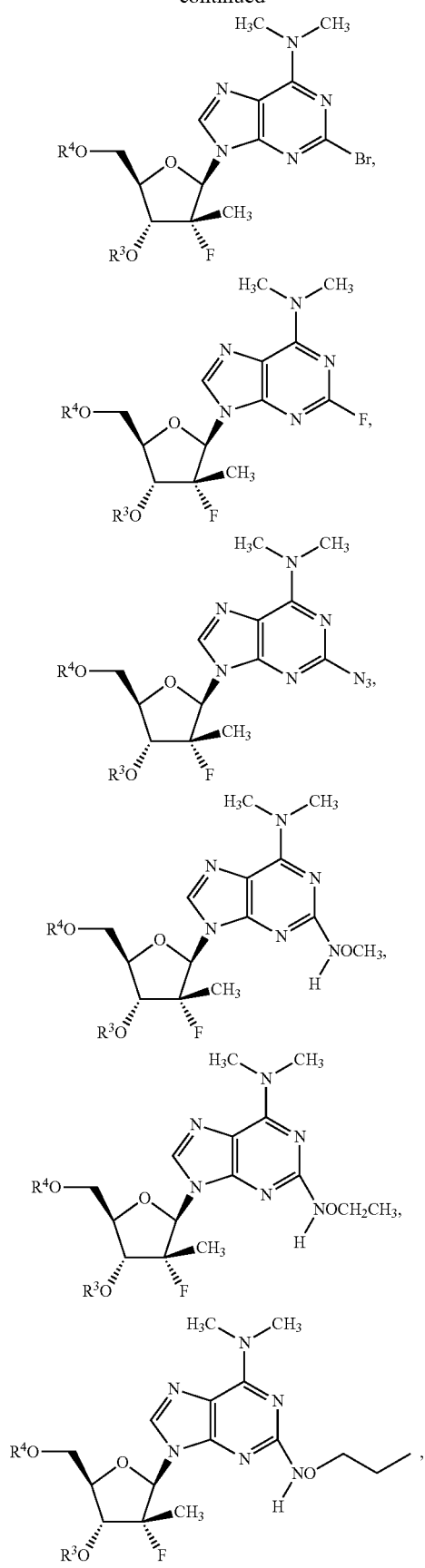
86
-continued
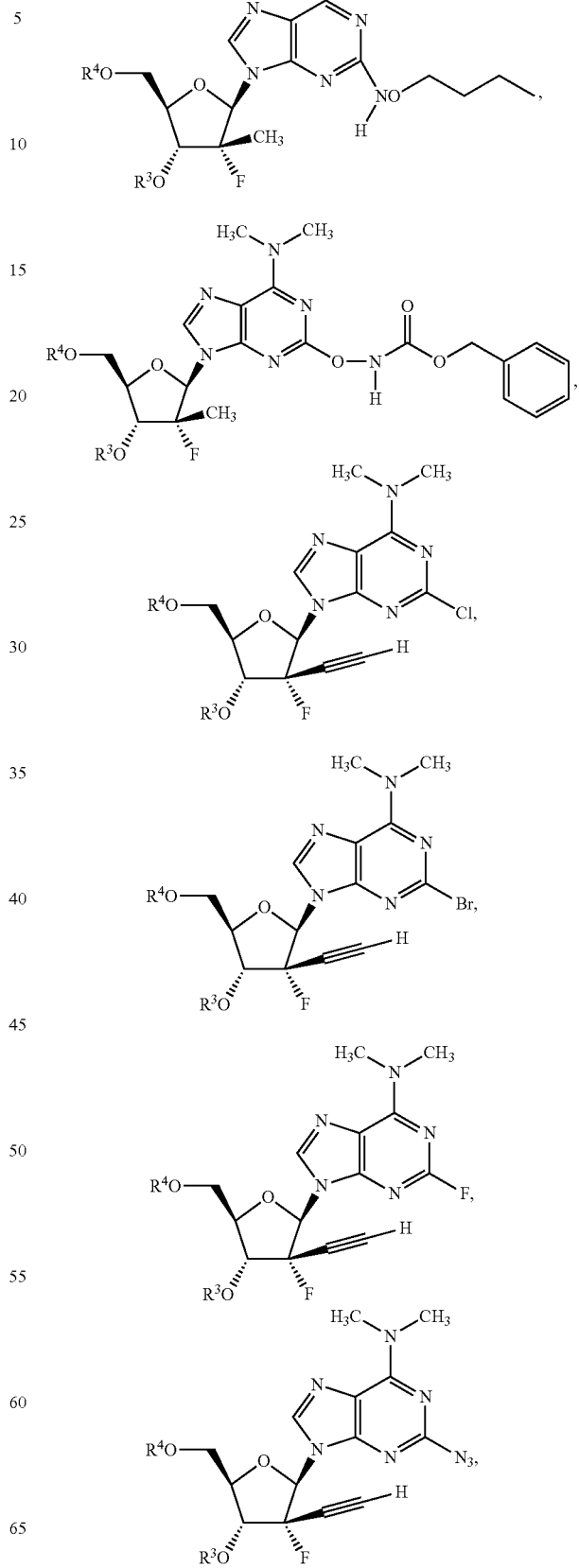

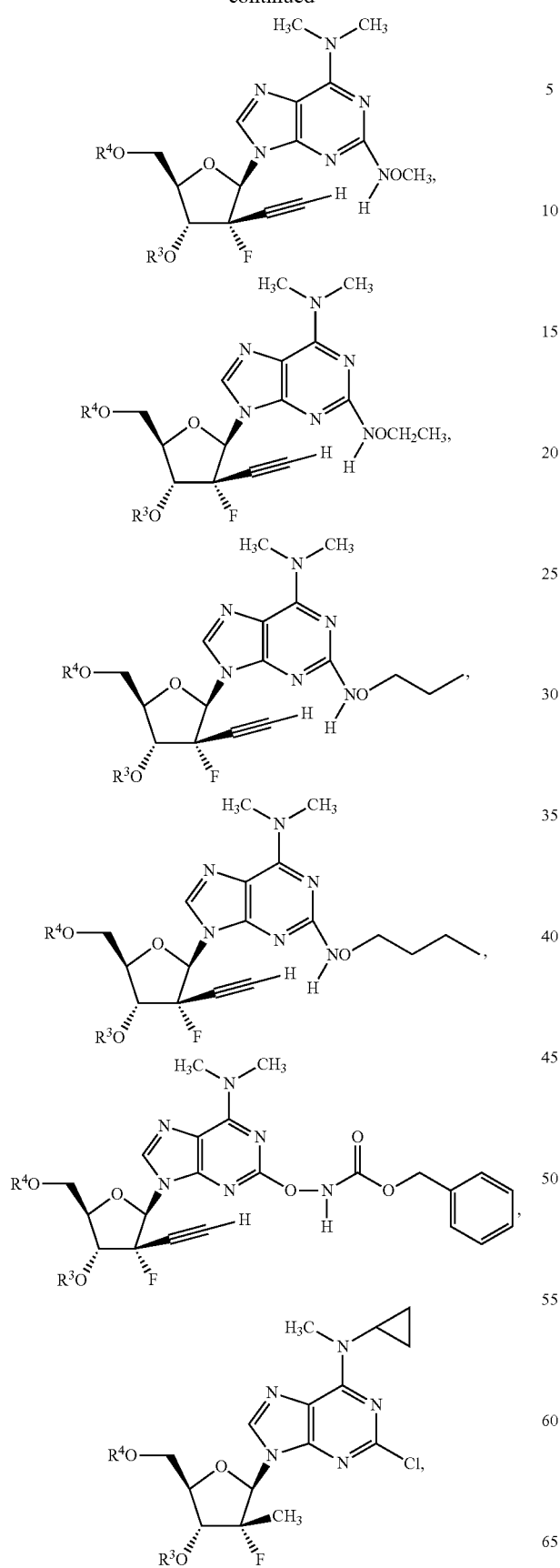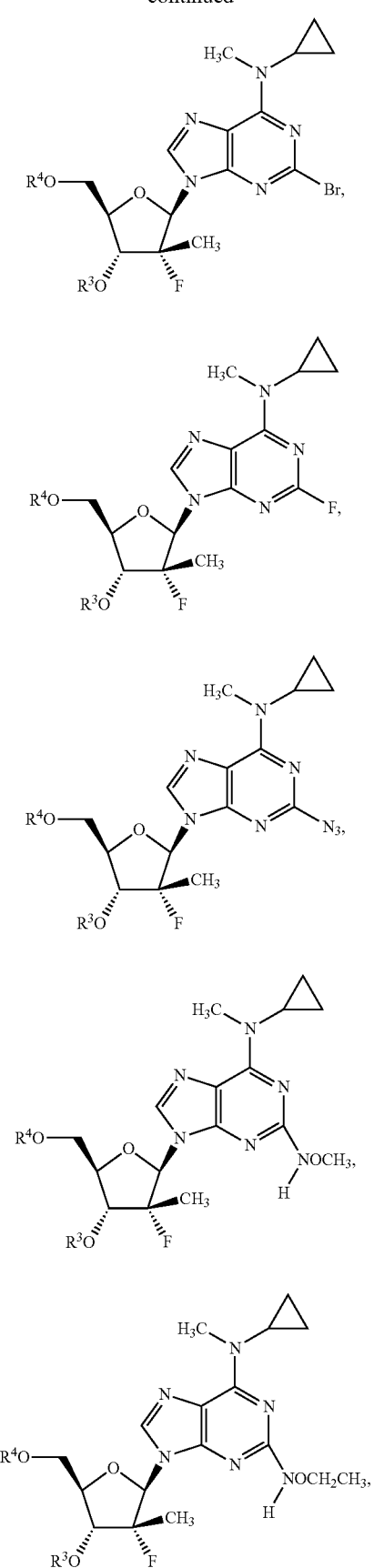

89
-continued
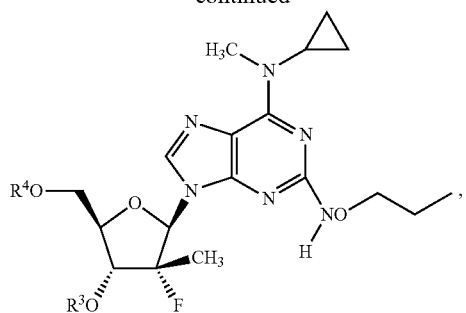
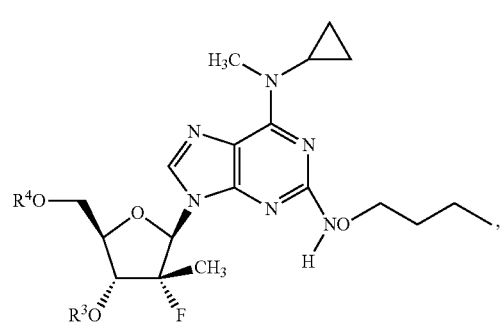
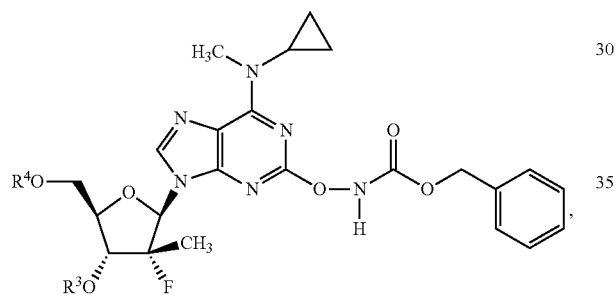
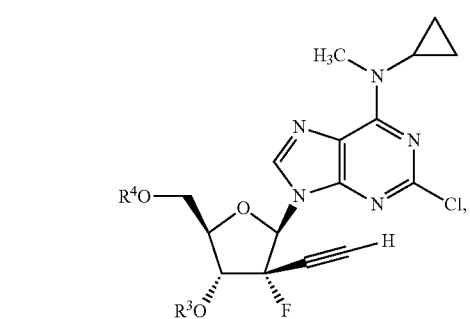
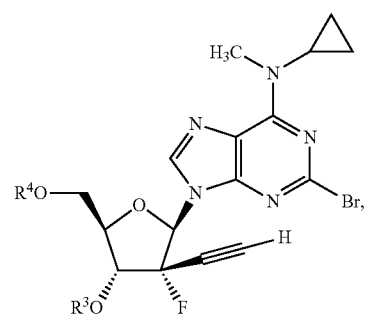
90
-continued
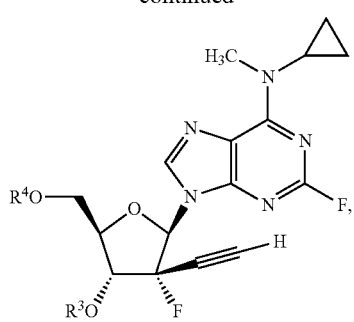
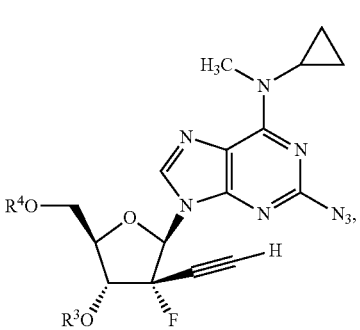
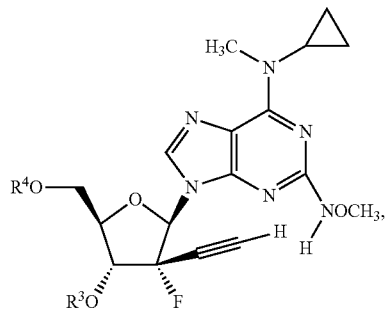
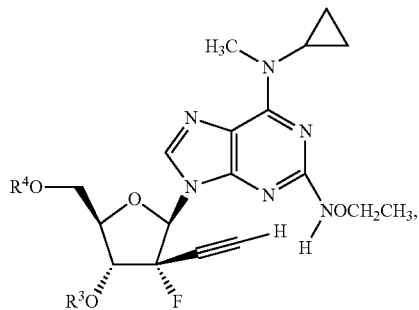
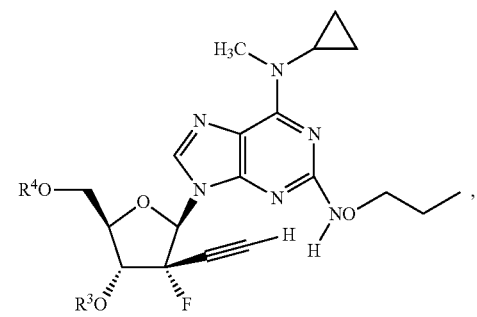

-continued
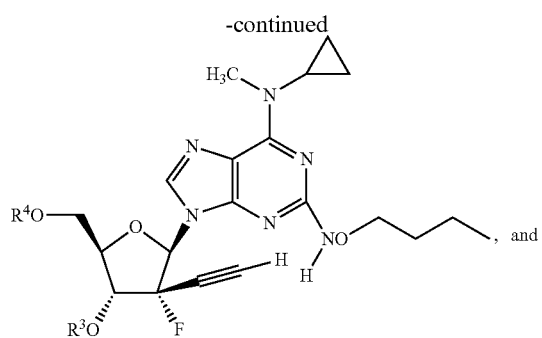
, and
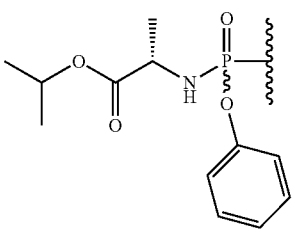
.
In some embodiments, $R^3$ is H and $R^4$ is
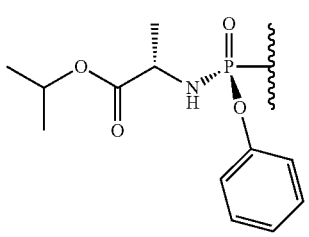
.
In some embodiments, $R^3$ is H and $R^4$ is
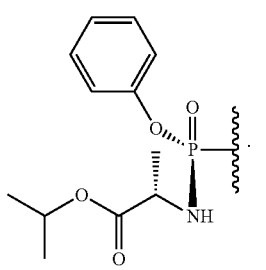 [SMILES: *[P@](=O)(N[C@@H](C)C(=O)OC(C)C)Oc1ccccc1]
.
In some embodiments, $R^3$ is H and $R^4$ is
In one embodiment, a compound of Formula II is provided. Non-limiting examples of compounds of Formula II include:
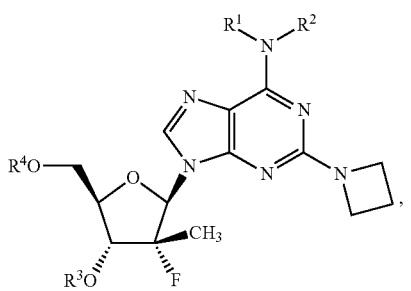
,
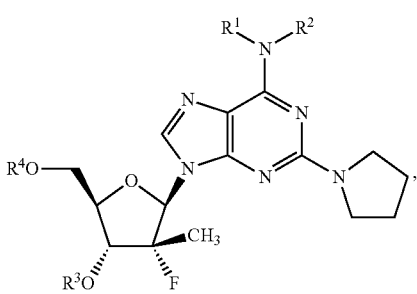
,
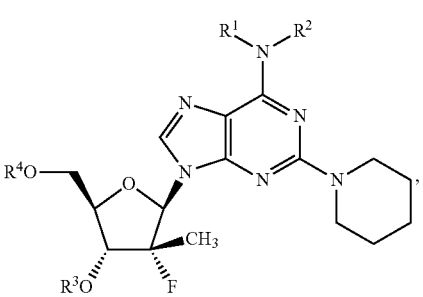
,
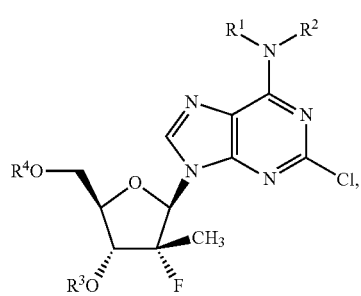
,
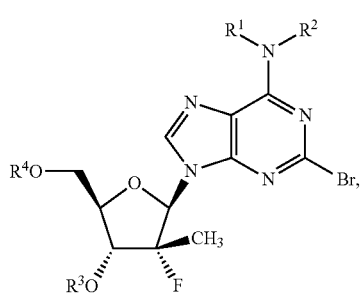
,

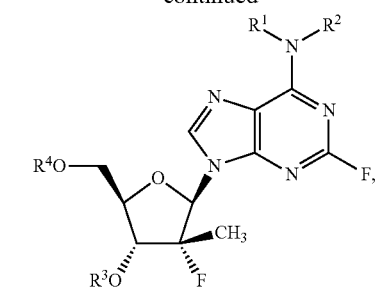
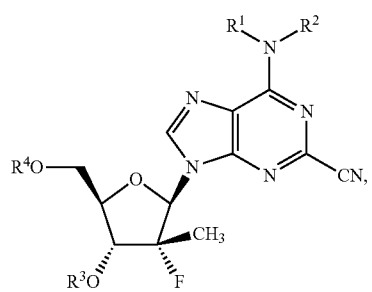
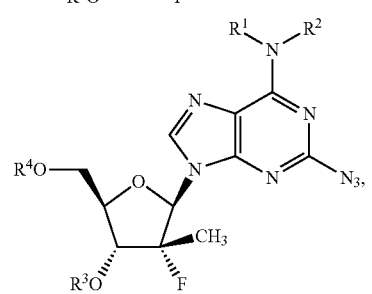
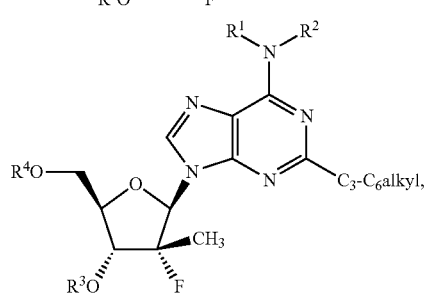
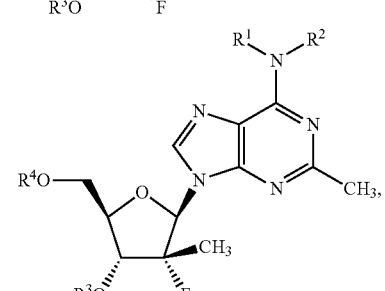
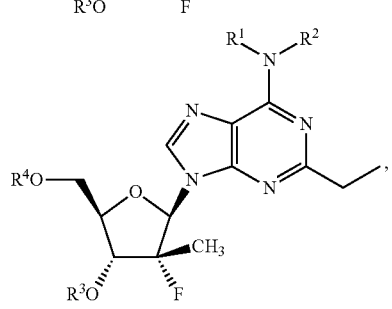
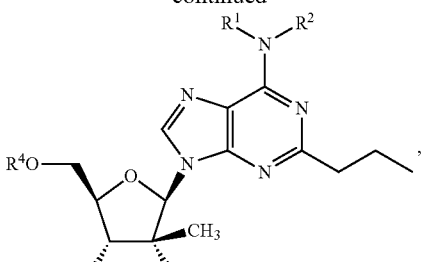
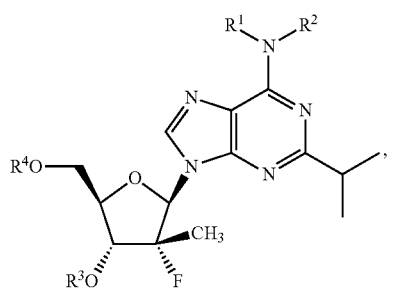
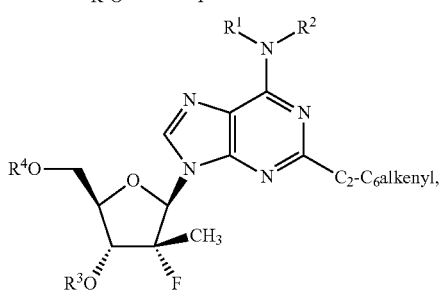
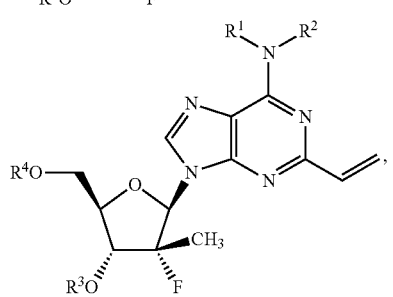
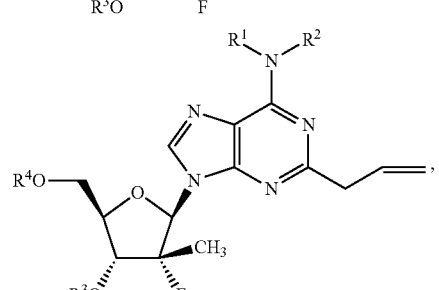
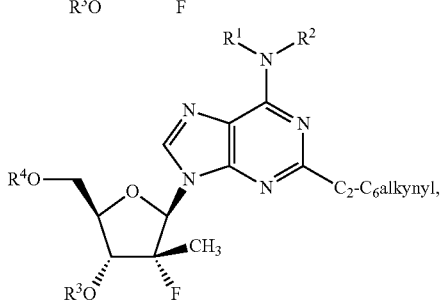

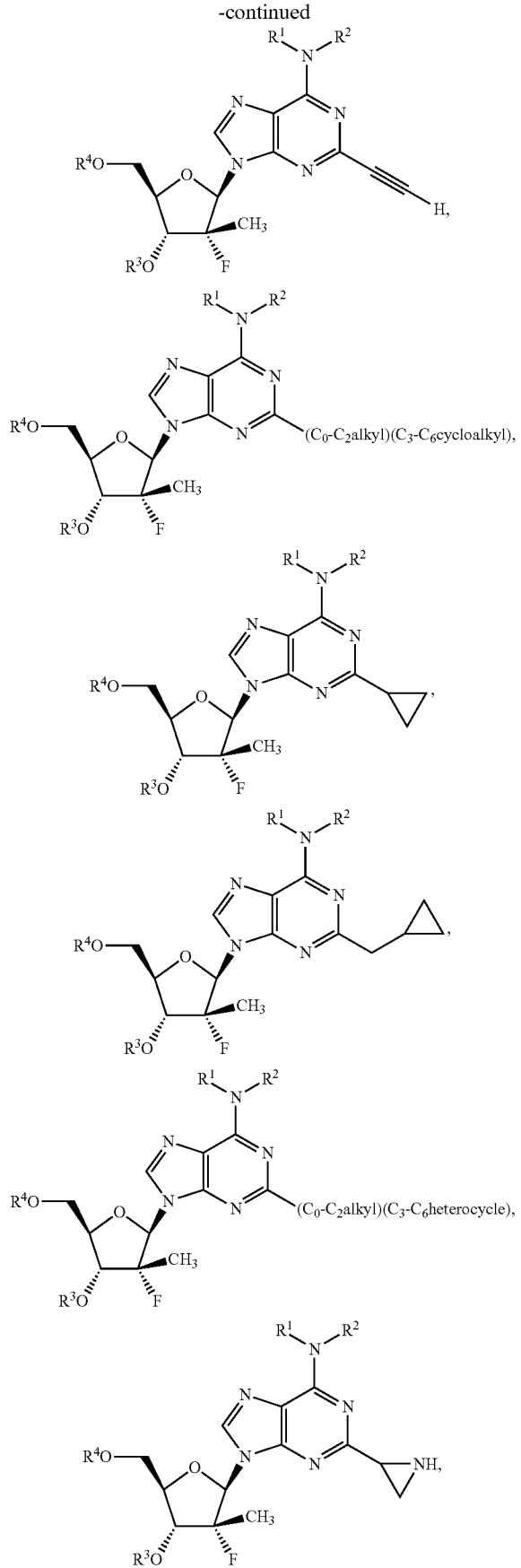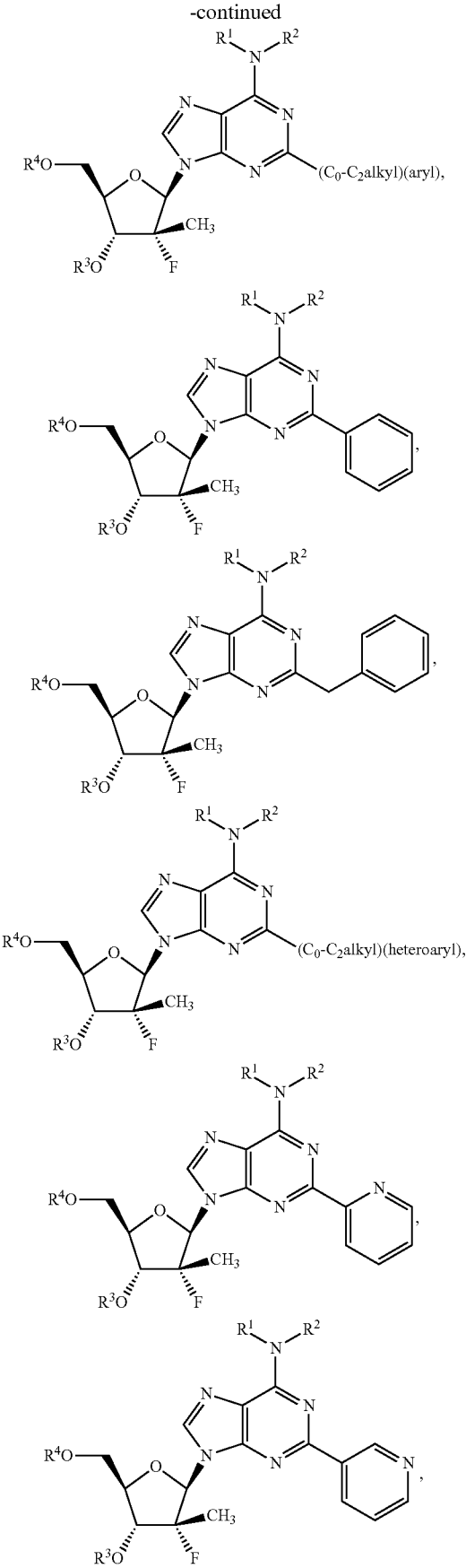

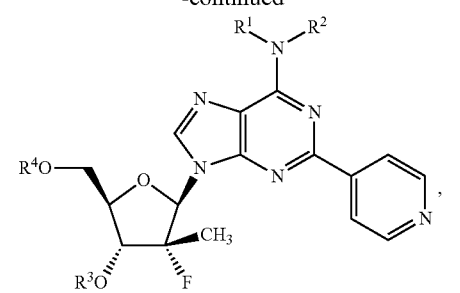
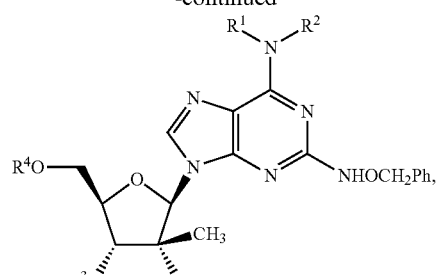
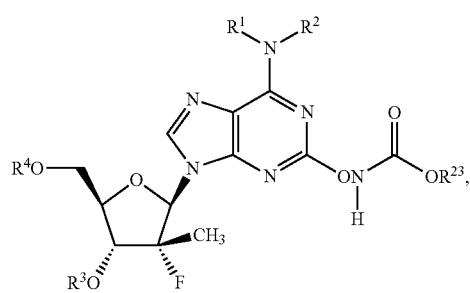
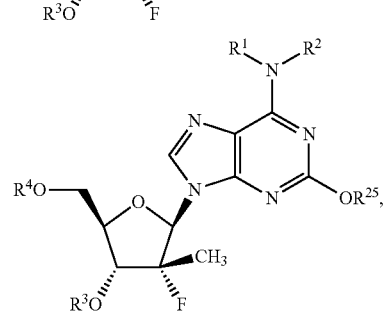
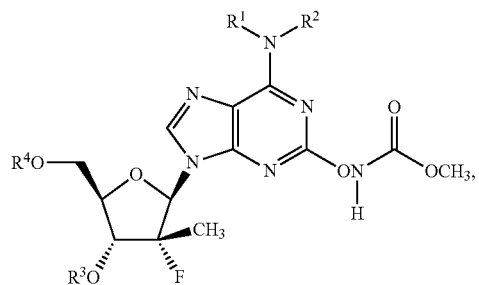
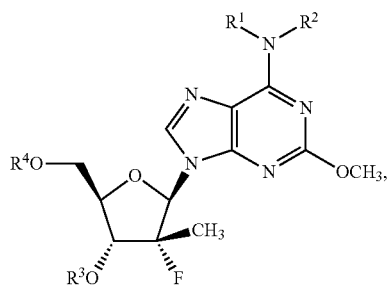
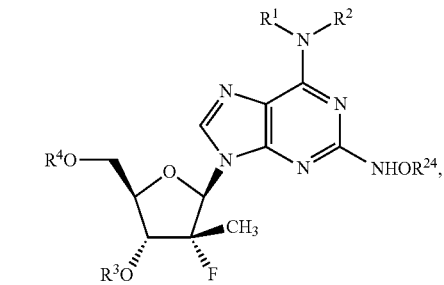
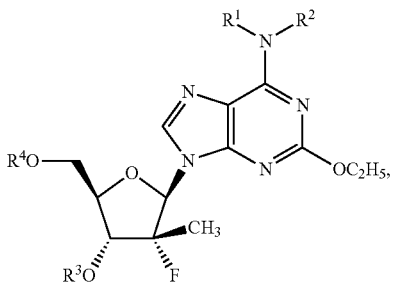
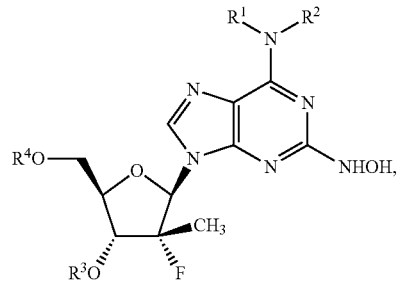
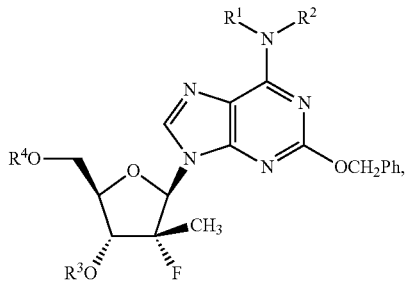
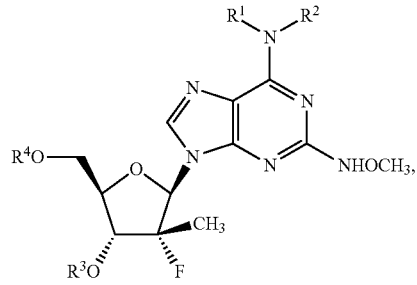
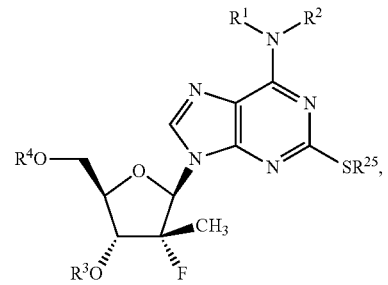

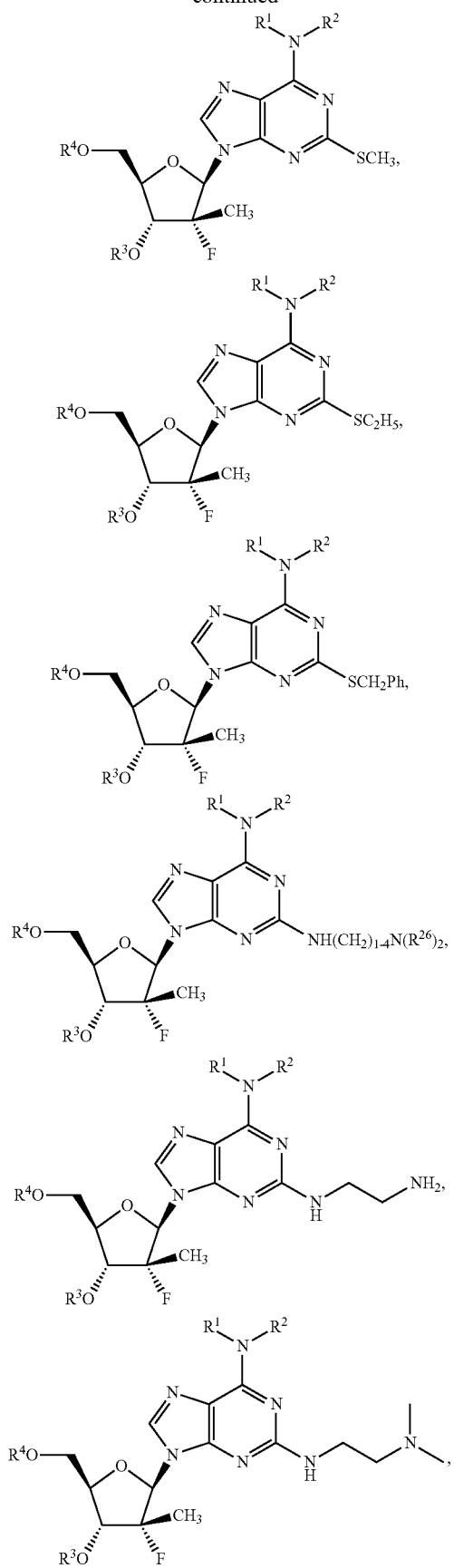
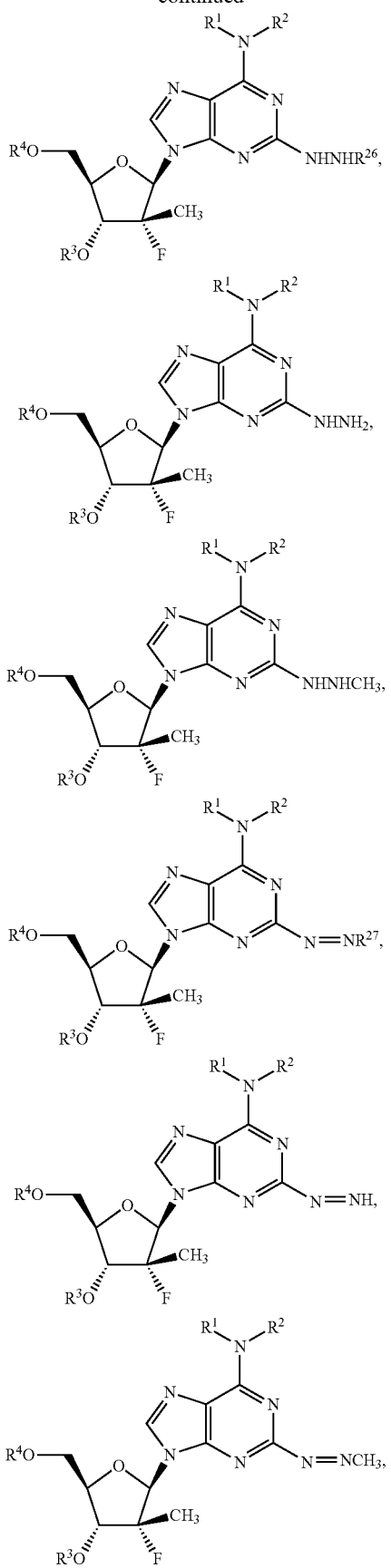

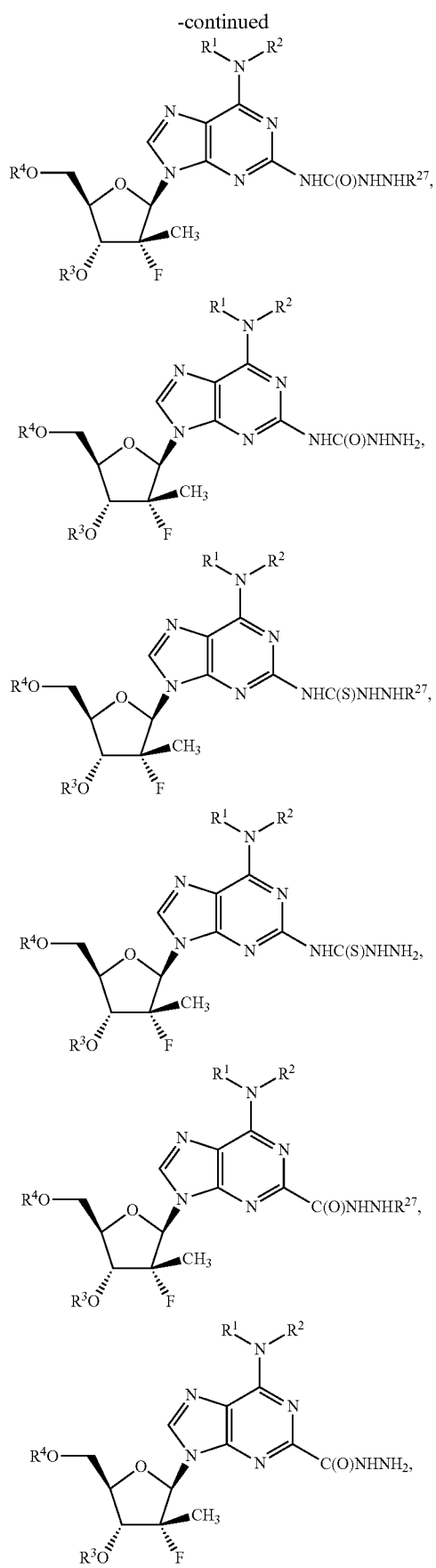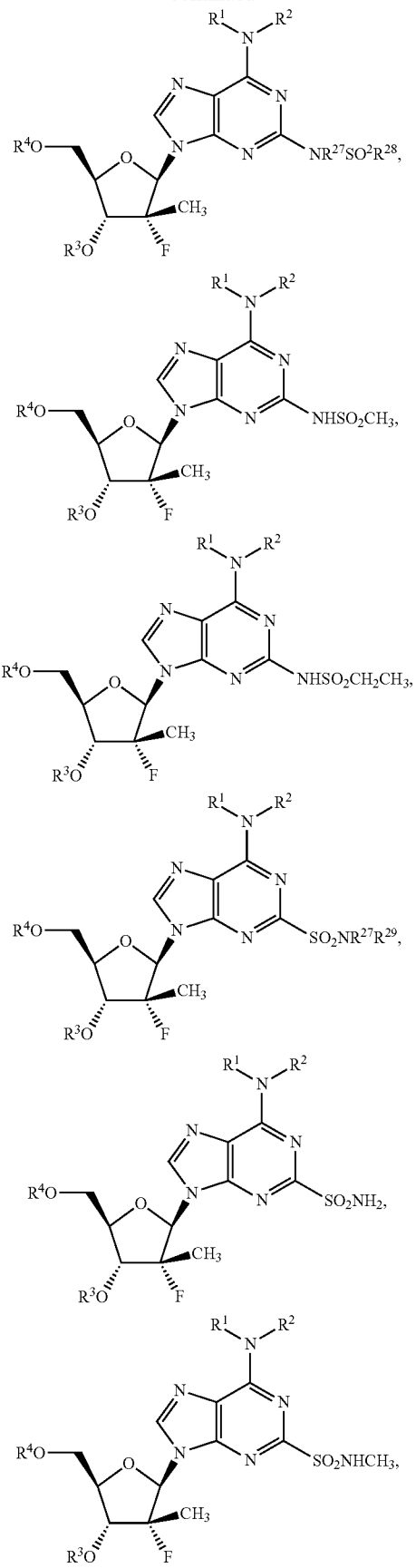

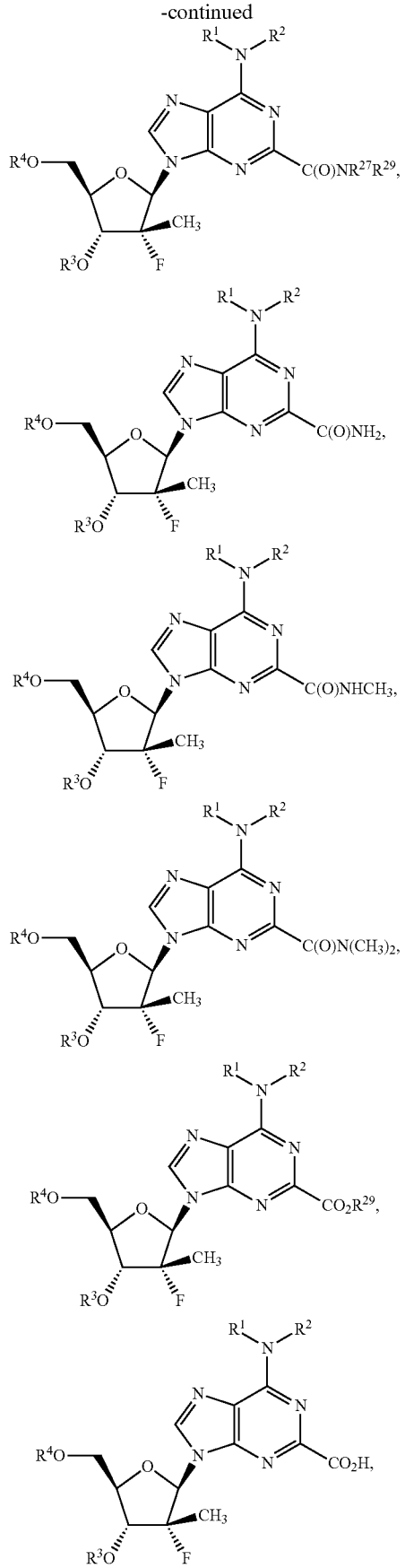
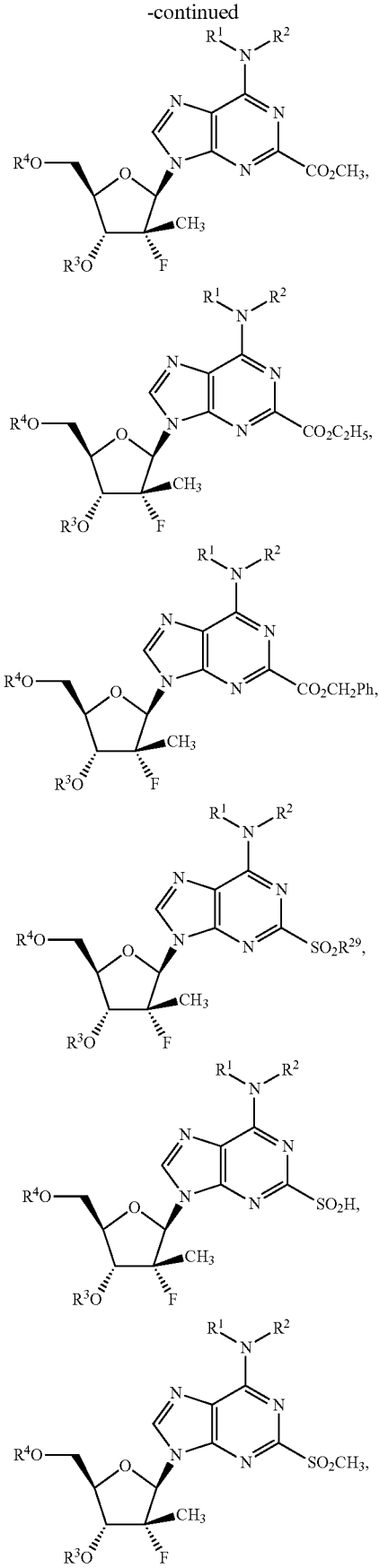

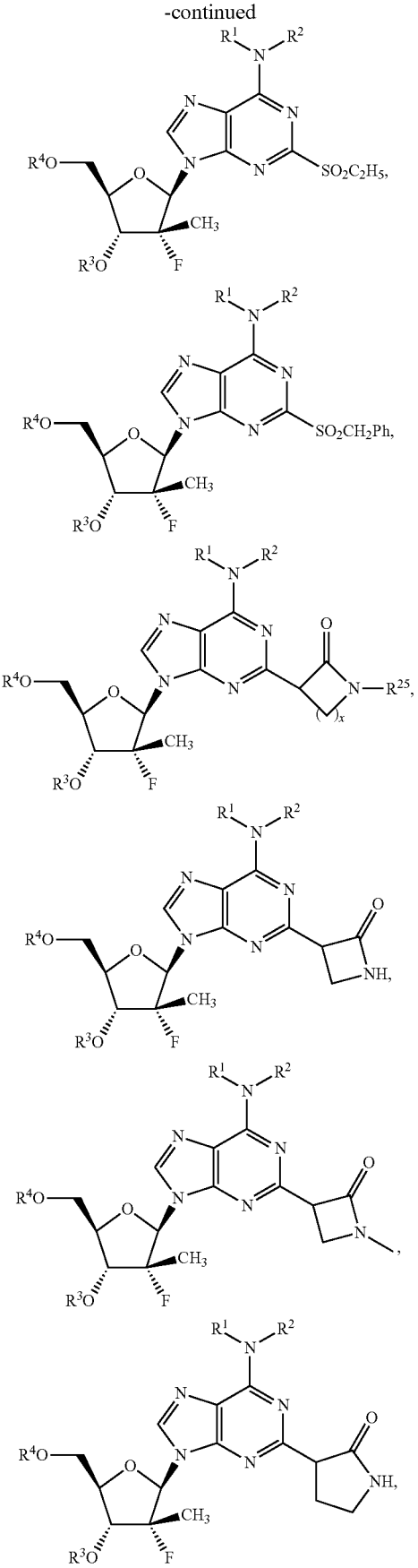
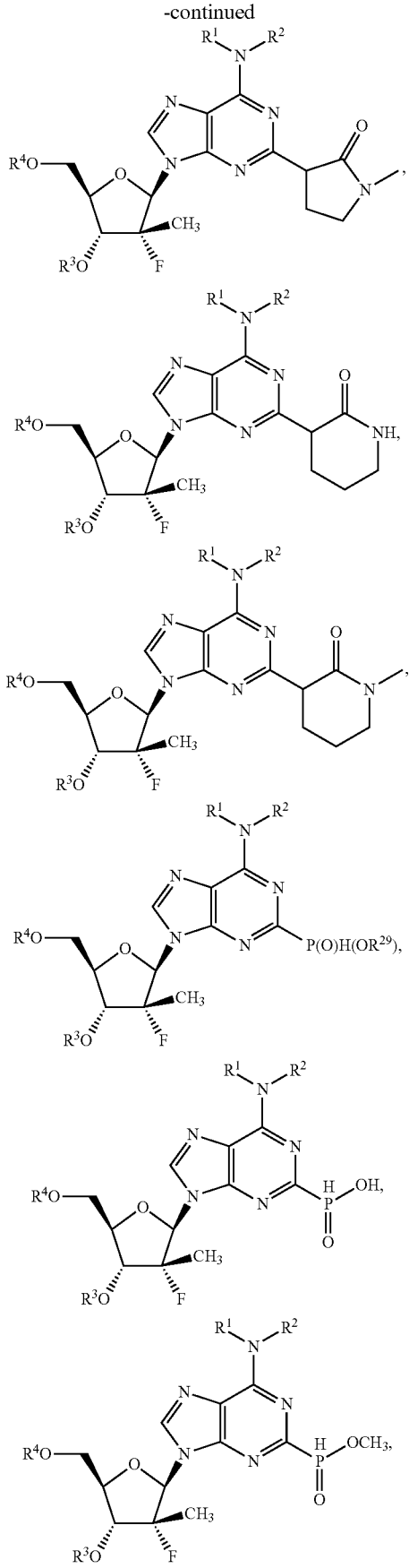

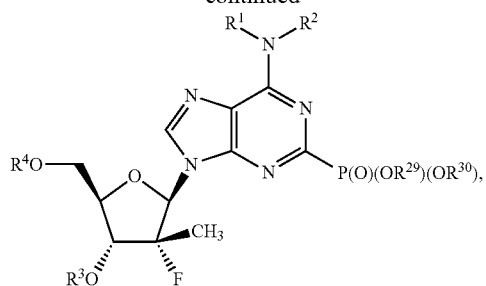
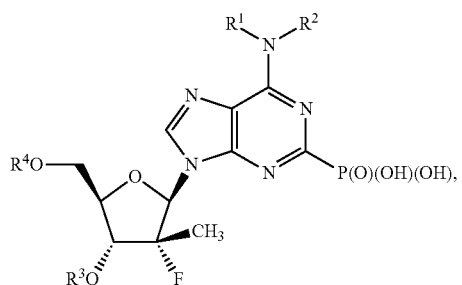
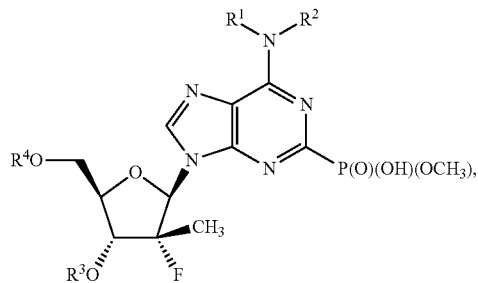
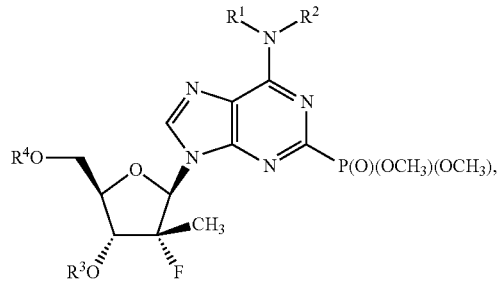
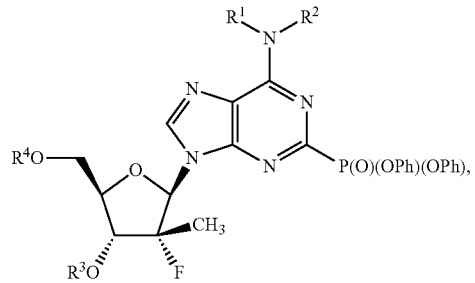
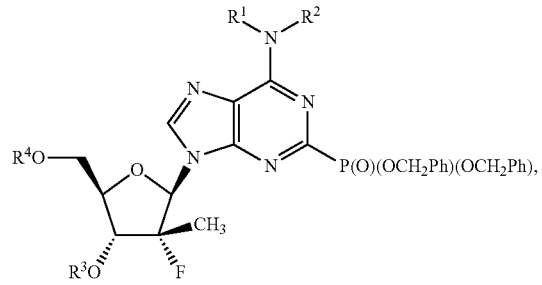
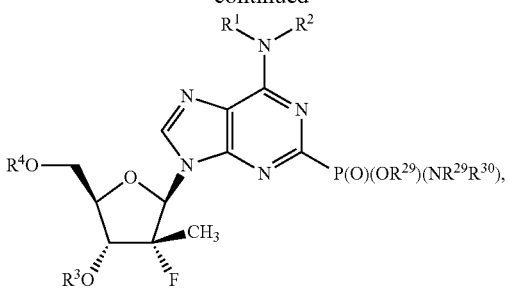
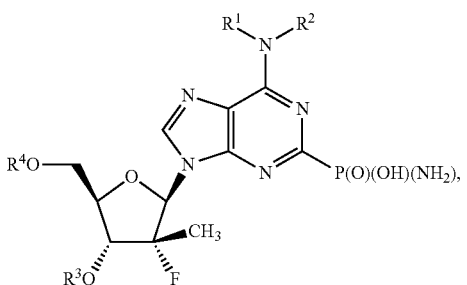
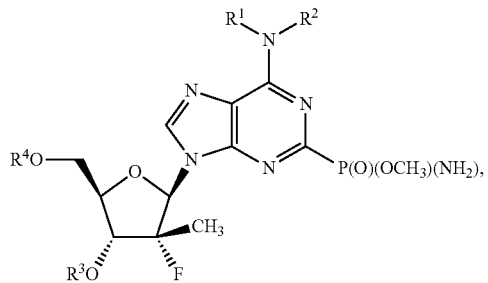
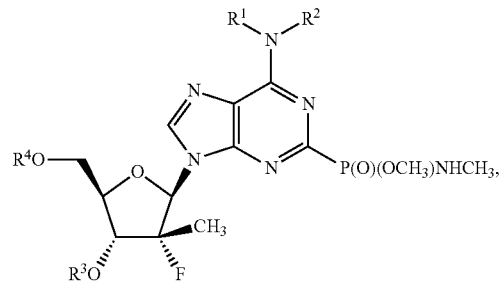
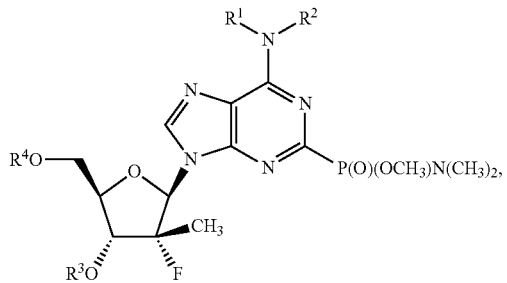
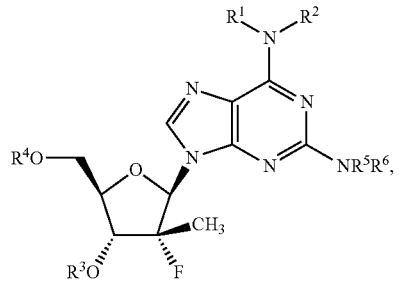

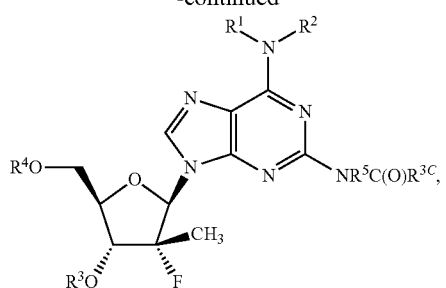
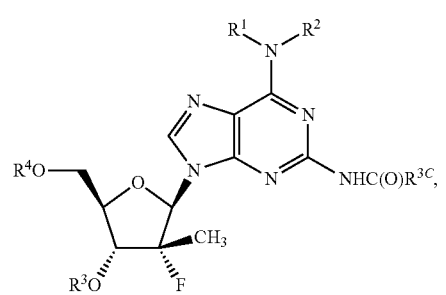
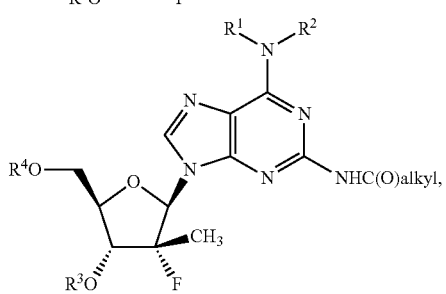
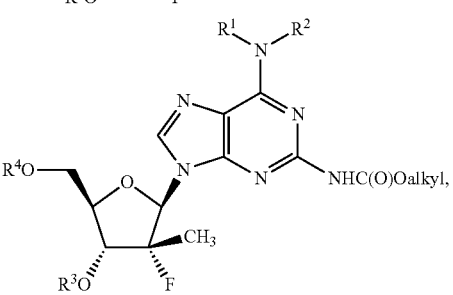
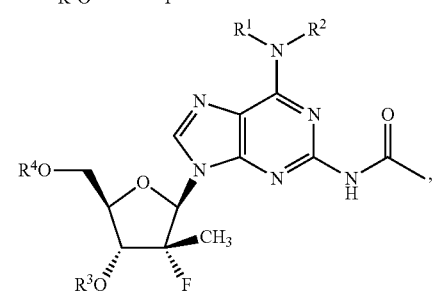
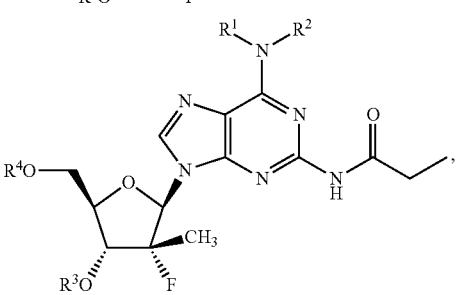
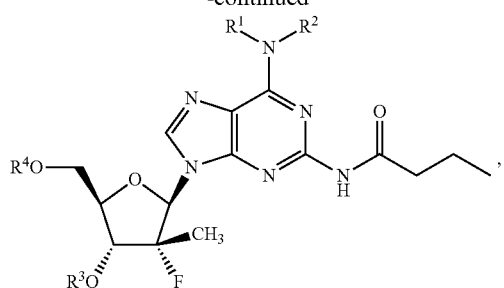
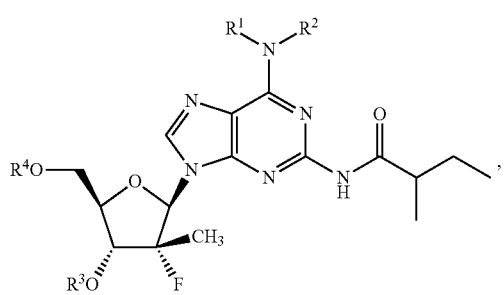
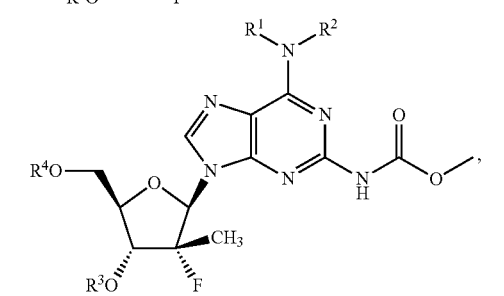
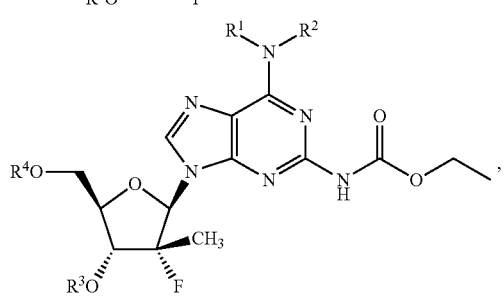
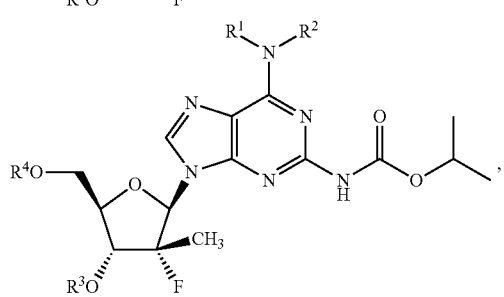
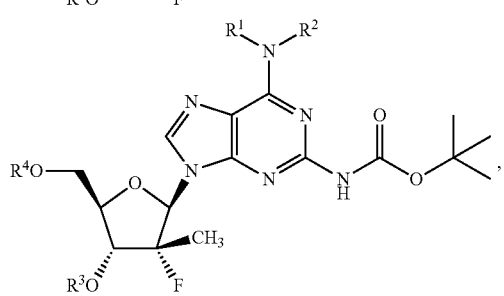

-continued
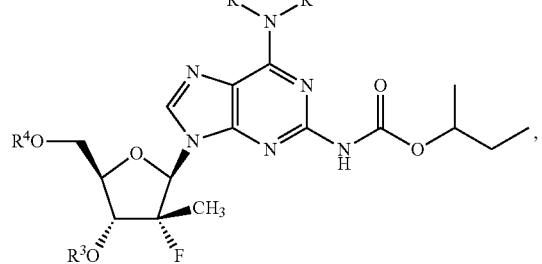,
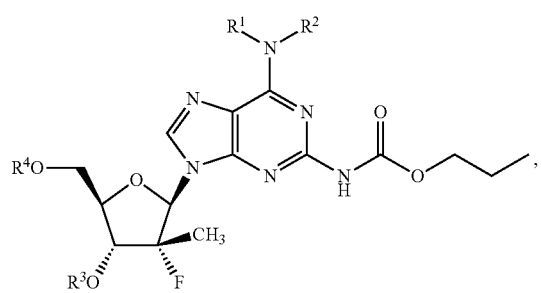,
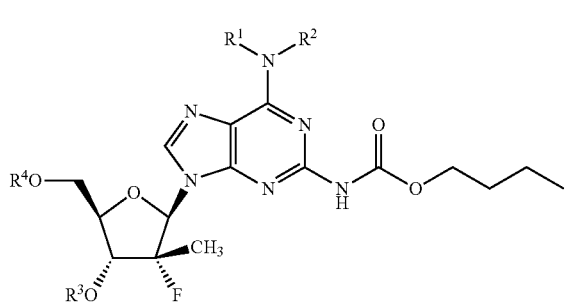,
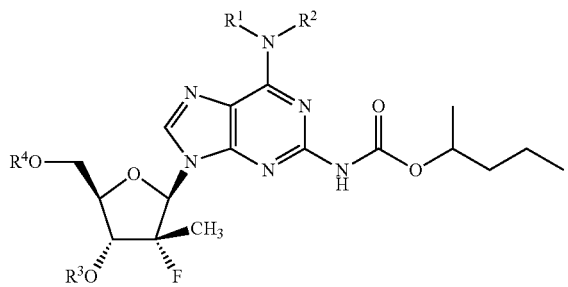,
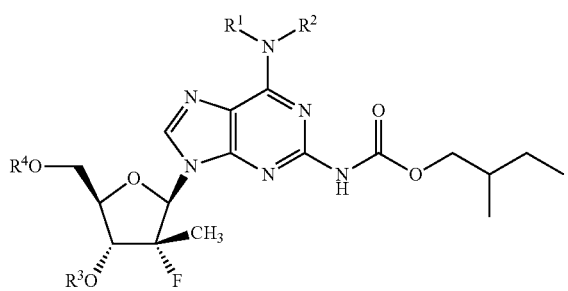,
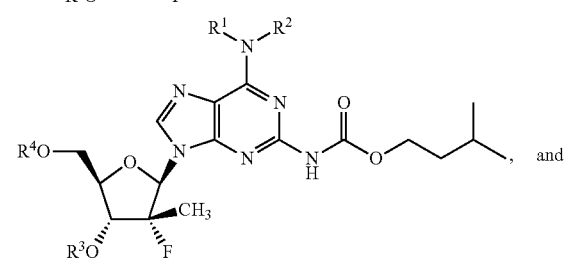, and
-continued
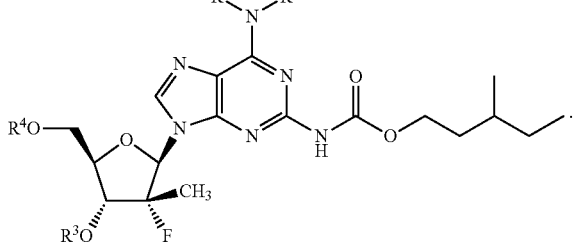.
In some embodiments, $R^3$ is H and $R^4$ is
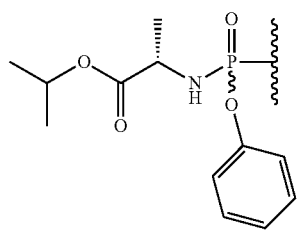
In some embodiments, $R^3$ is H and $R^4$ is
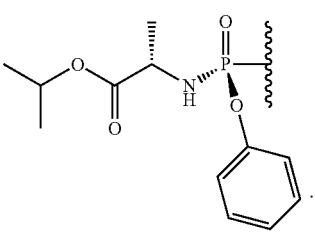 [SMILES: *[P@@](=O)(N[C@@H](C)C(=O)OC(C)C)Oc1ccccc1].
In some embodiments, $R^3$ is H and $R^4$ is
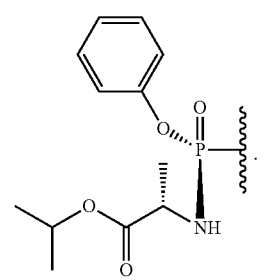 [SMILES: *[P@](=O)(N[C@@H](C)C(=O)OC(C)C)Oc1ccccc1]
In some embodiments, $R^1$ is $CH_3$, $R^2$ is H, $R^3$ is H and $R^4$ is
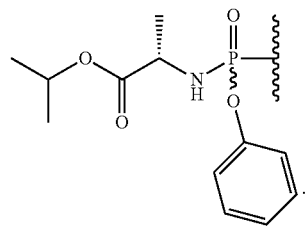 [SMILES: *P(=O)(N[C@@H](C)C(=O)OC(C)C)Oc1ccccc1].

In some embodiments, $R^1$ is $CH_3$, $R^2$ is H, $R^3$ is H and $R^4$ is

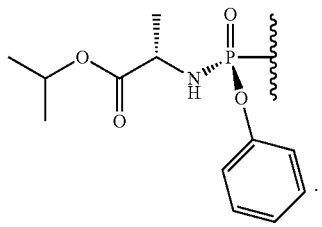 [SMILES: *[P@@](=O)(N[C@@H](C)C(=O)OC(C)C)Oc1ccccc1]

In some embodiments, $R^1$ is $CH_3$, $R^2$ is H, $R^3$ is H and $R^4$ is

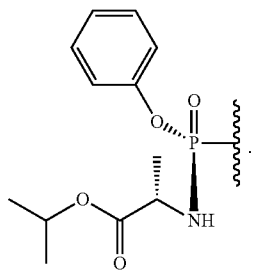 [SMILES: *[P@](=O)(N[C@@H](C)C(=O)OC(C)C)Oc1ccccc1]

In some embodiments, $R^1$ is $CH_3$, $R^2$ is $CH_3$, $R^3$ is H and $R^4$ is

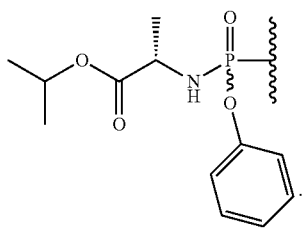 [SMILES: *P(=O)(N[C@@H](C)C(=O)OC(C)C)Oc1ccccc1]

In some embodiments, $R^1$ is $CH_3$, $R^2$ is $CH_3$, $R^3$ is H and $R^4$ is

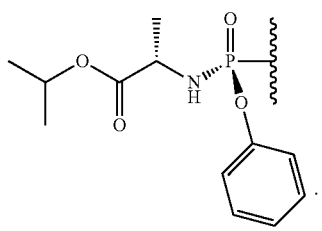 [SMILES: *[P@@](=O)(N[C@@H](C)C(=O)OC(C)C)Oc1ccccc1]

In some embodiments, $R^1$ is $CH_3$, $R^2$ is $CH_3$, $R^3$ is H and $R^4$ is

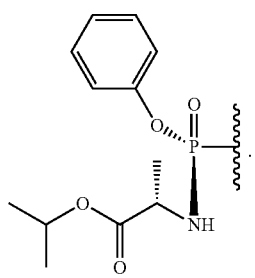 [SMILES: *[P@](=O)(N[C@@H](C)C(=O)OC(C)C)Oc1ccccc1]

In some embodiments, $R^1$ is cyclopropyl, $R^2$ is $CH_3$, $R^3$ is H and $R^4$ is

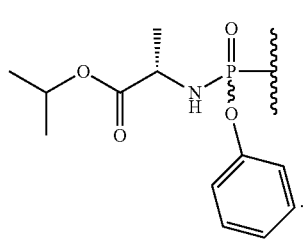 [SMILES: *P(=O)(N[C@@H](C)C(=O)OC(C)C)Oc1ccccc1]

In some embodiments, $R^1$ is cyclopropyl, $R^2$ is $CH_3$, $R^3$ is H and $R^4$ is

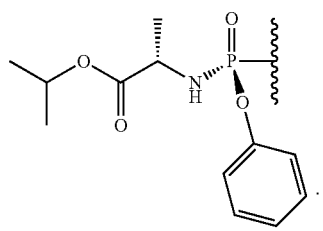 [SMILES: *[P@@](=O)(N[C@@H](C)C(=O)OC(C)C)Oc1ccccc1]

In some embodiments, $R^1$ is cyclopropyl, $R^2$ is $CH_3$, $R^3$ is H and $R^4$ is

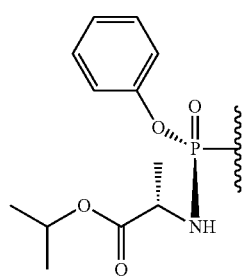

II. Definitions

The following terms are used to describe the present invention. In instances where a term is not specifically defined herein, that term is given an art-recognized meaning by those of ordinary skill applying that term in context to its use in describing the present invention.

The term "alkyl" shall mean within its context, a linear, or branch-chained fully saturated hydrocarbon radical or alkyl group which can be optionally substituted (for example, with halogen, including F). For example, an alkyl group can have 1, 2, 3, 4, 5, 6, 7 or 8 carbon atoms (i.e., $C_1$-$C_8$ alkyl), 1, 2, 3, 4, 5 or 6 carbon atoms (i.e., $C_1$-$C_6$ alkyl) or 1 to 4 carbon atoms (i.e., $C_1$-$C_4$ alkyl). Examples of suitable alkyl groups include, but are not limited to, methyl, ethyl, n-propyl, iso-propyl, n-butyl, isobutyl, sec-butyl, tert-butyl, pentyl, isopentyl, tert-pentyl, neopentyl, hexyl, 2-methylpentyl, 3-methylpentyl, 2,2-dimethylbutyl and 2,3-dimethylbutyl.

The term "alkenyl" refers to a non-aromatic hydrocarbon group which contains at least one double bond between adjacent carbon atoms and a similar structure to an alkyl group as otherwise described herein. For example, an alkenyl group can have 2 to 8 carbon atoms (i.e., $C_2$-$C_8$ alkenyl), or 2 to 4 carbon atoms (i.e., $C_2$-$C_4$ alkenyl).

Examples of suitable alkenyl groups include, but are not limited to, ethenyl or vinyl (—CH═CH$_2$), allyl (—CH$_2$CH═CH$_2$), 1-butenyl (—C═CH—CH$_2$CH$_3$) and 2-butenyl (—CH$_2$CH═CHCH$_2$). The alkenyl group can be optionally substituted as described herein.

The term "alkynyl" refers to a non-aromatic hydrocarbon group containing at least one triple bond between adjacent carbon atoms and a similar structure to an alkyl group as otherwise described herein. For example, an alkynyl group can have 2 to 8 carbon atoms (i.e., C$_2$-C$_8$ alkyne), or 2 to 4 carbon atoms (i.e., C$_2$-C$_4$ alkynyl). Examples of alkynyl groups include, but are not limited to, acetylenic or ethynyl and propargyl. The alkynyl group can be optionally substituted as described herein.

The term "acyl" refers to the moiety —C(O)R in which the carbonyl moiety is bonded to R, for example, —C(O) alkyl. R can be selected from alkoxy, alkyl, cycloalkyl, lower alkyl (i.e., C$_1$-C$_4$); alkoxyalkyl, including methoxymethyl; aralkyl—including benzyl, aryloxyalkyl—such as phenoxymethyl; aryl including phenyl optionally substituted with halogen, C$_1$ to C$_4$ alkyl or C$_1$ to C$_4$ alkoxy. In one embodiment, the term "acyl" refers to a mono, di or triphosphate.

The term "lower acyl" refers to an acyl group in which the carbonyl moiety is lower alkyl (i.e., C$_1$-C$_4$).

The term "alkoxy" refers to the group —OR' where —OR' is —O-alkyl, —O-alkenyl, —O-alkynyl, —O—(C$_0$-C$_2$)(cycloalkyl), —O—(C$_0$-C$_2$)(heterocyclo), —O—(C$_0$-C$_2$)(aryl), or —O—(C$_0$-C$_2$)(heteroaryl), each of which can be optionally substituted.

The term "amino" refers to the group —NH$_2$.

The term "amino acid" or "amino acid residue" refers to a D- or L-natural or non-naturally occurring amino acid. Representative amino acids include, but are not limited to, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine, among others.

The term "azido" refers to the group —N$_3$.

The term "aryl" or "aromatic", in context, refers to a substituted (as otherwise described herein) or unsubstituted monovalent aromatic radical having a single ring (e.g., phenyl or benzyl) or condensed rings (e.g., naphthyl, anthracenyl, phenanthrenyl, etc.) and can be bound to the compound according to the present invention at any available stable position on the ring(s) or as otherwise indicated in the chemical structure presented. The aryl group can be optionally substituted as described herein.

"Cycloalkyl", "carbocycle", or "carbocyclyl" refers to a saturated (i.e., cycloalkyl) or partially unsaturated (e.g., cycloakenyl, cycloalkadienyl, etc.) ring having 3 to 7 carbon atoms as a monocycle. Monocyclic carbocycles have 3 to 7 ring atoms, still more typically 5 or 6 ring atoms. Non-limiting examples of cycloalkyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, and 1-cyclo-hex-3-enyl.

The term "cyano" refers to the group —CN.

The term "halogen" or "halo" refers to chloro, bromo, fluoro or iodo.

A heteroaryl ring system is a saturated or unsaturated ring with one or more nitrogen, oxygen, or sulfur atoms in the ring (monocyclic) including but not limited to imidazole, furyl, pyrrole, furanyl, thiene, thiazole, pyridine, pyrimidine, purine, pyrazine, triazole, oxazole, or fused ring systems such as indole, quinoline, etc., among others, which may be optionally substituted as described above. Heteroaryl groups include nitrogen-containing heteroaryl groups such as pyrrole, pyridine, pyridone, pyridazine, pyrimidine, pyrazine, pyrazole, imidazole, triazole, triazine, tetrazole, indole, isoindole, indolizine, purine, indazole, quinoline, isoquinoline, quinolizine, phthalazine, naphthyridine, quinoxaline, quinazoline, cinnoline, pteridine, imidazopyridine, imidazotriazine, pyrazinopyridazine, acridine, phenanthridine, carbazole, carbazoline, perimidine, phenanthroline, phenacene, oxadiazole, benzimidazole, pyrrolopyridine, pyrrolopyrimidine and pyridopyrimidine; sulfur-containing aromatic heterocycles such as thiophene and benzothiophene; oxygen-containing aromatic heterocycles such as furan, pyran, cyclopentapyran, benzofuran and isobenzofuran; and aromatic heterocycles comprising two or more hetero atoms selected from among nitrogen, sulfur and oxygen, such as thiazole, thiadiazole, isothiazole, benzoxazole, benzothiazole, benzothiadiazole, phenothiazine, isoxazole, furazan, phenoxazine, pyrazoloxazole, imidazothiazole, thienofuran, furopyrrole, pyridoxazine, furopyridine, furopyrimidine, thienopyrimidine and oxazole, among others, all of which may be optionally substituted.

The term "heterocycle" or "heterocyclo" refers to a cyclic group which contains at least one heteroatom, i.e., O, N, or S, and may be aromatic (heteroaryl) or non-aromatic. Exemplary non-aromatic heterocyclic groups for use in the present invention include, for example, pyrrolidinyl, piperidinyl, piperazinyl, N-methylpiperazinyl, imidazolinyl, pyrazolidinyl, imidazolidinyl, morpholinyl, tetrahydropyranyl, azetidinyl, oxetanyl, oxathiolanyl, pyridone, 2-pyrrolidone, ethyleneurea, 1,3-dioxolane, 1,3-dioxane, 1,4-dioxane, phthalimide, and succinimide, among others, all of which may be optionally substituted.

The term "hydroxyl" refers to the group —OH.

The term "nitro" refers to the group —NO$_2$.

The term "pharmaceutically acceptable salt" or prodrug" is used throughout the specification to describe any pharmaceutically acceptable form (such as an ester, phosphoramidate, thiophosphoramidate, phosphate ester, salt of an ester, or a related group) of a β-D-2'-D-2'-α-fluoro-2'-β-C-substituted-2-modified-N$^6$-substituted purine nucleotide which, upon administration to a patient, provides the desired active compound. Examples of pharmaceutically acceptable salts are organic acid addition salts formed with acids, which form a physiological acceptable anion, for example, tosylate, methanesulfonate, acetate, citrate, malonate, tartrate, succinate, benzoate, ascorbate, α-ketoglutarate, and α-glycerophosphate. Suitable inorganic salts may also be formed, including sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium, or lithium) or alkaline earth metal (for example calcium) salts of carboxylic acids can also be made.

"Pharmaceutically acceptable prodrug" refers to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated, thiophoshoramidated, dethiophosphoramidated, phoshoramidated or dephosphoramidated to produce the active compound. The compounds of this invention possess antiviral activity against HCV, or are metabolized to a compound that exhibits such activity. The β-D-2'-D-2'-α-fluoro-2'-β-C-substituted-2-modified-$N^6$-substituted purine nucleoside can also be administered as a 5'-phosphoether lipid, a bisphosphoramidate, a 3',5'-cyclic phosphoramidate, a 3',5'-cyclic thiophosphoramidate, a DTE conjugate, a mixed phosphoramidate-SATE derivative or a "SATE" derivative.

The term "phosphonic acid" refers to the group —P(O)(OH)$_2$.

In one embodiment, the term purine or pyrimidine base includes, but is not limited to, adenine, $N^6$-alkylpurines, $N^6$-acylpurines (wherein acyl is —C(O)alkyl, —C(O)(aryl) $C_0$-$C_4$alkyl, or —C(O)($C_0$-$C_4$alkyl)aryl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, —$C^5$-acyl pyrimidine, —$C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include benzyl, trimethylsilyl, dimethylhexylsilyl, t-butyldimethylsilyl, t-butyldiphenylsilyl, trityl, alkyl groups, and acyl groups such as acetyl and propionyl; methanesulfonyl, and p-toluenesulfonyl. Alternatively, the purine or pyrimidine base can optionally be substituted such that it forms a viable prodrug, which can be cleaved in vivo. Examples of appropriate substituents include an acyl moiety.

The term "substituted" or "optionally substituted" indicates that the moiety can have at least one additional substituent including, but not limited to, halogen (F, Cl, Br, I), OH, phenyl, benzyl, $N_3$, CN, acyl, alkyl, including methyl; alkenyl, alkynyl, alkoxy, haloalkyl; including CHF$_2$, CH$_2$F and CF$_3$; etc. In one embodiment, the term "substituted" or "optionally substituted" indicates that the moiety can have at least one additional substituent including, but not limited to, azido, cyano, halogen (fluoro, chloro, bromo, or iodo), alkyl, alkenyl, alkynyl, cycloalkyl, heterocycle, aryl, heteroaryl, haloalkyl, hydroxyl, alkoxy, amino, —NH($C_1$-$C_6$ unsubstituted alkyl), —NH($C_1$-$C_6$ substituted alkyl), —NH—($C_0$-$C_2$alkyl)($C_3$-$C_8$cycloalkyl), —NH—($C_0$-$C_2$alkyl)($C_3$-$C_8$heterocycle), —NH—($C_0$-$C_2$alkyl)(aryl), —N($C_1$-$C_6$ unsubstituted alkyl)$_2$, —N($C_1$-$C_6$ unsubstituted alkyl)($C_1$-$C_6$ substituted alkyl), —N($C_1$-$C_6$ substituted alkyl)$_2$, —NH—($C_0$-$C_2$alkyl)($C_3$-$C_8$cycloalkyl), —NH—($C_0$-$C_2$alkyl)($C_3$-$C_8$heterocycle), —NH—($C_0$-$C_2$alkyl)(aryl), acyl, nitro, sulfonic acid, sulfate, phosphonic acid, phosphate, phosphonate, or thiol.

The term "sulfonate esters", represented by the formula, $R^{14}S(O)_2OR^{15}$, comprise $R^{14}$ wherein $R^{14}$ is alkyl, haloalkyl, aralkyl or aryl. $R^{15}$ is alkyl, aryl or aralkyl.

The term "sulfonic acid" refers to the group —SO$_2$OH.

The term "thiol" refers to the group —SH.

The term "nitrogen-protecting group" as used herein refers to a moiety that is covalently attached to nitrogen and which can be removed, and typically replaced with hydrogen, when appropriate. For example, a nitrogen-protecting group may be a group that is removed in vivo after administration to a host, in vitro by a cell, or it may be removed during a manufacturing process. Suitable nitrogen-protecting groups useful in the present invention are described by Greene and Wuts in Protective Groups in Organic Synthesis (1991) New York, John Wiley and Sons, Inc.

The term "oxygen-protecting group" as used herein refers to a moiety that is covalently attached to oxygen and which can be removed, and typically replaced with hydrogen, when appropriate. For example, an oxygen-protecting group may be a group that is removed in vivo after administration to a host, in vitro by a cell, or it may be removed during a manufacturing process. Suitable oxygen-protecting groups useful in the present invention are described by Greene and Wuts in Protective Groups in Organic Synthesis (1991) New York, John Wiley and Sons, Inc.

"Phosphate" refers to the group —OP(O)(OH)$_2$.

"Phosphate ester" refers to mono, di, and tri phosphates unless otherwise indicated.

The term "phosphoamidate", "phosphoramidate", or "phosphoroamidate" is a moiety that has a phosphorus bound to three oxygen groups and an amine (which may optionally be substituted). Suitable phosphoramidates useful in the present invention are described by Madela, Karolina and McGuigan in 2012, "Progress in the development of anti-hepatitis C virus nucleoside and nucleotide prodrugs", *Future Medicinal Chemistry* 4(5), pages 625-650 10:1021/jm300074y and Dominique, McGuigan and Balzarini in 2004, "Aryloxy Phosphoramidate Triesters as Pro-Tides", *Mini Reviews in Medicinal Chemistry* 4(4), pages 371-381. Additional phosphoramidates useful in the present invention are described in U.S. Pat. Nos. 5,233,031, 7,115,590, 7,547, 704, 7,879,815, 7,888,330, 7,902,202, 7,951,789, 7,964,580, 8,071,568; 8,148,349, 8,263,575, 8,324,179, 8,334,270, 8,552,021, 8,563,530, 8,580,765, 8,735,372, 8,759,318; EP 2120565; EP 1143995; U.S. Pat. Nos. 6,455,513; and 8,334, 270. Other phosphoramidates are described in the nucleoside patents described in the Background of the Invention.

Phosphoramidate groups for use in the present invention include those of the structures:

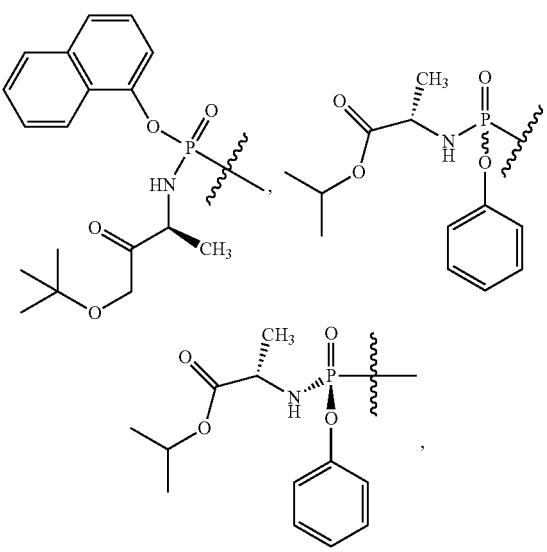

119
-continued

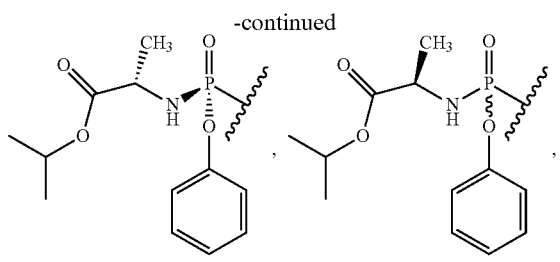
,

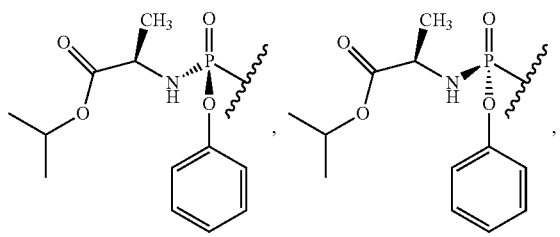
,

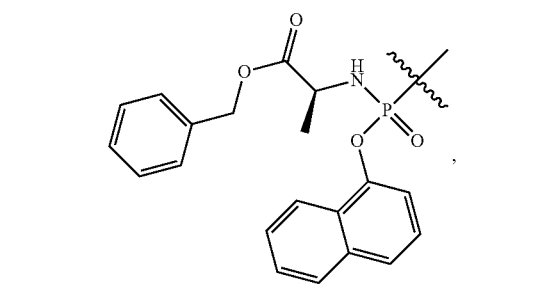
,

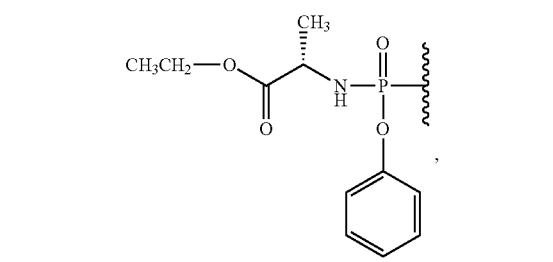
,

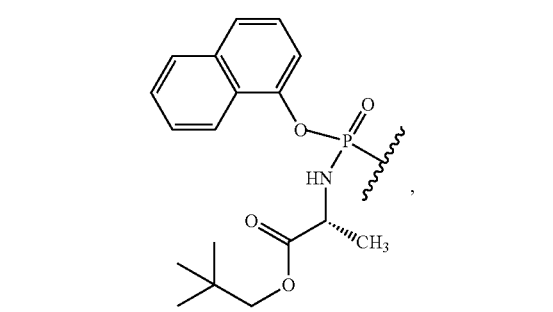
,

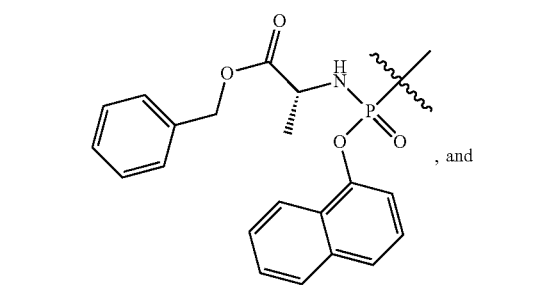
, and

120
-continued

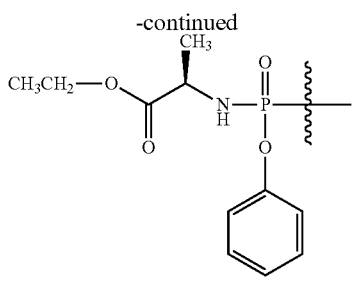

Other phosphoramidates for use in the present invention include those of the structure:

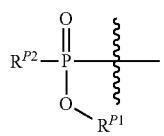

wherein:

$R^{P1}$ is an optionally substituted linear, branched, or cyclic alkyl group, or an optionally substituted aryl, heteroaryl or heterocyclic group or a linked combination thereof; and $R^{P2}$ is a —$NR^{N1}R^{N2}$ group or a B' group;

wherein:

$R^{N1}$ and $R^{N2}$ are each independently H, $C_{1-8}$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; which may be optionally substituted; or $R^{N1}$ and $R^{N2}$ along with the nitrogen atom to which that are attached, join to form a 3 to 7 membered heterocyclic ring;

B' is

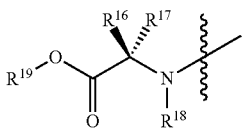

group;

wherein:

$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);

$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);

$R^{18}$ is hydrogen or $C_1$-$C_3$alkyl; or $R^{16}$ and $R^{17}$ can form a ($C_3$-$C_7$)cycloalkyl or ($C_3$-$C_7$) heterocyclic group; or $R^{18}$ and $R^{16}$ or $R^{17}$ can form $(C_3-C_6)$heterocyclic group; and $R^{19}$ is hydrogen, $(C_1-C_8)$alkyl, $(C_3-C_6)$alkenyl, $(C_3-C_6)$alkynyl, $(C_3-C_8\text{cycloalkyl})C_0-C_4\text{alkyl-}$, $(\text{aryl})C_0-C_4\text{alkyl-}$, $(C_3-C_6\text{heterocyclo})C_0-C_4\text{alkyl-}$, $(\text{heteroaryl})C_0-C_4\text{alky-}$; or B' is a

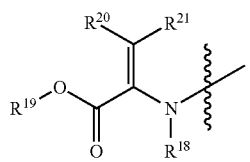

group;

wherein:

$R^{20}$ is hydrogen, $(C_1-C_3)$alkyl, $(C_3-C_8\text{cycloalkyl})C_0-C_4\text{alkyl-}$, $(\text{aryl})C_0-C_4\text{alkyl-}$, $(C_3-C_6\text{heterocyclo})C_0-C_4\text{alkyl-}$, or $(\text{heteroaryl})C_0-C_4\text{alky-}$;

$R^{21}$ is hydrogen, $(C_1-C_3)$alkyl, $(C_3-C_8\text{cycloalkyl})C_0-C_4\text{alkyl-}$, $(\text{aryl})C_0-C_4\text{alkyl-}$, $(C_3-C_6\text{heterocyclo})C_0-C_4\text{alkyl-}$, or $(\text{heteroaryl})C_0-C_4\text{alky-}$; and $R^{18}$ and $R^{19}$ are as defined above.

Preferred $R^{P1}$ groups include optionally substituted phenyl, naphthyl, and monocyclic heteroaryl groups, especially those groups (particularly lipophilic groups) which enhance bioavailability of the compounds in the cells of the patient and which exhibit reduced toxicity, enhanced therapeutic index and enhanced pharmacokinetics (the compounds are metabolized and excreted more slowly).

The term phosphoramidate is used throughout the specification to describe a group that is found at the 5' or 3' position of the furanose ring of the nucleoside compound and forms a prodrug form of the nucleoside compound. In one embodiment, phosphoramidates can be found at both the 5' and 3' position of the furanose ring of the nucleoside compound and form a prodrug form of the nucleoside compound. In another embodiment, the phosphoramidate found at the 5' position of the furanose ring of the nucleoside can form a cyclic phosphoramidate compound by forming a bond with the 3'-hydroxyl substituent at the 3' position of the furanose ring of the nucleoside compound and form a prodrug form of the nucleoside compound.

The term "thiophosphoramidate", "thiophosphoramidate", or "thiophosphoroamidate" is a moiety that has a phosphorus bound to sulfur, two oxygen groups and an amine (which may optionally be substituted). Thiophosphoramidates useful in the present invention are described in U.S. Pat. No. 8,772,474 and WO 2012/040124.

Thiophosphoramidate groups for use in the present invention include those of the structures:

-continued

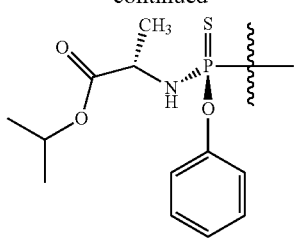

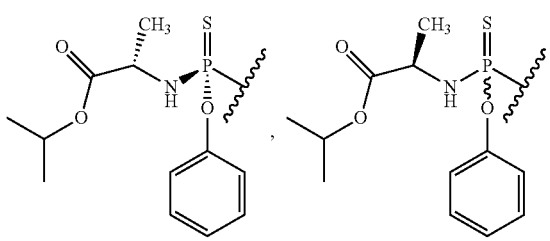

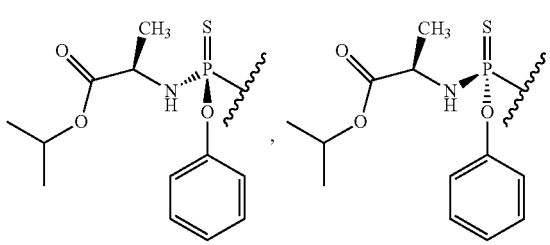

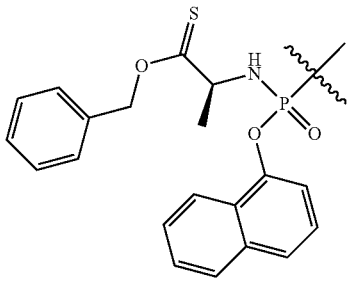

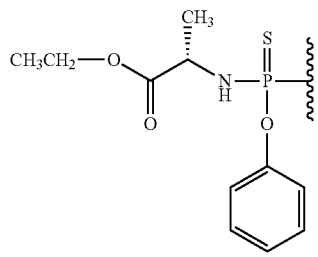

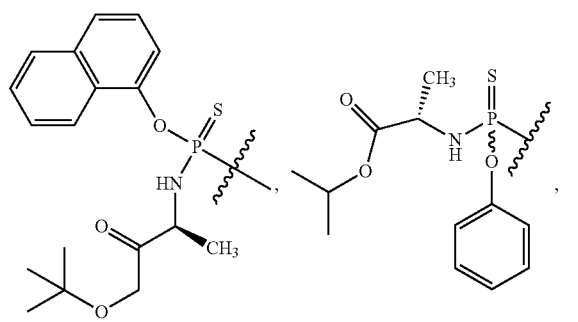

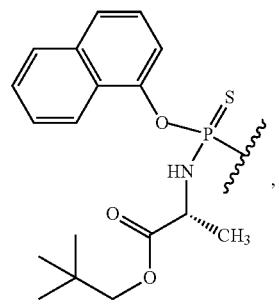

-continued

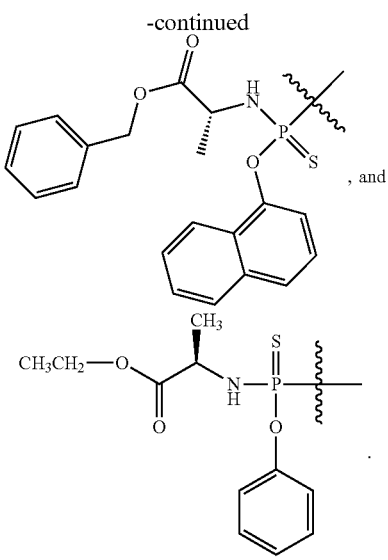, and

Other thiophosphoramidates include those of the structure:

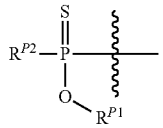

wherein:

$R^{P1}$ is an optionally substituted linear, branched, or cyclic alkyl group, or an optionally substituted aryl, heteroaryl or heterocyclic group or a linked combination thereof; and $R^{P2}$ is a —$NR^{N1}R^{N2}$ group or a B' group;

wherein:

$R^{N1}$ and $R^{N2}$ are each independently H, $C_1$-$C_8$alkyl, ($C_3$-$C_7$cycloalkyl)$C_0$-$C_4$alkyl-, (aryl)$C_0$-$C_4$alkyl-, ($C_3$-$C_6$heterocyclo)$C_0$-$C_4$alkyl-, or (heteroaryl)$C_0$-$C_4$alky-; or $R^{N1}$ and $R^{N2}$ along with the nitrogen atom to which that are attached, join to form a 3 to 7 membered heterocyclic ring;

B' is a

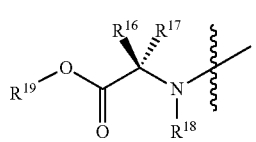

group;

wherein:

$R^{16}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{16}$ is hydrogen, methyl, isopropyl, or isobutyl);

$R^{17}$ is hydrogen, ($C_1$-$C_8$)alkyl, ($C_2$-$C_8$)alkenyl, ($C_2$-$C_8$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-, or the sidechain of an amino acid, for example a sidechain of an amino acid (as otherwise described herein) often selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan, or tyrosine (often $R^{17}$ is hydrogen, methyl, isopropyl, or isobutyl);

$R^{18}$ is hydrogen or $C_1$-$C_3$alkyl; or $R^{16}$ and $R^{17}$ can form a ($C_3$-$C_7$)cycloalkyl or ($C_3$-$C_7$) heterocyclic group; or $R^{18}$ and $R^{16}$ or $R^{17}$ can form ($C_3$-$C_6$) heterocyclic group; and $R^{19}$ is hydrogen, ($C_1$-$C_6$)alkyl, ($C_3$-$C_6$)alkenyl, ($C_3$-$C_6$) alkynyl, ($C_3$-$C_8$cycloalkyl)$C_0$-$C_4$alkyl-, (aryl)$C_0$-$C_4$alkyl-, ($C_3$-$C_6$heterocyclo)$C_0$-$C_4$alkyl-, (heteroaryl)$C_0$-$C_4$alky-; or B' is a group; and $R^8$, $R^{19}$, $R^{20}$ and $R^{21}$ are as defined above.

Preferred $R^{P1}$ groups include optionally substituted phenyl, naphthyl, and monocyclic heteroaryl groups, especially those groups (particularly lipophilic groups) which enhance bioavailability of the compounds into the cells of the patient and which exhibit reduced toxicity, enhanced therapeutic index and enhanced pharmacokinetics (the compounds are metabolized and excreted more slowly).

The thiophosphoramidate can be at the 5' or 3' position of the furanose ring of the nucleoside compound to form a prodrug form of the nucleoside compound. In one embodiment, thiophosphoramidates can be found at both the 5' and 3' position of the furanose ring of the nucleoside compound and form a prodrug form of the nucleoside compound. In another embodiment, the thiophosphoramidate found at the 5' position of the furanose ring of the nucleoside can form a cyclic thiophosphoramidate compound by forming a bond with the 3'-hydroxyl substituent at the 3' position of the furanose ring of the nucleoside compound and form a prodrug form of the nucleoside compound.

The term "D-configuration" as used in the context of the present invention refers to the principle configuration which mimics the natural configuration of sugar moieties as opposed to the unnatural occurring nucleosides or "L" configuration. The term "β" or "β anomer" is used with reference to nucleoside analogs in which the nucleoside base is configured (disposed) above the plane of the furanose moiety in the nucleoside analog.

The terms "coadminister" and "coadministration" or combination therapy are used to describe the administration of at least one of the 2'-deoxy-2'-α-fluoro-2'-β-C-nucleoside compounds according to the present invention in combination with at least one other active agent, for example where appropriate at least one additional anti-HCV agent, including other 2'-deoxy-2'-α-fluoro-2'-β-C-nucleoside agents which are disclosed herein. The timing of the coadministration is best determined by the medical specialist treating the patient. It is sometimes preferred that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

The term "host", as used herein, refers to a unicellular or multicellular organism in which a HCV virus can replicate, including cell lines and animals, and typically a human. The term host specifically refers to infected cells, cells transfected with all or part of a HCV genome, and animals, in particular, primates (including chimpanzees) and humans. In most animal applications of the present invention, the host is a human patient. Veterinary applications, in certain indications, however, are clearly anticipated by the present invention (such as chimpanzees). The host can be for example, bovine, equine, avian, canine, feline, etc.

Isotopic Substitution

The present invention includes compounds and the use of compounds with desired isotopic substitutions of atoms, at amounts above the natural abundance of the isotope, i.e., enriched. Isotopes are atoms having the same atomic number but different mass numbers, i.e., the same number of protons but a different number of neutrons. By way of general example and without limitation, isotopes of hydrogen, for example, deuterium ($^2$H) and tritium ($^3$H) may be used anywhere in described structures. Alternatively or in addition, isotopes of carbon, e.g., $^{13}$C and $^{14}$C, may be used. A preferred isotopic substitution is deuterium for hydrogen at one or more locations on the molecule to improve the performance of the drug. The deuterium can be bound in a location of bond breakage during metabolism (an α-deuterium kinetic isotope effect) or next to or near the site of bond breakage (a β-deuterium kinetic isotope effect). Achillion Pharmaceuticals, Inc. (WO/2014/169278 and WO/2014/169280) describes deuteration of nucleotides to improve their pharmacokinetics or pharmacodynamics, including at the 5-position of the molecule.

Substitution with isotopes such as deuterium can afford certain therapeutic advantages resulting from greater metabolic stability, such as, for example, increased in vivo half-life or reduced dosage requirements. Substitution of deuterium for hydrogen at a site of metabolic break down can reduce the rate of or eliminate the metabolism at that bond. At any position of the compound that a hydrogen atom may be present, the hydrogen atom can be any isotope of hydrogen, including protium ($^1$H), deuterium ($^2$H) and tritium ($^3$H). Thus, reference herein to a compound encompasses all potential isotopic forms unless the context clearly dictates otherwise.

The term "isotopically-labeled" analog refers to an analog that is a "deuterated analog", a "$^{13}$C-labeled analog," or a "deuterated/$^{13}$C-labeled analog." The term "deuterated analog" means a compound described herein, whereby a H-isotope, i.e., hydrogen/protium ($^1$H), is substituted by a H-isotope, i.e., deuterium ($^2$H). Deuterium substitution can be partial or complete. Partial deuterium substitution means that at least one hydrogen is substituted by at least one deuterium. In certain embodiments, the isotope is 90, 95 or 99% or more enriched in an isotope at any location of interest. In some embodiments it is deuterium that is 90, 95 or 99% enriched at a desired location. Unless indicated to the contrary, the deuteration is at least 80% at the selected location. Deuteration of the nucleoside can occur at any replaceable hydrogen that provides the desired results.

III. Methods of Treatment or Prophylaxis

Treatment, as used herein, refers to the administration of an active compound to a host that is infected with a HCV virus.

The term "prophylactic" or preventative, when used, refers to the administration of an active compound to prevent or reduce the likelihood of an occurrence of the viral disorder. The present invention includes both treatment and prophylactic or preventative therapies. In one embodiment, the active compound is administered to a host who has been exposed to and thus at risk of infection by a hepatitis C virus infection.

The invention is directed to a method of treatment or prophylaxis of a hepatitis C virus, including drug resistant and multidrug resistant forms of HCV and related disease states, conditions, or complications of an HCV infection, including cirrhosis and related hepatotoxicities, as well as other conditions that are secondary to a HCV infection, such as weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular cancer, among others. The method comprises administering to a host in need thereof an effective amount of at least one β-D-2'-D-2'-α-fluoro-2'-β-C-substituted-2-modified-N$^6$-substituted purine nucleotide as described herein, optionally in combination with at least one additional bioactive agent, for example, an additional anti-HCV agent, further in combination with a pharmaceutically acceptable carrier additive and/or excipient.

In yet another aspect, the present invention is a method for prevention or prophylaxis of a an HCV infection or a disease state or related or follow-on disease state, condition or complication of an HCV infection, including cirrhosis and related hepatotoxicities, weakness, loss of appetite, weight loss, breast enlargement (especially in men), rash (especially on the palms), difficulty with clotting of blood, spider-like blood vessels on the skin, confusion, coma (encephalopathy), buildup of fluid in the abdominal cavity (ascites), esophageal varices, portal hypertension, kidney failure, enlarged spleen, decrease in blood cells, anemia, thrombocytopenia, jaundice, and hepatocellular (liver) cancer, among others, said method comprising administering to a patient at risk with an effective amount of at least one compound according to the present invention as described above in combination with a pharmaceutically acceptable carrier, additive, or excipient, optionally in combination with another anti-HCV agent. In another embodiment, the active compounds of the invention can be administered to a patient after a hepatitis-related liver transplantation to protect the new organ.

The 5'-stabilized β-D-2'-D-2'-α-fluoro-2'-β-C-substituted-2-modified-N$^6$-substituted purine nucleotide can be administered if desired as any salt or prodrug that upon administration to the recipient is capable of providing directly or indirectly the parent compound, or that exhibits activity itself. Nonlimiting examples are the pharmaceutically acceptable salts and a compound, which has been modified at a function group, such as a hydroxyl or amine function, to modify the biological activity, pharmacokinetics, half-life, controlled delivery, lipophilicity, absorption kinetics, ease of phosphorylation to the active 5'-triphosphate or efficiency of delivery using a desired route of administration; of the compound. Methods to modify the properties of an active compound to achieve target properties are known to those of skill in the art or can easily be assessed by standard methods, for example, acylation, phosphorylation, thiophosphoramidation, phosphoramidation, phosphonation, alkylation, or pegylation.

IV. Pharmaceutical Compositions

In an aspect of the invention, pharmaceutical compositions according to the present invention comprise an anti-HCV virus effective amount of at least one of the 5′-stabilized β-D-2′-D-2′-α-fluoro-2′-β-C-substituted-2-modified-$N^6$-substituted purine nucleotide compounds described herein, optionally in combination with a pharmaceutically acceptable carrier, additive, or excipient, further optionally in combination or alternation with at least one other active compound.

In an aspect of the invention, pharmaceutical compositions according to the present invention comprise an anti-HCV effective amount of at least one of the active β-D-2′-D-2′-α-fluoro-2′-β-C-substituted-2-modified-$N^6$-substituted purine nucleotide compounds described herein, optionally in combination with a pharmaceutically acceptable carrier, additive, or excipient, further optionally in combination with at least one other antiviral, such as an anti-HCV agent.

The invention includes pharmaceutical compositions that include an effective amount to treat a hepatitis C virus infection, of one of the β-D-2′-D-2′-α-fluoro-2′-β-C-substituted-2-modified-$N^6$-substituted purine nucleotide compounds of the present invention or its salt or prodrug, in a pharmaceutically acceptable carrier or excipient. In an alternative embodiment, the invention includes pharmaceutical compositions that include an effective amount to prevent a hepatitis C virus infection, of one of the β-D-2′-D-2′-α-fluoro-2′-β-C-substituted-2-modified-$N^6$-substituted purine nucleotide compounds of the present invention or its salt or prodrug, in a pharmaceutically acceptable carrier or excipient.

One of ordinary skill in the art will recognize that a therapeutically effective amount will vary with the infection or condition to be treated, its severity, the treatment regimen to be employed, the pharmacokinetics of the agent used, as well as the patient or subject (animal or human) to be treated, and such therapeutic amount can be determined by the attending physician or specialist.

The 5′-stabilized β-D-2′-D-2′-α-fluoro-2′-β-C-substituted-2-modified-$N^6$-substituted purine nucleotide compounds according to the present invention can be formulated in an admixture with a pharmaceutically acceptable carrier. In general, it is preferable to administer the pharmaceutical composition in orally-administrable form, but certain formulations may be administered via a parenteral, intravenous, intramuscular, topical, transdermal, buccal, subcutaneous, suppository, or other route, including intranasal spray. Intravenous and intramuscular formulations are often administered in sterile saline. One of ordinary skill in the art may modify the formulations to render them more soluble in water or other vehicle, for example, this can be easily accomplished by minor modifications (salt formulation, esterification, etc.) which are well within the ordinary skill in the art. It is also well within the routineers' skill to modify the route of administration and dosage regimen of a particular compound in order to manage the pharmacokinetics of the present compounds for maximum beneficial effect in patients.

In certain pharmaceutical dosage forms, the prodrug form of the compounds, especially including acylated (acetylated or other), and ether (alkyl and related) derivatives, phosphate esters, thiophosphoramidates, phosphoramidates, and various salt forms of the present compounds, are preferred. One of ordinary skill in the art will recognize how to readily modify the present compounds to prodrug forms to facilitate delivery of active compounds to a targeted site within the host organism or patient. The routineer also will take advantage of favorable pharmacokinetic parameters of the prodrug forms, where applicable, in delivering the present compounds to a targeted site within the host organism or patient to maximize the intended effect of the compound.

The amount of compound included within therapeutically active formulations according to the present invention is an effective amount for treating the HCV infection, reducing the likelihood of a HCV infection or the inhibition, reduction, and/or abolition of HCV or its secondary effects, including disease states, conditions, and/or complications which occur secondary to HCV. In general, a therapeutically effective amount of the present compound in pharmaceutical dosage form usually ranges from about 0.001 mg/kg to about 100 mg/kg per day or more, more often, slightly less than about 0.1 mg/kg to more than about 25 mg/kg per day of the patient or considerably more, depending upon the compound used, the condition or infection treated and the route of administration. The active nucleoside compound according to the present invention is often administered in amounts ranging from about 0.1 mg/kg to about 15 mg/kg per day of the patient, depending upon the pharmacokinetics of the agent in the patient. This dosage range generally produces effective blood level concentrations of active compound which may range from about 0.001 to about 100, about 0.05 to about 100 micrograms/cc of blood in the patient.

Often, to treat, prevent or delay the onset of these infections and/or to reduce the likelihood of an HCV virus infection, or a secondary disease state, condition or complication of HCV, the compositions will be administered in oral dosage form in amounts ranging from about 250 micrograms up to about 500 mg or more at least once a day, for example, at least 25, 50, 100, 150, 250 or 500 milligrams, up to four times a day. The present compounds are often administered orally, but may be administered parenterally, topically, or in suppository form, as well as intranasally, as a nasal spray or as otherwise described herein.

In the case of the co-administration of the present compounds in combination with another anti-HCV compound as otherwise described herein, the amount of the compound according to the present invention to be administered ranges from about 0.01 mg/kg of the patient to about 500 mg/kg. or more of the patient or considerably more, depending upon the second agent to be co-administered and its potency against the virus, the condition of the patient and severity of the disease or infection to be treated and the route of administration. The other anti-HCV agent may for example be administered in amounts ranging from about 0.01 mg/kg to about 500 mg/kg. In certain preferred embodiments, these compounds may be often administered in an amount ranging from about 0.5 mg/kg to about 50 mg/kg or more (usually up to about 100 mg/kg), generally depending upon the pharmacokinetics of the two agents in the patient. These dosage ranges generally produce effective blood level concentrations of active compound in the patient.

For purposes of the present invention, a prophylactically or preventive effective amount of the compositions according to the present invention falls within the same concentration range as set forth above for therapeutically effective amount and is usually the same as a therapeutically effective amount.

Administration of the active compound may range from continuous (intravenous drip) to several oral or intranasal administrations per day (for example, Q.I.D.) or transdermal administration and may include oral, topical, parenteral, intramuscular, intravenous, sub-cutaneous, transdermal (which may include a penetration enhancement agent), buccal, and suppository administration, among other routes of administration. Enteric coated oral tablets may also be used to enhance bioavailability of the compounds for an oral route of administration. The most effective dosage form will depend upon the bioavailability/pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is often intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs, and solutions, suitable carriers and additives including water, glycols, oils, alcohols, flavoring agents, preservatives, coloring agents, and the like may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents, and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester prodrug forms of the nucleoside compounds according to the present invention.

In typical embodiments according to the present invention, the compounds and compositions are used to treat, prevent or delay a HCV infection or a secondary disease state, condition or complication of HCV.

V. Combination and Alternation Therapy

It is well recognized that drug-resistant variants of viruses can emerge after prolonged treatment with an antiviral agent. Drug resistance most typically occurs by mutation of a gene that encodes for an enzyme used in viral replication. The efficacy of a drug against an HCV infection, can be prolonged, augmented, or restored by administering the compound in combination or alternation with another, and perhaps even two or three other, antiviral compounds that induce a different mutation or act through a different pathway, from that of the principle drug. Alternatively, the pharmacokinetics, bio distribution, half-life, or other parameter of the drug can be altered by such combination therapy (which may include alternation therapy if considered concerted). Since the disclosed β-D-2'-D-2'-α-fluoro-2'-β-C-substituted-2-modified-$N^6$-substituted purine nucleotides are NS5B polymerase inhibitors, it may be useful to administer the compound to a host in combination with, for example a:

(1) Protease inhibitor, such as an NS3/4A protease inhibitor;
(2) NS5A inhibitor;
(3) Another NS5B polymerase inhibitor;
(4) NS5B non-substrate inhibitor;
(5) Interferon alfa-2a, which may be pegylated or otherwise modified, and/or ribavirin;
(6) Non-substrate-based inhibitor;
(7) Helicase inhibitor;
(8) Antisense oligodeoxynucleotide (S-ODN);
(9) Aptamer;
(10) Nuclease-resistant ribozyme;
(11) iRNA, including microRNA and SiRNA;
(12) Antibody, partial antibody or domain antibody to the virus, or
(13) Viral antigen or partial antigen that induces a host antibody response.

Non limiting examples of anti-HCV agents that can be administered in combination with the β-D-2'-D-2'-α-fluoro-2'-β-C-substituted-2-modified-$N^6$-substituted purine nucleotides of the invention are:

(i) protease inhibitors such as telaprevir (Incivek®), boceprevir (Victrelis™), simeprevir (Olysio™), paritaprevir (ABT-450), ACH-2684; AZD-7295; BMS-791325; danoprevir; Filibuvir; GS-9256; GS-9451; MK-5172; Setrobuvir; Sovaprevir; Tegobuvir; VX-135; VX-222 and ALS-220;
(ii) NS5A inhibitor such as ACH-2928, ACH-3102, IDX-719, daclatasvir, ledispasvir and Ombitasvir (ABT-267);
(iii) NS5B inhibitors such as ACH-3422; AZD-7295; Clemizole; ITX-5061; PPI-461; PPI-688, Sovaldi®, MK-3682, and mericitabine;
(iv) NS5B inhibitors such as ABT-333, MBX-700; and,
(v) Antibody such as GS-6624.

If the β-D-2'-D-2'-α-fluoro-2'-β-C-substituted-2-modified-$N^6$-substituted purine nucleotide is administered to treat advanced hepatitis C virus leading to liver cancer or cirrhosis, in one embodiment, the compound can be administered in combination or alternation with another drug that is typically used to treat hepatocellular carcinoma (HCC), for example, as described by Andrew Zhu in "New Agents on the Horizon in Hepatocellular Carcinoma" Therapeutic Advances in Medical Oncology, V 5(1), January 2013, 41-50. Examples of suitable compounds for combination therapy where the host has or is at risk of HCC include anti-angiogenic agents, sunitinib, brivanib, linifanib, ramucirumab, bevacizumab, cediranib, pazopanib, TSU-68, lenvatinib, antibodies against EGFR, mTor inhibitors, MEK inhibitors, and histone decetylace inhibitors.

Drugs that are currently approved for influenza are Amantadine, Rimantadine and Oseltamivir. Any of these drugs can be used in combination or alternation with an active compound provided herein to treat a viral infection susceptible to such. Ribavirin is used to treat measles, Influenza A, influenza B, parainfluenza, severe RSV bronchiolitis and SARS as well as other viral infections, and therefore is particularly useful in combination with the present compound for treatment of the host infected with a single stranded RNA virus. Palivizumab is approved for use in infants with high risk for RSV infection.

Currently, there are no approved drugs for West Nile virus. Physicians are recommended to provide intensive support therapy, which may involve hospitalization, intravenous fluids, use of a ventilator to assist breathing, medications to control seizures, brain swelling, nausea and vomiting, and the use of antibiotics to prevent bacterial infections for making the disease even worse. This highlights the importance of the present compounds for viral medical therapy.

VI. Process of Preparation of β-D-2'-D-2'-α-fluoro-2'-β-C-substituted-2-modified-N⁶-Substituted Purine Nucleotides of the Invention General methods for providing the compounds of the present invention are known in the art or described herein. The synthesis of 2'-chloro nucleotides is described in US 20150366888, WO 2014058801; WO 2015/066370 and WO 2015200219.

EXAMPLES

General Methods $^1$H, $^{19}$F and $^{31}$P NMR spectra were recorded on a 300 MHz Fourier transform Brücker spectrometer. Spectra were obtained from samples prepared in 5 mm diameter tubes in CDCl$_3$, CD$_3$OD or DMSO-d$_6$. The spin multiplicities are indicated by the symbols s (singlet), d (doublet), t (triplet), m (multiplet) and, br (broad). Coupling constants (J) are reported in Hz. MS spectra were obtained using electrospray ionization (ESI) on an Agilent Technologies 6120 quadrupole MS apparatus. The reactions were generally carried out under a dry nitrogen atmosphere using Sigma-Aldrich anhydrous solvents. All common chemicals were purchased from commercial sources.

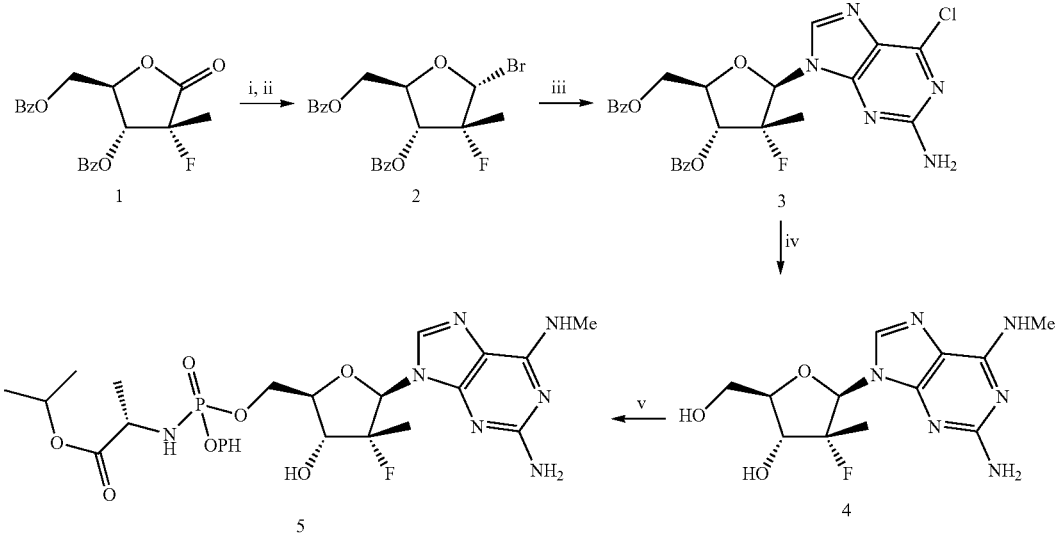

i) Li(OtBu)$_3$AlH, THF, -30° C. -> -15° C.; ii) PPh$_3$, CBr$_4$, DCM, -20° C. -> 0° C.; iii) 2-amino-6-chloropurine, tBuOK, tBuOH/MeCN 9:1, 65° C.; iv) MeNH$_2$ (33%), MeOH, 85° C.; v Isopropyl ((R,S)-(pentaflurorphenoxy)-phenoxy-phosphoryl-L-alaninate, tBuMgCl, THF, 0° C., -> r.t.

The following abbreviations are used in the synthetic schemes.
- CBr$_4$: Carbon tetrabromide
- DBU: 1,8-Diazabicyclo[5.4.0]undec-7-ene
- DCM: Dichloromethane
- THF: Tetrahydrofuran (THF), anhydrous
- EtOAc: Ethyl acetate
- EtOH: Ethanol
- Li(OtBu)$_3$AlH: Lithium tri-tert-butoxyaluminum hydride
- Na$_2$SO$_4$: Sodium sulphate (anhydrous)
- MeCN: Acetonitrile
- MeNH$_2$: Methylamine
- MeOH: Methanol
- Na$_2$SO$_4$: Sodium sulfate
- NaHCO$_3$: Sodium bicarbonate
- NH$_4$Cl: Ammonium chloride
- NH$_4$OH: Ammonium hydroxide
- PE: Petroleum ether
- Ph$_3$P: Triphenylphosphine
- Silica gel (230 to 400 mesh, Sorbent)
- t-BuMgCl: t-Butyl magnesium chloride
- t-BuOK: Sodium tert-butoxide
- t-BuOH: Tert-butanol

Example 1

Preparation of isopropyl ((((R,S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate Step 1. Preparation of ((2R,3R,4R,5R)-3-(benzoyloxy)-5-bromo-4-fluoro-4-methyltetrahydrofuran-2-yl)methyl benzoate (2)

To a solution of (2R)-3,5-di-O-benzoyl-2-fluoro-2-C-methyl-D-ribono-γ-lactone (24.8 g, 66.6 mmol) in dry THF (333 mL), under a nitrogen atmosphere and cooled to -30° C., was added lithium tri-tert-butoxyaluminum hydride (1.0 M in THF, 22.6 mL, 22.6 mmol) dropwise. After completion of the addition the reaction mixture was slowly warmed up to -15° C. over 90 min then EtOAc was added (300 mL) and the mixture was quenched with a saturated aq. NH$_4$Cl solution (200 mL). The resulting solution was filtered on Celite® and the filtrate was extracted twice with EtOAc. The combined organics were dried (Na$_2$SO$_4$), filtered and concentrated. The residue was taken up in dry DCM (225 mL) under a nitrogen atmosphere, cooled to -20° C., then PPh$_3$ (19.1 g, 72.8 mmol) was added. After 10 min of stirring at −20° C., CBr$_4$ (26.0 g, 78.4 mmol) was added and the reaction mixture was allowed to slowly warm up to 0° C. over 2 h. The resulting mixture was poured onto a silica gel column and eluted with PE/EtOAc (gradient 100:0 to 80:20). The fractions containing the α-bromofuranoside were collected and concentrated to afford the product 2 (18.1 g, 41.3 mmol, 62% over two steps) as a thick colorless oil.

$^1$H NMR (300 MHz, CDCl$_3$) δ 8.15-8.11 (m, 2H), 8.04-8.01 (m, 2H), 7.64-7.55 (m, 2H), 7.51-7.41 (m, 4H), 6.34 (d, J=1.6 Hz, 1H), 5.29 (dd, J=5.5, 3.1 Hz, 1H), 4.89-4.85 (m, 1H), 4.78 (dd, J=12.5, 3.2 Hz, 1H), 4.63 (dd, J=12.5, 4.5 Hz, 1H), 1.72 (d, J=21.6 Hz, 3H). $^{19}$F NMR (282 MHz, CDCl$_3$) δ −150.0.

Step 2. Preparation of (2R,3R,4R,5R)-5-(2-amino-6-chloro-9H-purin-9-yl)-2-(benzoyloxymethyl)-4-fluoro-4-methyltetrahydrofuran-3-yl benzoate (3)

2-Amino-6-chloropurine (2.63 g, 15.5 mmol) was suspended in t-BuOH (54 mL) under a nitrogen atmosphere. The reaction mixture was heated to 30° C. then potassium tert-butoxide (1.69 g, 15.1 mmol) was added. After 45 min a solution of bromofuranoside 2 (2.24 g, 5.12 mmol) dissolved in anhydrous MeCN (6 mL) was added, the reaction mixture was heated to 65° C. for 16 h then cooled down to room temperature. A saturated aq. NH$_4$Cl solution (70 mL) was added and the resulting solution was extracted with EtOAc (3×60 mL). The combined organics were dried (Na$_2$SO$_4$), filtered and concentrated. The residue was purified twice by column chromatography (gradient PE/EtOAc 80:20 to 0:100 then 60:40 to 20:80) to afford the product 3 (1.56 g, 2.96 mmol, 57%) as a white solid.

$^1$H NMR (300 MHz, CDCl$_3$) δ 8.05-8.02 (m, 2H), 7.95-7.92 (m, 2H), 7.88 (s, 1H), 7.63-7.57 (m, 1H), 7.53-7.41 (m, 3H), 7.35-7.30 (m, 2H), 6.43 (dd, J=22.6, 9.1 Hz, 1H), 6.12 (d, J=18.3 Hz, 1H), 5.34 (br s, 2H), 5.00 (dd, J=11.9, 4.5 Hz, 1H), 4.79-4.73 (m, 1H), 4.60 (dd, J=11.9, 5.3 Hz, 1H), 1.34 (d, J=22.6 Hz, 3H). $^{19}$F NMR (282 MHz, CDCl$_3$) δ −157.0. MS (ESI) m/z calcd. for C$_{25}$H$_{22}$FN$_5$O$_5$ [M+H]$^+$ 526.9; found 527.0.

Step 3. Preparation of (2R,3R,4R,5R)-5-(2-amino-6-(methylamino)-9H-purin-9-yl)-4-fluoro-2-(hydroxymethyl)-4-methyltetrahydrofuran-3-ol (4)

To a solution of compound 3 (575 mg, 1.09 mmol) in MeOH (9 mL) was added methylamine (33% in absolute EtOH, 1.7 mL, 1.81 mmol). The reaction mixture was heated to 85° C. in a sealed tube for 16 h, cooled down to room temperature and concentrated. The residue was purified by column chromatography (gradient DCM/MeOH 100:0 to 85:15) then reverse phase column chromatography (gradient H$_2$O/MeOH 100:0 to 0:100) to afford the product 4 (286 mg, 0.91 mmol, 84%) as a white solid.

$^1$H NMR (300 MHz, CD$_3$OD) δ 8.06 (s, 1H), 6.11 (d, J=18.1 Hz, 1H), 4.41 (dd, J=24.4, 9.1 Hz, 1H), 4.07-4.01 (m, 2H), 3.86 (dd, J=12.9, 3.3 Hz, 1H), 3.04 (br s, 3H), 1.16 (d, J=22.3 Hz, 3H). $^{19}$F NMR (282 MHz, CD$_3$OD) δ −163.7. MS (ESI) m/z calcd. for C$_{12}$H$_9$FN$_6$O$_3$ [M+H]$^+$ 313.1; found 313.2.

Step 4. Preparation of isopropyl ((((R,S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate (5)

To a solution of compound 4 (114 mg, 365 µmol) in dry THF (4 mL), under a nitrogen atmosphere and cooled to 0° C. was added t-butyl magnesium chloride (1.0 M in THF, 0.66 mL, 660 µmol) dropwise over 10 min. The reaction mixture was stirred 15 min at 0° C. then another 15 min at room temperature. The reaction mixture was cooled down to 0° C. then a solution of isopropyl ((R,S)-(pentafluorophenoxy)-phenoxy-phosphoryl)-L-alaninate, Ross, B. S., Reddy, P. G., Zhang, H. R., Rachakonda, S., and Sofia, M. J., J. Org. Chem., (2011), (253 mg, 558 µmol) dissolved in dry THF (1 mL) was added dropwise over 10 min. The reaction mixture was stirred at 0° C. for 30 min followed by 18 h at room temperature then quenched with a saturated aq. NH$_4$Cl solution (4 mL) and extracted with EtOAc (3×5 mL). The combined organics were dried, filtered (Na$_2$SO$_4$) and concentrated. The residue was purified by column chromatography (gradient DCM/MeOH 100:0 to 90:10) then reverse phase column chromatography (gradient H$_2$O/MeOH 100:0 to 0:100) to afford product 5 (a mixture of diastereomers, 101 mg, 174 µmol, 48%) as a white solid.

$^1$H NMR (300 MHz, CD$_3$OD) δ 7.83 (s, 0.55H), 7.82 (s, 0.45H), 7.38-7.16 (m, 5H), 6.15 (d, J=18.5 Hz, 0.45 H), (d, J=18.8 Hz, 0.55 H), 4.99-4.88 (overlapped with H$_2$O, m, 1H), 4.65-4.36 (m, 3H), 4.25-4.17 (m, 1H), 3.97-3.85 (m, 1H), 3.05 (br s, 3H), 1.32-1.28 (m, 3H), 1.25-1.15 (m, 9H). $^{19}$F NMR (282 MHz, CD$_3$OD) δ −162.8 (s), −163.3 (s). $^{31}$P NMR (121 MHz, CD$_3$OD) δ 4.10 (s), 3.99 (s). MS (ESI) m/z calcd. for C$_{24}$H$_{34}$FN$_7$O$_7$P [M+H]$^+$ 582.2; found 582.2.

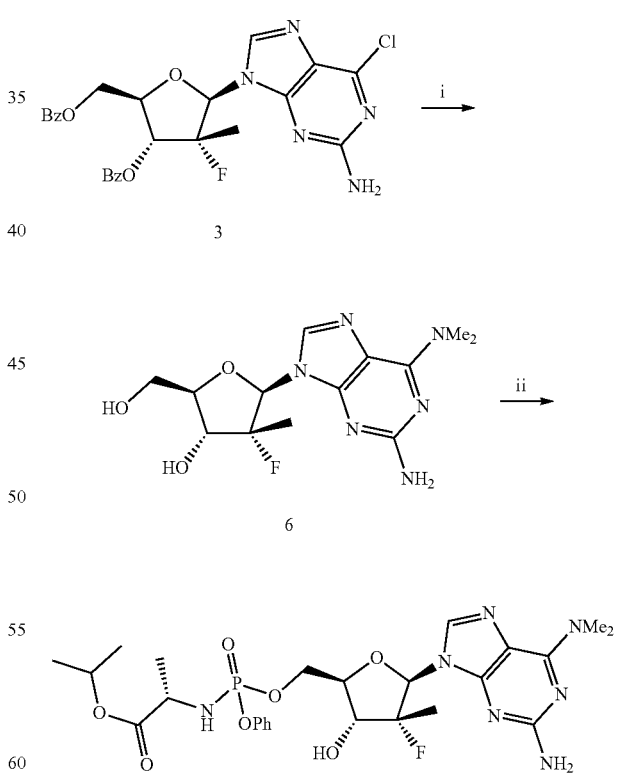

i) Me$_2$NH·HCl, DBU, MeOH, 85° C.; v) Isopropyl ((R,S)-(pentafluorophenoxy)-phenoxy-phosphoryl)-L-alaninate, tBuMgCl, THF, 0° C.

Example 2

Preparation of isopropyl ((((R,S)-(2R,3R,4R,5R)-5-(2-Amino-6-(dimethylamino)-9H-purin-9-yl)-4-fluoro-3-hydroxy-4-methyltetrahydrofuran-2-yl)methoxy)-phenoxy-phosphoryl)-L-alaninate (7)

Step 1. Preparation of (2R,3R,4R,5R)-5-(2-amino-6-(dimethylamino)-9H-purin-9-yl)-4-fluoro-2-(hydroxymethyl)-4-methyltetrahydrofuran-3-ol (6)

To a solution of compound 3, from Example 1, (500 mg, 0.95 mmol) in MeOH (6 mL) was added dimethylamine hydrochloride (783 mg, 9.6 mmol) and 1,8-diazabicyclo[5.4.0]undec-7-ene (1.43 mL, 9.6 mmol). The reaction mixture was heated at 85° C. in a sealed tube for 6 h, cooled down to room temperature and concentrated. The residue was purified by column chromatography (gradient DCM/MeOH 100:0 to 85:15) then by reverse phase column chromatography (gradient $H_2O$/MeOH 100:0 to 0:100) to afford product 6 (200 mg, 0.61 mmol, 64%) as a white solid.

$^1$H NMR (300 MHz, $CD_3OD$) δ 8.07 (s, 1H), 6.14 (d, J=18.1 Hz, 1H), 4.41 (dd, J=24.4, 9.2 Hz, 1H), 4.08-4.02 (m, 2H), 3.87 (dd, J=12.8, 2.9 Hz, 1H), 3.42 (br s, 6H), 1.16 (d, J=22.0 Hz, 3H). $^{19}$F NMR (282 MHz, $CD_3OD$) δ -163.8. MS (ESI) m/z calcd. for $C_{13}H_{20}FN_6O_3$ [M+H]$^+$ 327.2; found 327.2.

Step 2. Preparation of isopropyl ((((R,S)-(2R,3R,4R,5R)-5-(2-amino-6-(dimethylamino)-9H-purin-9-yl)-4-fluoro-3-hydroxy-4-methyltetrahydrofuran-2-yl)methoxy)-phenoxy-phosphoryl)-L-alaninate (7)

To a solution of compound 6 (80 mg, 245 μmol) in dry THF (4 mL), under a nitrogen atmosphere and cooled to 0° C. was added tert-butyl magnesium chloride (1.0 M in THF, 0.64 mL, 640 μmol) drop-wise over 10 min. The reaction mixture was stirred 15 min at 0° C. then another 15 min at room temperature. The reaction mixture was cooled down to 0° C. then a solution of isopropyl ((R,S)-(pentafluorophenoxy)-phenoxy-phosphoryl)-L-alaninate (167 mg, 367 μmol) dissolved in dry THF (4 mL) was added drop-wise over 10 min. The reaction mixture was stirred at 0° C. for 30 min and 18 h at room temperature. The reaction was quenched with a saturated aq. $NH_4Cl$ solution (4 mL) and extracted with EtOAc (3×5 mL). The combined organics were dried, filtered ($Na_2SO_4$) and concentrated. The residue was purified by column chromatography (gradient DCM/MeOH 100:0 to 90:10) and then by reverse phase column chromatography (gradient $H_2O$/MeOH 100:0 to 0:100) to afford the product 7 (mixture of diastereomers, 35 mg, 58 μmol, 24%) as a white solid.

$^1$H NMR (300 MHz, $CD_3OD$) δ 7.83 (s, 0.5H), 7.82 (s, 0.5H), 7.34-7.16 (m, 5H), 6.15 (d, J=18.7 Hz, 0.5 H), 6.13 (d, J=18.8 Hz, 0.5 H), 4.99-4.85 (overlapped with $H_2O$, m, 1H), 4.65-4.26 (m, 3H), 4.27-4.12 (m, 1H), 3.99-3.81 (m, 1H), 3.42, 3.41 (2br s, 6H), 1.36-1.25 (m, 3H), 1.24-1.11 (m, 9H). $^{19}$F NMR (282 MHz, $CD_3OD$) δ -162.7 (s), -163.2 (s). $^{31}$P NMR (121 MHz, $CD_3OD$) δ 4.08 (s), 4.00 (s). MS (ESI) m/z calcd. for $C_{25}H_{36}FN_7O_7P$ [M+H]$^+$ 596.5; found 596.2.

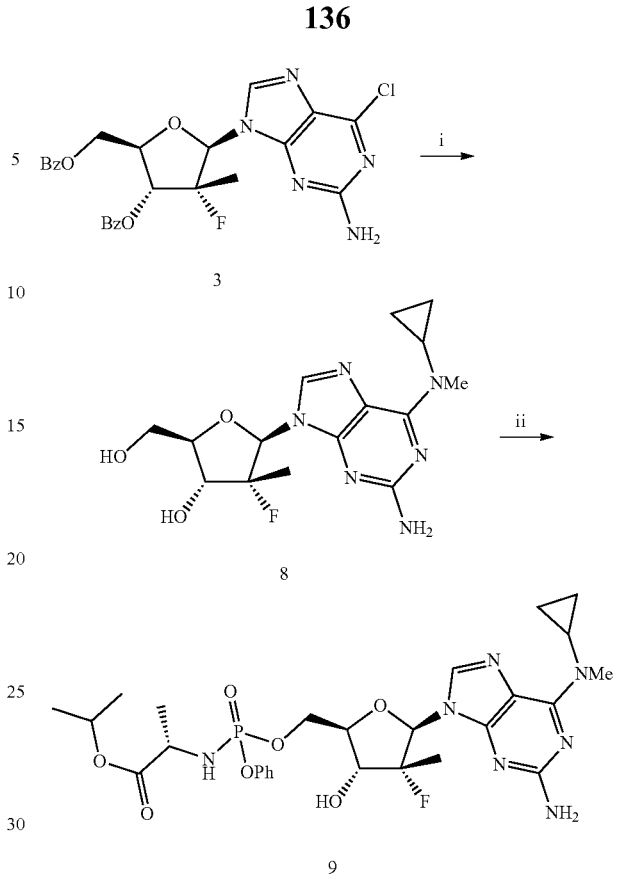

i) a) N-Methylcyclopropylamine hydrochloride, $Et_3N$, MeOH, 100° C.; b) $NH_4OH$, MeOH, 100° C.; ii) Isopropyl ((R,S)-(pentafluorophenoxy)-phenoxy-phosphoryl)-L-alaninate, tBuMgCl, THF, 0° C.

Example 3

Preparation of Isopropyl ((((R,S)-(2R,3R,4R,5R)-5-(2-amino-6-(N-methyl-cyclopropylamino)-9H-purin-9-yl)-4-fluoro-3-hydroxy-4-methyltetrahydrofuran-2-yl)methoxy)-phenoxy-phosphoryl)-L-alaninate (9)

Step 1. Preparation of (2R,3R,4R,5R)-5-(2-Amino-6-(N-methylcyclopropylamino)-9H-purin-9-yl)-4-fluoro-2-(hydroxymethyl)-4-methyltetrahydrofuran-3-ol (8)

To a solution of compound 3 (600 mg, 1.14 mmol) in MeOH (10 mL) was added N-methylcyclopropylamine hydrochloride (366 mg, 3.40 mmol) and triethylamine (470 μL, 3.40 mmol). The reaction mixture was heated at 100° C. in a sealed tube for 15 h and cooled down to room temperature. An aqueous solution containing 30% $NH_4OH$ (4 mL) was added and the reaction mixture was heated at 100° C. in a sealed tube for 2 h, cooled down and concentrated. The residue was purified by column chromatography (gradient DCM/MeOH 100:0 to 90:10) to afford product 8 (351 mg, 0.99 mmol, 87%) as a white solid.

$^1$H NMR (300 MHz, $CD_3OD$) δ 8.13 (s, 1H), 6.15 (d, J=18.0 Hz, 1H), 4.40 (dd, J=24.3, 9.0 Hz, 1H), 4.06-4.02 (m, 2H), 3.89-3.83 (m, 1H), 3.32 (m, 3H), 3.18-3.11 (m, 1H), 1.16 (d, J=22.2 Hz, 3H), 0.96-0.89 (m, 2H), 0.74-0.69 (m, 2H). $^{19}$F NMR (282 MHz, $CD_3OD$) δ -163.8. MS (ESI) m/z calcd. for $C_{15}H_{22}FN_6O_3$ [M+H]$^+$ 353.2; found 353.2.

Step 2. Preparation of isopropyl ((((R,S)-(2R,3R, 4R,5R)-5-(2-amino-6-(N-methyl-cyclopropy-lamino)-9H-purin-9-yl)-4-fluoro-3-hydroxy-4-methyltetrahydrofuran-2-yl)methoxy)-phenoxy-phosphoryl)-L-alaninate (9)

To a solution of compound 8 (200 mg, 0.57 mmol) in dry THF (15 mL) at 0° C. was added tert-butyl magnesium chloride (1.0 M in THF, 680 µL, 0.68 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (283 mg, 0.62 mmol) dissolved in dry THF (4 mL) was added dropwise over 10 min. The reaction mixture was stirred at 0° C. for 30 min and 18 h at room temperature. The reaction was quenched with a saturated aq. NH$_4$Cl solution (4 mL) and extracted with EtOAc (3×5 mL). The combined organics were dried over Na$_2$SO$_4$ and concentrated. The residue was purified by column chromatography (gradient DCM/MeOH 100:0 to 90:10) and then by reverse phase column chromatography (gradient H$_2$O/MeOH 100:0 to 0:100) to afford product 9 (mixture of 2 diastereoisomers, 160 mg, 0.26 mmol, 45%) as a white solid.

$^1$H NMR (300 MHz, CD$_3$OD) δ 7.85 (m, 1H), 7.38-7.16 (m, 5H), 6.18 (d, J=18.6 Hz) and 6.16 (d, J=18.9 Hz, 1H), 4.95-4.90 (overlapped with H$_2$O, m, 1H), 4.58-4.47 (m, 3H), 4.22-4.19 (m, 1H), 3.95-3.87 (m, 1H), 3.36-3.34 (overlapped with MeOH, m, 3H), 3.19-3.12 (m, 1H), 1.32-1.22 (m, 12H), 0.96-0.89 (m, 2H), 0.74-0.69 (m, 2H). $^{31}$P NMR (121 MHz, CD$_3$OD) δ 4.11 (s), 4.02 (s). MS (ESI) m/z calcd. for C$_{27}$H$_{28}$FN$_7$O$_7$P [M+H]$^+$ 622.2; found 622.2.

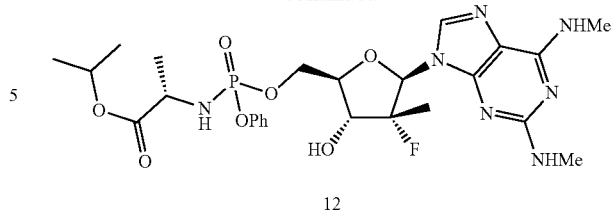

i) 2,6-dichloropurine, tBuOK, tBuOH/MeCN, 65° C.; ii) MeNH$_2$, MeOH, 130° C.; iii) Isopropyl ((R,S)-(pentafluorophenoxy)-phenoxy-phosphoryl)-L-alaninate, tBuMgCl, THF, 0° C. to RT Example 4

Preparation of isopropyl ((((R,S)-(2R,3R,4R,5R)-5-(2,6-bis-methylamino-9H-purin-9-yl)-4-fluoro-3-hydroxy-4-methyltetrahydrofuran-2-yl)methoxy)-phenoxy-phosphoryl)-L-alaninate (12)

Step 1. Preparation of (2R,3R,4R,5R)-5-(2,6-di-chloro-9H-purin-9-yl)-2-(benzoyloxymethyl)-4-fluoro-4-methyltetrahydrofuran-3-yl benzoate (10)

The compound 2,6-dichloropurine (1.30 g, 6.86 mmol) was suspended in t-BuOH (25 mL) under a nitrogen atmosphere. Potassium tert-butoxide (778 mg, 6.92 mmol) was added portion-wise then the reaction mixture was stirred at room temperature. After 1 h, a solution of bromofuranoside 2 (1.0 g, 2.29 mmol) dissolved in anhydrous MeCN (20 mL) was added and the reaction mixture was heated at 65° C. overnight and then cooled down to room temperature. A saturated aq. NH$_4$Cl solution was added and the resulting solution was extracted with EtOAc (3 times). The combined organics were dried over Na$_2$SO$_4$ and concentrated. The residue was purified by column chromatography (gradient PE/EtOAc 100:0 to 0:100) to afford product 10 (148 mg, 0.27 mmol, 12%) as a sticky solid.

$^1$H NMR (300 MHz, CDCl$_3$) δ 8.31 (s, 1H), 8.12-8.09 (m, 2H), 8.02-7.99 (m, 2H), 7.64-7.39 (m, 6H), 6.38 (d, J=17.2 Hz, 1H), 6.02 (dd, J=21.2, 8.9 Hz, 1H), 4.90-4.68 (m, 3H), 1.33 (d, J=22.4 Hz, 3H). $^{19}$F NMR (282 MHz, CDCl$_3$) δ -158.0. MS (ESI) m/z calcd. for C$_{25}$H$_{20}$Cl$_2$FN$_4$O$_5$ [M+H]$^+$ 546.4; found 546.3.

Step 2. Preparation of (2R,3R,4R,5R)-5-(2,6-bis-methylamino-9H-purin-9-yl)-4-fluoro-2-(hydroxymethyl)-4-methyltetrahydrofuran-3-ol (11)

A solution of compound 10 (148 mg, 0.27 mmol) in methylamine (33% in EtOH, 30 mL) was heated at 130° C. in a sealed tube for 4 days, cooled down to room temperature and concentrated. The residue was purified by column chromatography (gradient DCM/MeOH 100:0 to 50:50) followed by reverse phase column chromatography (gradient H$_2$O/MeOH 100:0 to 0:100) to afford product 11 (33 mg, 0.10 mmol, 37%) as a white solid. $^1$H NMR (300 MHz, CD$_3$OD) δ 8.00 (s, 1H), 6.12 (d, J=18.5 Hz, 1H), 4.51 (dd, J=24.4, 9.5 Hz, 1H), 4.06-3.85 (m, 3H), 3.04 (s, 3H), 2.93 (s, 3H), 1.20 (d, J=22.4 Hz, 3H). $^{19}$F NMR (282 MHz, CD$_3$OD) δ -163.2. MS (ESI) m/z calcd. for C$_{13}$H$_{20}$FN$_6$O$_3$ [M+H]$^+$ 327.2; found 327.2.

Step 3. Preparation of isopropyl ((((R,S)-(2R,3R, 4R,5R)-5-(2,6-bis-methylamino-9H-purin-9-yl)-4-fluoro-3-hydroxy-4-methyltetrahydrofuran-2-yl)methoxy)-phenoxy-phosphoryl)-L-alaninate (12)

To a solution of compound 11 (55 mg, 0.17 mmol) in dry THF (2 mL) at 0° C. was added tert-butyl magnesium

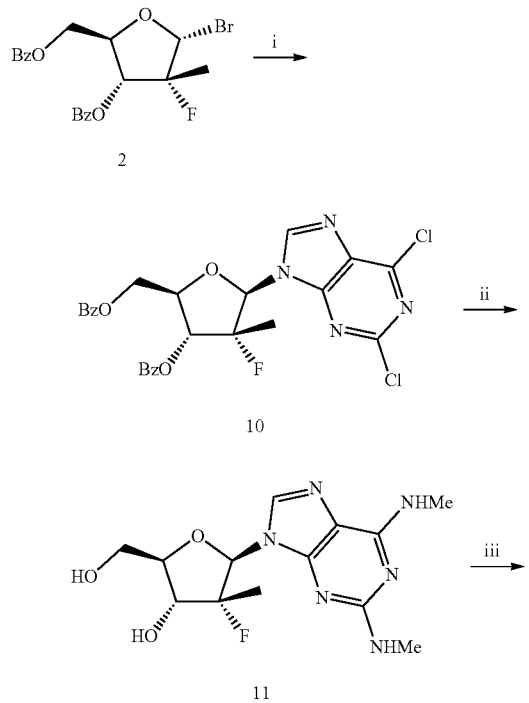

chloride (1 M in THF, 304 μL, 0.30 mmol) dropwise over 10 min. The reaction mixture was stirred 15 min at 0° C. and then 15 min at room temperature. The solution was cooled down to 0° C. and a solution of isopropyl ((R,S)-(pentafluorophenoxy)-phenoxy-phosphoryl)-L-alaninate (115 mg, 0.25 mmol) dissolved in dry THF (1 mL) was dropwise added over 10 min. The mixture was warmed slowly to room temperature and stirred for 4 days. The reaction was quenched with a saturated aq. NH$_4$Cl solution and extracted with EtOAc (3 times). The combined organics were dried over Na$_2$SO$_4$ and concentrated. The residue was purified by column chromatography (gradient DCM/MeOH 100:0 to 50:50) to yield product 12 (mixture of diastereomers, 13 mg, 0.02 mmol, 13%) as a white solid. $^1$H NMR (300 MHz, CD$_3$OD) δ 7.78 (s, 1H), 7.35-7.12 (m, 5H), 6.13 (d, J=19.1 Hz, 0.53H), 6.10 (d, J=19.2 Hz, 0.47H), 4.99-4.78 (overlapped with H$_2$O, m, 1H), 4.72-4.46 (m, 3H), 4.24-4.15 (m, 1H), 3.79-3.92 (m, 1H), 3.02 (br s, 3H), 2.92 (s+s, 3H), 1.29-1.11 (m, 12H). $^{19}$F NMR (282 MHz, CD$_3$OD) δ −162.0 (s), −162.3 (s). $^{31}$P NMR (121 MHz, CD$_3$OD) δ 3.97 (s), 3.89 (s). MS (ESI) m/z calcd. for C$_{25}$H$_{36}$FN$_7$O$_7$P [M+H]$^+$ 596.6; found 596.2.

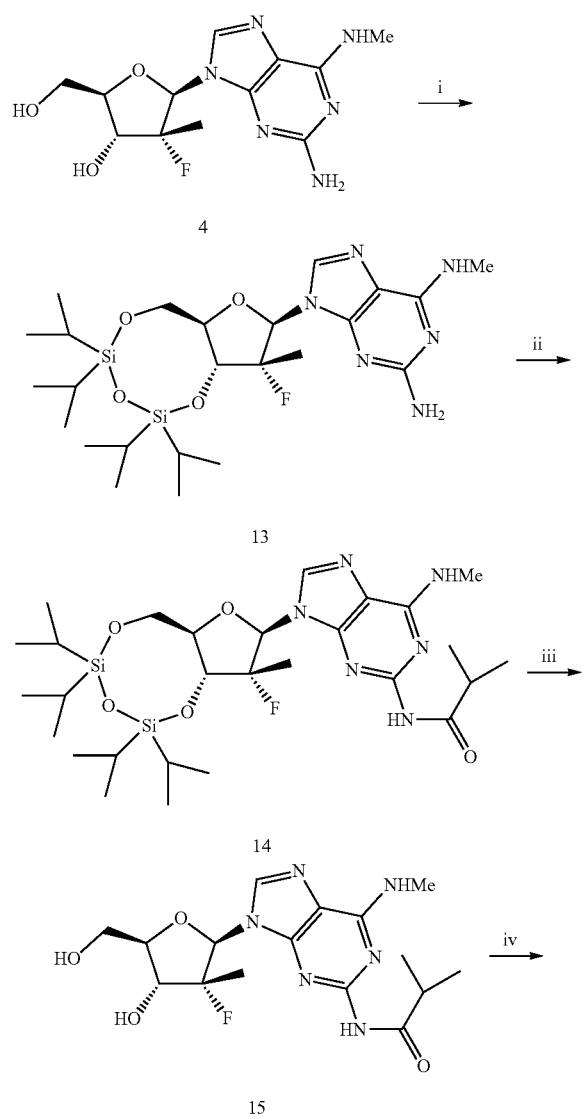

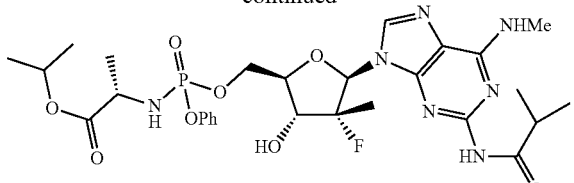

i) TIPDSCl$_2$, imiazole, DMF; ii) isobutyryl chloride, pyridine; iii) TBAF, THF; iv) Isopropyl ((R,S)-(pentafluorophenoxy)-phenoxy-phosphoryl)-L-alaninate, tBuMgCl, THF, 0° C.

Example 5

Preparation of isopropyl (((((R,S)-(2R,3R,4R,5R)-5-(2-isobutyramido-6-methylamino-9H-purin-9-yl)-4-fluoro-3-hydroxy-4-methyltetrahydrofuran-2-yl)methoxy)-phenoxy-phosphoryl)-L-alaninate (16)

Step 1. Preparation of Compound 13

To a solution of compound 4 (286 mg, 0.92 mmol) and imidazole (370 mg, 5.43 mmol) in dry DMF (6 mL) at 0° C. was added 1,3-dichloro-1,1,3,3-tetraisopropyldisiloxane (300 μL, 0.94 mmol). The reaction mixture was stirred for 2 h at RT, diluted with EtOAc (50 mL and the suspension was washed with saturated aq. NH$_4$Cl solution and brine (40 mL each). The organics were dried over Na$_2$SO$_4$ and concentrated. The residue was purified by column chromatography (gradient PE/EtOAc 7:3 to 3:7) to afford product 13 (283 mg, 0.51 mmol, 56%) as a white solid. MS (ESI) m/z calcd. for C$_{24}$H$_{44}$FN$_6$O$_4$Si$_2$ [M+H]$^+$ 555.8, found 555.2.

Step 2. Preparation of Compound 14

To a solution of compound 13 (200 mg, 0.36 mmol) in dry pyridine (3 mL) at 0° C. was added isobutyryl chloride (38 μL, 0.36 mmol). The reaction mixture was stirred for 2 h at RT. The reaction was quenched by the addition of water (500 μL). The mixture was concentrated and co-evaporated with toluene (3×10 mL). The residue was purified by column chromatography (gradient PE/EtOAc 1:0 to 1:1) to afford product 14 (99 mg, 0.16 mmol, 44%) as a white solid. MS (ESI) m/z calcd. for C$_{28}$H$_{50}$FN$_6$O$_5$Si$_2$ [M+H]$^+$ 625.9; found 625.3.

Step 3. Preparation of (2R,3R,4R,5R)-5-(2-isobutyramido-6-methylamino-9H-purin-9-yl)-4-fluoro-2-(hydroxymethyl)-4-methyltetrahydrofuran-3-ol (15)

To a solution of compound 14 (90 mg, 0.14 mmol) in dry THF (2 mL) was added tetrabutylammonium fluoride (1 M in THF, 38 μL, 0.38 mmol). The mixture was stirred for 2 h at RT and concentrated. The residue was purified by column chromatography (gradient DCM/MeOH 10:0 to 9:1) followed by reverse phase column chromatography (gradient H$_2$O/MeOH 100:0 to 0:100) to give product 15 (42 mg, 0.11 mmol, 77%) as a white solid. $^1$H NMR (300 MHz, CD$_3$OD) δ 8.31 (s, 1H), 6.29 (d, J=17.9 Hz, 1H), 4.70-4.60 (m, 1H), 4.07-3.98 (m, 2H), 3.89 (dd, J=12.5, 3.4 Hz, 1H), 3.10 (br s, 3H), 2.87 (br s, 1H), 1.23-1.16 (m, 9H). $^{19}$F NMR (282 MHz, CD$_3$OD) δ −163.8. MS (ESI) m/z calcd. for C$_{16}$H$_{24}$FN$_6$O$_4$ [M+H]$^+$ 383.4; found 383.2.

Step 4. Preparation of isopropyl ((((R,S)-(2R,3R, 4R,5R)-5-(2-isobutyramido-6-methylamino-9H-purin-9-yl)-4-fluoro-3-hydroxy-4-methyltetrahydrofuran-2-yl)methoxy)-phenoxy-phosphoryl)-L-alaninate (16)

To a solution of compound 15 (27 mg, 0.07 mmol) in dry THF (1 mL) at 0° C. was added t-butyl magnesium chloride (1.0 M in THF, 130 μL, 0.13 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (50 mg, 0.11 mmol) dissolved in dry THF (1 mL) was added dropwise over 10 min. The reaction mixture was stirred at 0° C. for 30 min followed by 18 h at room temperature then quenched with a saturated aq. $NH_4Cl$ solution (2 mL) and extracted with EtOAc (3×5 mL). The combined organics were dried over $Na_2SO_4$ and concentrated. The residue was purified by column chromatography (gradient DCM/MeOH 100:0 to 95:5) then reverse phase column chromatography (gradient $H_2O$/MeOH 100:0 to 0:100) to afford product 16 (mixture of 2 diastereoisomers, 25 mg, 0.04 mmol, 54%) as a white solid.

$^1$H NMR (300 MHz, $CD_3OD$) δ 8.05 (s, 1H), 7.33-7.13 (m, 5H), 6.27 (d, J=18.6 Hz) and 6.21 (d, J=19.1 Hz, 1H), 5.10-4.95 (m, 1H), 4.93-4.78 (overlapped with $H_2O$, m, 1H), 4.60-4.42 (m, 2H), 4.26-4.18 (m, 1H), 3.90-3.80 (m, 1H), 3.09 (br s, 3H), 2.84-2.80 (m, 1H), 1.33-1.15 (m, 18H). $^{31}$P NMR (121 MHz, $CD_3OD$) δ 3.69 (s). $^{31}$P NMR (121 MHz, $CD_3OD$) δ 4.11 (s), 3.99 (s). MS (ESI) m/z calcd. for $C_{28}H_{40}FN_7O_8P$ [M+H]$^+$ 652.6; found 652.3.

Example 6

Preparation of isopropyl ((((R,S)-(2R,3R,4R,5R)-5-(2-amino-6-(N-methyl-ethylamino)-9H-purin-9-yl)-4-fluoro-3-hydroxy-4-methyltetrahydrofuran-2-yl)methoxy)-phenoxy-phosphoryl)-L-alaninate (18)

Step 1. Preparation of (2R,3R,4R,5R)-5-(2-amino-6-(N-methyl-ethylamino)-9H-purin-9-yl)-4-fluoro-2-(hydroxymethyl)-4-methyltetrahydrofuran-3-ol (17)

To a solution of compound 3 (150 mg, 0.29 mmol) in MeOH (4 mL) was added N-methylethylamine (245 μL, 2.90 mmol). The reaction mixture was heated at 100° C. in a sealed tube for 15 h, cooled down to room temperature and concentrated. The residue was purified by column chromatography (gradient DCM/MeOH 100:0 to 90:10) to afford product 31 (89 mg, 0.26 mmol, 89%) as a white solid.

$^1$H NMR (300 MHz, $CD_3OD$) δ 8.06 (s, 1H), 6.13 (d, J=18.0 Hz, 1H), 4.40 (dd, J=24.9, 8.7 Hz, 1H), 4.11-4.01 (m, 4H), 3.98-3.83 (m, 1H), 3.34 (br. s, 3H), 1.24-1.11 (m, 6H). $^{19}$F NMR (282 MHz, $CD_3OD$) δ −163.7. MS (ESI) m/z calcd. for $C_{14}H_{22}FN_6O_3$ [M+H]$^+$ 341.2; found 341.2.

Step 2. Preparation of isopropyl ((((R,S)-(2R,3R, 4R,5R)-5-(2-amino-6-(N-methyl-ethylamino)-9H-purin-9-yl)-4-fluoro-3-hydroxy-4-methyltetrahydrofuran-2-yl)methoxy)-phenoxy-phosphoryl)-L-alaninate (18)

To a solution of compound 17 (30 mg, 0.09 mmol) in dry THF (2 mL) at 0° C. was added tert-butyl magnesium chloride (1.0 M in THF, 110 μL, 0.11 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (48 mg, 0.11 mmol) dissolved in dry THF (1 mL) was added dropwise over 10 min. The reaction mixture was stirred at 0° C. for 30 min and 18 h at room temperature. The reaction was quenched with a saturated aq. $NH_4Cl$ solution (4 mL) and extracted with EtOAc (3×5 mL). The combined organics were dried over $Na_2SO_4$ and concentrated. The residue was purified by column chromatography (gradient DCM/MeOH 100:0 to 90:10) to afford the product 18 (mixture of 2 diastereoisomers, 22 mg, 0.04 mmol, 40%) as a white solid.

$^1$H NMR (300 MHz, $CD_3OD$) δ 7.69 (m, 1H), 7.26-7.04 (m, 5H), 6.05 (d, J=18.6 Hz) and 6.03 (d, J=18.9 Hz, 1H), 4.86-4.79 (overlapped with $H_2O$, m, 1H), 4.50-4.32 (m, 3H), 4.12-4.06 (m, 1H), 3.96-3.79 (m, 3H), 3.25 (br. s, 3H), 1.24-1.02 (m, 15H). $^{31}$P NMR (121 MHz, $CD_3OD$) δ 4.07 (s), 4.00 (s). MS (ESI) m/z calcd. for $C_{26}H_{38}FN_7O_7P$ [M+H]$^+$ 609.3; found 609.2.

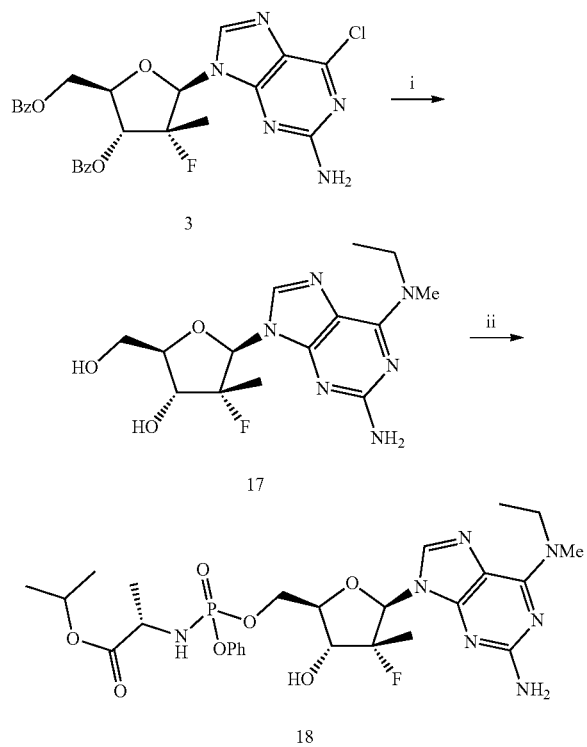

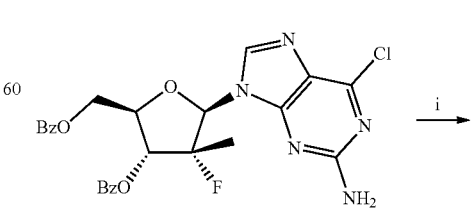

i) N-Methylethylamine, MeOH, 100° C.; ii) Isopropyl ((R,S)-(pentafluorophenoxy)-phenoxy-phosphoryl)-L-alaninate, tBuMgCl, THF, 0° C.

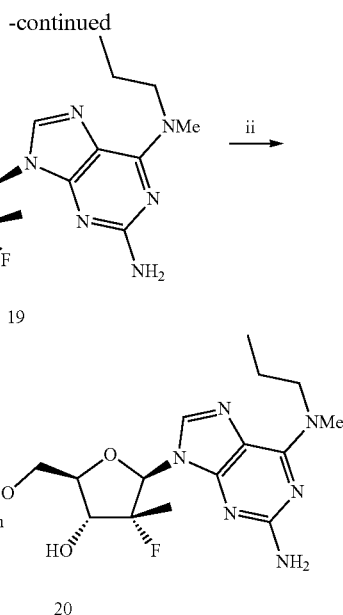

19

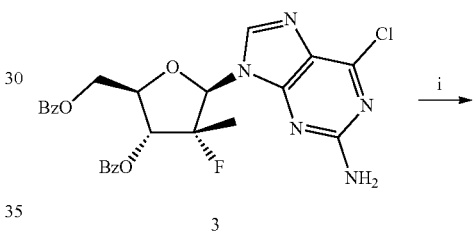

20 i) N-Methylpropylamine, MeOH, 100° C.; ii) Isopropyl ((R,S)-(pentafluorophenoxy)-phenoxy-phosphoryl)-L-alaninate, tBuMgCl, THF, 0° C.

Example 7

Preparation of isopropyl ((((R,S)-(2R,3R,4R,5R)-5-(2-amino-6-(N-methyl-propylamino)-9H-purin-9-yl)-4-fluoro-3-hydroxy-4-methyltetrahydrofuran-2-yl)methoxy)-phenoxy-phosphoryl)-L-alaninate (20)

Step 1. Preparation of (2R,3R,4R,5R)-5-(2-amino-6-(N-methyl-propylamino)-9H-purin-9-yl)-4-fluoro-2-(hydroxymethyl)-4-methyltetrahydrofuran-3-ol (19)

To a solution of compound 3 (150 mg, 0.29 mmol) in MeOH (4 mL) was added N-methylpropylamine (295 µL, 2.90 mmol). The reaction mixture was heated at 100° C. in a sealed tube for 15 h, cooled down to room temperature and concentrated. The residue was purified by column chromatography (gradient DCM/MeOH 100:0 to 90:10) then reverse phase column chromatography (gradient H$_2$O/MeOH 100:0 to 0:100) to afford product 19 (80 mg, 0.23 mmol, 78%) as a white solid.

$^1$H NMR (300 MHz, CD$_3$OD) δ 8.04 (s, 1H), 6.13 (d, J=18.3 Hz, 1H), 4.40 (dd, J=24.2, 9.2 Hz, 1H), m, 4.06-3.84 (m, 5H), 1.68 (sept, J=7.5 Hz, 2H), 1.15 (d, J=22.2 Hz, 3H), 0.93 (t, J=7.5 Hz, 3H). $^{19}$F NMR (282 MHz, CD$_3$OD) δ −163.8. MS (ESI) m/z calcd. for C$_{15}$H$_{24}$FN$_6$O$_3$ [M+H]$^+$ 355.2; found 355.2.

Step 2. Preparation of isopropyl ((((R,S)-(2R,3R,4R,5R)-5-(2-amino-6-(N-methyl-propylamino)-9H-purin-9-yl)-4-fluoro-3-hydroxy-4-methyltetrahydrofuran-2-yl)methoxy)-phenoxy-phosphoryl)-L-alaninate (20)

To a solution of compound 19 (30 mg, 0.09 mmol) in dry THF (2 mL) at 0° C. was added tert-butyl magnesium chloride (1.0 M in THF, 110 µL, 0.11 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (46 mg, 0.11 mmol) dissolved in dry THF (1 mL) was added dropwise over 10 min. The reaction mixture was stirred at 0° C. for 30 min and 18 h at room temperature. The reaction was quenched with a saturated aq. NH$_4$Cl solution (4 mL) and extracted with EtOAc (3×5 mL). The combined organics were dried over Na$_2$SO$_4$ and concentrated. The residue was purified by column chromatography (gradient DCM/MeOH 100:0 to 90:10) to afford product 20 (mixture of 2 diastereoisomers, 22 mg, 0.03 mmol, 33%) as a white solid.

$^1$H NMR (300 MHz, CD$_3$OD) δ 7.78, 7.77 (s+s, 1H), 7.37-7.13 (m, 5H), 6.15 (d, J=18.6 Hz) and 6.13 (d, J=18.9 Hz, 1H), 4.97-4.89 (overlapped with H$_2$O, m, 1H), 4.63-4.30 (m, 3H), 4.22-4.14 (m, 1H), 4.02-3.84 (m, 2H), 1.74-1.63 (3H, m), 1.32-1.27 (m, 3H), 1.23-1.13 (m, 9H), 0.94 (t, J=7.4 Hz) and 0.93 (t, J=7.4 Hz, 3H). $^{31}$P NMR (121 MHz, CD$_3$OD) δ 4.05 (s), 4.00 (s). MS (ESI) m/z calcd. for C$_{27}$H$_{40}$FN$_7$O$_7$P [M+H]$^+$ 623.3; found 623.2.

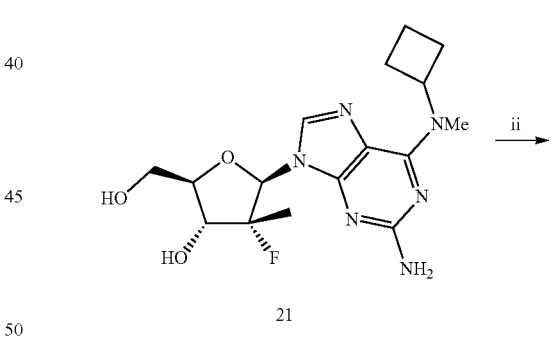

21

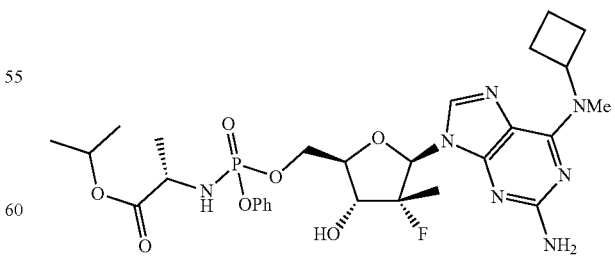

22 i) a) N-Methylcyclobutylamine hydrochloride, Et$_3$N, MeOH, 100° C.; b) NH$_4$OH, MeOH, 100° C.; ii) Isopropyl ((R,S)-(pentafluorophenoxy)-phenoxy-phosphoryl)-L-alaninate, tBuMgCl, THF, 0° C.

Example 8

Preparation of Isopropyl ((((R,S)-(2R,3R,4R,5R)-5-(2-amino-6-(N-methyl-cyclobutylamino)-9H-purin-9-yl)-4-fluoro-3-hydroxy-4-methyltetrahydrofuran-2-yl)methoxy)-phenoxy-phosphoryl)-L-alaninate (22)

Step 1. Preparation of (2R,3R,4R,5R)-5-(2-amino-6-(N-methyl-cyclobutylamino)-9H-purin-9-yl)-4-fluoro-2-(hydroxymethyl)-4-methyltetrahydrofuran-3-ol (21)

To a solution of compound 3 (150 mg, 0.29 mmol) in MeOH (4 mL) was added N-methylcyclobutylamine hydrochloride (105 mg, 0.90 mmol) and triethylamine (190 µL, 1.00 mmol). The reaction mixture was heated at 100° C. in a sealed tube for 15 h and cooled down to room temperature. An aqueous solution containing 30% $NH_4OH$ (1 mL) was added and the reaction mixture was heated at 100° C. in a sealed tube for 2 h, cooled down and concentrated. The residue was purified by column chromatography (gradient DCM/MeOH 100:0 to 90:10) to afford product 21 (90 mg, 0.25 mmol, 86%) as a pale yellow solid.

$^1$H NMR (300 MHz, $CD_3OD$) δ 8.09 (s, 1H), 6.14 (d, J=18.0 Hz, 1H), 5.80-5.70 (m, 1H), 4.44-4.33 (m, 1H), 4.06-4.02 (m, 2H), 3.88-3.84 (m, 1H), 3.34 (s, 3H), 2.38-2.19 (m, 4H), 1.79-1.71 (m, 2H), 1.17 (d, J=22.2 Hz, 3H). $^{19}$F NMR (282 MHz, $CD_3OD$) δ −163.8. MS (ESI) m/z calcd. for $C_{16}H_{24}FN_6O_3$ $[M+H]^+$ 367.2; found 367.2.

Step 2. Preparation of isopropyl ((((R,S)-(2R,3R,4R,5R)-5-(2-amino-6-(N-methyl-cyclobutylamino)-9H-purin-9-yl)-4-fluoro-3-hydroxy-4-methyltetrahydrofuran-2-yl)methoxy)-phenoxy-phosphoryl)-L-alaninate (22)

To a solution of compound 21 (50 mg, 0.14 mmol) in dry THF (2 mL) at 0° C. was added tert-butyl magnesium chloride (1.0 M in THF, 210 µL, 0.21 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (74 mg, 0.16 mmol) dissolved in dry THF (2 mL) was added dropwise over 10 min. The reaction mixture was stirred at 0° C. for 30 min and 18 h at room temperature. The reaction was quenched with a saturated aq. $NH_4Cl$ solution (4 mL) and extracted with EtOAc (3×5 mL). The combined organics were dried over $Na_2SO_4$ and concentrated. The residue was purified by column chromatography (gradient DCM/MeOH 100:0 to 90:10) and then by reverse phase column chromatography (gradient $H_2O$/MeOH 100:0 to 0:100) to afford product 22 (mixture of 2 diastereoisomers, 24 mg, 0.04 mmol, 28%) as a white solid.

$^1$H NMR (300 MHz, $CD_3OD$) δ 7.79 (s, 0.2H), 7.77 (s, 0.8H), 7.38-7.12 (m, 5H), 6.18 (d, J=17.6 Hz) and 6.16 (d, J=17.5 Hz, 1H), 4.95-4.81 (m, 2H), 4.62-4.43 (m, 3H), 4.25-4.18 (m, 1H), 3.96-3.83 (m, 1H), 3.38 (s) and 3.36 (s, 3H), 2.38-2.21 (m, 4H), 1.75-1.63 (m, 2H), 1.32-1.16 (m, 12H). $^{31}$P NMR (121 MHz, $CD_3OD$) δ 4.04 (s), 3.97 (s). MS (ESI) m/z calcd. for $C_{28}H_{40}FN_7O_7P$ $[M+H]^+$636.3; found 636.2.

Modification of the 2-amino Moiety in the Active Compounds

One of ordinary skill in the art can add a substituent to the 2-amino purine moiety by methods well known to those skilled in the art. One non-limiting process is provided here, and others can be easily adapted. ((2R,3R,4R,5R)-3-(benzoyloxy)-5-bromo-4-fluoro-4-methyltetrahydrofuran-2-yl) methyl benzoate, is treated with commercially available 2,6-dichloropurine, a base and a mixture of organic solvents at an elevated temperature to generate (2R,3R,4R,5R)-5-(2,6-dichloro-9H-purin-9-yl)-2-(benzoyloxymethyl)-4-fluoro-4-methyltetrahydrofuran-3-yl benzoate. In one embodiment, the base is potassium tert-butoxide. In one embodiment, the mixture of organic solvents comprises tert-butanol and acetonitrile. The compound, (2R,3R,4R,5R)-5-(2,6-dichloro-9H-purin-9-yl)-2-(benzoyloxymethyl)-4-fluoro-4-methyltetrahydrofuran-3-yl benzoate is treated with an amine, a base and an organic solvent at ambient temperature to generate 2-chloro-$N^6$-substituted purines. In one embodiment, the amine is methylamine. In one embodiment, the base is triethylamine. In one embodiment, the organic solvent is ethanol. One skilled in the art will also recognize that upon treatment with an amine and base, the benzoate groups on the nucleoside will simultaneously be removed to generate the deprotected furanose moiety. 2-Chloro-$N^6$-substituted purines can then be treated with an amine, and an organic solvent in a sealed tube at an elevated temperature of about 100° C. to generate $N^2,N^6$-disubstituted purine nucleosides of the present invention. In one embodiment, the amine is methylamine. In one embodiment, the organic solvent is ethanol. $N^2,N^6$-Disubstituted purine nucleosides of the present invention can be treated with a base, isopropyl ((R,S)-(pentafluorophenoxy)-phenoxy-phosphoryl)-L-alaninate and an organic solvent at a reduced temperature to generate compounds of Formula I-V. In one embodiment, the base is tert-butyl magnesium chloride. In one embodiment, the organic solvent is tetrahydrofuran.

Preparation of Stereospecific Phosphorus Enantiomers

Certain of the active compounds described herein have a chiral phosphorus moiety. Any of the active compounds described herein can be provided as an isolated phosphorus enantiomeric form, for example, at least 80, 90, 95 or 98% of the R or S enantiomer, using methods known to those of skill in the art. For example, there are a number of publications that describe how to obtain such compounds, including but not limited to column chromatography, for example as described in Example 17 below and U.S. Pat. Nos. 8,859,756; 8,642,756 and 8,333,309 to Ross, et al.

Example 9

Separation of the Stereoisomers of Compound 5

The stereoisomers of Compound 5 were separated on a Phenominex Luna column using the following conditions:

Column: Phenominex Luna 5 micron C18 (2) 250×10 mm part# OOG-4252-BO
Sample concentration: Approximately 50 mg/ml in acetonitrile
Injection volume: 50 µl
Mobile phase A: HPLC grade water
Mobile phase B: HPLC grade acetonitrile.
Flow: 5 ml/min
UV: 283 nm
Gradient:

| Time | % B |
|---|---|
| 0 | 2 |
| 40 | 50 |
| 41 | 50 |
| 41.1 | 2 |
| 45 | 2 |

Run time: 45 minutes
Column Temperature: 40° C.
A sample chromatogram of a semi-prep run is illustrated in FIG. 1.
The combined fractions were evaluated using an analytical column with the following conditions:
Column: Phenominex Luna 5 micron C18 (2) 250×2 mm part# OOG-4252-BO
Injection volume: 10 μl
Mobile phase A: HPLC grade water
Mobile phase B: HPLC grade acetonitrile.
Flow: 0.2 ml/min
UV: 283 nm
Gradient:

| Time | % B |
|------|-----|
| 0    | 2   |
| 30   | 50  |
| 40   | 50  |
| 40.1 | 2   |
| 45   | 2   |

Run time: 45 minutes
Column Temperature: 40° C.
The combined fractions for each stereoisomer were evaporated to dryness using a rotovap with a bath temperature of 30° C. The resulting solids were dissolved in 1 ml of acetonitrile, transferred into 1.7 ml microcentrifuge tubes and the solvent evaporated on the vacuum centrifuge at a temperature of 30° C.
The data on the final samples are as follows:
1. First eluding peak: Compound 5 #1 (5-1) (21.7 mgs—97.8% ee).
2. Second eluding Peak: Compound 5 #2 (5-2) (13.2 mgs—95.90/% ee).
The final weights of the 1$^{st}$ and 2$^{nd}$ peak correspond well to their percentages in the original mixture. (62.2% and 37.8% respectively).
Stereospecific Syntheses of Compounds of Formula I-VII

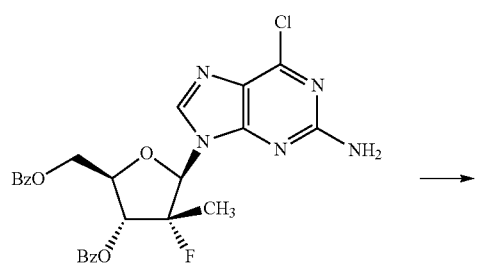

3

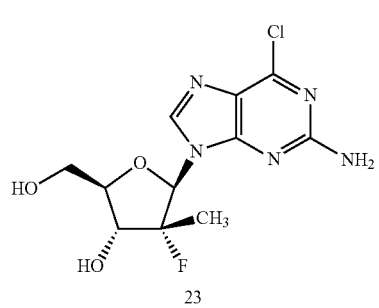

23

Example 10

Preparation of (2R,3R,4R,5R)-5-(2-amino-6-chloro-9H-purin-9-yl)-2-(hydroxymethyl)-4-fluoro-4-methyltetrahydrofuran-3-ol (23)

Step 1. Preparation of (2R,3R,4R,5R)-5-(2-amino-6-chloro-9H-purin-9-yl)-2-(hydroxymethyl)-4-fluoro-4-methyltetrahydrofuran-3-ol (23)

The compound (2R,3R,4R,5R)-5-(2-amino-6-chloro-9H-purin-9-yl)-2-(benzoyloxymethyl)-4-fluoro-4-methyltetrahydrofuran-3-yl benzoate, 3, (80 g, 140 mmol) was added to a solution of trimethylamine in methanol (7 M, 800 mL) and stirred at RT overnight. The mixture was concentrated and then purified by column chromatography (DCM:MeOH=100:1) to afford (2R,3R,4R,5R)-5-(2-amino-6-chloro-9H-purin-9-yl)-2-(hydroxymethyl)-4-fluoro-4-methyl-tetrahydrofuran-3-ol (23) (40 g, 90%).

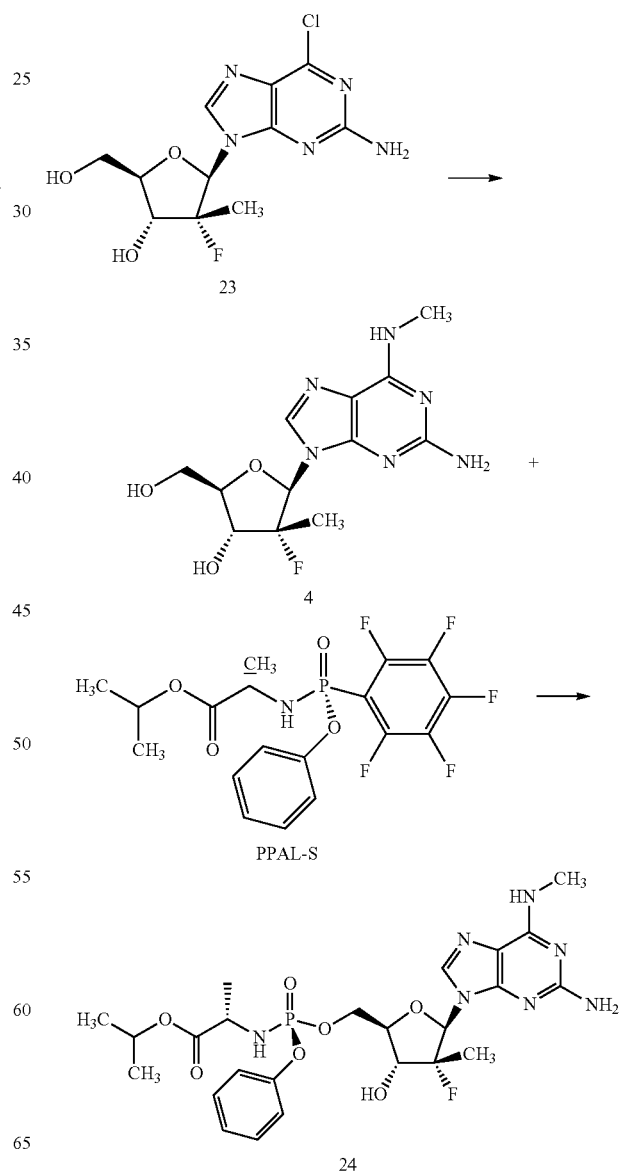

Example 11

Preparation of ((((S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate

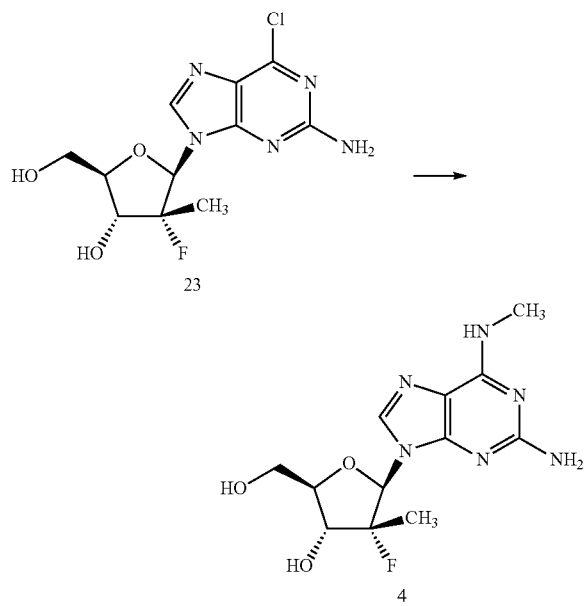

Step 1. Preparation of (2R,3R,4R,5R)-5-(2-amino-6-(methylamino)-9H-purin-9-yl)-4-fluoro-3-hydroxy-4-methyltetrahydrofuran-3-ol (4)

To a solution of (2R,3R,4R,5R)-5-(2-amino-6-chloro-9H-purin-9-yl)-2-(hydroxymethyl)-4-fluoro-4-methyl-tetrahydrofuran-3-ol (2.0 g, 1.0 eq) in dioxane (15 mL) was added MeNH$_2$ aqueous solution (5.0 eq). After stirring overnight at RT, TLC showed that the starting material was consumed. The mixture was concentrated and purified by column chromatography (DCM:MeOH=40:1-30:1) to afford (2R,3R,4R,5R)-5-(2-amino-6-(methylamino)-9H-purin-9-yl)-4-fluoro-3-hydroxy-4-methyltetrahydrofuran-3-ol as a white powder (1.6 g, 81.6%). [M+H]$^+$; =313.5

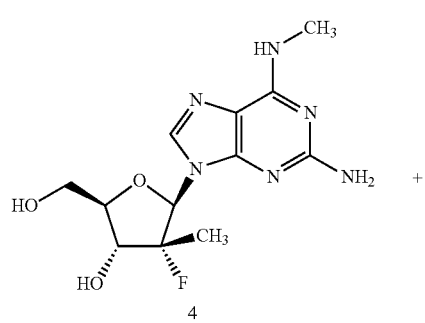

+

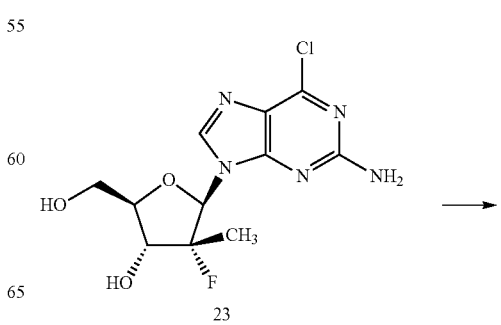

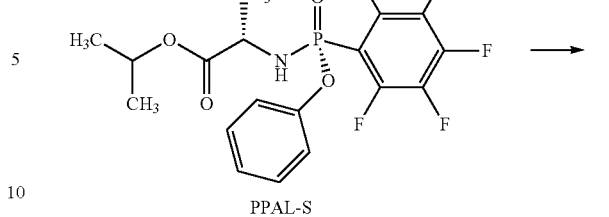

PPAL-S

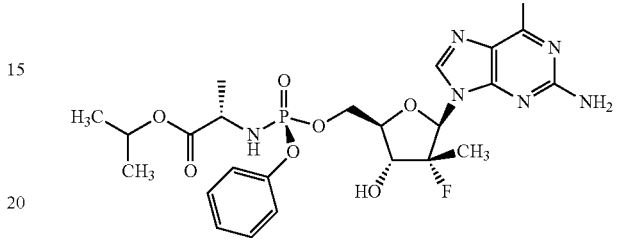

24

Step 2. Preparation of ((((S)-(2R,3R,4R,5R)-5-(2-amino-6-(methylamino)-9H-purin-9-yl)-4-fluoro-3-hydroxy-4-methyltetrahydrofuran-2-yl)methoxy)-phenoxy-phosphoryl)-L-alaninate The compound (2R,3R,4R,5R)-5-(2-amino-6-(methylamino)-9H-purin-9-yl)-4-fluoro-3-hydroxy-4-methyltetrahydrofuran-3-ol (1.47 g, 1.0 eq) and PPAL-S (2.35 g, 1.1 eq) were dissolved in anhydrous THF (29 mL). After cooling the mixture to −10° C., t-BuMgCl (5.8 mL, 1.7 M, 2.1 eq) was slowly added under a blanket of N$_2$. After stirring at RT for 45 min, the mixture was quenched with aq. saturated NH$_4$Cl, and extracted with EtOAc (20 mL×3). The combined organic layers were washed with water, brine (30 mL), dried over anhydrous Na$_2$SO$_4$ and concentrated. The crude product was purified by column chromatography (DCM:MeOH=50:1-20:1) to afford ((((S)-(2R,3R,4R,5R)-5-(2-amino-6-(methylamino)-9H-purin-9-yl)-4-fluoro-3-hydroxy-4-methyl-tetrahydrofuran-2-yl)methoxy)-phenoxy-phosphoryl)-L-alaninate as a white powder (1.1 g, 40.3%).

$^1$H NMR (400 MHz, CD$_3$OD) δ 7.81 (s, 1H), 7.33-7.16 (m, 5H), 6.10 (d, J=18.4 Hz, 1H), 4.90-4.84 (m, 5H), 4.55-4.46 (m, 3H), 4.20-4.16 (m, 1H), 3.91-3.87 (m, 1H), 3.30 (m, 1H), 3.03 (s, 3H), 1.30-1.20 (m, 12H). [M+H]$^+$=582.8.

151

-continued

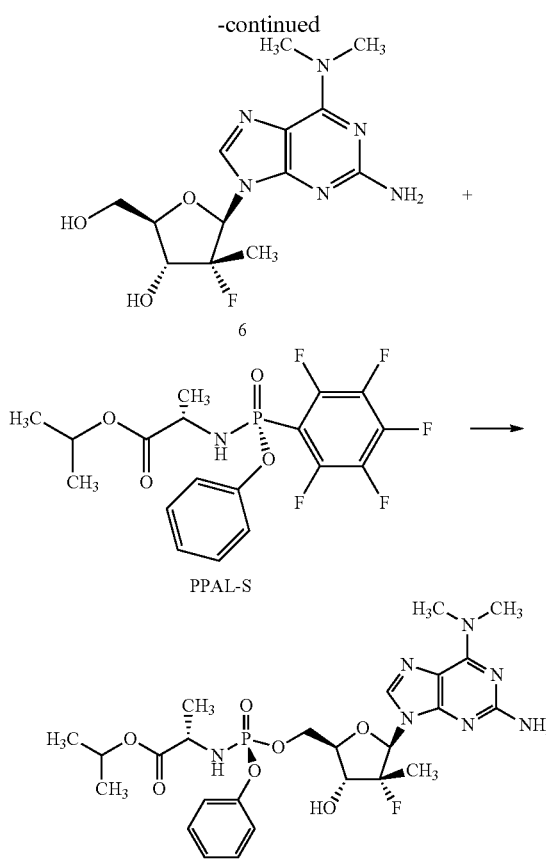

Example 12

Preparation of isopropyl ((((S)-(2R,3R,4R,5R)-5-(2-amino-6-(dimethylamino)-9H-purin-9-yl)-4-fluoro-3-hydroxy-4-methyltetrahydrofuran-2-yl)methoxy)-phenoxy-phosphoryl)-L-alaninate (25)

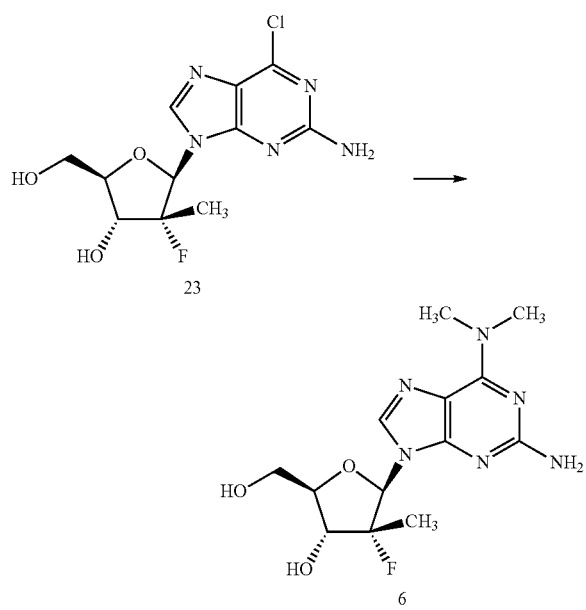

152

Step 1. Preparation of (2R,3R,4R,5R)-5-(2-amino-6-(dimethylamino)-9H-purin-9-yl)-4-fluoro-3-hydroxy-4-methyltetrahydrofuran-3-ol To a solution of (2R,3R,4R,5R)-5-(2-amino-6-chloro-9H-purin-9-yl)-2-(hydroxymethyl)-4-fluoro-4-methyl-tetrahydrofuran-3-ol (2.8 g, 8 mmol) in dioxane (20 mL) was added dimethylamine aqueous solution (5 mL). After stirring at RT for 3 h, TLC showed that the starting material was consumed. The mixture was concentrated and purified by column chromatography (DCM:MeOH=60:1) to afford (2R,3R,4R,5R)-5-(2-amino-6-(dimethylamino)-9H-purin-9-yl)-4-fluoro-3-hydroxy-4-methyltetrahydrofuran-3-ol (2.2 g).

$^1$H NMR (400 MHz, CD$_3$OD) δ 8.08 (s, 1H), 6.13 (d, J=18.0 Hz, 1H), 4.43 (dd, J=9.2, 9.2 Hz, 1H), 4.06 (d, J=10.8 Hz, 2H), 3.90 (m, 1H), 3.37 (s, 3H), 3.06 (s, 3H), 1.18 (d, J=22 Hz, 3H).

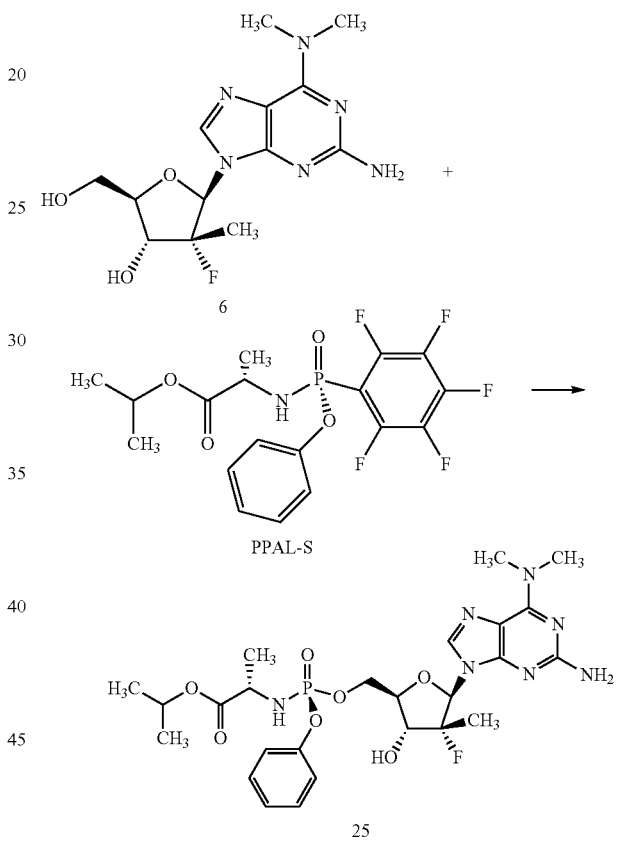

Step 2. Preparation of isopropyl ((((S)-(2R,3R,4R,5R)-5-(2-amino-6-(dimethylamino)-9H-purin-9-yl)-4-fluoro-3-hydroxy-4-methyltetrahydrofuran-2-yl)methoxy)-phenoxy-phosphoryl)-L-alaninate (25)

The compound (2R,3R,4R,5R)-5-(2-amino-6-(dimethylamino)-9H-purin-9-yl)-4-fluoro-3-hydroxy-4-methyltetrahydrofuran-3-ol (8 g, 1.0 eq) and PPAL-S (11.1 g, 1 eq) were dissolved in anhydrous THF (100 mL). The mixture was cooled to −5-0° C. and t-BuMgCl (30.5 mL, 1.7 M, 2.1 eq) was slowly added under a N$_2$ atmosphere. After stirring at RT for 2 h, the mixture was quenched with aq. saturated NH$_4$Cl solution and extracted with EtOAc (70 mL×3). The combined organic layers were washed with water, brine (30 mL), dried over anhydrous Na$_2$SO$_4$ and concentrated. The crude product was purified by column chromatography (DCM:MeOH=50:1) to afford isopropyl ((((S)-(2R,3R,4R,5R)-5-(2-amino-6-(dimethylamino)-9H-purin-9-yl)-4- fluoro-3-hydroxy-4-methyltetrahydrofuran-2-yl)methoxy)-phenoxy-phosphoryl)-L-alaninate as a white powder (9.5 g, 65%).

¹H NMR (400 MHz, CD₃OD) δ 7.81 (s, 1H), 7.35-7.19 (m, 5H), 6.15 (d, J=18.8 Hz, 1H), 4.90 (m, 1H), 4.54-4.49 (m, 3H), 4.22-4.19 (m, 1H), 3.90 (m, 1H), 3.43 (s, 3H), 1.32 (d, J=7.2 Hz, 3H), 1.24-1.17 (m, 9H). ³¹P NMR (160 MHz, CD₃OD) δ 3.89.

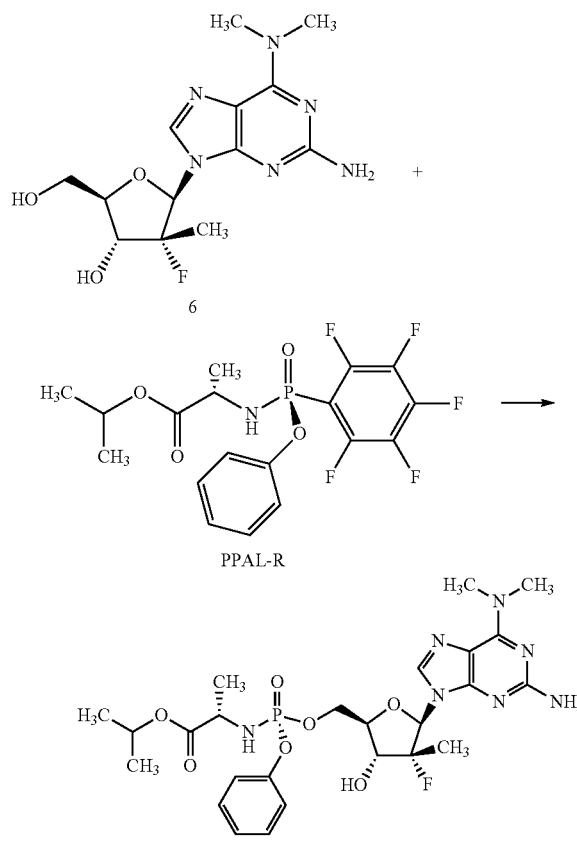

Example 13

Preparation of isopropyl ((((R)-(2R,3R,4R,5R)-5-(2-amino-6-(dimethylamino)-9H-purin-9-yl)-4-fluoro-3-hydroxy-4-methyltetrahydrofuran-2-yl)methoxy)-phenoxy-phosphoryl)-L-alaninate (26)

The compound (2R,3R,4R,5R)-5-(2-amino-6-(dimethylamino)-9H-purin-9-yl)-4-fluoro-3-hydroxy-4-methyltetrahydrofuran-3-ol (3 g, 1.0 eq) and PPAL-R (4.17 g, 1 eq) were dissolved in anhydrous THF (60 mL). The mixture was cooled to −5-0° C. and t-BuMgCl (11.4 mL, 1.7 M, 2.1 eq) was slowly added under a N₂ atmosphere. After stirring at RT for 16 h, the mixture was quenched with aq. saturated NH₄Cl solution and extracted with EtOAc (50 mL×3). The combined organic layers were washed with water, brine (30 mL), dried over anhydrous Na₂SO₄ and concentrated. The crude product was purified by column chromatography (DCM:MeOH=50:1) to afford isopropyl ((((R)-(2R,3R,4R,5R)-5-(2-amino-6-(dimethylamino)-9H-purin-9-yl)-4-fluoro-3-hydroxy-4-methyltetrahydrofuran-2-yl)methoxy)-phenoxy-phosphoryl)-L-alaninate as a white powder (2.2 g, 41%).

¹H NMR (400 MHz, CD₃OD) δ 7.8 (s, 1H), 7.35-7.29 (m, 5H), 6.18 (d, J=18.8 Hz, 1H), 4.92 (m, 1H), 4.60 (m, 1H), 4.51-4.23 (m, 3H), 3.90 (m, 1H), 3.44 (s, 6H), 1.29(d, J=6 Hz, 3H), 1.22-1.16(m, 10H). ³¹P NMR (160 MHz, CD₃OD) δ 3.98.

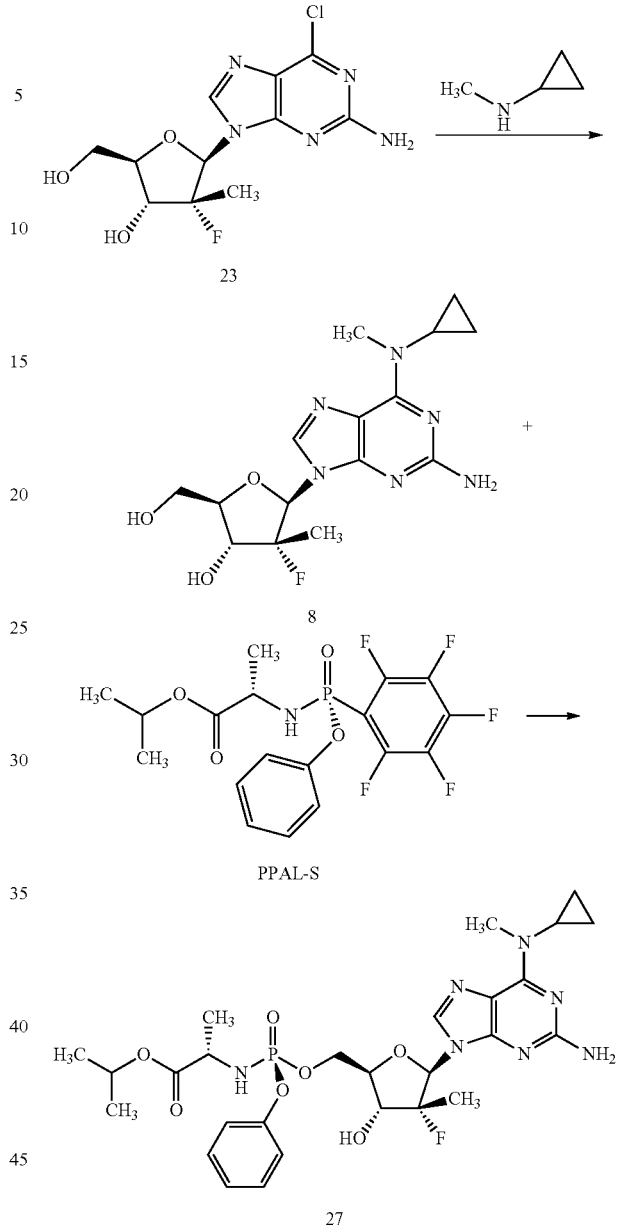

Example 14

Preparation of isopropyl (((((S)-(2R,3R,4R,5R)-5-(2-amino-6-(methylcyclopropanamino)-9H-purin-9-yl)-4-fluoro-3-hydroxy-4-methyltetrahydrofuran-2-yl)methoxy)-phenoxy-phosphoryl)-L-alaninate

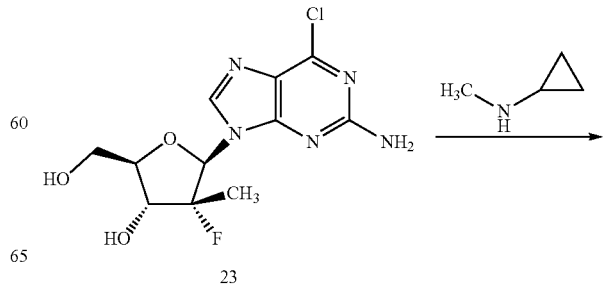

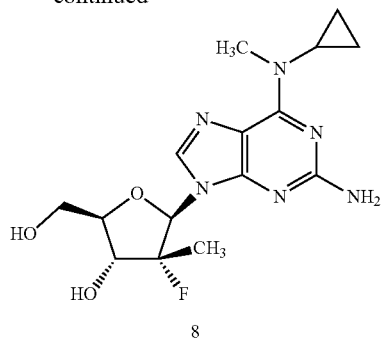

8

Step 1: Preparation of (2R,3R,4R,5R)-5-(2-amino-6-(methylcyclopropanamino)-9H-purin-9-yl)-4-fluoro-3-hydroxy-4-methyltetrahydrofuran-3-ol (8)

$K_2CO_3$ (53 g, 500 mmol) was added to N-methylcyclopropanamine hydrochloride in aqueous solution (100 mL). After stirring at RT for 10 min, a solution of (2R,3R,4R,5R)-5-(2-amino-6-chloro-9H-purin-9-yl)-2-(hydroxymethyl)-4-fluoro-4-methyl-tetrahydrofuran-3-ol (35 g, 109 mmol) in dioxane (300 mL) was added. The mixture was stirred at RT for 16 h and HPLC indicated that the reaction was complete. The mixture was concentrated and purified by column chromatography (DCM:MeOH=60:1) to afford (2R,3R,4R,5R)-5-(2-amino-6-(methylcyclopropanamino)-9H-purin-9-yl)-4-fluoro-3-hydroxy-4-methyltetrahydrofuran-3-ol (30 g, 82%).

$^1$H NMR (400 MHz, CD$_3$OD) δ 8.16 (s, 1H), 6.17 (d, J=18.0 Hz, 1H), 4.41 (dd, J=9.2, 9.2 Hz, 1H), 4.06 (m, 2H), 3.90 (m, 1H), 3.37 (s, 3H), 3.16 (m, 1H), 1.18 (d, J=22.4 Hz, 3H), 0.94 (m, 2H), 0.74 (m, 2H). [M+H]$^+$=353.2.

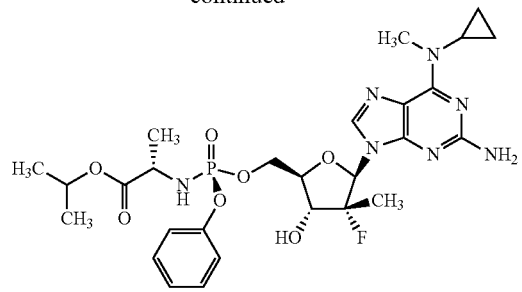

27

Step 2: Preparation of isopropyl ((((S)-(2R,3R,4R,5R)-5-(2-amino-6-(methylcyclopropanamino)-9H-purin-9-yl)-4-fluoro-3-hydroxy-4-methyltetrahydrofuran-2-yl)methoxy)-phenoxy-phosphoryl)-L-alaninate The compound (2R,3R,4R,5R)-5-(2-amino-6-(methylcyclopropanamino)-9H-purin-9-yl)-4-fluoro-3-hydroxy-4-methyltetrahydrofuran-3-ol (8 g, 1.0 eq) and PPAL-S (10.3 g, 1 eq) were dissolved in anhydrous THF (100 mL). After cooling the mixture to −5-0° C., t-BuMgCl (28 mL, 1.7 M, 2.1 eq) was slowly added under a N$_2$ atmosphere. The mixture was stirred at RT for 1 h, quenched with aq. saturated NH$_4$Cl solution, and extracted with EtOAc (70 mL×3). The combined organic layers were washed with water, brine (30 mL), dried over anhydrous Na$_2$SO$_4$ and concentrated. The crude product was purified by column chromatography (DCM:MeOH=100:1 to −50:1) to afford isopropyl ((((S)-(2R,3R,4R,5R)-5-(2-amino-6-(methylcyclopropanamino)-9H-purin-9-yl)-4-fluoro-3-hydroxy-4-methyltetrahydrofuran-2-yl)methoxy)-phenoxy-phosphoryl)-L-alaninate as a white powder (9.5 g, 65%).

$^1$H NMR (400 MHz, CD$_3$OD) δ 7.86 (s, 1H), 7.35-7.19 (m, 5H), 6.17 (d, J=19.2 Hz, 1H), 4.91 (m, 1H), 4.52 (m, 3H), 4.21 (m, 1H), 3.93 (m, 1H), 3.35 (s, 3H), 3.16 (m, 1H), 2.0 (s, 1H), 1.26-1.16 (m, 12H), 0.93 (m, 2H), 0.73 (m, 2H).
$^{31}$P NMR (160 MHz, CD$_3$OD) δ 3.90

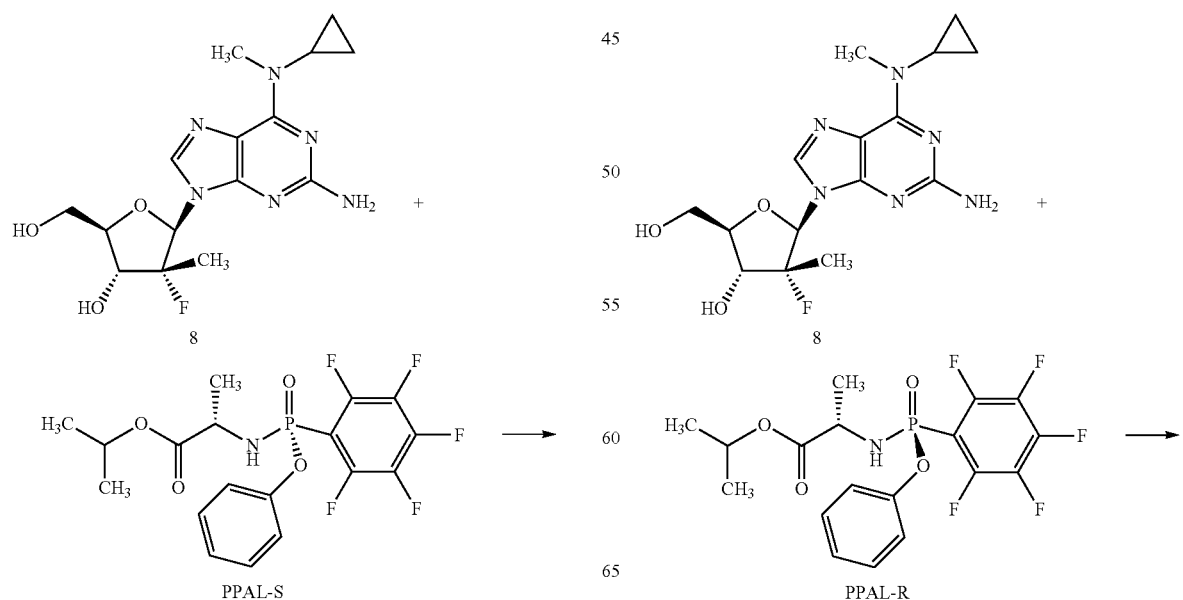

-continued

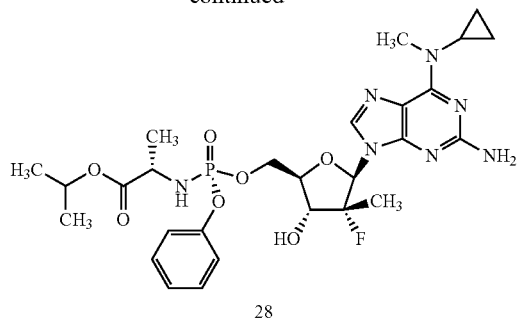

28

Example 15

Preparation of isopropyl ((((R)-(2R,3R,4R,5R)-5-(2-amino-6-(methylcyclopropanamino)-9H-purin-9-yl)-4-fluoro-3-hydroxy-4-methyltetrahydrofuran-2-yl)methoxy)-phenoxy-phosphoryl)-L-alaninate The compound (2R,3R,4R,5R)-5-(2-amino-6-(methylcyclopropanamino)-9H-purin-9-yl)-4-fluoro-3-hydroxy-4-methyltetrahydrofuran-3-ol (3 g, 1.0 eq) and PPAL-R (2.8 g, 1 eq) were dissolved in anhydrous THF (60 mL). After cooling the mixture to −5-0° C., t-BuMgCl (7.6 mL, 1.7 M, 2.1 eq) was slowly added under N$_2$. Then the mixture was stirred at RT for 1 h and quenched with aq. saturated NH$_4$Cl solution, and extracted with EtOAc (50 mL×3). The combined organic layers were washed with water, brine (30 mL), dried over anhydrous Na$_2$SO$_4$ and concentrated. The crude product was purified by column chromatography (DCM:MeOH=100:1 to 50:1) to afford the product as a white powder (3 g, 55%).

$^1$H NMR (400 MHz, CD$_3$OD) δ 7.81 (s, 1H), 7.30-7.25 (m, 5H), 6.16 (d, J=24.8 Hz, 1H), 4.84 (m, 1H), 4.84-4.50 (m, 3H), 4.22-4.19 (m, 1H), 3.88 (m, 1H), 3.33 (s, 3H), 3.14 (m, 1H), 2.0 (s, 1H), 1.28-1.13 (m, 12H), 0.92 (m, 2H), 0.90 (m, 2H). $^{31}$P NMR (160 MHz, CD$_3$OD) δ 3.99.

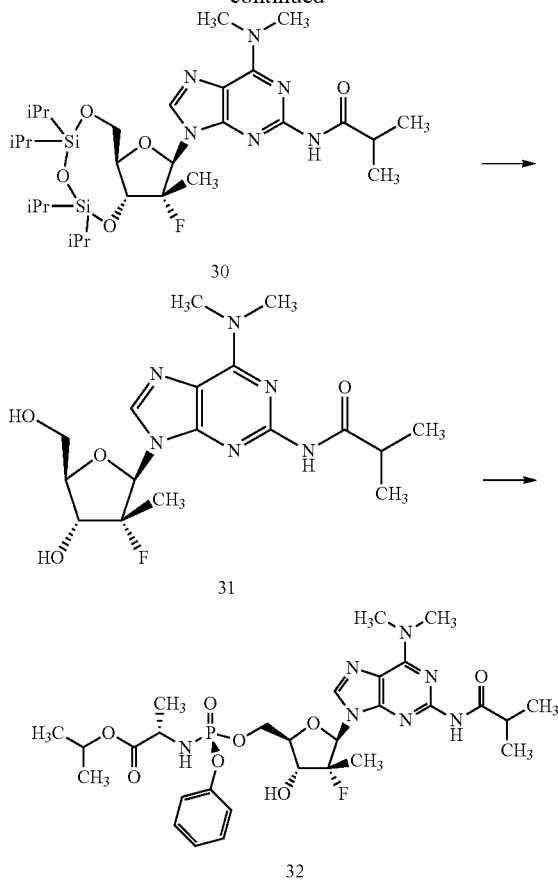

Example 16

Preparation of Compound 32

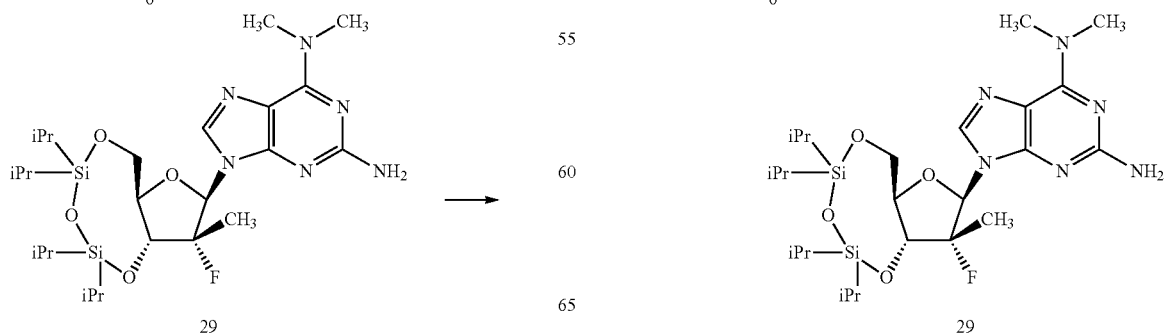

Step 1. Preparation of Compound 29

To a solution of 6 (3.0 g, 1.0 eq) in pyridine (30 mL) was added TIPDSCl$_2$ (4.35 g, 1.5 eq) at 0° C. After stirring at RT for 4 h, TLC showed that starting material was consumed. The mixture was diluted with EtOAc, washed with 1M aq. HCl solution, saturated NaHCO$_3$ aqueous solution, brine, dried over anhydrous Na$_2$SO$_4$ and concentrated to afford 29 as a yellow oil (6.3 g, 100%).

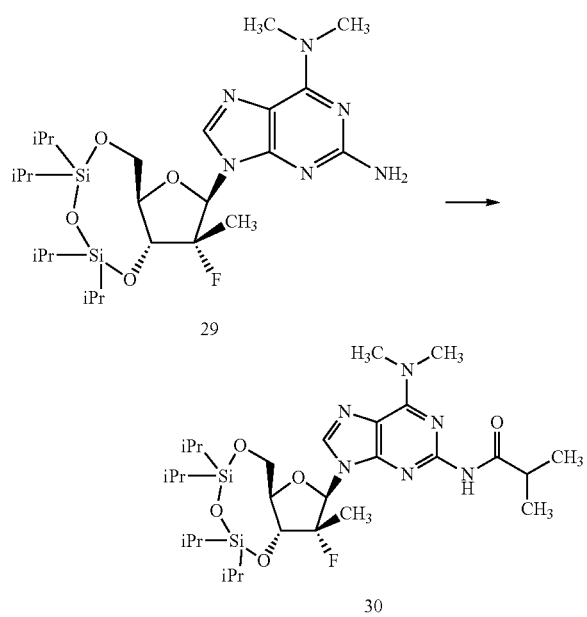

Step 2. Preparation of Compound 30

To a mixture of Compound 29 (800 mg, 1.0 eq), DMAP (16 mg, 0.1 eq), pyridine (1.6 mL) and DCM (10 mL) was added isobutyryl chloride (209 mg, 1.5 eq) at 0° C. After stirring at RT for 2 h, TLC showed that the starting material was consumed. The mixture was quenched with water, washed with aq. 1M HCl solution, saturated NaHCO$_3$ aqueous solution, brine, dried over anhydrous Na$_2$SO$_4$ and concentrated. The crude product was purified by column chromatography to afford the product, 30, as a white oil (563 mg, 62.3%).

$^1$H NMR (400 MHz, CDCl$_3$) δ 7.98 (s, 1H), 787 (s, 1H), 6.20 (d, J=16.0 Hz, 1H), 4.32-4.07 (m, 4H), 3.50 (s, 6H), 2.3 (m, 1H), 1.29-1.05 (m, 45H).

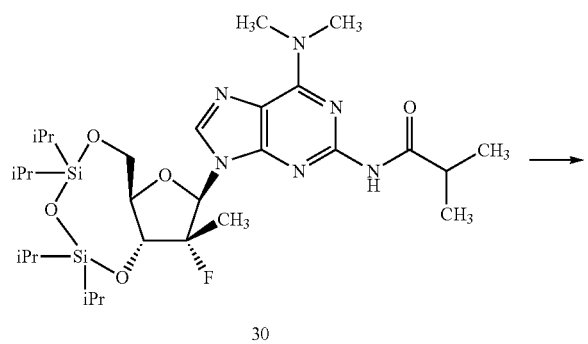

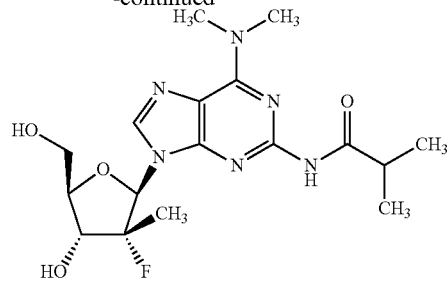

Step 3. Preparation of Compound 31

To a mixture of 30 (560 mg, 1.0 eq) in THF (10 mL) was added Et$_3$N.3HF (706 mg, 5 eq) and Et$_3$N (890 mg, 10 eq) at RT. After stirring at RT for 1.5 h, TLC showed that the starting material was consumed. The mixture was concentrated and purified by column chromatography to afford 31 as a white powder (288 mg, 83%).

$^1$H NMR (400 MHz, CDCl$_3$) δ 7.72 (s, 1H), 5.96 (d, J=44.0 Hz, 1H), 5.22 (m, 1H), 4.13-3.99 (m, 4H), 3.42 (s, 6H), 2.83-2.63 (m, 2H), 1.29-1.17 (m, 9H).

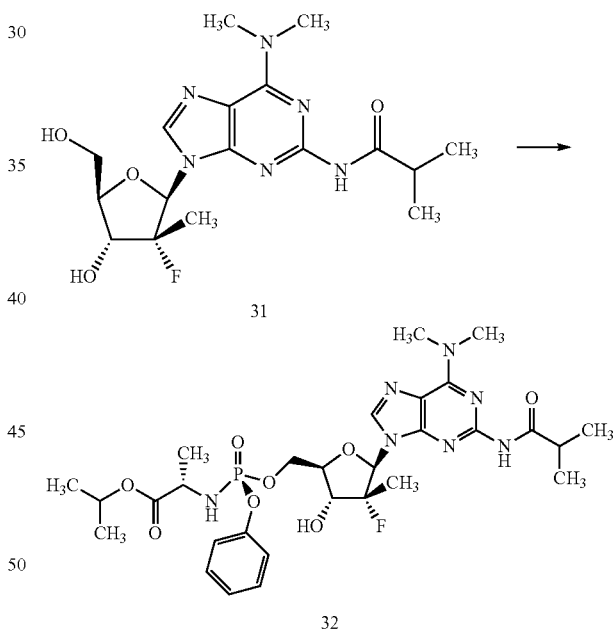

Step 4. Preparation of Compound 32

Compound 31 (280 mg, 1.0 eq) and PPAL-S (320 mg, 1 eq) were dissolved in anhydrous THF (10 mL). After cooling the mixture to −5° C., t-BuMgCl (0.87 mL, 1.7 M, 2.1 eq) was slowly added under a N$_2$ atmosphere. The mixture was stirred at RT for 2 h, quenched with aq. saturated NH$_4$Cl solution, and extracted with EtOAc (10 mL×3). The combined organic layers were washed with water, brine (20 mL), dried over anhydrous Na$_2$SO$_4$ and concentrated. The crude product was purified by column chromatography to afford the product as a white powder (260 mg, 50%).

¹H NMR (400 MHz, CD₃OD) δ 7.98 (s, 1H), 7.25 (m, 5H), 6.23 (d, J=18.8 Hz, 1H), 4.52 (m, 3H), 4.38 (m, 1H), 3.81 (m, 1H), 3.75 (m, 1H), 3.48 (s, 6H), 2.81 (m, 1H), 1.32 (m, 18H). [M+H]⁺=666.9.

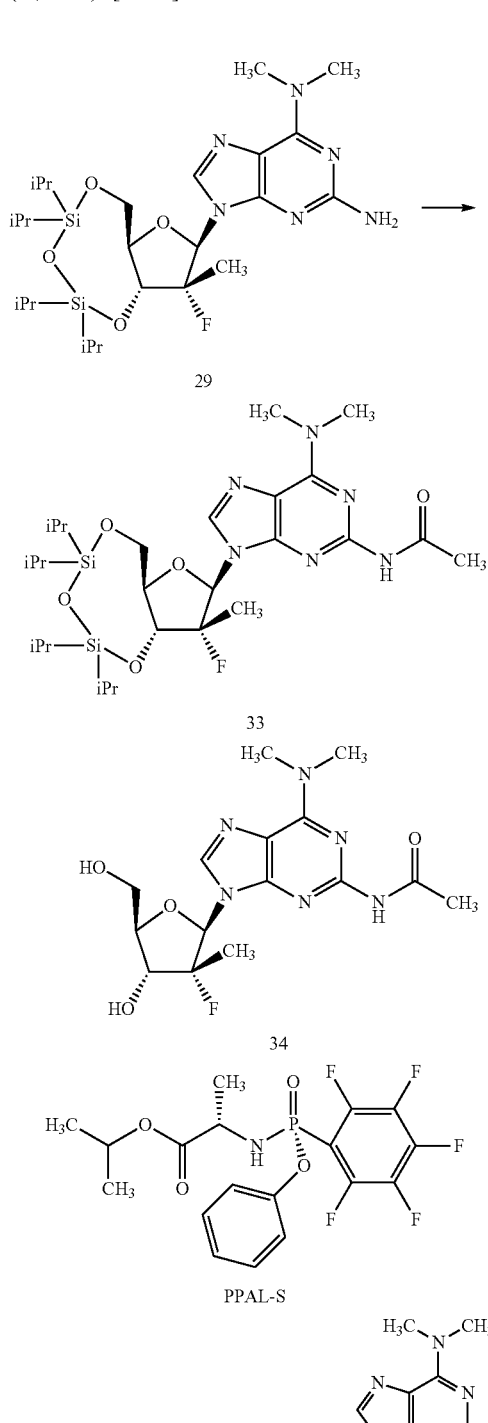

Example 17

Preparation of Compound 35

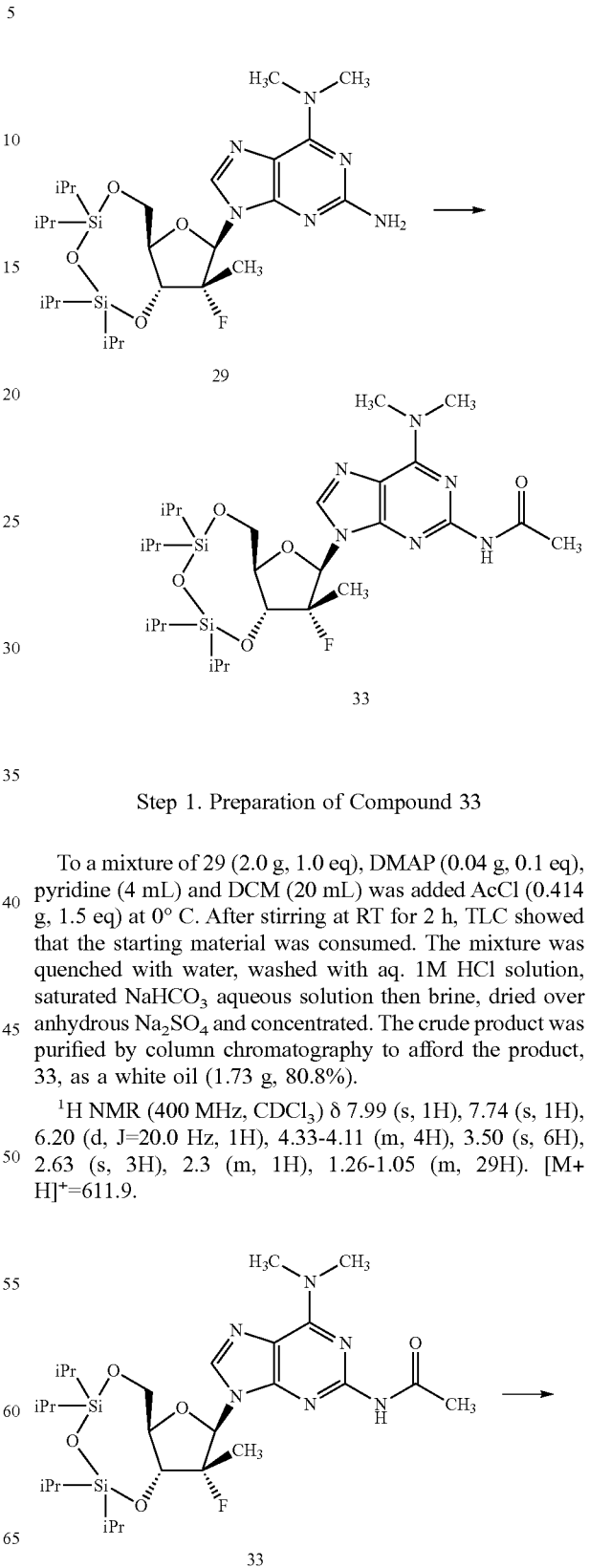

Step 1. Preparation of Compound 33

To a mixture of 29 (2.0 g, 1.0 eq), DMAP (0.04 g, 0.1 eq), pyridine (4 mL) and DCM (20 mL) was added AcCl (0.414 g, 1.5 eq) at 0° C. After stirring at RT for 2 h, TLC showed that the starting material was consumed. The mixture was quenched with water, washed with aq. 1M HCl solution, saturated NaHCO₃ aqueous solution then brine, dried over anhydrous Na₂SO₄ and concentrated. The crude product was purified by column chromatography to afford the product, 33, as a white oil (1.73 g, 80.8%).

¹H NMR (400 MHz, CDCl₃) δ 7.99 (s, 1H), 7.74 (s, 1H), 6.20 (d, J=20.0 Hz, 1H), 4.33-4.11 (m, 4H), 3.50 (s, 6H), 2.63 (s, 3H), 2.3 (m, 1H), 1.26-1.05 (m, 29H). [M+H]⁺=611.9.

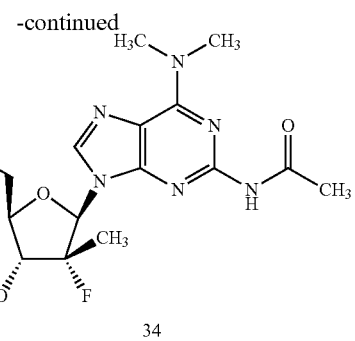

34

Step 2. Preparation of Compound 34

To a mixture of 33 (1.58 g, 1.0 eq) in THF (20 mL) was added Et$_3$N.3HF (2.1 g, 5 eq) and Et$_3$N (2.6 g, 10 eq) at RT. After stirring at RT for 1.5 h, TLC showed that the starting material was consumed. The mixture was concentrated and purified by column chromatography to afford 34 as a white powder (782 mg, 82%). [M+H]+=369.6.

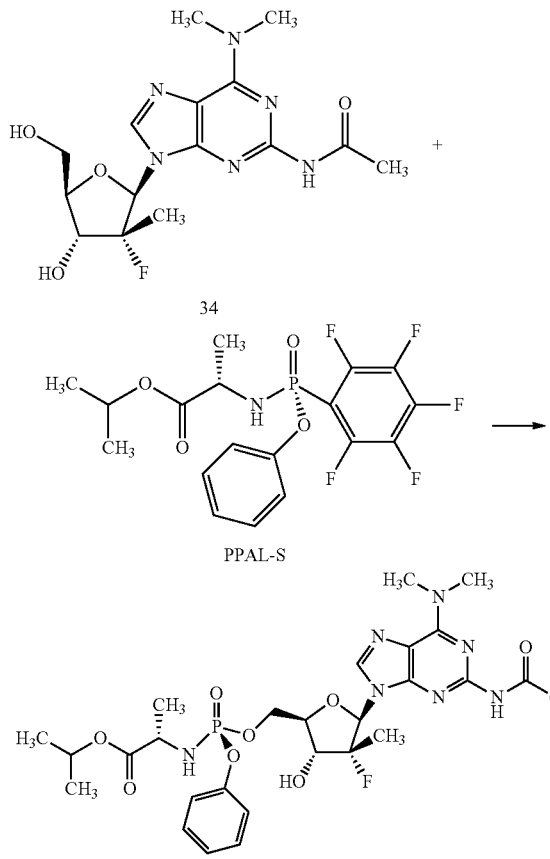

Step 3. Preparation of Compound 35

Compound 34 (136 mg, 1.0 eq) and PPAL-S (184 mg, 1.1 eq) were dissolved in anhydrous THF (3 mL). After cooling the mixture to −5° C., i-BuMgCl (0.5 mL, 1.7 M, 2.1 eq) was slowly added under a N$_2$ atmosphere. The mixture was stirred at RT for 30 min, quenched with aq. saturated NH$_4$Cl solution and extracted with EtOAc (10 mL×3). The combined organic layers were washed with water, brine (20 mL), dried over anhydrous and concentrated. The crude product was purified by column chromatography (DCM:MeOH=50:1-20:1) to afford the phosphoramidate 35 as a white powder (150 mg, 63.8%).

$^1$H NMR (400 MHz, CD$_3$OD) δ 7.81 (s, 1H), 7.35-7.16 (m, 5H), 6.10 (d, J=18.4 Hz, 1H), 4.87 (m, 1H), 4.52-4.46 (m, 3H), 4.21 (m, 1H), 3.91-3.87 (m, 1H), 3.03 (s, 3H), 1.30-1.13 (m, 12H). $^{31}$P NMR (160 MHz, CD$_3$OD) δ 3.84. $^{19}$F NMR (376 MHz, CD$_3$OD) δ −162.79.

Synthesis of β-D-2'-deoxy-2'-α-fluoro-2'-β-ethynyl-N'-substituted-2,6-diaminopurine nucleotides

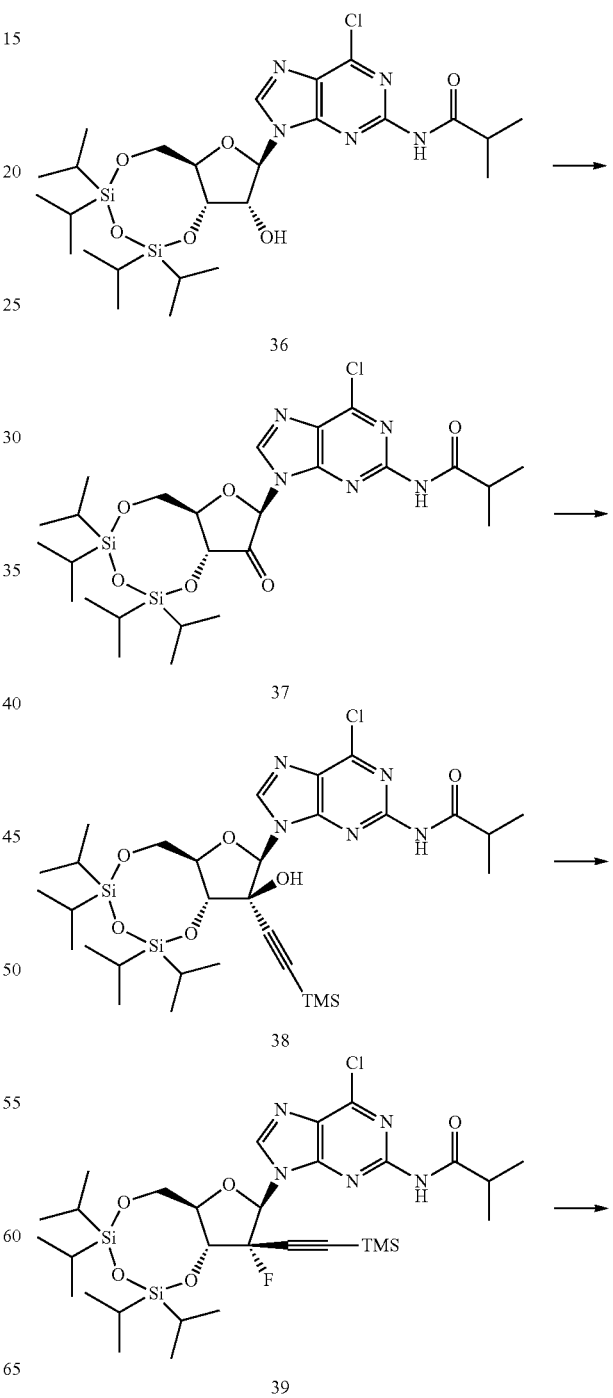

-continued

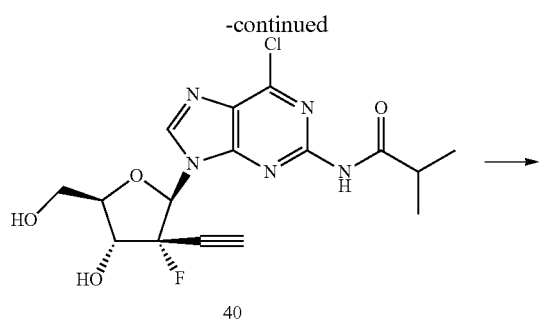
40

Target compound at that temperature for 2 h, TLC showed the starting material was consumed. DCM (600 mL) was added, and then TMSCl (85 mL, 2 eq.) was added dropwise at 0-5° C. After stirring at that temperature for 2 h, TLC showed the intermediate was consumed.

Isobutyryl chloride was added dropwise at 0-5° C. After stirring at that temperature for 2 h, TLC showed the intermediate was consumed. Water was added, and the content was extracted with DCM. The organic phase was then washed with 0.5 N HCl to remove pyridine. After the pH of the content was washed to 5~6, pTSA.H$_2$O (9.2 g, 484.5 mmol) was added at 0-5° C. After stirring at that temperature for 1 h, TLC showed the intermediate was consumed. Water was then added, and the organic phase was washed with water, saturated aqueous NaHCO$_3$ and brine. After being dried over Na$_2$SO$_4$, the solvent was removed in vacuo. The residue was then purified with column chromatography (PE/EA=100-10/1) to afford the product as a light yellow solid (82 g, 40%).

$^1$H NMR (400 MHz, DMSO-d$_6$) δ 10.88 (s, 1H), 8.55 (s, 1H), 5.91 (d, J=1.6 Hz, 1H), 5.53 (d, J=4.6 Hz, 1H), 4.72-4.58 (m, 2H), 4.16 (dd, J=12.4, 4.8 Hz, 1H), 4.00 (ddd, J=7.7, 4.8, 2.6 Hz, 1H), 3.93 (dd, J=12.4, 2.7 Hz, 1H), 2.78 (h, J=6.9 Hz, 1H), 1.26-1.12 (m, 3H), 1.10 (d, J=6.7 Hz, 6H), 1.09-0.88 (m, 24H).

Example 18

General route to β-D-2'-deoxy-2'-α-fluoro-2'-β-ethynyl-N'-substituted-2,6-diaminopurine nucleotides

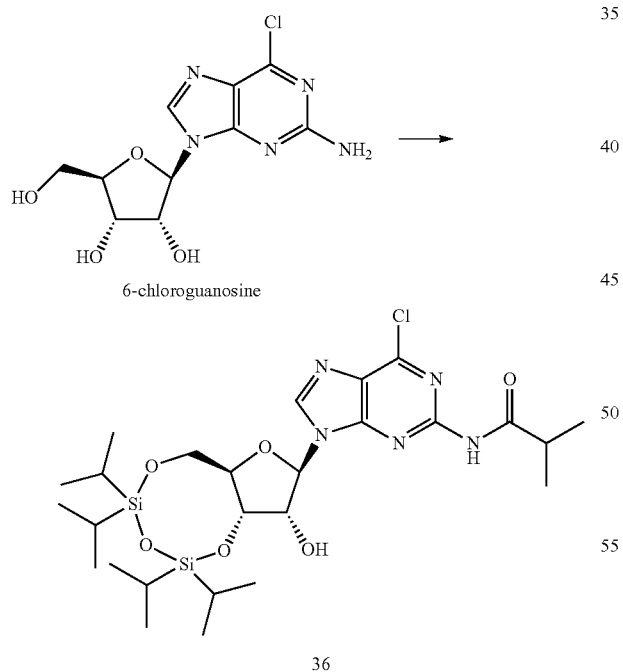

6-chloroguanosine

36

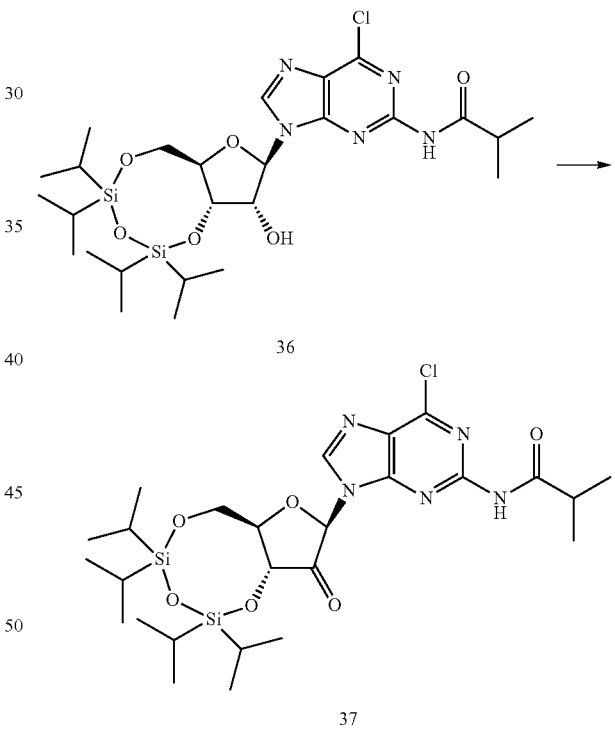

36

37

Step 1. Preparation of Compound 36

To a solution of 6H-choroguanosine (100 g, 332 mmol) in pyridine (400 mL) was added TPDSCl$_2$ (110 mL, 1.05 eq.) dropwise at −5~5° C. under a N$_2$ atmosphere. After stirring

Step 2. Preparation of Compound 37

To a solution of 36 (10.0 g, 16.3 mmol) in DCM (100 mL) was added Dess-Martin periodinane at rt and the reaction was stirred for 12 h. TLC showed the starting material was consumed. The reaction mixture was then diluted with DCM (200 mL) and washed with saturated aqueous Na$_2$S$_2$O$_3$ and brine. The organic phase was then dried over Na$_2$SO$_4$ and concentrated to afford crude 37 as a light yellow solid (12 g). The crude 53 can be used directly in the next step without purification

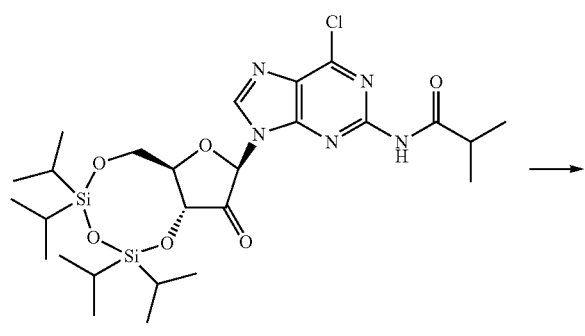

37

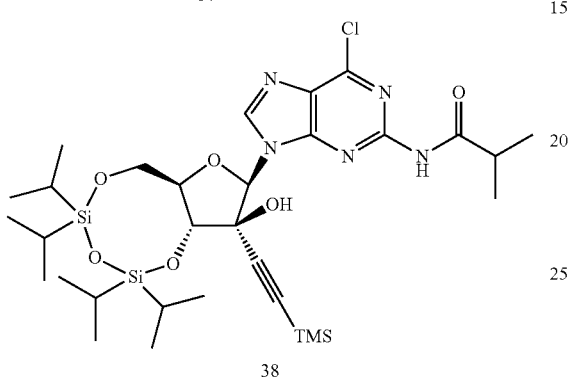

38

Step 3. Preparation of Compound 38

To a solution of ethynyltrimethylsilane (18.6 mL, 142.7 mmol) in THF (240 mL) was added n-BuLi (46 mL, 2.5 M, 115.0 mmol) dropwise at −15~−20° C. under a $N_2$ atmosphere. After stirring for 30 min, the reaction was cooled to −70° C., and 37 (crude, 16.3 mmol) in THF (60 mL) was added at that temperature. The content was then warmed to 0° C. TLC showed the starting material was consumed. Saturated aqueous $NH_4Cl$ was added, and the reaction was extracted with EA (100 mL) three times. The organic phase was combined and then washed with brine, then further dried over $Na_2SO_4$. After being concentrated in vacuo, the residue was purified by column chromatography (PE/EA=100->10/1) to afford a light yellow solid (6.0 g, 52%).

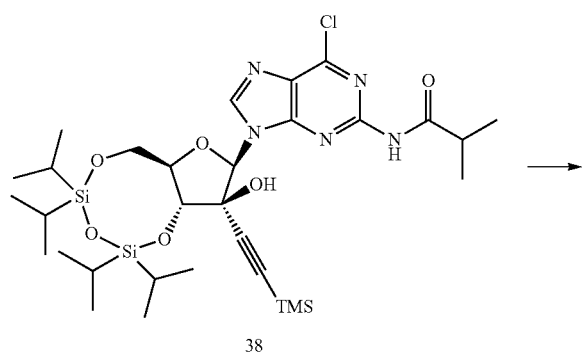

38

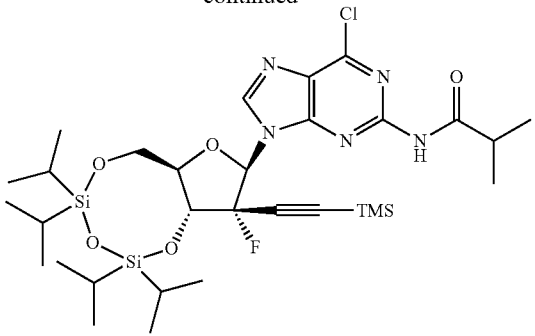

39

Step 4. Preparation of Compound 39

To a solution of 38 (6.0 g, 8.4 mmol) in DCM (240 mL) was added pyridine (4.2 mL, 52.9 mmol) under a $N_2$ atmosphere. The reaction was cooled to −70° C., and DAST (12 mL, 90.4 mmol) was added. The content was then warmed to −30° C. TLC showed that the starting material was consumed. The reaction was poured into saturated aqueous $NaHCO_3$, and then extracted with DCM (200 mL). The organic phase was washed with brine and dried over $Na_2SO_4$. After being concentrated in vacuo, the residue was purified with column chromatography (PE/EA=100->10/1) to afford a light yellow solid (3.8 g, 63%).

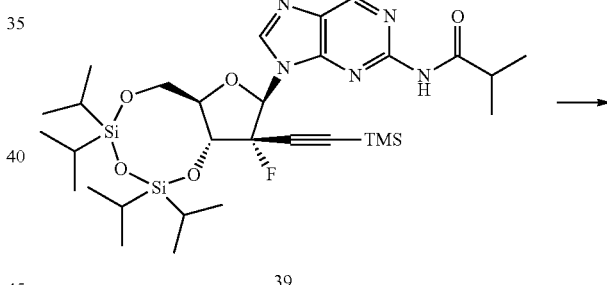

39

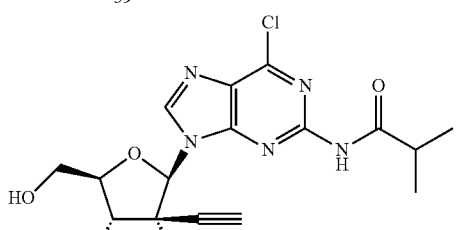

40

Step 5. Preparation of Compound 40

To a solution of 39 (3.8 g, 5.3 mmol) in THF (120 mL) was added AcOH (1.3 g, 22 mmol) and TBAF (4.2 g, 15.9 mmol) at rt. The reaction was stirred at rt for 30 min. TLC showed the starting material was consumed. After being concentrated in vacuo, the residue was purified with column chromatography (EA) to afford the product as a white solid (2.0 g, 95%).

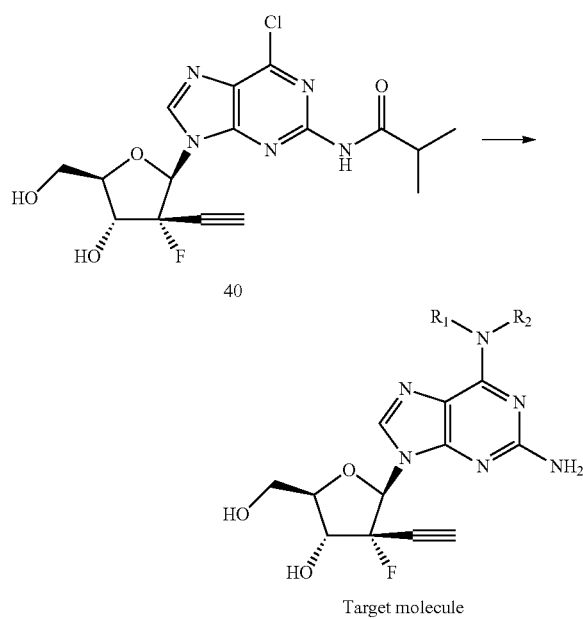

General Procedure for Amino Displacement and Deprotection:

To a solution of 40 (350 mg, 0.88 mmol) in dioxane (20 mL) was added the methanol or water solution of the corresponding amine (free base or salt as hydrochloride plus DIEA) at rt. The content was stirred at rt for 1-12 h. TLC showed the starting material was consumed. After being concentrated in vacuo, the residue was used directly in the next step without purification. The above mentioned residue was dissolved in methanol (10 mL). Aqueous NaOH (2.5 N, 10 mL) was added. After stirring overnight at rt, TLC showed that starting material was consumed. The pH of the content was adjusted to 7-8 with 1 N HCl. The solution was concentrated and purified with column chromatography (DCM/MeOH=100->20/1) to afford the product as an off-white solid (yield: 40-80% over two steps). Table 1 illustrates the structures of compounds 57-63 and the corresponding mass spectral and $^1$H NMR for the respective compounds.

TABLE 1

| Compound No. | Structure | $^1$H NMR/MS |
|---|---|---|
| 41 | 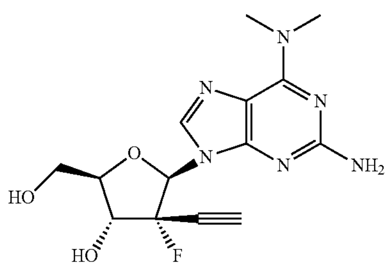 [SMILES: C#C[C@@]1(F)[C@H](O)[C@@H](CO)O[C@H]1n1cnc2c(N(C)C)nc(N)nc21] | $^1$H NMR (400 MHz, Methanol-$d_4$) δ 8.05 (s, 1H), 6.27 (d, J = 16.9 Hz, 1H), 4.75 (dd, J = 21.7, 9.1 Hz, 1H), 4.06 (dd, J = 11.0, 2.4 Hz, 2H), 3.87 (dd, J = 13.1, 3.2 Hz, 1H), 3.42 (s, 6H), 3.37 (s, 2H), 3.18 (d, J = 5.4 Hz, 1H). [M + H]$^+$ = 336.9 |
| 42 | 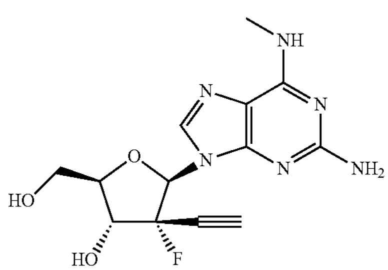 [SMILES: C#C[C@@]1(F)[C@H](O)[C@@H](CO)O[C@H]1n1cnc2c(NC)nc(N)nc21] | $^1$H NMR (400 MHz, DMSO-$d_6$) δ 7.94 (s, 1H), 7.30 (s, 1H), 6.20-6.09 (m, 2H), 5.98 (s, 2H), 5.33 (t, J = 5.3 Hz, 1H), 4.57 (dt, J = 22.1, 8.0 Hz, 1H), 4.12 (q, J = 5.3 Hz, 1H), 3.91 (d, J = 9.3 Hz, 1H), 3.70 (t, J = 8.6 Hz, 1H), 3.36 (s, 1H), 3.18 (d, J = 5.2 Hz, 2H), 2.89 (d, J = 7.0 Hz, 3H). [M + H]$^+$ = 323.0 |
| 43 | 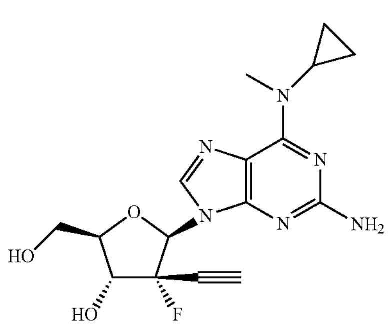 [SMILES: C#C[C@@]1(F)[C@H](O)[C@@H](CO)O[C@H]1n1cnc2c(N(C)C3CC3)nc(N)nc21] | $^1$H NMR (400 MHz, Methanol-$d_4$) δ 8.11 (s, 1H), 6.29 (d, J = 16.9 Hz, 1H), 4.76 (dd, J = 21.7, 9.0 Hz, 1H), 4.10-4.01 (m, 2H), 3.87 (dd, J = 13.1, 3.1 Hz, 1H), 3.37 (s, 1H), 3.24-3.11 (m, 2H), 1.00-0.87 (m, 2H), 0.74 (td, J = 4.6, 2.8 Hz, 2H). [M + H]$^+$ = 363.0 |

TABLE 1-continued

| Compound No. | Structure | $^1$H NMR/MS |
|---|---|---|
| 44 | (structure shown) | $^1$H NMR (400 MHz, Methanol-$d_4$) δ 8.07 (s, 1H), 6.26 (d, J = 16.9 Hz, 1H), 4.76 (dd, J = 21.8, 9.3 Hz, 1H), 4.11-4.01 (m, 2H), 3.89 (d, J = 3.0 Hz, 1H), 3.89-3.75 (m, 1H), 3.37 (s, 2H), 3.21 (d, J = 5.4 Hz, 1H), 2.97-2.86 (m, 1H), 1.00-0.77 (m, 2H), 0.67-0.46 (m, 2H). [M + H]$^+$ = 348.8 |

Example 19

Preparation of isopropyl ((((R,S)-(2R,3R,4R,5R)-5-(2-amino-6-dimethylamino-9H-purin-9-yl)-4-fluoro-3-hydroxy-4-ethynyltetrahydrofuran-2-yl)methoxy)-phenoxy-phosphoryl)-L-alaninate

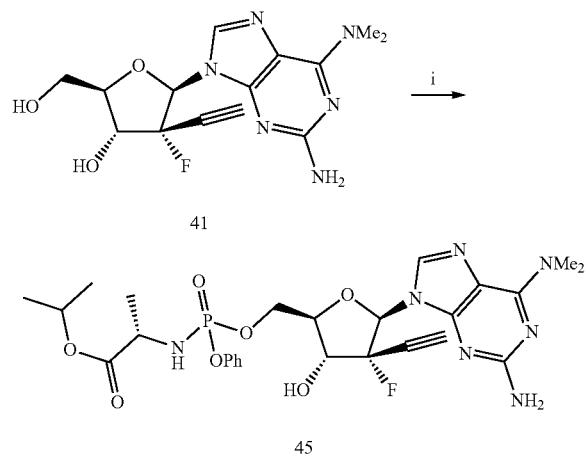

i) Isopropyl ((R,S)-(pentafluorophenoxy)-phenoxy-phosphoryl)-L-alaninate, tBuMgCl, THF, 0° C.

Step 1. Preparation of isopropyl ((((R,S)-(2R,3R,4R,5R)-5-(2-amino-6-dimethylamino-9H-purin-9-yl)-4-fluoro-3-hydroxy-4-ethynyltetrahydrofuran-2-yl)methoxy)-phenoxy-phosphoryl)-L-alaninate To a solution of compound 41 (30 mg, 0.09 mmol) in dry THF (2 mL) at 0° C. was added tert-butyl magnesium chloride (1.0 M in THF, 125 μL, 0.13 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (49 mg, 0.11 mmol) dissolved in dry THF (2 mL) was added dropwise over 10 min. The reaction mixture was stirred at 0° C. for 30 min and 18 h at room temperature. The reaction was quenched with a saturated aq. NH$_4$Cl solution (4 mL) and extracted with EtOAc (3×5 mL). The combined organics were dried over Na$_2$SO$_4$ and concentrated. The residue was purified by column chromatography (gradient DCM/MeOH 100:0 to 90:10) to afford the product (mixture of 2 diastereoisomers, 12 mg, 0.02 mmol, 24%) as a white solid.

$^1$H NMR (300 MHz, CD$_3$OD) δ 7.79 (s, 0.45H), 7.77 (s, 0.55H), 7.36-7.14 (m, 5H), 6.28 (d, J=17.4 Hz) and 6.26 (d, J=17.5 Hz, 1H), 5.00-4.44 (m, 5H), 4.23-4.16 (m, 1H), 3.69-3.81 (m, 1H), 3.42 (bs, 3H), 3.40 (bs, 3H), 1.32-1.26 (m, 3H), 1.20-1.15 (m, 6H). $^{31}$P NMR (121 MHz, CD$_3$OD) δ 4.04 (s), 3.98 (s). MS (ESI) m/z calcd. for C$_{26}$H$_{34}$FN$_7$O$_7$P [M+H]$^+$ 606.2; found 606.2.

Example 20

Preparation of isopropyl ((((R,S)-(2R,3R,4R,5R)-5-(2-amino-6-methylamino-9H-purin-9-yl)-4-fluoro-3-hydroxy-4-ethynyltetrahydrofuran-2-yl)methoxy)-phenoxy-phosphoryl)-L-alaninate

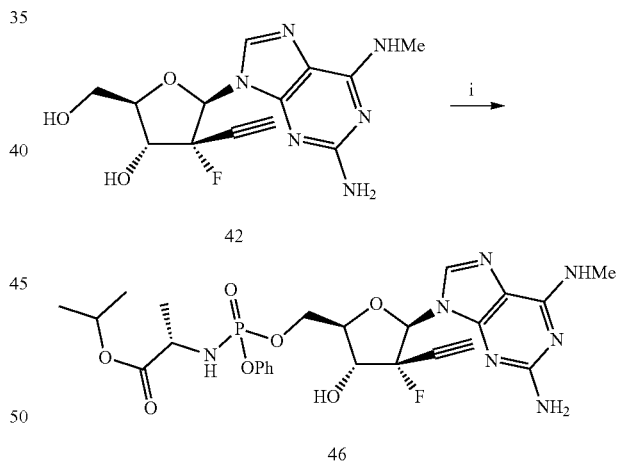

i) Isopropyl ((R,S)-(pentafluorophenoxy)-phenoxy-phosphoryl)-L-alaninate, tBuMgCl, THF, 0° C.

Step 1. Preparation of isopropyl ((((R,S)-(2R,3R,4R,5R)-5-(2-amino-6-methylamino-9H-purin-9-yl)-4-fluoro-3-hydroxy-4-ethynyltetrahydrofuran-2-yl)methoxy)-phenoxy-phosphoryl)-L-alaninate To a solution of compound 42 (30 mg, 0.09 mmol) in dry THF (2 mL) at 0° C. was added tert-butyl magnesium chloride (1.0 M in THF, 125 μL, 0.13 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (49 mg, 0.11 mmol) dissolved in dry THF (2 mL) was added dropwise over 10 min. The reaction mixture was stirred at 0° C. for 30 min and 18 h at room temperature. The reaction was quenched with a saturated aq. NH$_4$Cl solution (4 mL) and extracted with EtOAc (3×5 mL). The combined organics were dried over Na$_2$SO$_4$ and concentrated. The residue was purified by column chromatography (gradient DCM/MeOH 100:0 to 90:10) to afford the product (mixture of 2 diastereoisomers, 9 mg, 0.02 mmol, 18%) as a white solid.

$^1$H NMR (300 MHz, CD$_3$OD) δ 7.81, 7.79 (0.9s+0.1s, 1H), 7.36-7.14 (m, 5H), 6.26 (d, J=17.4 Hz, 0.1H) and 6.24 (d, J=17.4 Hz, 0.9H), 4.93-4.89 (overlapped with H$_2$O, m, 1H), 4.80-4.78 (m, 1H), 4.53-4.49 (m, 2H), 4.21-4.18 (m, 1H), 3.95-3.84 (m, 1H), 3.23-3.20 (m, 1H), 3.04 (bs, 1H), 1.31-1.14 (m, 9H). $^{31}$P NMR (121 MHz, CD$_3$OD) δ 4.06 (s), 3.97 (s). MS (ESI) m/z calcd. for C$_{25}$H$_{32}$FN$_7$O$_7$P [M+H]$^+$ 592.2; found 592.2.

Example 21

Preparation of isopropyl (((((R,S)-(2R,3R,4R,5R)-5-(2-amino-6-(N-methylcyclopropylamino)-9H-purin-9-yl)-4-fluoro-3-hydroxy-4-ethynyltetrahydrofuran-2-yl)methoxy)-phenoxy-phosphoryl)-L-alaninate

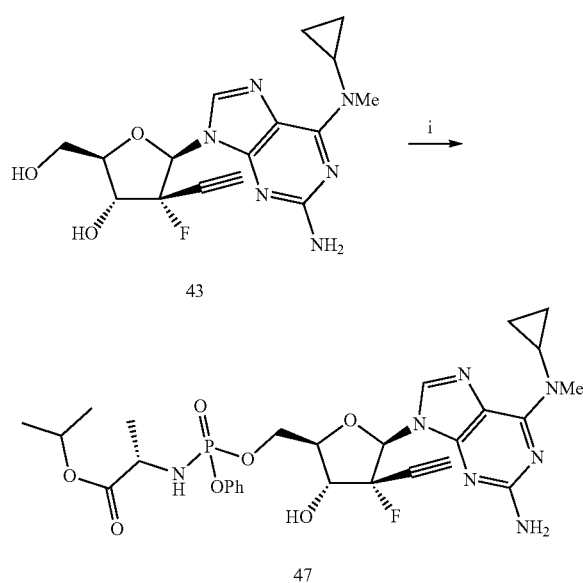

i) Isopropyl ((R,S)-(pentafluorophenoxy)-phenoxy-phosphoryl)-L-alaninate, tBuMgCl, THF, 0° C.

Step 1. Preparation of isopropyl (((((R,S)-(2R,3R,4R,5R)-5-(2-amino-6-(N-methylcyclopropylamino)-9H-purin-9-yl)-4-fluoro-3-hydroxy-4-ethynyltetrahydrofuran-2-yl)methoxy)-phenoxy-phosphoryl)-L-alaninate To a solution of compound 43 (40 mg, 0.11 mmol) in dry THF (2 mL) at 0° C. was added tert-butyl magnesium chloride (1.0 M in THF, 160 μL, 0.16 mmol) dropwise over 10 min. The reaction mixture was stirred 15 min at 0° C. then another 15 min at room temperature. The reaction mixture was cooled down to 0° C. and a solution of isopropyl ((R,S)-(pentafluorophenoxy)-phenoxy-phosphoryl)-L-alaninate (55 mg, 0.12 mmol) dissolved in dry THF (2 mL) was added dropwise over 10 min. The reaction mixture was stirred at 0° C. for 30 min and 18 h at room temperature. The reaction was quenched with a saturated aq. NH$_4$Cl solution (4 mL) and extracted with EtOAc (3×5 mL). The combined organics were dried over Na$_2$SO$_4$ and concentrated. The residue was purified by column chromatography (gradient DCM/MeOH 100:0 to 90:10) to afford the product (mixture of 2 diastereoisomers, 18 mg, 0.03 mmol, 26%) as a white solid.

$^1$H NMR (300 MHz, CD$_3$OD) δ 7.84, 7.82 (s+s, 1H), 7.35-7.14 (m, 5H), 6.30 (d, J=17.4 Hz) and 6.26 (d, J=17.6 Hz, 1H), 4.99-4.89 (overlapped with H$_2$O, m, 1H), 4.82-4.69 (m, 1H), 4.59-4.46 (m, 2H), 4.21 (m, 1H), 3.96-3.82 (m, 1H), 3.24-3.22 (m, 1H), 3.17-3.11 (m, 1H) 1.31-1.26 (m, 3H), 1.20-1.15 (m, 6H), 0.93-0.89 (m, 2H), 0.75-0.68 (m, 2H). $^{31}$P NMR (121 MHz, CD$_3$OD) δ 4.06 (s), 3.98 (s). MS (ESI) m/z calcd. for C$_{28}$H$_{36}$FN$_7$O$_7$P [M+H]$^+$ 632.2; found 632.2.

Example 22

Preparation of PPAL-S

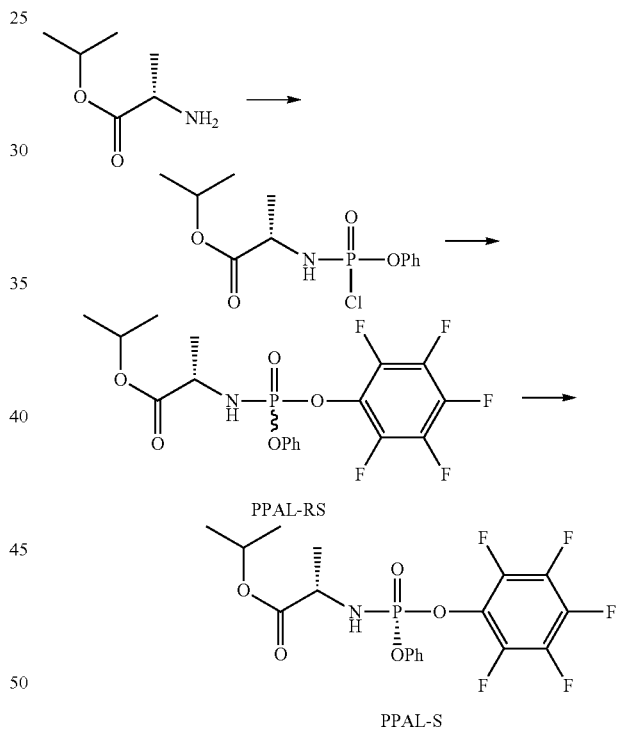

Step 1. Preparation of Racemic PPAL

To a stirred solution of phenyl dichlorophosphate (250 g) in EtOAc (800 mL) was added isopropyl L-alaninate (200 g) in triethylamine (120 g) at −10° C. The reaction was stirred at −10° C. for 1 h. The compound 2,3,4,5,6-pentafluorophenol (220 g) in triethylamine (120 g) and EtOAc (400 mL) was added at −5° C. and stirred at that temperature for 0.5 h. The reaction mixture was allowed to warm to 25° C. and stirred at that temperature for 2 h. The solution was filtrated and washed with EtOAc (2×200 mL), and the combined organic phases were evaporated under vacuum to afford the solid PPAL-RS (racemate).

Step 2. Preparation of PPAL-RS

To a stirred solution of PPAL-RS in EtOAc (200 mL) and in-heptane (1.4 L) was added 2,3,4,5,6-pentafluorophenol (10.1 g) in triethylamine (6 g), and stirring was continued for about 4-8 h. After the R-isomer of the solid was less than 0.5%, the solid was filtered. The solid was dissolved in EtOAc (4 L), washed with water (2×100 mL), brine (1 L), dried over anhydrous $Na_2SO_4$, and filtered. The solvent was removed under vacuum to afford the PPAL-S (350 g).

$^1$H NMR (400 MHz, DMSO-d6) δ=7.42-7.40 (m, 2H), 7.24-7.22 (m, 3H), 6.87 (dd, J=14.1, 9.9 Hz, 1H), 4.90-4.84 (m, 1H), 3.94-3.88 (m, 1H), 1.27 (dd, J=7.1, 1.1 Hz, 3H), 1.15 (dd, J=6.2, 1.2 Hz, 6H) ppm. $^{13}$P NMR (160 MHz, DMSO-d6) δ=0.37 ppm.

Example 23

Preparation of PPAL-R

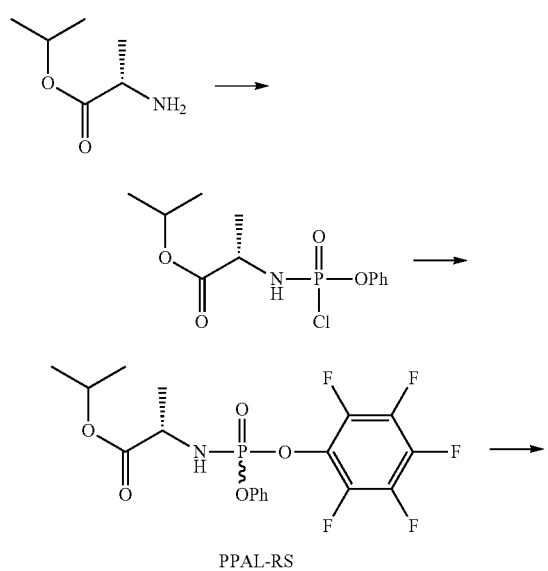

PPAL-RS

PPAL-R

To a three-necked round bottom flask fitted with a mechanic stirrer were added phenyl dichlorophosphate (189.6 g, 0.90 mol) and anhydrous EtOAc (750 mL). The solution was cooled to −10° C. under a nitrogen atmosphere. Iso-propyl L-alaninate (118 g, 0.90 mmol) and triethylamine (100 g, 1.1 eq) were added to the above solution. A pre-cooled (below 10° C.) mixture of 2,3,4,5,6-pentafluorophenol (165 g, 1 eq) and triethylamine (90.5 g, 1 eq) in EtOAc (300 mL) was added to the mixture via an addition funnel at −5° C. and the resulting mixture was stirred between 20-25° C. for 1 hour. The white precipitate (TEA.HCl) was filtered off and rinsed with EtOAc. The filtrate was concentrated under reduced pressure to yield PPAL-RS about 280 g (S/R=1/1) as a white solid PPAL-RS (280 g) was triturated in 300 mL of heptane/EtOAc (20:1) at room temperature for 5 min. The white suspension was filtered and the solid was rinsed with a mixture of heptane/EtOAc (20:1). The filtrate was cooled to 8° C. and the solid was collected by filtration. Crude PPAL-R (10 g) was obtained with 95% chiral purity. The crude product was purified following above step. PPAL-R (5 g) was obtained in NLT 98% chiral purity.

$^1$H NMR (400 MHz, DMSO-$d_6$) δ=7.43-7.39 (m, 2H), 7.27-7.22 (m, 3H), 6.87 (dd, J=14.1, 9.9 Hz, 1H), 4.89-4.85 (m, 1H), 3.95-3.90 (m, 1H), 1.27 (dd, J=7.1, 1.1 Hz, 3H), 1.14 (dd, J=6.2, 1.2 Hz, 6H). $^{31}$P NMR (160 MHz, DMSO-$d_6$) δ=0.35.

Example 24

Preparation of Compound 52

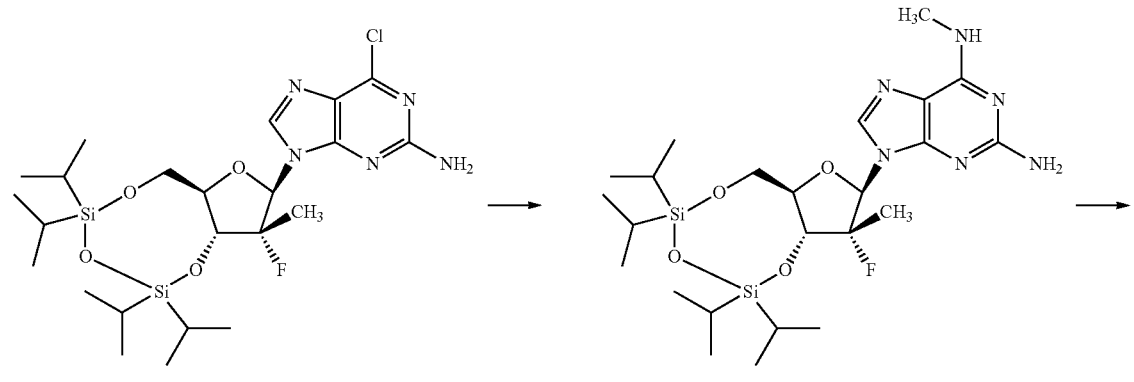

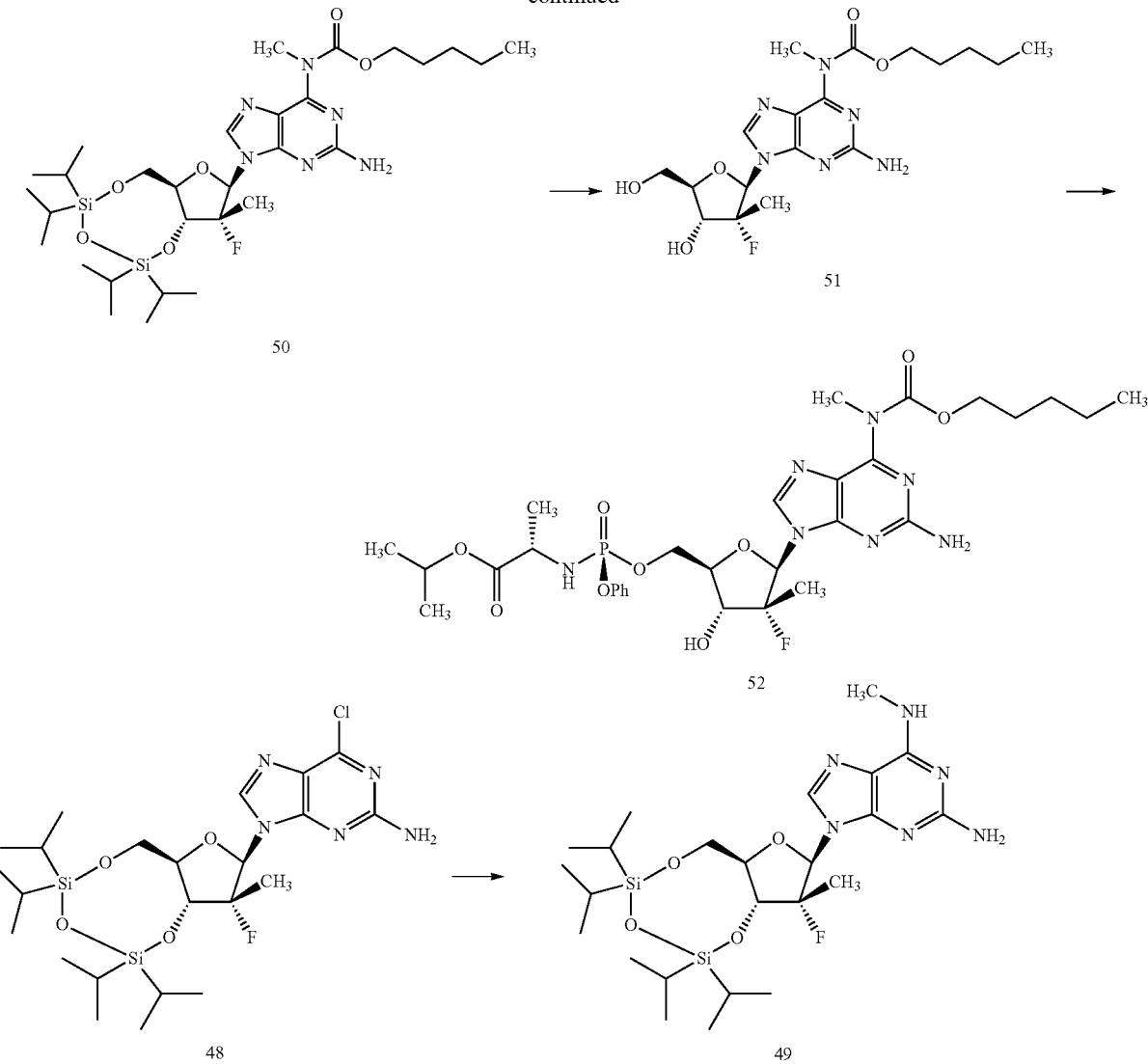

Step 1. Preparation of Compound 49

To a solution of 48 (1.81 g, 3.23 mmol) in dioxane (18 mL) was added 40% aqueous $CH_3NH_2$ solution (16.2 mmol). The reaction was stirred at 40° C. for 2 h. The mixture was concentrated, diluted with EtOAc (50 mL), washed with water and brine. The organic layer was dried over anhydrous $Na_2SO_4$, filtered and concentrated to afford a white solid 49 (1.66 g, 92%).

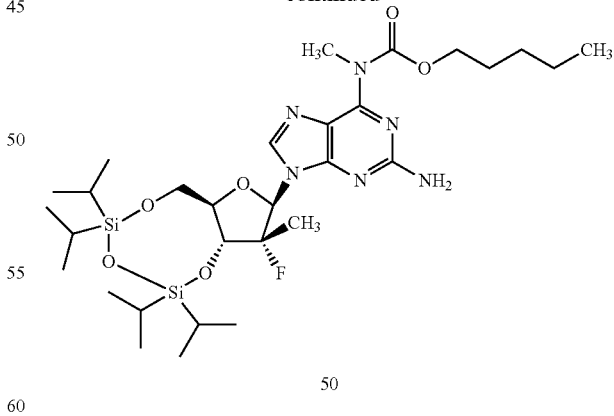

Step 2. Preparation of Compound 50

To a solution of 49 (1.34 g, 2.42 mmol) and 1-methylimidazole (794 mg, 9.68 mmol) in DCM (14 mL) was slowly added pentyl chloroformate (547 mg, 3.63 mmol) at 0° C. The reaction was stirred at r.t overnight. The mixture was concentrated, and purified by column chromatography (PE:EtOAc=5:1-2:1) to afford 50 (1.01 g, 62%) as a white solid.

¹HNMR (400 MHz, DMSO) δ 7.96 (s, 1a), 6.73 (s, 1K), 6.06-6.10 (d, J=16.0 Hz, 1H), 4.09-4.30 (m, 2H), 3.97-4.09 (m, 4H), 3.28 (s, 3H), 1.39-1.46 (m, 2H), 1.0-1.2 (m, 35H), 0.73-0.76 (t, J=8.0 Hz, 3H).

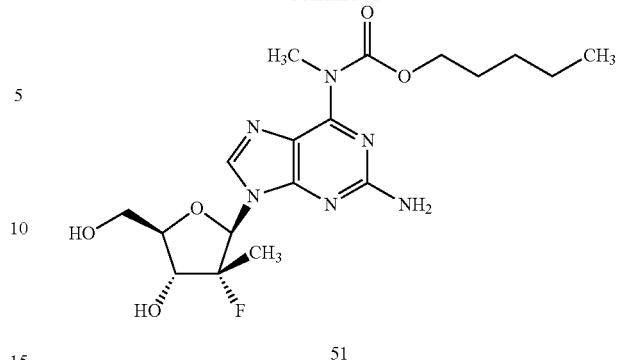

51

Step 3. Preparation of Compound 51

To a solution of 50 (1.00 g, 1.5 mmol) in THF (11 mL) was added Et₃N (2.0 mL, 15 mmol) and Et₃N.3HF (1.21 g, 7.5 mmol) at 0° C. The reaction was stirred at r.t for 1.5 h. The mixture was concentrated, and purified by column chromatography (MeOH:CH₂Cl₂=50:1) to afford 75 (460 mg, 72.2%) as a white powder.

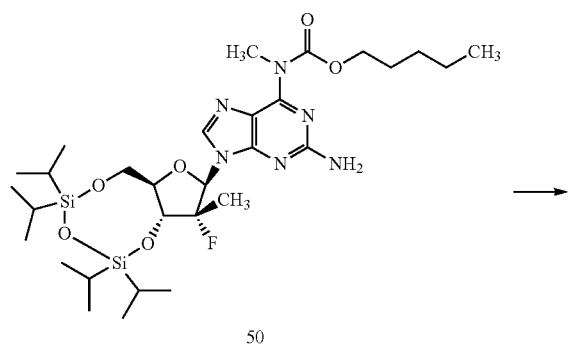

50

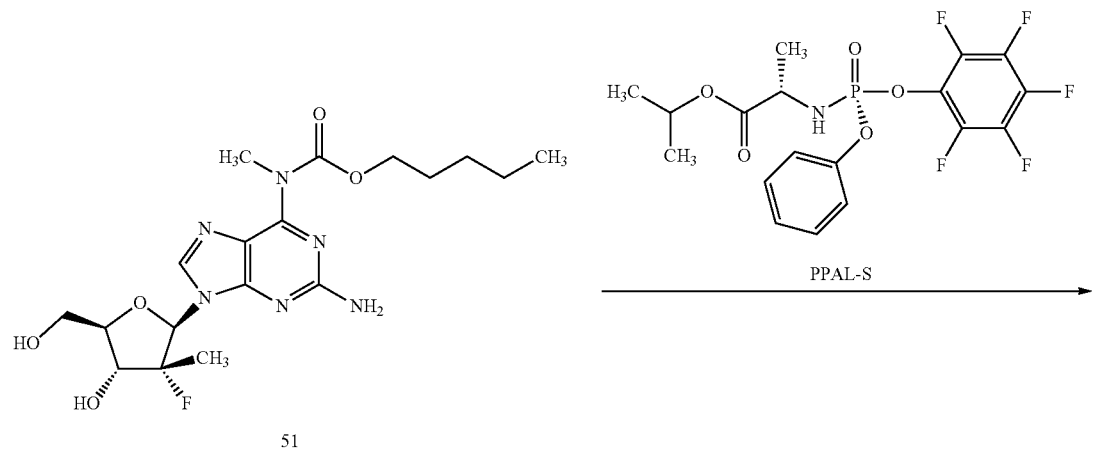

51

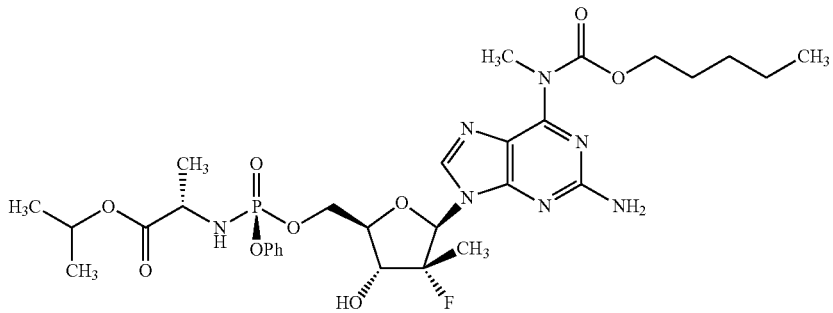

52

Step 4. Preparation of Compound 52

To a solution of 51 (460 mg, 1.08 mmol) and PPAL-S (538 mg, 1.19 mmol) in anhydrous THF (9 mL) was slowly added t-BuMgCl (2.27 mmol) at 5-10° C. under $N_2$. The reaction was stirred at r.t for 40 min. The mixture was quenched with aq. saturated $NH_4Cl$ solution, extracted with EtOAc, washed with aq. 5% $K_2CO_3$ solution and brine, dried over anhydrous $Na_2SO_4$, filtered and concentrated. The crude product was purified by column chromatography ($CH_2Cl_2$:MeOH=15:1) to afford 52 (280 mg, 37.3%) as a white solid.

$^1$H NMR (400 MHz, DMSO) δ 8.12 (s, 1H), 7.34-7.38 (m, 2H), 7.18-7.23 (m, 3H), 6.74 (s, 2H), 6.11-6.16 (d, J=16.0 Hz, 1H), 5.99-6.05 (m, 1H), 5.84 (m, 1H), 4.77-4.81 (m, 1H), 4.30-4.41 (m, 3H), 4.03-4.11 (m, 3H), 3.78-3.80 (m, 1H), 3.3 (s, 3H), 1.44-1.51 (m, 2H), 1.00-1.21 (m, 16H), 0.76-0.80 (t, J=8.0 Hz, 3H). [M+H]$^+$=696.6.

Example 25

Preparation of Compound 56

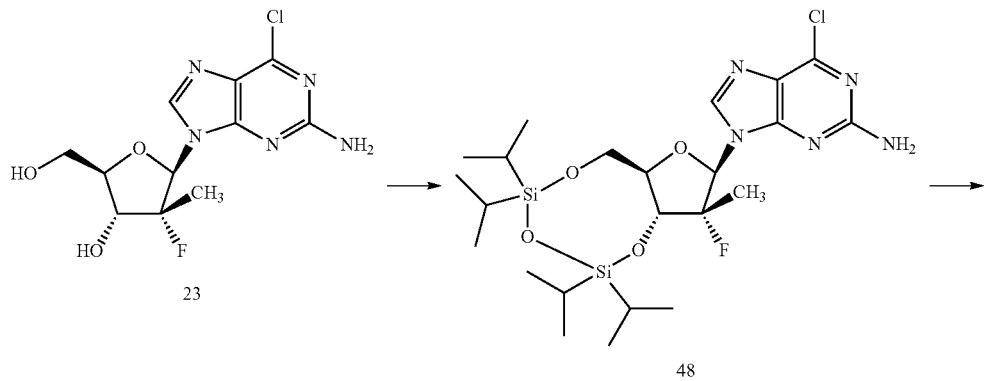

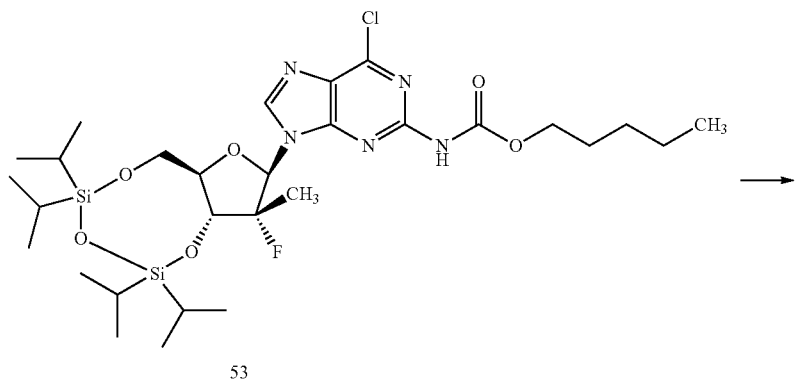

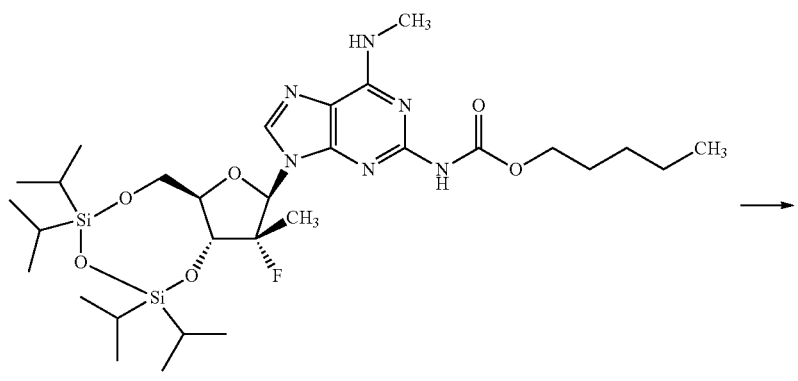

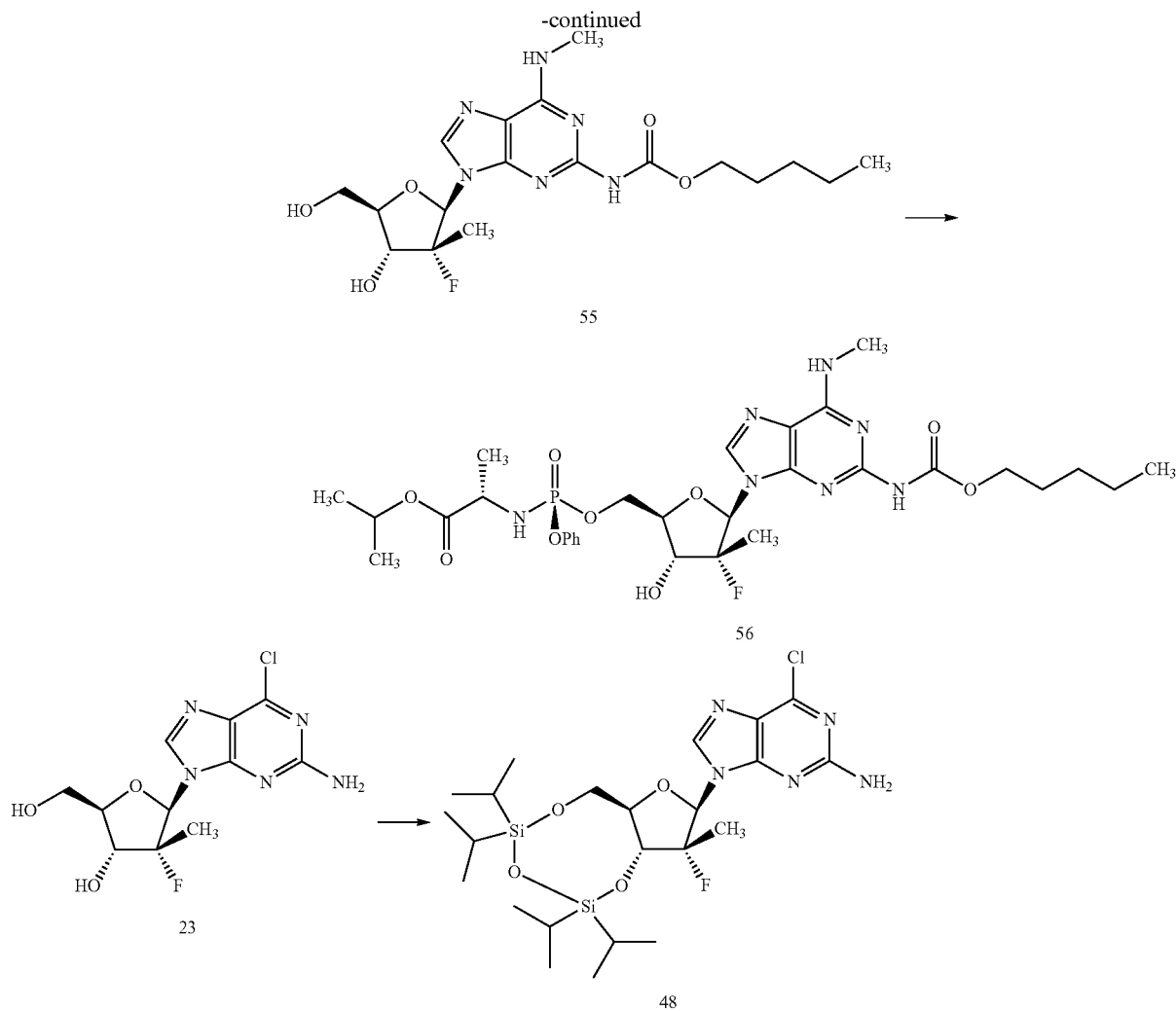

Step 1. Preparation of Compound 48

To a solution of 23 (600 mg, 1 eq) in pyridine (30 mL) was added TIPDSCl$_2$ (1.5 eq) at 0° C. The resulting solution was allowed to stand at room temperature for 2 h. The mixture was quenched with ice water and extracted with EtOAc. The organic layer was washed with 1M aq. HCl solution, saturated aqueous sodium bicarbonate and saturated aqueous sodium chloride, dried over anhydrous sodium sulfate, and concentrated to yield the crude residue. The residue was purified by chromatography (MeOH:CH$_2$Cl$_2$=1:50) to afford 48 (998 mg, 94.4%) as a white solid form.

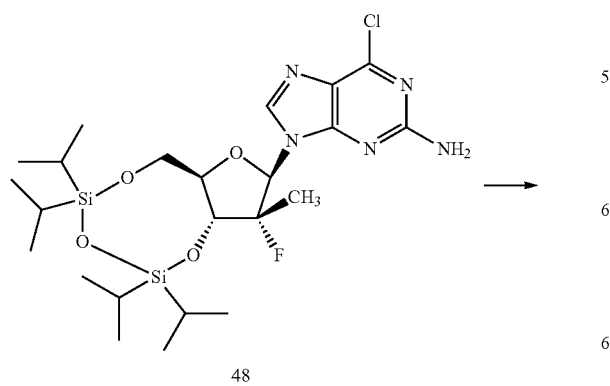

Step 2. Preparation of Compound 53

A mixture of 48 (800 mg, 1 eq), pyridine (3.2 mL), DMAP (34.9 mg, 0.2 eq) in DCM (20 mL) was stirred at room temperature. N-amyl chloroformate (3.2 mL) was added dropwise at 0° C., and the mixture was stirred at room temperature for 1 day. The organic layer was washed with 1M aqueous HCl solution, saturated aqueous sodium bicarbonate and saturated aqueous sodium chloride, dried over anhydrous sodium sulfate, and evaporated in vacuo. The residue was purified by chromatography on silica gel (MeOH:CH$_2$Cl$_2$=1:50) to afford 53 (255 mg, 26% as a white solid foam.

was chromatographed on silica gel (methanol:dichloromethane=1:40) to afford 54 (220 mg, 81.7%) as a white solid foam.

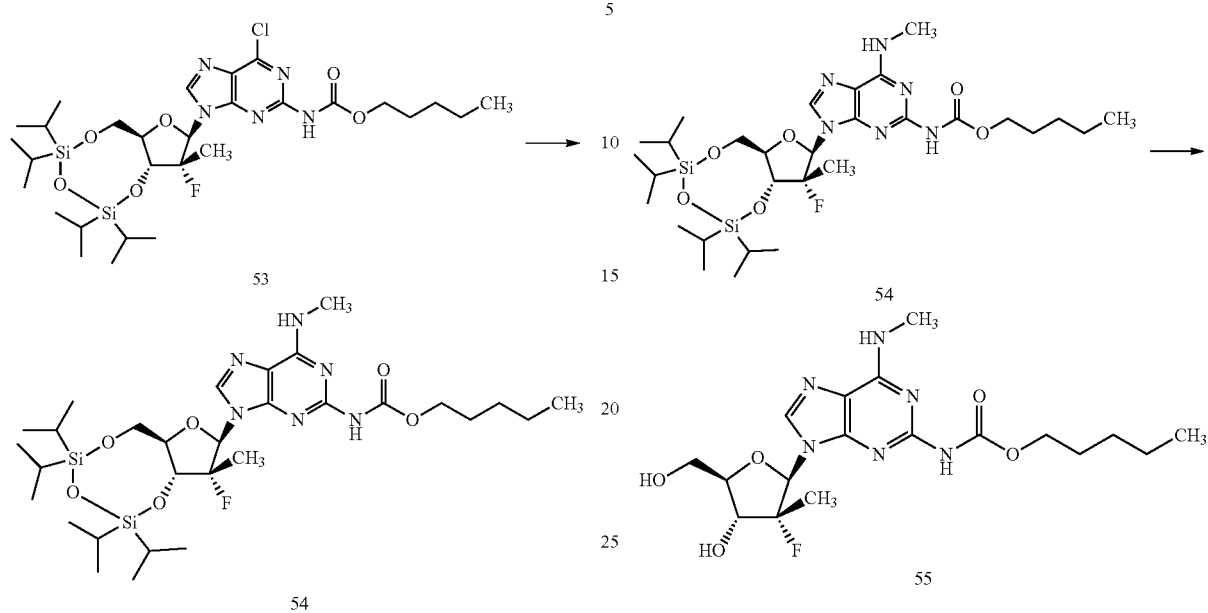

Step 3. Preparation of Compound 54

To the solution of 53 (270 mg, 1 eq) in 1,4-dioxane (10 mL), was dropwise added 40%/aqueous CH$_3$NH$_2$ solution (225.7 mg, 5 eq). The mixture was stirred for 2 h at room temperature and then concentrated in vacuo. The residue

Step 4. Preparation of Compound 55

Triethylamine (1011.9 mg, 10 eq) and Et$_3$N.3HF (806.05 mg, 5 eq) were added to an ice-cooled solution of 54 (668 mg, 1 eq) in THF (10 mL), the mixture was stirred for 2 h at room temperature. The mixture was concentrated and chromatographed on silica gel (MeOH:CH$_2$Cl$_2$=1:30) to afford 55 (492 mg, 84%) as a white solid foam.

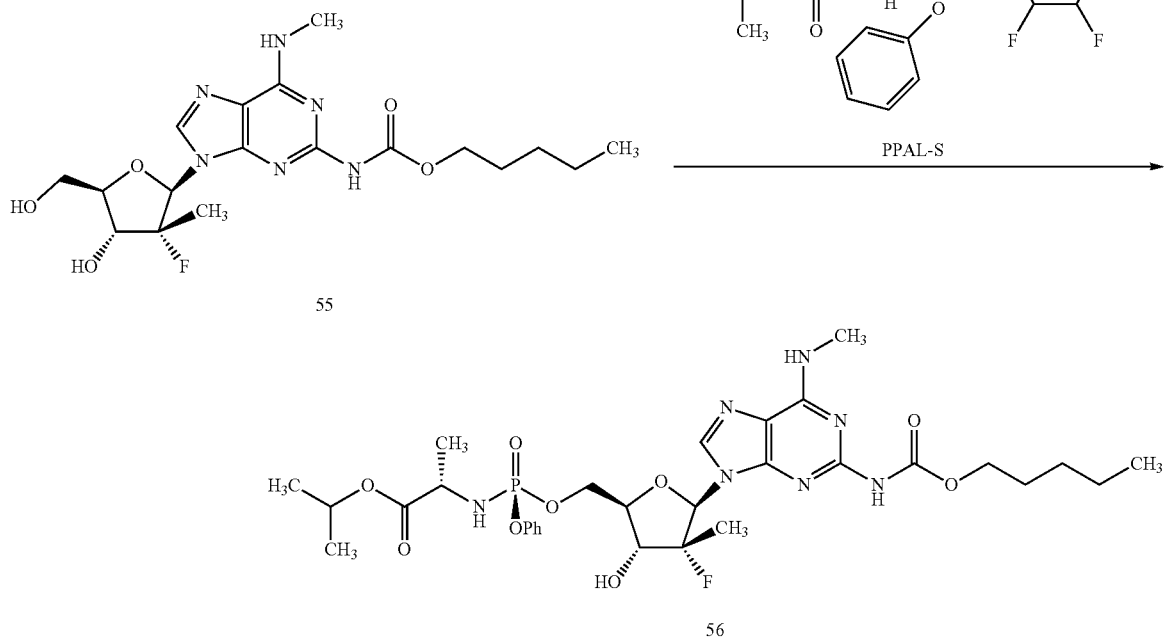

Step 5. Preparation of Compound 56

To the mixture of 55 (113 mg, 1 eq) and PPAL-S (120 mg, 1 eq) in THF (4 mL) was dropwise added 1.7 M t-BuMgCl in THF (0.327 mL, 2.1 eq) at −10° C. The mixture was stirred at room temperature for 1 h, and then quenched with saturated aq. NH₄Cl solution. The aqueous phase was extracted with EtOAc and the organic phase was washed with brine, dried and concentrated to obtain crude residue. The residue was subjected to flash chromatography to afford 56 (126 mg, 68.5%) as a white solid.

$^1$H NMR (400 MHz, DMSO) δ 8.00 (s, 1H), 7.10-7.45 (m, 5H), 6.15-6.20 (d, J=20.0 Hz, 1H), 5.00-5.25 (s, 1H), 4.80-4.86 (m, 1H), 4.45-4.70 (m, 2H), 4.12-4.19 (m, 3H), 3.80-3.85 (m, 1H), 3.04 (s, 3H), 1.60-1.75 (m, 2H), 1.10-1.40 (m, 16H), 0.76-0.80 (t, J=8.0 Hz, 3H).
$^{31}$P NMR (160 MHz, DMSO) δ 3.57. [M+H]⁺=696.5.

Example 26

Preparation of Compound 60

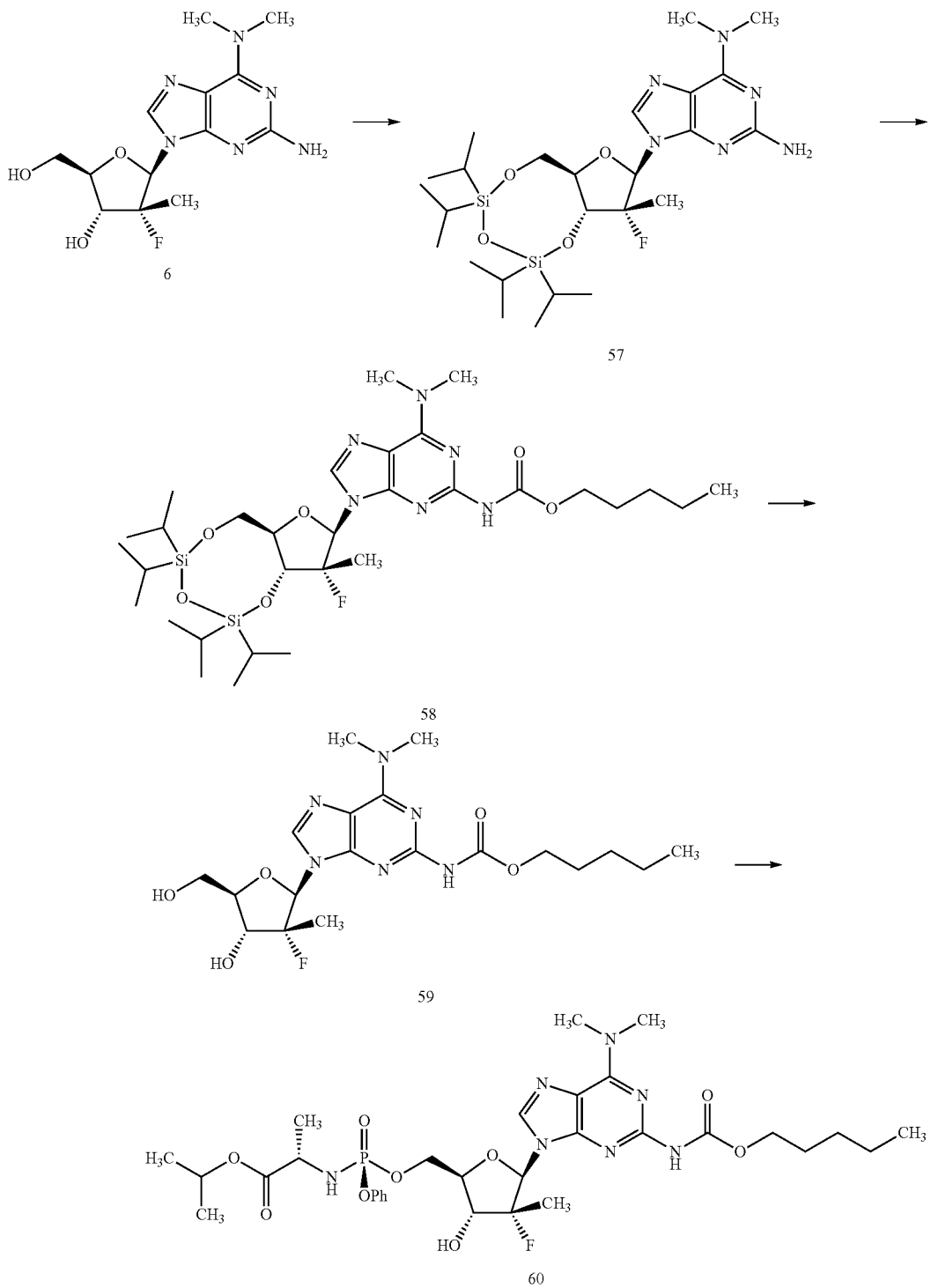

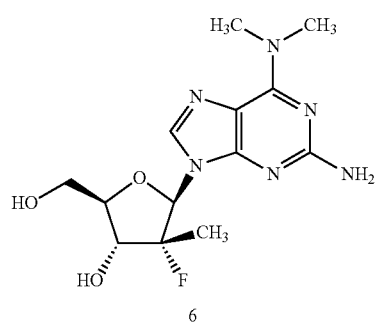

6

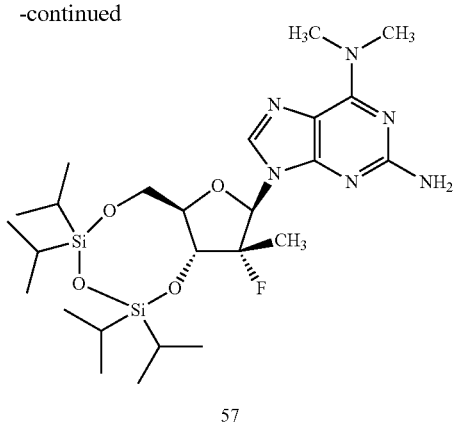

57

Step 1. Preparation of Compound 57

To a solution of 6 (20 g, 1 eq) in CH$_3$CN (100 mL) was added imidazole (16.6 g), TIPDSCl$_2$ (28.9 g, 1.5 eq) in sequence at 5±5° C. The resulting solution was allowed to stand at room temperature for 4 h. The mixture was quenched with ice water and extracted with EtOAc. The organic layer was washed with water, saturated aqueous sodium bicarbonate and saturated aqueous sodium chloride, dried over anhydrous sodium sulfate, and concentrated to afford the crude residue (32 g).

Step 2. Preparation of Compound 58

To the solution of 57 (9.8 g, 1 eq) in THF (4 mL) was dropwise added 1.7 M t-BuMgCl in THF (50 mL, 4.8 eq) at 0-5° C. The mixture was stirred at room temperature for 0.5 h, and n-amyl chloroformate (2.7 g, 1.05 eq) was slowly added. The mixture was stirred at 0-5° C. for 3-4 h. The mixture was quenched with saturated aq. NH$_4$Cl solution. The aqueous phase was extracted with EtOAc (200 mL) and the organic phase was washed with brine, dried and concentrated to obtain 58 (10.7 g) as oil.

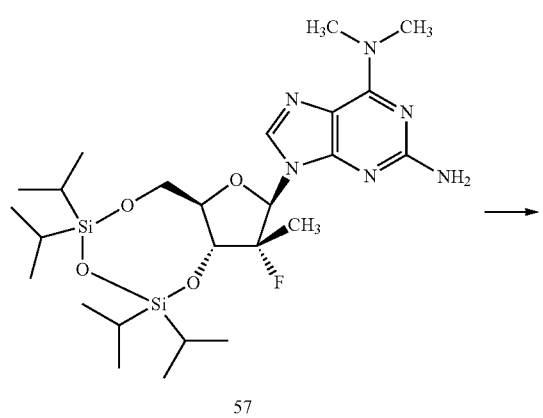

57

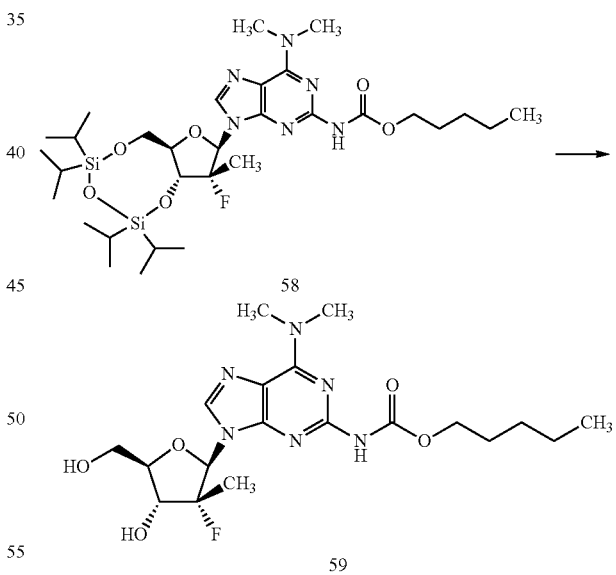

58

59

Step 3. Preparation of Compound 59

Triethylamine (10.119 g) and Et$_3$N.3HF (8.6 g, 5 eq) were added to an ice-cooled solution of 58 (7.3 g, 1 eq) in THF (100 mL) and the mixture was stirred for 1 h at room temperature. The mixture was concentrated and chromatographed on silica gel (MeOH:CH$_2$Cl$_2$=1:30) to afford 59 (4.3 g, 91%) as a white solid.

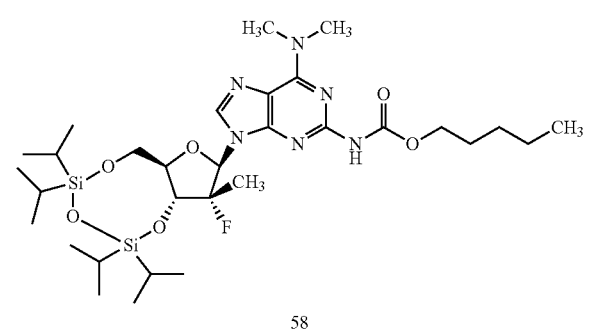

58

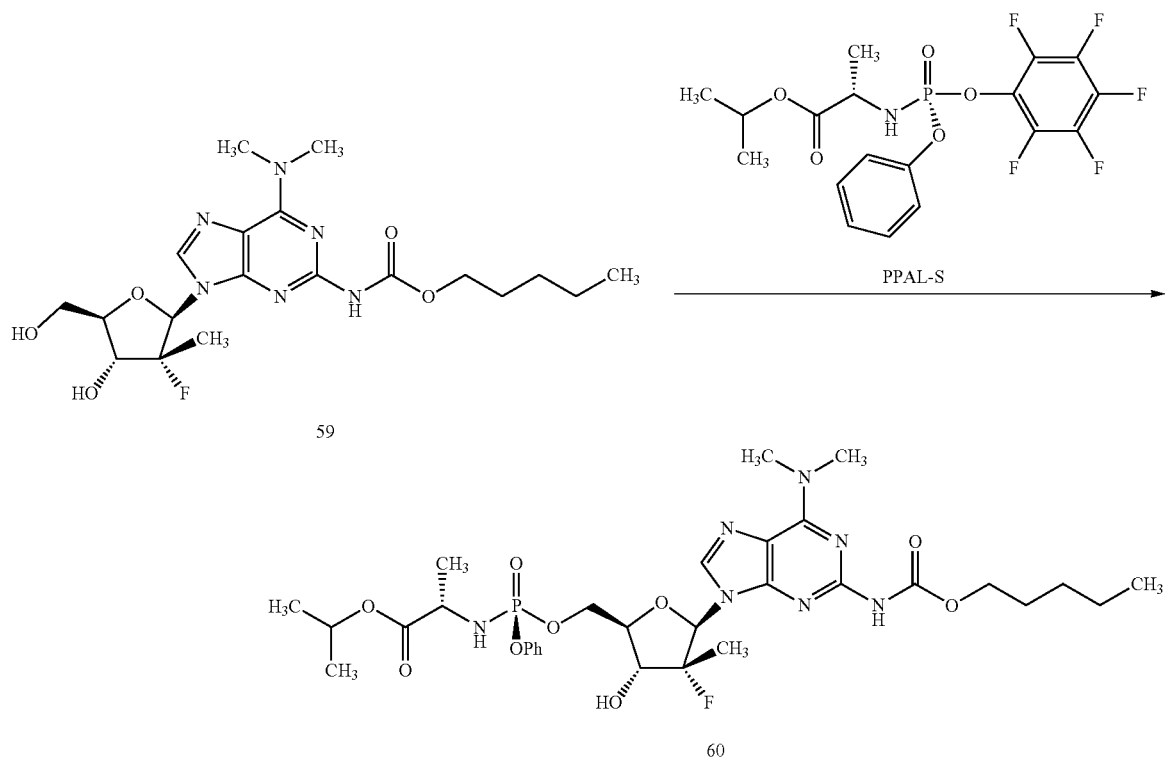

Step 4. Preparation of Compound 60

To the mixture of 59 (2 g, 1 eq) and PPAL-S (2.3 g, 1.1 eq) in THF (40 mL) was dropwise added 1.7 M t-BuMgCl in THF (5.6 mL, 2.1 eq) at −5° C. The mixture was stirred at −20±5° C. for 1 h, and then quenched with saturated aq. NH$_4$Cl solution. The aqueous phase was extracted with EtOAc and the organic phase was washed with brine, dried and concentrated to obtain crude residue. The residue was subjected to flash chromatography to afford 60 (1.5 g, 47%) as a white solid.

$^1$H NMR (400 MHz, CD$_3$OD) δ 7.9 (s, 1H), 7.1~7.2 (m, 5H), 6.2 (d, J=20 Hz, 1H), 5.1 (br, 1H), 4.84 (m, 1H), 4.49 (m, 2H), 4.16 (m, 1H), 4.13 (m, 2H), 3.86 (m, 1H), 3.45 (br, 6H), 1.70 (m, 2H), 1.26 (m, 4H), 1.20 (m, 6H), 1.14 (m, 6H), 0.93 (m, 3 H). [M+H]$^+$=710.5.

Biological Data

Example 27

Assay Methodology and Additional Biological Data

Figure 2:
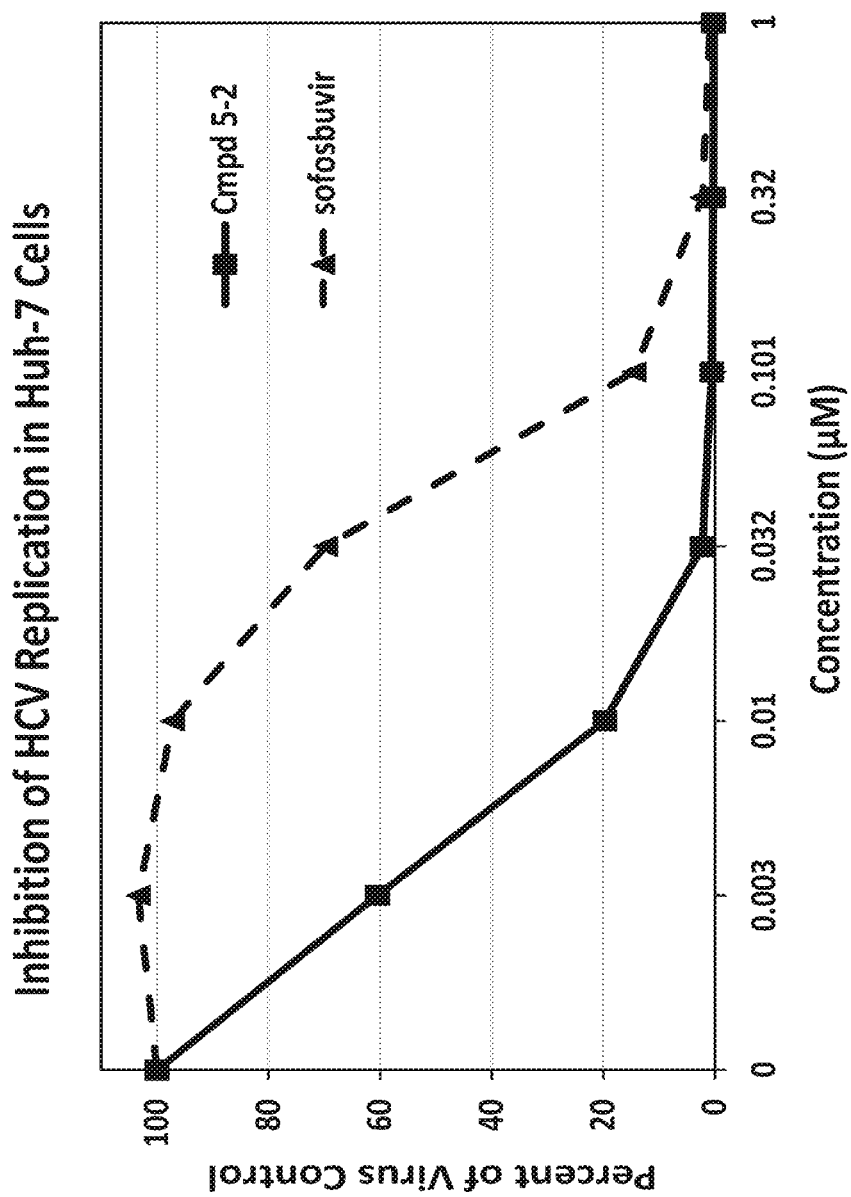
FIG. 2 is a graph of the HCV replication inhibition curves for Compound 5-2 (Table 7) and Sofosbuvir. Compound 5-2 has an $EC_{50}$=4 nM, a $TC_{50}$ greater than one hundred micromolar and a therapeutic index of greater than 25,000. Sofosbuvir has an $EC_{50}$=53 nM, a $TC_{50}$ greater than one hundred micromolar and a therapeutic index greater than 1,920. The y-axis is the percent of virus control and the x-axis is the concentration of drug in μM.
Figure 3:
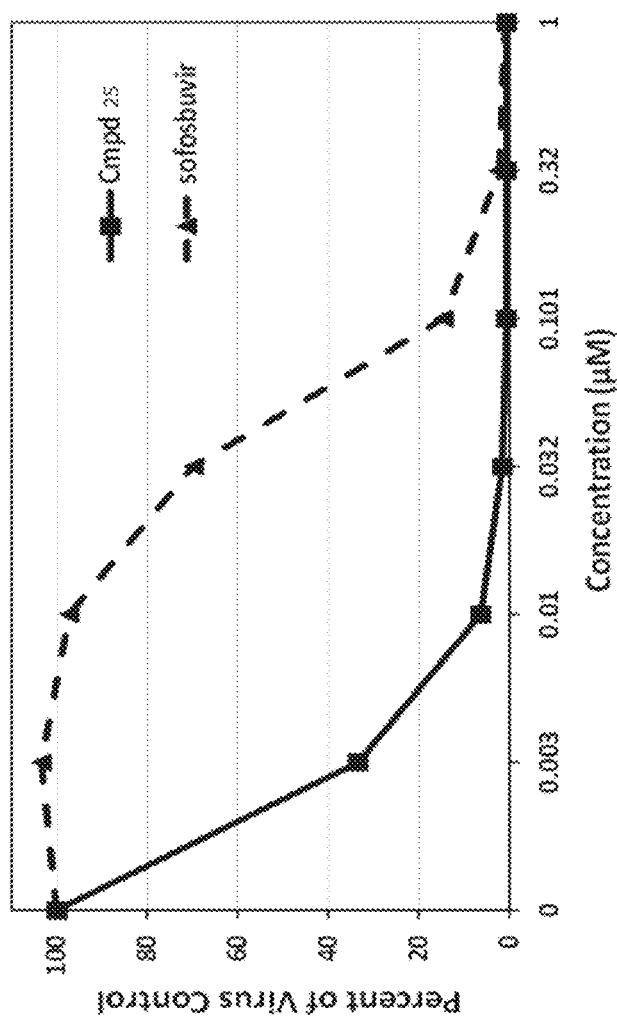
FIG. 3 is a graph of the HCV replication inhibition curves for Compound 25 (Table 7) and Sofosbuvir. As described in Example 27, Compound 25 has an $EC_{50}$=4 nM, a $TC_{50}$ of greater than 100 μM, and a therapeutic index of greater than 25,000. Sofosbuvir has an $EC_{50}$=53 nM, a $TC_{50}$ greater than one hundred micromolar and a therapeutic index greater than 1,920. The y-axis is the percent of virus control and the x-axis is the concentration of drug in μM.
Figure 4:
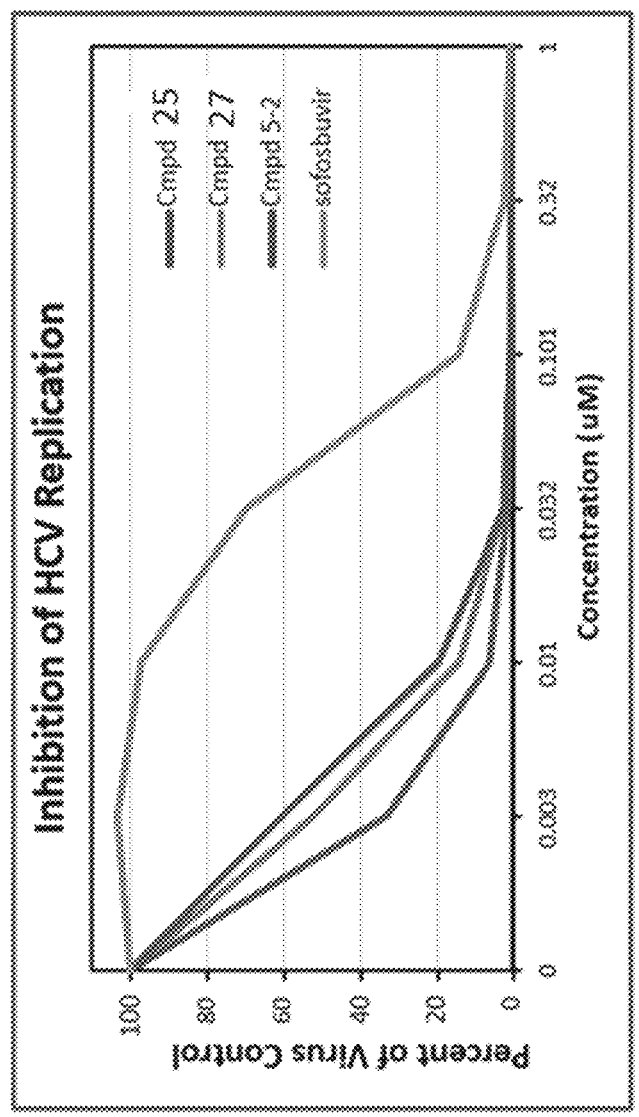
FIG. 4 is an intra-assay comparison of the anti-HCV activity for Compounds 5-2, 25, 27 (Table 7) and Sofosbuvir. The y-axis is the percent of virus control and the x-axis is the concentration of drug in μM. See, Example 27.

Huh-7 luc/neo ET cells bearing a discistronic HCV genotype 1b luciferase reporter replicon were plated at 7.5×10$^3$ cells/ml in duplicate 96-well plates for the parallel determination of antiviral efficacy (EC$_{50}$) and cytotoxicity (TC$_{50}$). The plates were cultured for 24 hours prior to the addition of compounds. Six serial one half log dilutions of the test articles (high test concentration of 100.0 μM or high test concentration of 1.0 μM) and human interferon-alpha2b (high test 10.0 U/ml) were prepared in cell culture medium and added to the cultured cells in triplicate wells for each dilution. Six wells in the test plates received medium alone as an untreated control. Following 72 hours of culture in the presence of compound, one of the plates was used for the determination of cytotoxicity by staining with XTT and the other for antiviral efficacy by determination of luciferase reporter activity. Cytotoxicity and efficacy data were collected and imported into a customized Excel workbook for determination of the TC$_{50}$ and EC$_{50}$ values. Data for compounds of Formula I-VII are illustrated in Table 7 below. In addition, FIG. 2 illustrates the HCV replication inhibition curves for Compound 5-2 and Sofosbuvir. As can be seen in FIG. 2, Compound 5-2 has an EC$_{50}$=4 nM, while Sofosbuvir has an EC$_{50}$=53 nM. The y-axis is the percent of virus control and the x-axis is the concentration of drug in μM. FIG. 3 illustrates the HCV replication inhibition curves for Compound 25 and Sofosbuvir. Compound 25 has an EC$_{50}$=4 nM and Sofosbuvir has an EC$_{50}$=53 nM. The y-axis is the percent of virus control and the x-axis is the concentration of drug in μM. FIG. 4 illustrates an intra-assay comparison of the anti-HCV activity for Compounds 5-2, 25, 27 and Sofosbuvir. The y-axis is the percent of virus control and the x-axis is the concentration of drug in μM.

Various patient-derived HCV genotypes containing wild-type and resistance-associated variants were used to determine their relative replication sensitivity to test compounds. Replicon resistance test vectors (RTVs) containing the NS5B genomic regions were prepared using viral RNA isolated from plasma of HCV patients. Each NS5B region was amplified by reverse-transcription polymerase chain reaction and cloned into an HCV replicon RTV which was then transferred by electroporation into Huh-7 cells. After incubation in the absence and presence of serially diluted test compounds for 72-96 hr, viral replication was measured by luciferase activity and 50% inhibitory concentrations (IC$_{50}$ values) were determined.

Table 2 reports the IC$_{50}$ and IC$_{95}$ values for compound 25, 27, 5-2 and Sofosbuvir against various clinical isolates containing wild-type and resistance-associated variants.

All compounds were significantly more effective against HCV replication than sofosbuvir and neither 25, 27 nor 5-2 compound showed any evidence of cross-resistance to L159F, L159F and S282T, and C316N mutants.

All compounds were significantly more effective against HCV replication than sofosbuvir and neither 25, 27, nor 5-2 compounds showed any evidence of cross-resistance to S282T variant.

TABLE 2

Antiviral Activity of Test Compounds in Patient-derived HCV Genotypes

| HCV Genotype | NS5B Mutation | Test Compound | $IC_{50}$ Value (nM) | $IC_{95}$ Value (nM) | Fold Change in $IC_{50}$ from Sofosbuvir | Fold Change in $IC_{95}$ from Sofosbuvir |
|---|---|---|---|---|---|---|
| 1a | none | sofosbuvir | 62.7 | 507.7 | | |
| | | 25 | 4.4 | 31.3 | 14.2 | 16.2 |
| | | 27 | 4.2 | 26.4 | 15.0 | 19.3 |
| | | 5-2 | 10.5 | 60.8 | 6.0 | 8.4 |
| 1b | none | sofosbuvir | 86.0 | 642.2 | 1.0 | |
| | | 25 | 5.9 | 32.0 | 1.0 | 20.0 |
| | | 27 | 5.0 | 28.9 | 0.9 | 22.2 |
| | | 5-2 | 10.6 | 72.4 | 0.8 | 8.9 |
| 2a | none | sofosbuvir | 22.5 | 195.1 | | |
| | | 25 | 2.7 | 22.2 | 8.4 | 8.8 |
| | | 27 | 2.9 | 16.2 | 7.9 | 12.0 |
| | | 5-2 | 6.2 | 45.4 | 3.6 | 4.3 |
| 2b | none | sofosbuvir | 44.8 | 295.3 | | |
| | | 25 | 3.0 | 14.9 | 15.2 | 19.9 |
| | | 27 | 3.1 | 14.7 | 14.4 | 20.1 |
| | | 5-2 | 6.3 | 32.5 | 7.1 | 9.1 |
| 3a-1 | none | sofosbuvir | 125.9 | 689.8 | | |
| | | 25 | 5.1 | 27.8 | 24.5 | 24.8 |
| | | 27 | 4.4 | 25.4 | 28.4 | 27.2 |
| | | 5-2 | 11.8 | 59.3 | 10.7 | 11.6 |
| 3a-2 | none | sofosbuvir | 123.5 | 808.1 | | |
| | | 25 | 4.7 | 24.2 | 26.3 | 33.4 |
| | | 27 | 4.5 | 23.3 | 27.5 | 34.6 |
| | | 5-2 | 10.4 | 56.5 | 11.9 | 14.3 |
| 4a | none | sofosbuvir | 74.9 | 681.4 | | |
| | | 25 | 4.6 | 33.0 | 16.2 | 20.7 |
| | | 27 | 3.6 | 38.1 | 20.7 | 17.9 |
| | | 5-2 | 9.9 | 74.4 | 7.5 | 9.2 |
| 4d | none | sofosbuvir | 93.7 | 1019.7 | | |
| | | 25 | 5.9 | 44.2 | 16.0 | 23.1 |
| | | 27 | 5.6 | 38.4 | 16.7 | 26.6 |
| | | 5-2 | 14.0 | 79.9 | 6.7 | 12.8 |
| 1a | L159F | sofosbuvir | 114.7 | 1067.5 | | |
| | | 25 | 5.2 | 40.4 | 22.0 | 26.4 |
| | | 27 | 5.1 | 36.2 | 22.3 | 29.5 |
| | | 5-2 | 13.0 | 95.3 | 8.8 | 11.2 |
| 1a | L159F and S282T | sofosbuvir | 1619.9 | 16950.9 | | |
| | | 25 | 17.2 | 158.5 | 94.0 | 107.0 |
| | | 27 | 14.9 | 141.6 | 108.4 | 119.7 |
| | | 5-2 | 38.7 | 313.5 | 41.9 | 54.1 |
| 1b | C316N | sofosbuvir | 73.9 | 472.8 | | |
| | | 25 | 3.2 | 18.1 | 23.1 | 26.2 |
| | | 27 | 3.1 | 16.5 | 23.5 | 28.7 |
| | | 5-2 | 7.7 | 42.7 | 9.6 | 11.1 |

A transient transfection assay was performed to determine the sensitivity of the wild type S282T mutant of HCV to test compounds. Huh-7 cells were electroporated in the presence of RNA transcribed from wild type or S282T HCV replicon plasmids from the T7 promoter. The transfected cells were seeded in to 96-well plates at $7.5 \times 10^3$ cells per well in Dulbecco's Modified Eagle's medium. After 24 hr of incubation, medium was removed and replaced with fresh medium containing no or various concentrations of test compounds. Following an additional 96-hr incubation, the anti-HCV activity was measured by luciferase endpoint with Britelite™ Plus luminescence reporter gene kit (Perkin Elmer, Shelton, Conn.). Duplicate plates were treated and incubated in parallel for assessment of cellular toxicity by staining with the tetrazolium dye XTT.

Table 3 reports the $IC_{50}$ and $IC_{95}$ values for compounds 25, 27, 5-2 and Sofosbuvir against HCV wild type and S282T replicons.

TABLE 3

Antiviral Activity of Test Compounds in a HCV Transient Infection Assay

| Compound | NS5B Mutation | $IC_{50}$ Value (nM) | $IC_{95}$ value (nM) | Fold change in $IC_{50}$ from Sofosbuvir | Fold change in $IC_{95}$ from Sofosbuvir |
|---|---|---|---|---|---|
| 5-2 | None | 1.4 | 9.98 | 26 | 22.2 |
| | S282T | 2.8 | 20.6 | 99.3 | >48.5 |
| 25 | None | <1 | 2.7 | >36.4 | 80.7 |
| | S282T | <1 | 9.4 | >278 | >106.4 |
| 27 | None | <1 | 4.1 | >36.4 | 53.2 |
| | S282T | <1 | 11.8 | >278 | >84.7 |
| Sofosbuvir | None | 36.4 | 218 | | |
| | S282T | 278 | >1000 | | |

The stability of selected compounds in fresh human whole blood and in human liver S9 fraction was determined in incubations containing 10 μM test compound. After incubations of 0, 30, 60 min, and up to 120 min, aliquots were removed and immediately extracted with 3 volumes of ice-cold methanol/acetonitrile (1:1, v/v). Extracts were centrifuged and supernatants were analyzed by LC-MS/MS for concentrations of unchanged test compound and potential metabolites.

Figure 5:
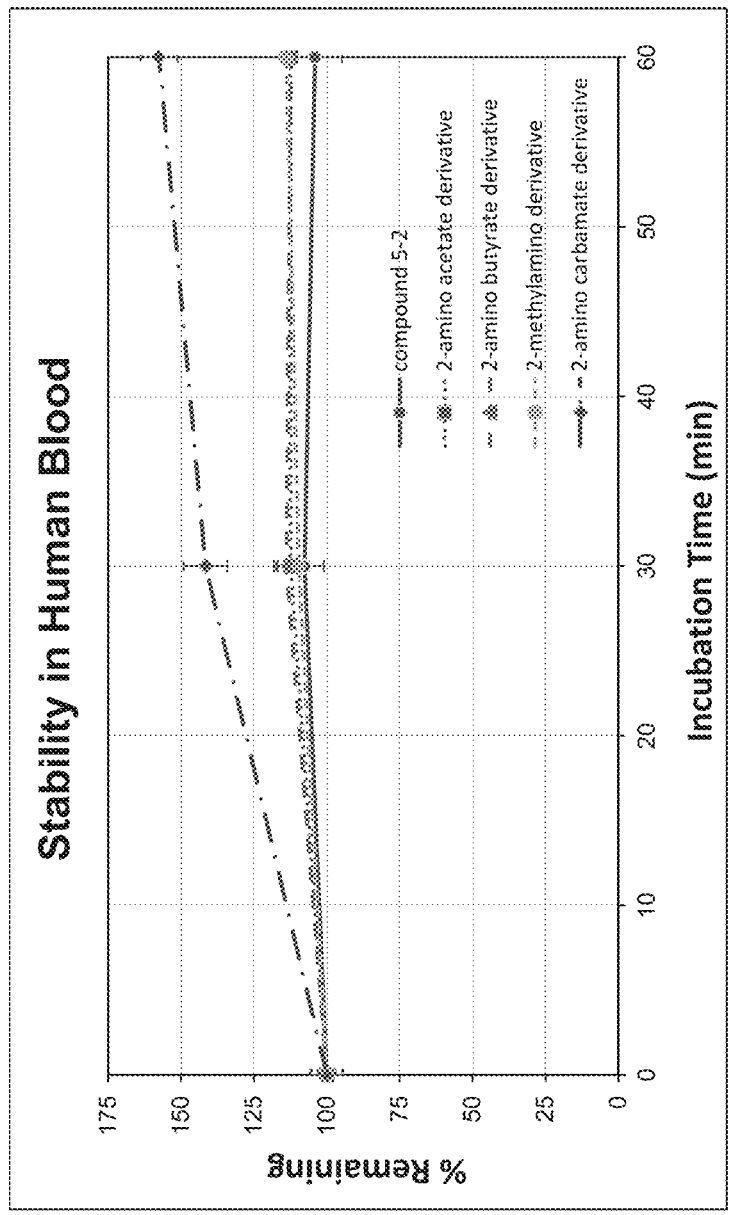
FIG. 5 is a graph that shows the stability of compounds 5-2; the $N^2$-acetate of compound 5-2, the $N^2$-butyrate of compound 5-2; the $N^2$-methyl derivative of compound 5-2; and the $N^2$-n-pentylcarbamate of compound 5-2 in human blood. The x axis is incubation time measured in minutes and the y axis is the measurement of the percent of the parent compound remaining.

FIG. 5 illustrates the excellent stability of compound 5-2 and all 2-amino derivatives in human blood.

Figure 6:
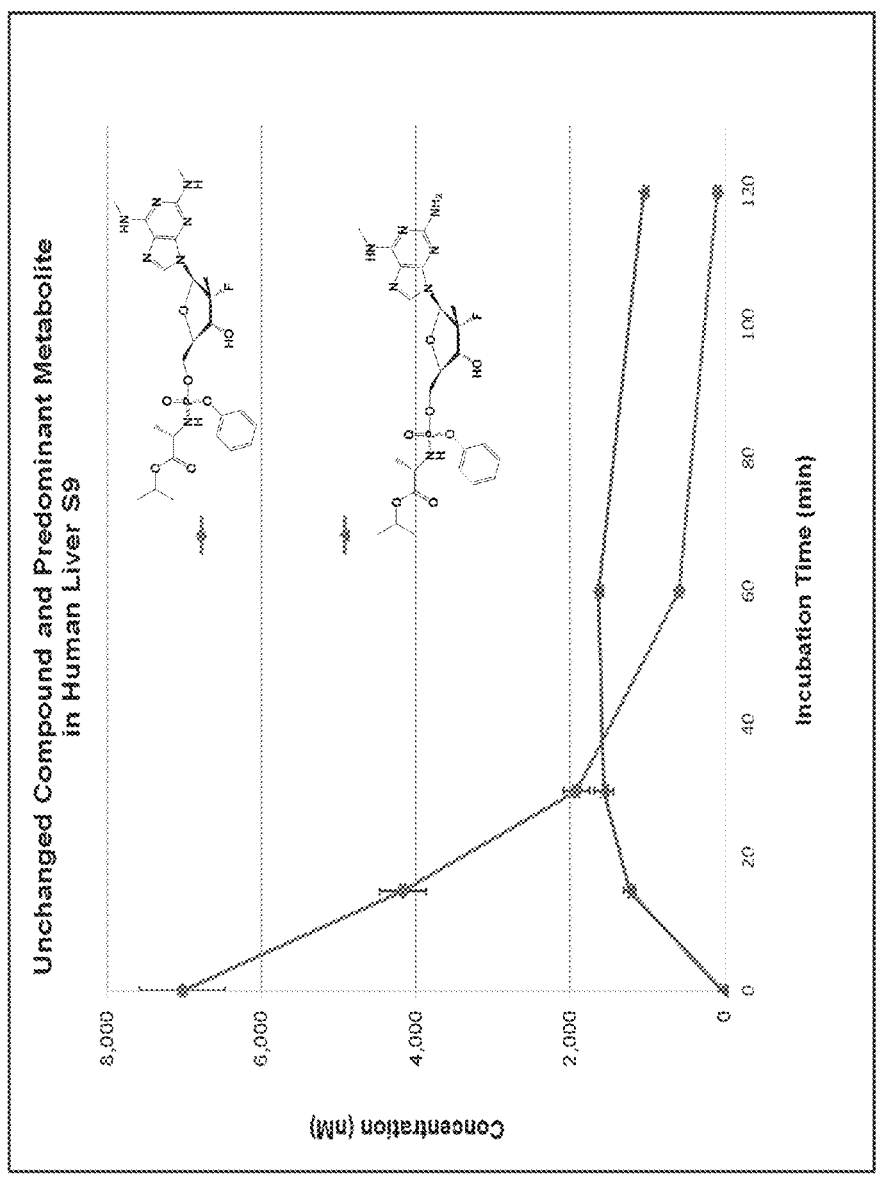
FIG. 6 is a graph showing the in vitro time course dealkylation of 2'-deoxy-2'-α-fluoro-2'-β-methyl-$N^2$-methyl-$N^6$-methyl-2,6-diaminopurine nucleoside phosphoramidate to 2'-deoxy-2'-α-fluoro-2'-β-methyl-$N^6$-methyl-2,6-diaminopurine nucleoside phosphoramidate in the presence of a human liver S9 fraction. The x axis is measured in minutes and the y axis is the measurement of the concentration of the compound remaining in nM.
Figure 7:
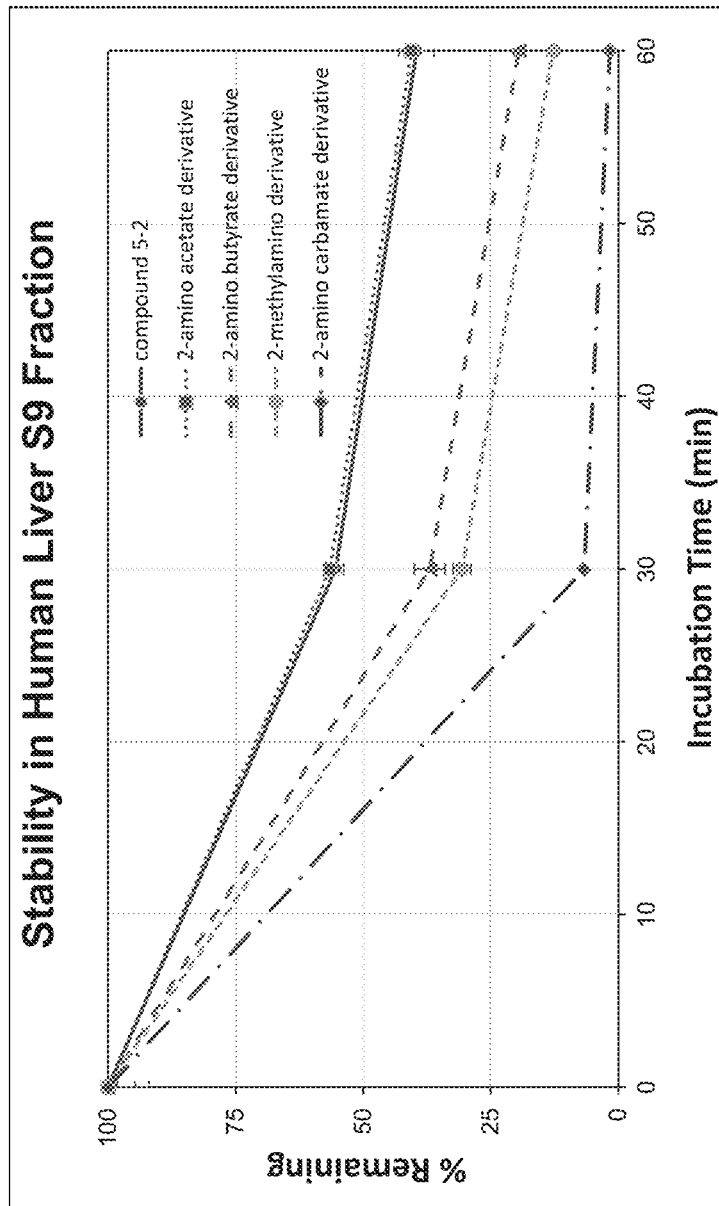
FIG. 7 is a graph showing the stability of compounds 5-2; the $N^2$-acetate of compound 5-2, the $N^2$-butyrate of compound 5-2; the $N^2$-methyl derivative of compound 5-2; and the $N^2$-n-pentylcarbamate of compound 5-2 in the presence of a human liver S9 fraction. The x axis is measured in minutes and the y axis is the measurement of percent compound remaining.

Interestingly, FIG. 6 illustrates the in vitro time course dealkylation of the 2'-deoxy-2'-α-fluoro-2'-β-methyl-$N^2$-methyl-$N^6$-methyl-2,6-diaminopurine nucleoside phosphoramidate to 2'-deoxy-2'-α-fluoro-2'-β-methyl-$N^6$-methyl-2,6-diaminopurine nucleoside phosphoramidate with a human liver S9 fraction. Furthermore, unexpected, faster, and a more extensive rate of cleavage of the carbamate moiety by human liver S9 fraction was observed as compared to compound 5-2 and its other 2-amino derivatives (FIG. 7).

Example 28

HCV (Gt1b) NS5B Polymerase Assay

Inhibition of HCV (gt1b) NS5B polymerase was determined in triplicate by measuring de novo polymerization in reaction mixtures containing serial dilutions of TA, in vitro transcribed viral RNA complementary to the HCV (−) strand 3'UTR region, polymerase, radiolabeled ribonucleotide, 250 µM non-competing rNTPs, and 1 µM competing rNTP. TA concentrations that produced 50% inhibition ($IC_{50}$) were determined from resulting inhibition curves.

Example 29

Human Bone Marrow Progenitor Cell Assay

Fresh human bone marrow progenitor cells (Invitrogen) suspended in either BFU-E or GM-CSF-specific culture medium were added, at $10^5$ cells/well, to triplicate serial dilutions of TA in 6-well plates. After 14-day incubations, colony counts were used to determine $CC_{50}$ values. BFU-E colonies were confirmed using the benzidene technique.

Compounds 25, 27 and 5-2 show no cytotoxicity against bone marrow stem cells in vitro.

Example 30 iPS Cardiomyocyte Assay iPS Cardiomyocytes (Cellular Dynamics) were seeded in microliter plates at $1.5 \times 10^4$ cells per well. After 48-hr incubation, cells were washed and maintenance medium containing serially diluted TA was added in triplicate. After incubating for an additional 3 days, cell viability was measured by staining with XTT and $CC_{50}$ values were calculated.

Compounds 25, 27 and 5-2 show no cytotoxicity against iPS cardiomyocytes in vitro.

Example 31

Human DNA Polymerase Assays

Inhibition of human DNA polymerases α, β and γ (CHIMERx) was determined in triplicate in reaction mixtures of serially diluted TA, 0.05 mM dCTP, dTTP, and dATP, 10 µCi [$^{32}$P]-α-dGTP (800 Ci/mmol), 20 µg activated calf thymus DNA and additional reagents specific for each polymerase. After 30-min incubations, incorporation of [α-$^{32}$P]-GTP was measured and resulting incubation curves were used to calculate $IC_{50}$ values.

The triphosphate, β-D-2'-deoxy-2'-α-fluoro-2'-β-methyl-guanine triphosphate, as well as the triphosphate analogs of compounds 25, 27 and 5-2 do not inhibit human DNA polymerases α, β or γ.

Example 32

Human Hepatocyte Co-Cultures

Cytotoxicity and hepatocyte health were assessed in triplicate by measuring ALT leakage, urea production, albumin secretion and cellular ATP contents in micro-patterned human hepatocyte co-cultures (HepatoPac®, Hepregen Corporation) prepared by seeding cryopreserved female human hepatocytes (single donor) and 3T3 J2 mouse fibroblasts in microtiter plates according to procedures established by Hepregen. Culture media was replaced with fresh media containing TA, test article, (0, 1, 10 or 30 µM) every 2 or 3 days through day 16. Spent culture media was assayed for ALT and urea content on days 2, 5, 7, 9, 12, 16 and 21 and for albumin content on days 2, 5, 7 and 9. Cellular ATP levels were measured on days 9 and 21. ATP signals in stromal-only control cultures (murine 3T3 fibroblasts) were subtracted from those of human HepatoPac co-cultures to obtain hepatocyte-specific effects. See, Table 4, 5 and 6 below.

Compound 5-2 at concentrations up to 30 µM, showed no signs of cytotoxicity as measured by ALT leakage, albumin secretion, urea production and cellular ATP content when incubated for up to 12 days with micro-patterned co-cultured human hepatocytes. The minor indications of cytotoxicity detected with extended exposure (up to 21 days of culture) were significantly less than those observed with sofosbuvir. See, Table 4, 5 and 6 below.

INX-189 was highly cytotoxic to human co-cultured hepatocytes, showing decreased albumin secretion as early as day 2 and cytotoxicity by all measures. Sofosbuvir showed more cytotoxicity than AT-511 under the same conditions.

TABLE 4

Effect of Test Article on Cellular ATP Concentrations

| | 50% Inhibitory Concentration ($IC_{50}$) - µM | |
| --- | --- | --- |
| Test Article | Day 9 | Day 21 |
| Cmpd 5-2 | >30 | 12.8 |
| Sofosbuvir | 8.6 | 2.3 |
| INX-189 | 8.1 | 0.1 |

TABLE 5

Effect of Test Articles on Albumin Secretion

| | 50% Inhibitory Concentration ($IC_{50}$) - µM | | | |
| --- | --- | --- | --- | --- |
| Test Article | Day 2 | Day 5 | Day 7 | Day 9 |
| Cmpd 5-2 | >30 | >30 | >30 | >30 |
| Sofosbuvir | >30 | 19.5 | 10.9 | 9.3 |
| INX-189 | 13.6 | 3.1 | 3.2 | 2.4 |

TABLE 6

Effect of Test Articles on Albumin Secretion

| Test Article | 50% Inhibitory Concentration (IC$_{50}$) - µM | | | | | | |
|---|---|---|---|---|---|---|---|
| | Day 2 | Day 5 | Day 7 | Day 9 | Day 12 | Day 16 | Day 21 |
| Cmpd 5-2 | >30 | >30 | >30 | >30 | >30 | 24.2 | 14.5 |
| Sofosbuvir | >30 | >30 | >30 | 12.1 | 6.8 | 2.7 | 2.3 |
| INX-189 | >30 | 4.2 | 1.8 | 1.8 | 1.3 | <<1 | <<1 |

Example 33

Metabolic Studies

The metabolism of compounds 25, 27 and 5-2, at a concentration of 10 µM, were investigated in fresh primary cultures of human, dog and mouse hepatocytes. Plated hepatocytes from humans (XenoTech, mixed gender, pooled from 10 donors), male Beagle dog (BioreclamationIVT), and male ICR/CD-1 mice (BioreclamationIVT, 8 donors) in 6-well plates with matrigel overlay were incubated in singlet with 10 µM TA. After 2, 4, 6, 8 or 24 hr, intracellular levels of nucleotide prodrugs and their potential metabolites (prodrugs, monophosphates, triphosphates and nucleosides) were quantitated by LC-MS/MS. Concentrations below the lower limit of quantitation (1.5 pmol/10$^6$ cells for prodrugs, monophosphates and nucleosides and 12 pmol/10$^6$ cells for triphosphates) were extrapolated from the standard curves.

The compound β-D-2'-deoxy-2'-α-fluoro-2'-β-methyl-guanine triphosphate is the predominant metabolite of compounds 25, 27 and 5-2 observed in cultured human hepatocytes and is a potent inhibitor of the HCV (gt1b) NS5B polymerase, with an IC$_{50}$ of 0.15 µM.

Figure 8:
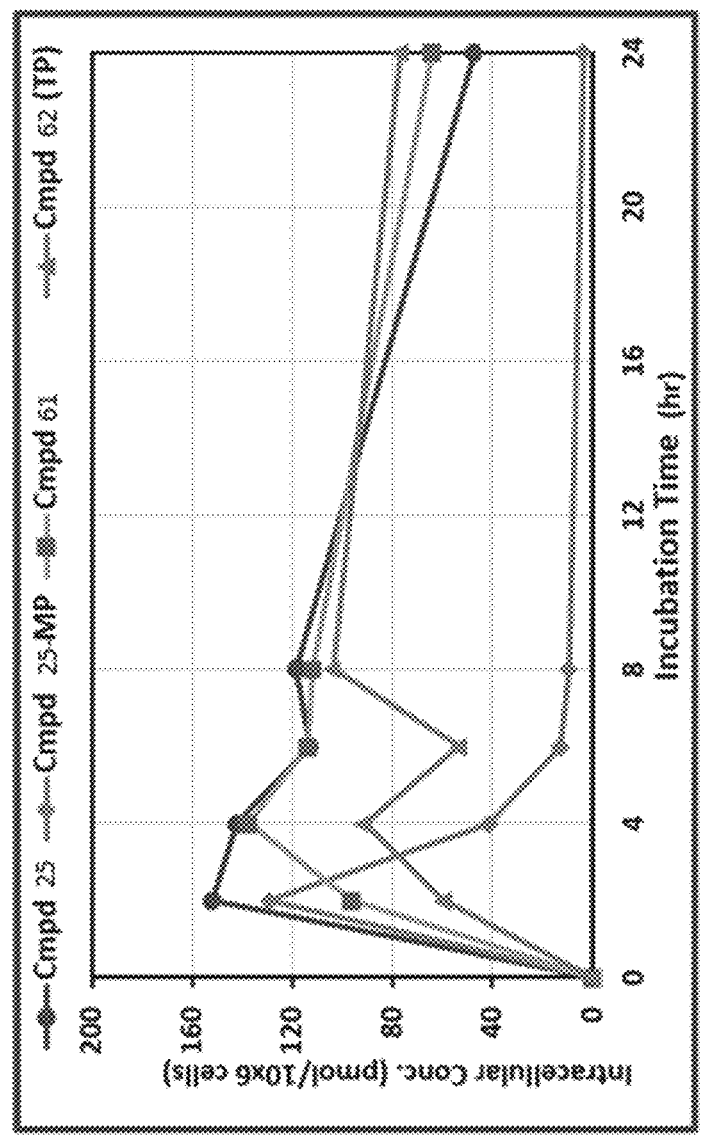
FIG. 8 shows the predominant Compound 25 metabolites generated in human hepatocytes. The x axis is incubation time in hours. The y axis is intracellular concentration in pmol/$10^6$ cells. See Example 33.

FIG. 8 shows the predominant Compound 25 metabolites in human hepatocytes.

Figure 9:
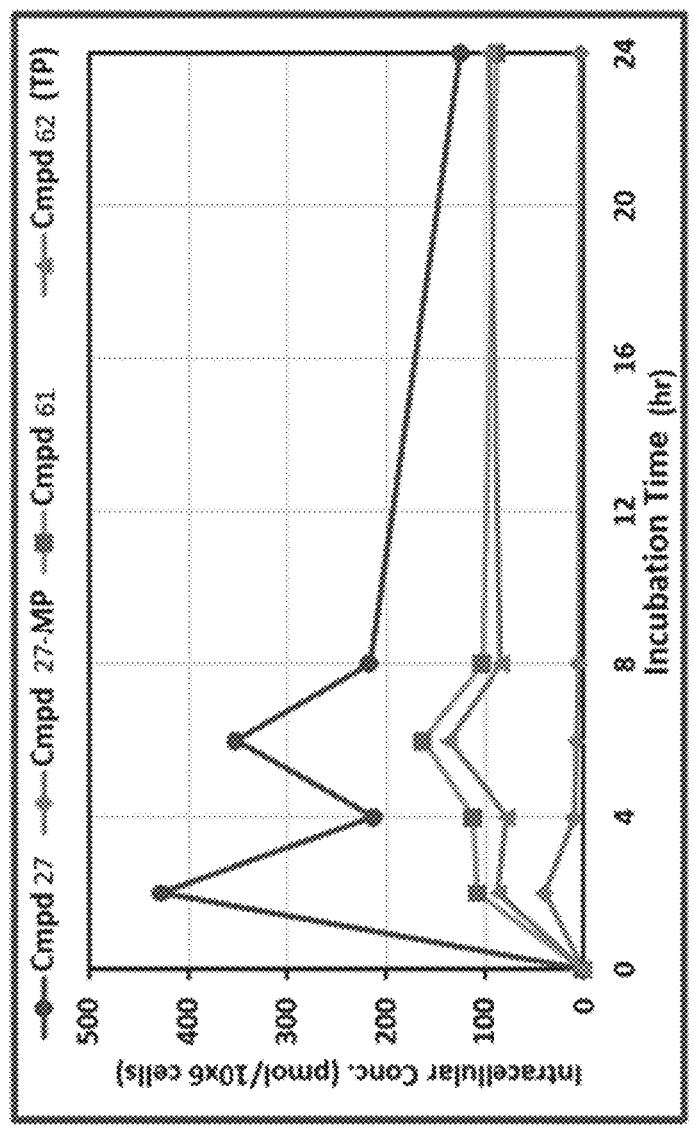
FIG. 9 shows the predominant Compound 27 metabolites generated in human hepatocytes. The x axis is incubation time in hours. The y axis is intracellular concentration in pmol/$10^6$ cells. See Example 33.

FIG. 9 shows the predominant Compound 27 metabolites in human hepatocytes.

Figure 10:
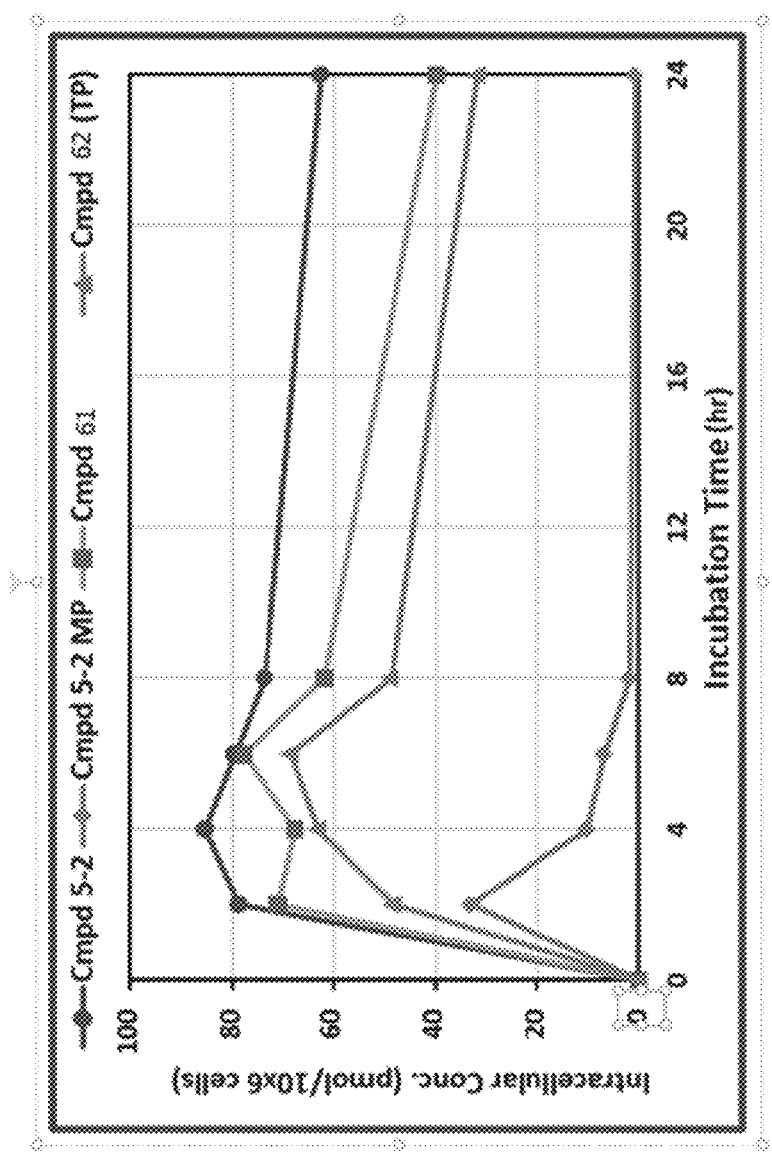
FIG. 10 shows the predominant Compound 5-2 metabolites generated in human hepatocytes. The x axis is incubation time in hours. The y axis is intracellular concentration in pmol/$10^6$ cells. See Example 33.

FIG. 10 shows the predominant Compound 5-2 metabolites in human hepatocytes.

Figure 11:
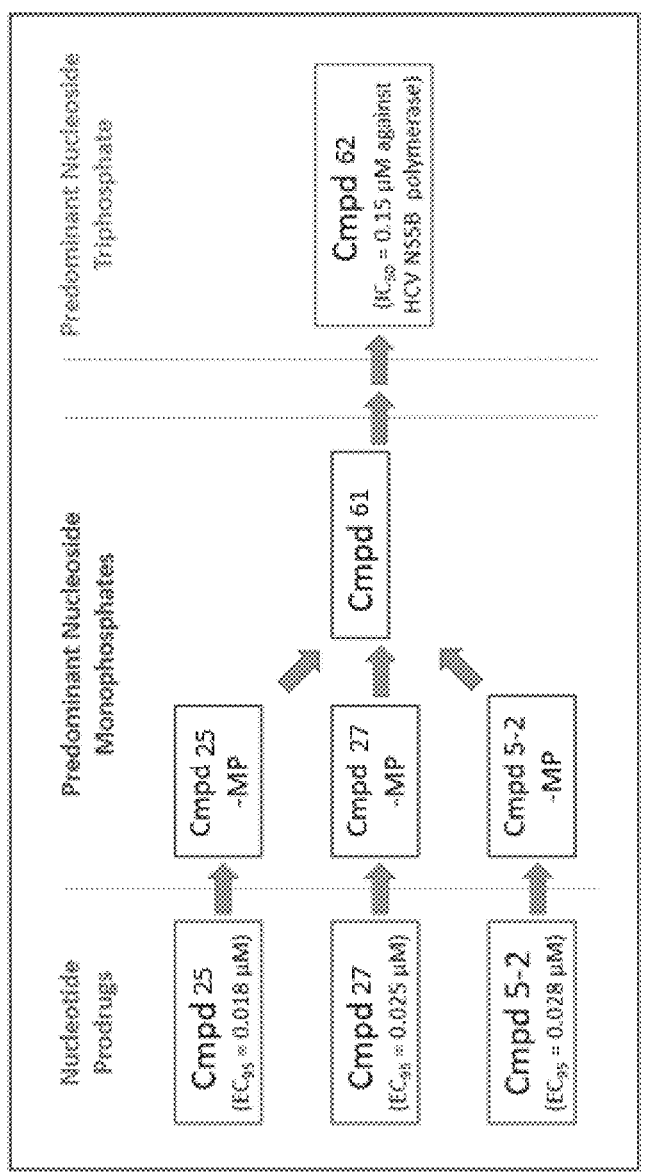
FIG. 11 is a graph showing the activation pathways for Compounds 25, 27 and 5-2. As can be seen, Compounds 25, 27 and 5-2 are converted to their corresponding monophosphate analogs which are subsequently metabolized to a common MP analog; β-D-2'-deoxy-2'-α-fluoro-2'-β-methyl-guanine monophosphate. The monophosphate is then stepwise phosphorylated to the active triphosphate: β-D-2'-deoxy-2'-α-fluoro-2'-β-methyl-guanine triphosphate. See Example 33.

FIG. 11 illustrates the activation pathways for Compounds 25, 27 and 5-2. As can be seen, Compounds 25, 27 and 5-2 are converted to their corresponding monophosphate analogs which are subsequently metabolized to a common MP analog; β-D-2'-deoxy-2'-α-fluoro-2'-β-methyl-guanine monophosphate (Compound 61). The monophosphate is then stepwise phosphorylated to the active triphosphate: β-D-2'-deoxy-2'-α-fluoro-2'-β-methyl-guanine triphosphate (Compound 62).

Example 34

Controls

INX-189 (INX-08189/BMS-986094) and sofosbuvir were used as controls in the Examples above.

The two most potent nucleotide prodrugs, Compounds 25 and 27, demonstrated excellent selectivity, with CC$_{50}$ values greater than 100 µM in Huh-7 cells, human bone marrow stem cells and human cardiomyocytes. No inhibition of human DNA polymerase α, β or γ, no activity against other RNA or DNA viruses, and no toxicity in all host cell lines was observed at concentrations up to 100 µM.

Table 7 is a table illustrating the compounds tested in a HCV Replicon Assay along with the EC$_{50}$/EC$_{95}$ (µM) and CC$_{50}$ (µM) results.

TABLE 7

Replicon Assay Results for Compounds Tested.

| Cmpd No. | Structure | HCV Replicon EC$_{50}$/EC$_{95}$ (µM) | HCV Replicon CC$_{50}$ (µM) | Fold increase in activity compared to parent nucleoside |
|---|---|---|---|---|
| | | 6.7 | >100 | |
| | | 2.1/9.04 | >100 | 3 |

TABLE 7-continued

Replicon Assay Results for Compounds Tested.

| Cmpd No. | Structure | HCV Replicon EC$_{50}$/EC$_{95}$ (μM) | HCV Replicon CC$_{50}$ (μM) | Fold increase in activity compared to parent nucleoside |
|---|---|---|---|---|
| 4 | 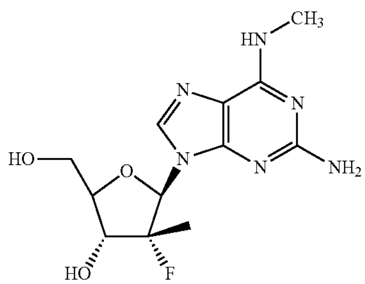 [SMILES: CNc1nc(N)nc2c1ncn2[C@@H]1OC(CO)[C@@H](O)[C@@]1(C)F] | 15.7 | >100 | |
| 5 | 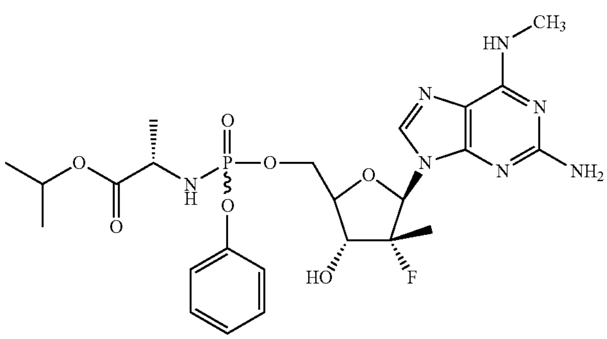 | 0.026/0.124 | >100 | >600 |
| 5-1 | 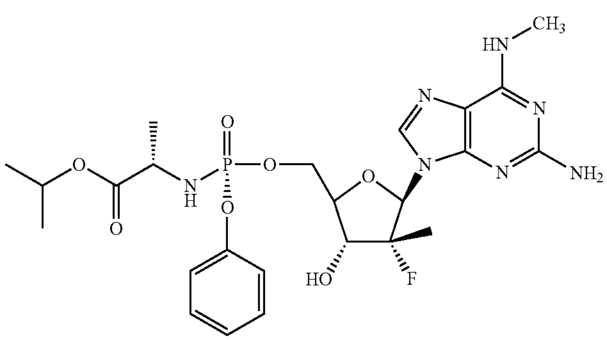 [SMILES: CNc1nc(N)nc2c1ncn2[C@@H]1OC(CO[P@](=O)(N[C@@H](C)C(=O)OC(C)C)Oc2ccccc2)[C@@H](O)[C@@]1(C)F] | 0.0551/0.282 | >100 | >280 |
| 5-2 | 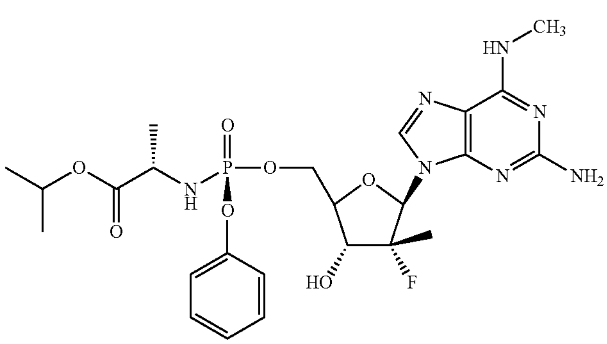 [SMILES: CNc1nc(N)nc2c1ncn2[C@@H]1OC(CO[P@@](=O)(N[C@@H](C)C(=O)OC(C)C)Oc2ccccc2)[C@@H](O)[C@@]1(C)F] | 0.004/0.028 | >100 | >3,900 |

TABLE 7-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 6 | 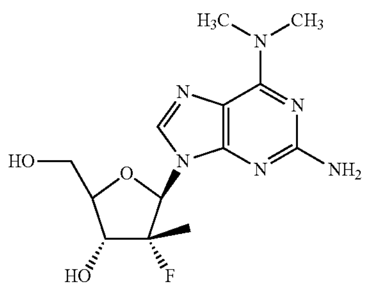 [SMILES: CN(C)c1nc(N)nc2c1ncn2[C@@H]1OC(CO)[C@@H](O)[C@@]1(C)F] | 10.7 | >100 | |
| 7 | 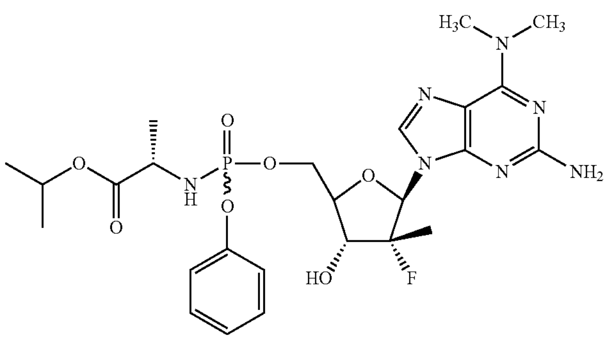 [SMILES: CC(C)OC(=O)[C@H](C)NP(=O)(OCC1O[C@@H](n2cnc3c(N(C)C)nc(N)nc32)[C@](C)(F)[C@@H]1O)Oc1ccccc1] | 0.0121/0.071 | >100 | >890 |
| 8 | 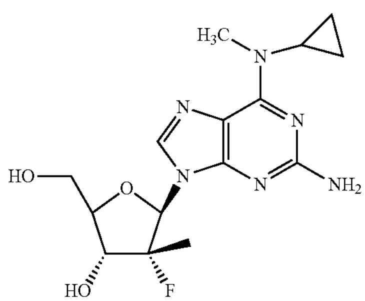 [SMILES: CN(c1nc(N)nc2c1ncn2[C@@H]1OC(CO)[C@@H](O)[C@@]1(C)F)C1CC1] | 5.56 | >100 | |
| 9 | 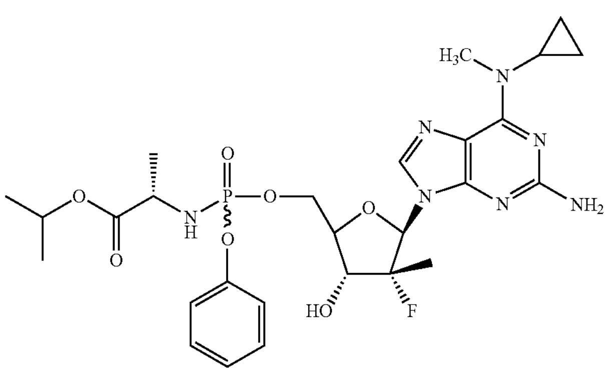 [SMILES: CC(C)OC(=O)[C@H](C)NP(=O)(OCC1O[C@@H](n2cnc3c(N(C)C4CC4)nc(N)nc32)[C@](C)(F)[C@@H]1O)Oc1ccccc1] | 0.0091/0.054 | >100 | >600 |

TABLE 7-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 15 | 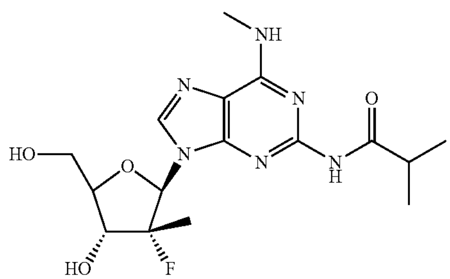 [SMILES: CNc1nc(NC(=O)C(C)C)nc2c1ncn2[C@@H]1OC(CO)[C@@H](O)[C@@]1(C)F] | >100 | >100 | |
| 16 | 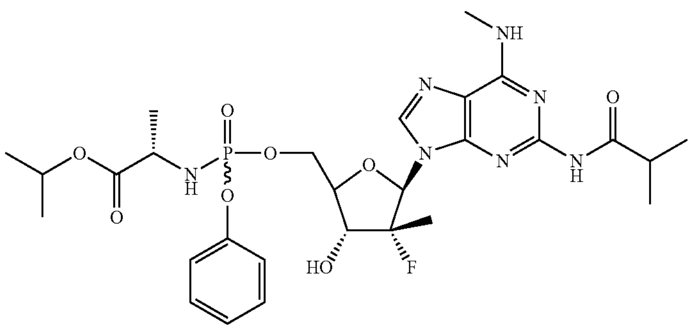 [SMILES: CNc1nc(NC(=O)C(C)C)nc2c1ncn2[C@@H]1OC(COP(=O)(N[C@@H](C)C(=O)OC(C)C)Oc2ccccc2)[C@@H](O)[C@@]1(C)F] | 0.576/3.69 | >100 | |
| 17 | 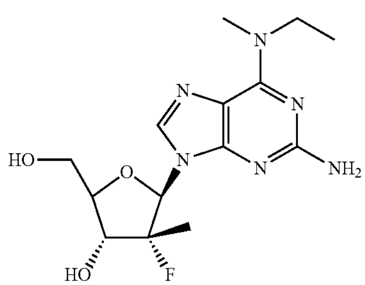 [SMILES: CCN(C)c1nc(N)nc2c1ncn2[C@@H]1OC(CO)[C@@H](O)[C@@]1(C)F] | 11.5/65.4 | >100 | |
| 18 | 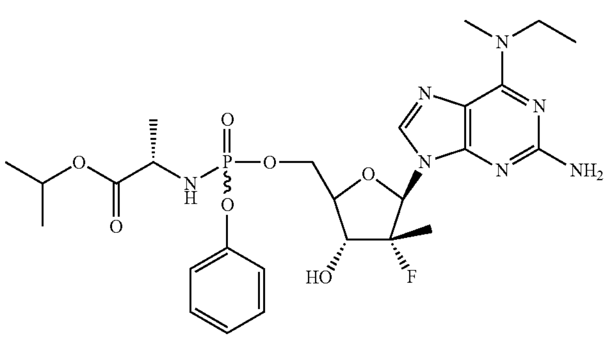 [SMILES: CCN(C)c1nc(N)nc2c1ncn2[C@@H]1OC(COP(=O)(N[C@@H](C)C(=O)OC(C)C)Oc2ccccc2)[C@@H](O)[C@@]1(C)F] | 0.048/0.219 | 90.0 | |

TABLE 7-continued

Replicon Assay Results for Compounds Tested.

| Cmpd No. | Structure | HCV Replicon EC$_{50}$/EC$_{95}$ (μM) | HCV Replicon CC$_{50}$ (μM) | Fold increase in activity compared to parent nucleoside |
|---|---|---|---|---|
| 19 | 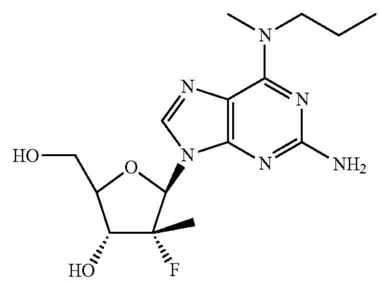 [SMILES: CCCN(C)c1nc(N)nc2c1ncn2[C@@H]1OC(CO)[C@@H](O)[C@@]1(C)F] | 7.47 | >100 | |
| 20 | 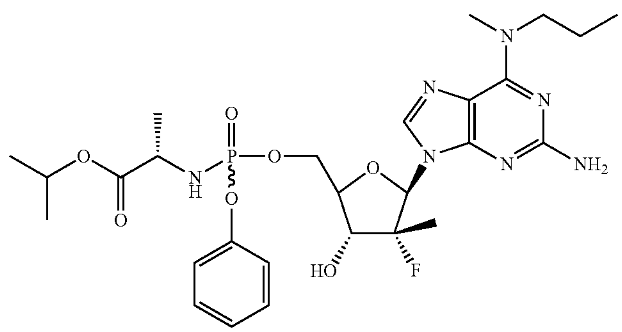 [SMILES: CCCN(C)c1nc(N)nc2c1ncn2[C@@H]1OC(COP(=O)(N[C@@H](C)C(=O)OC(C)C)Oc2ccccc2)[C@@H](O)[C@@]1(C)F] | 0.073/0.315 | >100 | |
| 25 | 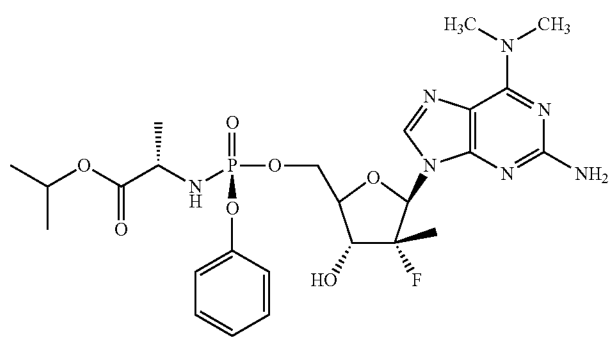 [SMILES: CC(C)OC(=O)[C@H](C)N[P@](=O)(OCC1O[C@@H](n2cnc3c(N(C)C)nc(N)nc32)[C@](C)(F)[C@@H]1O)Oc1ccccc1] | 0.004/0.019 | >100 | >2,600 |
| 26 | 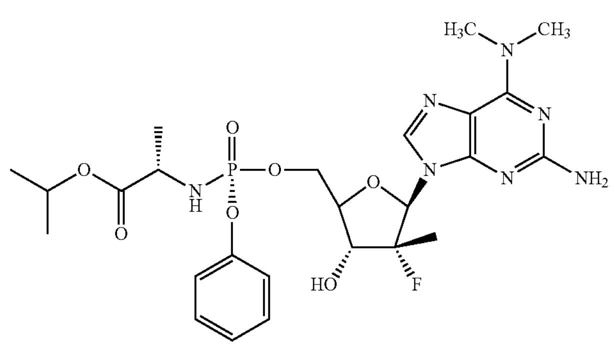 [SMILES: CC(C)OC(=O)[C@H](C)N[P@@](=O)(OCC1O[C@@H](n2cnc3c(N(C)C)nc(N)nc32)[C@](C)(F)[C@@H]1O)Oc1ccccc1] | 0.0351/0.057 | >100 | |

TABLE 7-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 27 | 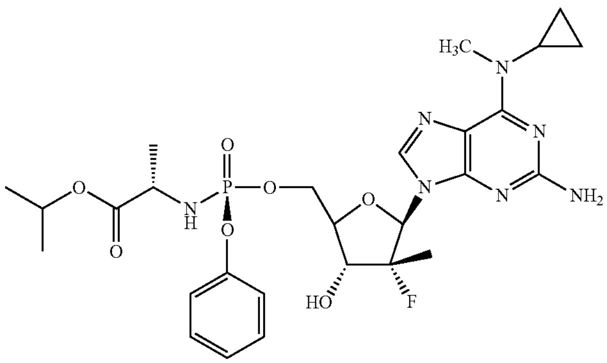 [SMILES: CC(C)OC(=O)[C@H](C)N[P@](=O)(OCC1O[C@@H](n2cnc3c(N(C)C4CC4)nc(N)nc32)[C@](C)(F)[C@@H]1O)Oc1ccccc1] | 0.005/0.025 | >100 | >1,100 |
| 28 | 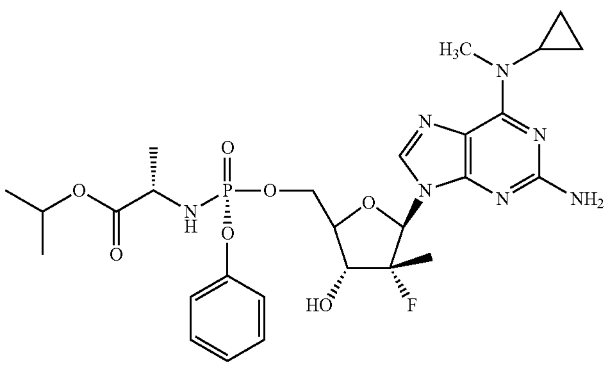 [SMILES: CC(C)OC(=O)[C@H](C)N[P@@](=O)(OCC1O[C@@H](n2cnc3c(N(C)C4CC4)nc(N)nc32)[C@](C)(F)[C@@H]1O)Oc1ccccc1] | 0.014/0.076 | >100 | |
| 41 | 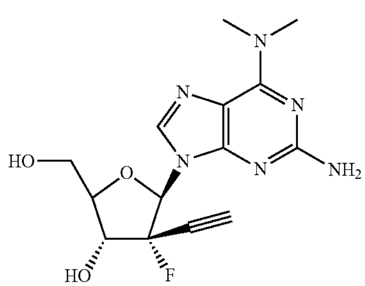 [SMILES: C#C[C@@]1(F)[C@H](O)C(CO)O[C@H]1n1cnc2c(N(C)C)nc(N)nc21] | 0.508/25.1 | | 21.8 |
| 42 | 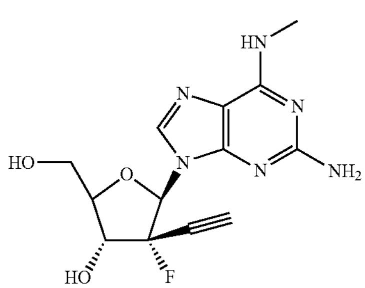 [SMILES: C#C[C@@]1(F)[C@H](O)C(CO)O[C@H]1n1cnc2c(NC)nc(N)nc21] | 4.18/20.4 | >100 | |

TABLE 7-continued

Replicon Assay Results for Compounds Tested.

| Cmpd No. | Structure | HCV Replicon $EC_{50}/EC_{95}$ (μM) | HCV Replicon $CC_{50}$ (μM) | Fold increase in activity compared to parent nucleoside |
|---|---|---|---|---|
| 43 | 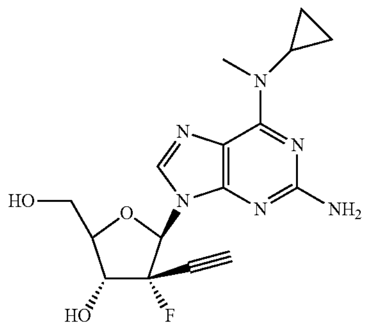 [SMILES: C#C[C@@]1(F)[C@H](O)C(CO)O[C@H]1n1cnc2c(N(C)C3CC3)nc(N)nc21] | 6.43/24.7 | 21.6 | |
| 45 | 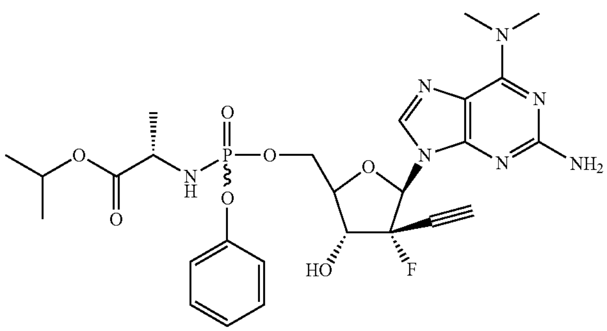 [SMILES: C#C[C@@]1(F)[C@H](O)C(COP(=O)(N[C@@H](C)C(=O)OC(C)C)Oc2ccccc2)O[C@H]1n1cnc2c(N(C)C)nc(N)nc21] | 0.16/0.876 | 0.68 | |
| 46 | 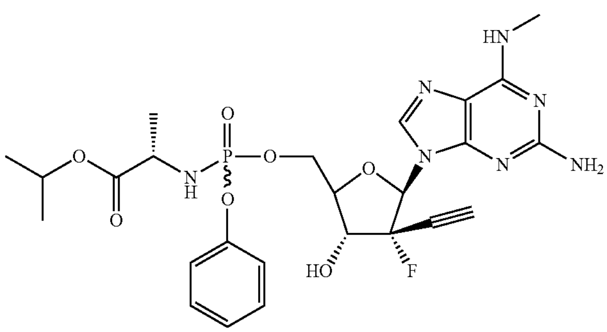 [SMILES: C#C[C@@]1(F)[C@H](O)C(COP(=O)(N[C@@H](C)C(=O)OC(C)C)Oc2ccccc2)O[C@H]1n1cnc2c(NC)nc(N)nc21] | 0.224/0.961 | >100 | |
| 47 | 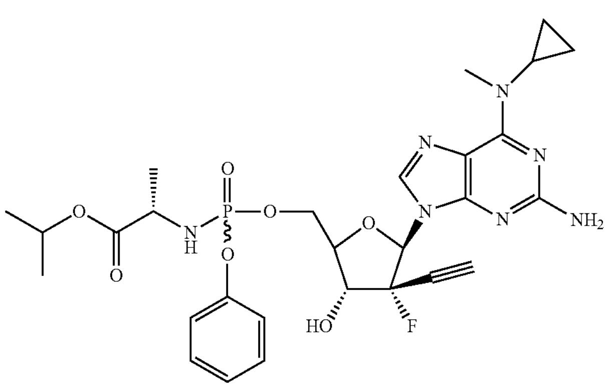 [SMILES: C#C[C@@]1(F)[C@H](O)C(COP(=O)(N[C@@H](C)C(=O)OC(C)C)Oc2ccccc2)O[C@H]1n1cnc2c(N(C)C3CC3)nc(N)nc21] | 0.338/1.72 | 1.68 | |

TABLE 7-continued

Replicon Assay Results for Compounds Tested.

| Cmpd No. | Structure | HCV Replicon EC$_{50}$/EC$_{95}$ (μM) | HCV Replicon CC$_{50}$ (μM) | Fold increase in activity compared to parent nucleoside |
|---|---|---|---|---|
| 61 | 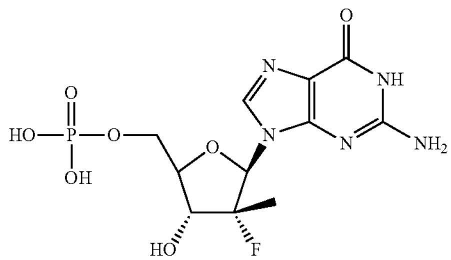 [SMILES: C[C@@]1(F)[C@H](O)C(COP(=O)(O)O)O[C@H]1n1cnc2c(=O)[nH]c(N)nc21] | | | |
| 62 | 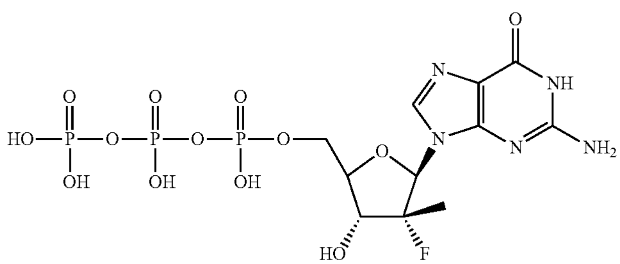 [SMILES: C[C@@]1(F)[C@H](O)C(COP(=O)(O)OP(=O)(O)OP(=O)(O)O)O[C@H]1n1cnc2c(=O)[nH]c(N)nc21] | | | |
| | Sofosbuvir | 0.052/0.310 | >100 | |
| | PSI-352938 | 0.045/0.259 | >100 | |

The β-D-2'-D-2'-α-fluoro-2'-β-C-substituted-2-modified-N$^6$-substituted purine nucleotides described herein exhibit significant activity against the HCV virus. Compounds according to the present invention are assayed for desired relative activity using well-known and conventional assays found in the literature.

For example, anti-HCV activity and cytotoxicity of the compounds may be measured in the HCV subgenomic RNA replicon assay system in Huh7 ET cells. (See, Korba, et al., *Antiviral Research* 2008, 77, 56). The results can be summarized in comparison to a positive control, 2'-C-Me-cytosine {2'-C-Me-C} (Pierra, et al., *Journal of Medicinal Chemistry* 2006, 49, 6614.

Another in-vitro assay for anti-hepatitis C virus activity is described in U.S. Pat. No. 7,718,790 by Stuyver, et al., and assigned to Pharmasset, Inc.

This specification has been described with reference to embodiments of the invention. Given the teaching herein, one of ordinary skill in the art will be able to modify the invention for a desired purpose and such variations are considered within the scope of the invention.

We claim:

1. A pharmaceutical composition comprising an anti-HCV effective amount of a compound of the formula:

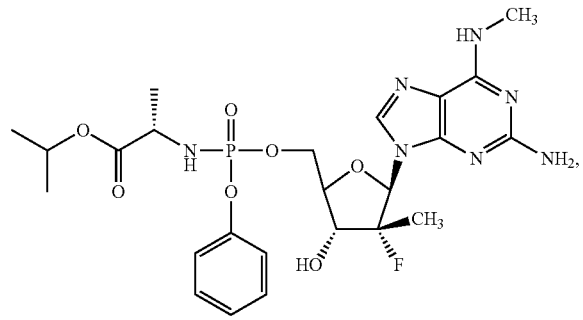 [SMILES: CNc1nc(N)nc2c1ncn2[C@@H]1OC(COP(=O)(N[C@@H](C)C(=O)OC(C)C)Oc2ccccc2)[C@@H](O)[C@@]1(C)F]

in a pharmaceutically acceptable carrier.

2. The pharmaceutical composition of claim 1, comprising an effective amount of a compound of the formula:

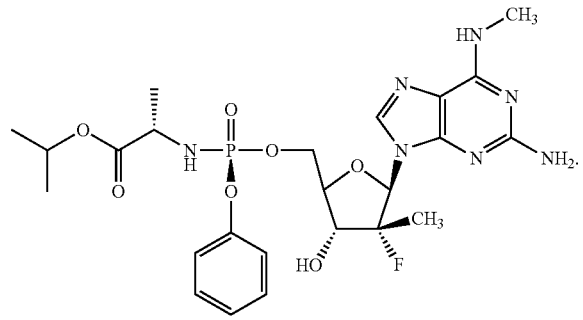

3. The pharmaceutical composition of claim 1, comprising an effective amount of a compound of the formula:

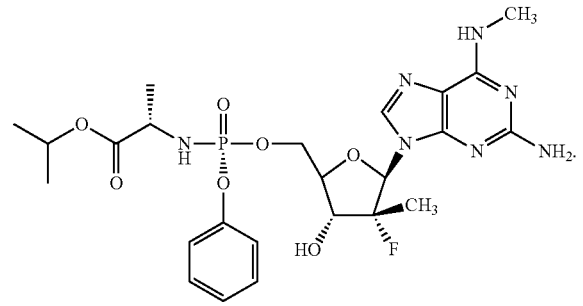 [SMILES: CNc1nc(N)nc2c1ncn2[C@@H]1OC(CO[P@](=O)(N[C@@H](C)C(=O)OC(C)C)Oc2ccccc2)[C@@H](O)[C@@]1(C)F]

4. The pharmaceutical composition of claim 1, in a dosage form.
5. The pharmaceutical composition of claim 4, in an oral dosage form.
6. The pharmaceutical composition of claim 5, in a tablet.
7. The pharmaceutical composition of claim 5, in a capsule.
8. The pharmaceutical composition of claim 2, in a dosage form.
9. The pharmaceutical composition of claim 8, in an oral dosage form.
10. The pharmaceutical composition of claim 9, in a tablet.
11. The pharmaceutical composition of claim 9, in a capsule.
12. The pharmaceutical composition of claim 3, in a dosage form.
13. The pharmaceutical composition of claim 12, in an oral dosage form.
14. The pharmaceutical composition of claim 13, in a tablet.
15. The pharmaceutical composition of claim 13, in a capsule.
16. A pharmaceutical composition comprising an anti-HCV effective amount of a compound of the formula:

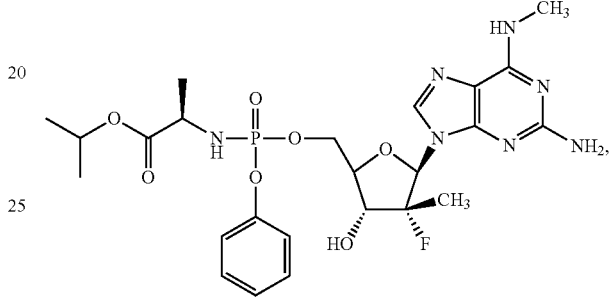

in a pharmaceutically acceptable carrier.

17. The pharmaceutical composition of claim 16, comprising an effective amount of a compound of the formula:

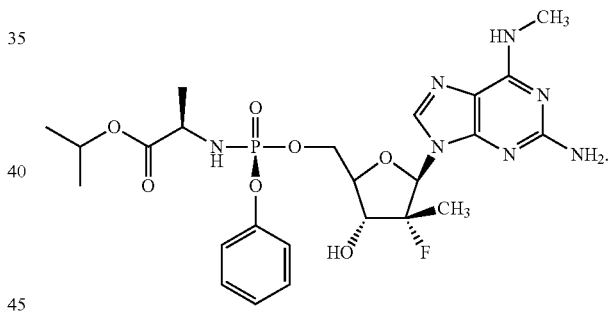

18. The pharmaceutical composition of claim 16, comprising an effective amount of a compound of the formula:

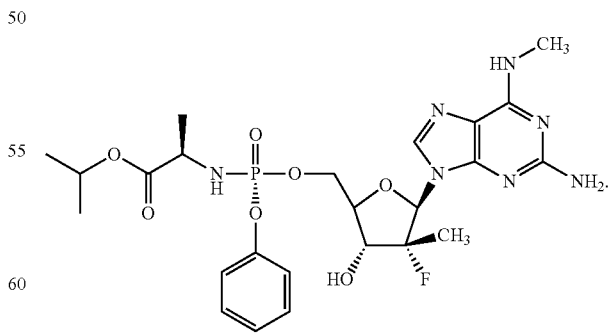

19. The pharmaceutical composition of claim 16, in a dosage form.
20. The pharmaceutical composition of claim 19, in an oral dosage form.

21. The pharmaceutical composition of claim 20, in a tablet.

22. The pharmaceutical composition of claim 20, in a capsule.

23. The pharmaceutical composition of claim 17, in a dosage form.

24. The pharmaceutical composition of claim 23, in an oral dosage form.

25. The pharmaceutical composition of claim 24, in a tablet.

26. The pharmaceutical composition of claim 24, in a capsule.

27. The pharmaceutical composition of claim 18, in a dosage form.

28. The pharmaceutical composition of claim 27, in an oral dosage form.

29. The pharmaceutical composition of claim 28, in a tablet.

30. The pharmaceutical composition of claim 28, in a capsule.

* * * * *